US008207194B2

(12) United States Patent
Honda et al.

(10) Patent No.: US 8,207,194 B2
(45) Date of Patent: Jun. 26, 2012

(54) COMPOUNDS HAVING A 4-PYRIDYLALKYLTHIO GROUP AS A SUBSTITUENT

(75) Inventors: Takahiro Honda, Ikoma (JP); Hisashi Tajima, Ikoma (JP); Yoshimasa Sasabuchi, Ikoma (JP); Kenji Kawashima, Ikoma (JP); Kazuyoshi Okamoto, Ikoma (JP); Minoru Yamamoto, Ikoma (JP); Masakazu Ban, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 546 days.

(21) Appl. No.: 12/381,290

(22) Filed: Mar. 10, 2009

(65) Prior Publication Data

US 2009/0286786 A1 Nov. 19, 2009

Related U.S. Application Data

(62) Division of application No. 10/548,283, filed as application No. PCT/JP2004/002812 on Mar. 5, 2004, now Pat. No. 7,534,802.

(30) Foreign Application Priority Data

Mar. 7, 2003 (JP) ................... 2003-062042
Jan. 20, 2004 (JP) ................... 2004-011602

(51) Int. Cl.
*A61K 31/47* (2006.01)
*C07D 401/02* (2006.01)
*C07D 213/02* (2006.01)

(52) U.S. Cl. ........ 514/307; 514/314; 514/357; 546/168; 546/174; 546/337

(58) Field of Classification Search .................. None
See application file for complete search history.

(56) References Cited

U.S. PATENT DOCUMENTS

| 4,970,224 | A | 11/1990 | Jacobson et al. |
| 6,329,372 | B1 | 12/2001 | Head et al. |
| 6,380,214 | B1 | 4/2002 | Gant et al. |
| 2005/0113450 | A1 | 5/2005 | Thorarensen et al. |
| 2007/0149574 | A1 | 6/2007 | Honda et al. |

FOREIGN PATENT DOCUMENTS

| CA | 2350208 A1 | 5/2000 |
| DE | 39 29 673 A1 | 3/1991 |
| EP | 0 337 815 A1 | 10/1989 |
| EP | 0 422 369 A2 | 4/1991 |
| JP | 02-129173 A1 | 5/1990 |
| JP | 02-501051 A | 1/2002 |
| JP | 03-500401 A | 1/2003 |
| WO | WO 97/30035 A1 | 8/1997 |
| WO | WO 98/35958 A1 | 8/1998 |
| WO | WO 98/50356 A1 | 11/1998 |
| WO | WO 00/27819 A2 | 5/2000 |
| WO | WO 00/27819 A3 | 5/2000 |
| WO | WO 01/55114 A1 | 8/2001 |
| WO | WO 02/062295 A2 | 8/2002 |
| WO | WO 02/066470 A1 | 8/2002 |
| WO | WO 2004/078723 A | 1/2003 |
| WO | WO 03/040096 A2 | 5/2003 |
| WO | WO 2004/018414 A2 | 3/2004 |
| WO | WO 2004/018428 A1 | 3/2004 |

OTHER PUBLICATIONS

*Molecular Medicine*, vol. 35, special issue, "Molecular Mechanism of Symptoms and Pathema"; Nakayama, Shoten, 73-74, (1998).
*Protein, Nucleic Acid, Enzyme*, "The Most Advanced Development of New Drugs"; Kyoritsu Shuppan, 1182-1187, (2000).
R. Ponci et al., *II Farmaco-Ed. Sc.*, 18, 288 (1963).
Frank D. King, "Bioisosteres, Conformational Restriction, and Pro-drugs—Case History: An Example of conformational Restriction Approach," *Med. Chem. Principle and Practice*, (1994), pp. 206-208.
Chinese Office Action dated Feb. 6, 2009, which issued in the counterpart Chinese Patent Application No. 2005800449908, and an English-language translation thereof.

*Primary Examiner* — Zinna Northington Davis
(74) *Attorney, Agent, or Firm* — Holtz, Holtz, Goodman & Chick, P.C.

(57) ABSTRACT

A compound having the following formula [I] or a pharmaceutically acceptable salt thereof:

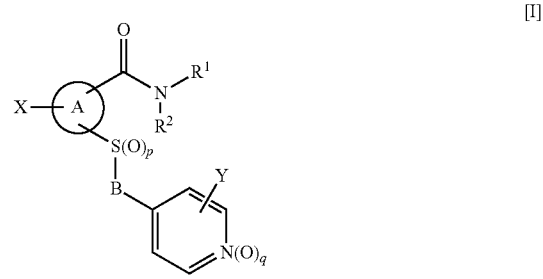

wherein A is benzene or an aromatic five-membered heterocycle which optionally is fused with a cycloalkane ring; B is an alkylene; $R^1$ and $R^2$ are hydrogen, hydroxy, alkoxy, aryloxy, alkyl, cycloalkyl, aryl, heterocycle, amino, alkylamino, arylamino or acyl, or $R^1$ and $R^2$ join together to form a heterocycle; X and Y are hydrogen, halogen, hydroxy, alkoxy, aryloxy, alkyl, cycloalkyl, aryl, mercapto, alkylthio, arylthio, carboxyl, an ester of carboxyl, an amide of carboxyl, cyano or nitro; p is 0, 1 or 2; and q is 0 or 1. The compound is useful for treating diseases in which angiogenesis or augmentation of vascular permeability is involved.

7 Claims, No Drawings

COMPOUNDS HAVING A 4-PYRIDYLALKYLTHIO GROUP AS A SUBSTITUENT

CROSS-REFERENCE TO RELATED APPLICATIONS

This application is a divisional application of application Ser. No. 10/548,283 filed Sep. 1, 2005 (U.S. Pat. No. 7,534,802) (the entire contents of which are hereby incorporated by reference herein), which is the United States national phase application of International application PCT/JP2004/002812 filed Mar. 5, 2004 (the entire contents of which are hereby incorporated by reference herein).

TECHNICAL FIELD

The present invention relates to novel compounds having a 4-pyridylalkylthio group as a substituent or salts thereof which are useful as pharmaceuticals. These compounds are useful as therapeutic agents for diseases in which angiogenesis or augmentation of vascular permeability is involved, particularly as therapeutic agents for cancer, rheumatoid arthritis, age-related macular degeneration, diabetic retinopathy, retinopathy of prematurity, retinal vein occlusion, polyploid choroidal angiopathy, diabetic macular edema, psoriasis vulgaris, pultaceous arteriosclerosis and the like.

BACKGROUND ART

Angiogenesis is a phenomenon wherein a new vascular network is formed from existing blood vessels and is observed mainly in fine blood vessel. Angiogenesis is originally a physiological phenomenon and is essential for blood vessel formation at a viviparous period, but it is usually observed only at a limited site such as endometrium or follicle or at a limited period such as a wound healing process in adults. However, pathologic angiogenesis is caused in diseases such as cancer, rheumatoid arthritis, age-related macular degeneration, diabetic retinopathy, retinopathy of prematurity, retinal vein occlusion, polyploid choroidal angiopathy, diabetic macular degeneration, psoriasis vulgaris and pultaceous arteriosclerosis, and pathologic angiogenesis closely relates to the progress of pathema of these diseases. It is considered that angiogenesis is adjusted by balance between its promotive factor and inhibitory factor, and angiogenesis is caused by losing of the balance. (See Molecular Medicine vol. 35, special issue, "Molecular Mechanism of Symptom and Pathema", Nakayama Shoten, 73-74 (1998) and Protein, Nucleic Acid, Enzyme, extra number, "The Most Advanced Development of New Drugs", Kyoritsu Shuppan, 1182-1187 (2000).)

A vascular endothelial growth factor (hereinafter abbreviated as "VEGF") is a factor which specifically acts on a receptor (Flt-1, KDR/Flk-1 or the like) existing on the surface of vascular endothelial cells, thereby promoting growth and migration of the vascular endothelial cells, construction of a capillary vessel network due to vasculogenesis. VEGF also augments vascular permeability, and plays an important role in occurrence of angiogenesis. Accordingly, there have been many reports on attempts to treat diseases in which angiogeniesis and the augmentation of vascular permeability are involved by inhibiting VEGF to control the occurrence of angiogenesis and the augmentation of vascular permeability. Examples of drugs to be used for the treatment are 2-indolinone derivatives (WO 98/50356), phthalazine derivatives (WO 98/35958), quinazoline derivatives (WO 97/30035), anthranilic acid amide derivatives (WO 00/27819), 2-aminonicotinic acid derivatives (WO 01/55114) and the like. However, compounds which have 4-pyridylalkylthio group as a substituent aren't described in these patent documents at all.

On the other hand, Il Farmaco-Ed. Sc., 18, 288 (1963) and WO 02/066470 report compounds having chemical structures relatively close to those of the compounds having 4-pyridylalkylthio as a substituent. The compounds disclosed in Il Farmaco-Ed. Sc., 18, 288 (1963) are benzoic acid amide derivatives having 3-pyridylalkylthio, and antibacterial actions are recited as their use. WO 02/066470 relates to substituted alkylamine derivatives and their pharmaceutical use, and discloses compounds having enormous combinations of chemical structures. WO 02/066470 discloses a derivative having 4-pyridylalkylamino as one example among those compounds, but does not describe 4-pyridylalkylthio derivatives at all.

DISCLOSURE OF THE INVENTION

It was a very interesting subject to study synthesis of novel compounds having 4-pyridylalkylthio as a substituent and to find pharmacological actions of the compounds.

Studying synthesis of the novel compounds having 4-pyridylalkylthio as a substituent, the present inventors succeeded in preparing many novel compounds. Further, studying variously pharmacological actions of these compounds, they found that the compounds have cell growth inhibitory effects, tumor growth inhibitory effects, paw edema inhibitory effects or choroidal neovascularization inhibitory effects, and are useful as therapeutic agents for diseases in which angiogenesis or augmentation of vascular permeability is involved, particularly as therapeutic agents for cancer, rheumatoid arthritis, age-related macular degeneration, diabetic retinopathy, retinopathy of prematurity, retinal vein occlusion, polyploid choroidal angiopathy, diabetic macular edema, psoriasis vulgaris, pultaceous arteriosclerosis and the like to complete the present invention.

The present invention provides the novel compounds having 4-pyridylalkylthio as a substituent or salts thereof which are useful as pharmaceuticals. In particular, the novel compounds having 4-pyridylalkylthio as a substituent of the present invention have excellent cell growth inhibitory effects, tumor growth inhibitory effects, paw edema inhibitory effects or choroidal neovascularization inhibitory effects, and are useful as therapeutic agents for the diseases in which angiogenesis or augmentation of vascular permeability is involved, for example, cancer, rheumatoid arthritis, age-related macular degeneration, diabetic retinopathy, retinopathy of prematurity, retinal vein occlusion, polyploid choroidal angiopathy, diabetic macular edema, psoriasis vulgaris, pultaceous arteriosclerosis and the like.

BEST MODE FOR CARRYING OUT THE INVENTION

The present invention relates to compounds represented by the general formula [I] or salts thereof (hereinafter referred to as "the present compound" as far as there is no proviso) and pharmaceutical compositions comprising the present compound. In more detail, the present invention relates to therapeutic agents comprising the present compounds as active ingredients for diseases in which angiogenesis or augmentation of vascular permeability is involved, for example, as therapeutic agents for cancer, rheumatoid arthritis, age-related macular degeneration, diabetic retinopathy, retinopathy of prematurity, retinal vein occlusion, polyploid choroidal angiopathy, diabetic macular edema, psoriasis vulgaris, pultaceous arteriosclerosis and the like,

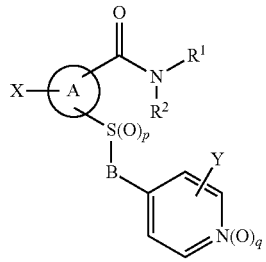

wherein the ring "A" is a benzene ring, or an aromatic five-membered heterocycle or an aromatic six-membered heterocycle which can be fused with a cycloalkane ring;
"B" is alkylene;
$R^1$ and $R^2$, the same or different, are hydrogen, hydroxy, substituted or unsubstituted alkoxy, substituted or unsubstituted aryloxy, substituted or unsubstituted alkyl, substituted or unsubstituted cycloalkyl, substituted or unsubstituted aryl, substituted or unsubstituted heterocycles, amino, substituted or unsubstituted alkylamino, substituted or unsubstituted arylamino, or substituted or unsubstituted acyl;
$R^1$ and $R^2$ can join together to form a substituted or unsubstituted heterocycle;
X and Y, the same or different, are one or plural groups selected from hydrogen, halogen, hydroxy, substituted or unsubstituted alkoxy, substituted or unsubstituted aryloxy, substituted or unsubstituted alkyl, substituted or unsubstituted cycloalkyl, substituted or unsubstituted aryl, mercapto, substituted or unsubstituted alkylthio, substituted or unsubstituted arylthio, carboxyl or ester thereof or amide thereof, cyano and nitro;
p is 0, 1 or 2; and
q is 0 or 1.
The same definitions are applied hereinafter.

The respective groups defined above are described in detail below.

The cycloalkane ring is a cycloalkane ring having three to eight carbon atoms. Specific examples of cycloalkane-rings are a cyclopropane ring, a cyclobutane ring, a cyclopentane ring, a cyclohexane ring, a cycloheptane ring, a cyclooctane ring and the like.

The aromatic five-membered heterocycle is a monocyclic aromatic five-membered heterocycle having one to three heteroatoms selected from a nitrogen atom, an oxygen atom and a sulfur atom in the ring. Specific examples of aromatic five-membered heterocycles are a pyrrole ring, a pyrazole ring, an imidazole ring and a [1,2,3]triazole ring, which have nitrogen atom(s) in the ring; a furan ring, which has an oxygen atom in the ring; a thiophene ring, which has a sulfur atom in the ring; an oxazole ring and an isoxazole ring, which have a nitrogen atom and an oxygen atom in the ring; and a thiazole ring and an isothiazole ring, which have a nitrogen atom and a sulfur atom in the ring, preferably a pyrazole ring, a furan ring and a thiophene ring, more preferably a thiophene ring.

The aromatic five-membered heterocycle fused with the cycloalkane ring is a fused ring wherein the aromatic five-membered heterocycle is fused with the cycloalkane ring.

The aromatic six-membered heterocycle is a monocyclic aromatic six-membered heterocycle having one to four nitrogen atoms in the ring. Specific examples of aromatic six-membered heterocycles are a pyridine ring, a pyridazine ring, a pyrimidine ring, a pyrazine ring, a [1,2,3]triazine ring, a [1,2,4]triazine ring and [1,2,3,4]tetrazine ring, preferably a pyridine ring and a pyrazine ring, more preferably a pyridine ring.

The aromatic six-membered heterocycle fused with the cycloalkane ring is a fused ring wherein the aromatic six-membered heterocycle is fused with the cycloalkane ring.

The alkylene is straight-chain or branched alkylene having one to eight carbon atoms. Specific examples of alkylene are methylene, ethylene, propylene, tetramethylene, pentamethylene, hexamethylene, heptamethylene octamethylene, methylmethylene, dimethylmethylene, 2-methyltrimethylene and the like.

The alkoxy is straight-chain or branched alkoxy having one to eight carbon atoms. Specific examples of alkoxy are methoxy, ethoxy, n-propoxy, n-butoxy, n-pentoxy, n-hexyloxy, n-heptyloxy, n-octyloxy, isopropoxy, isobutoxy, sec-butoxy, tert-butoxy, isopentoxy and the like.

The alkyl is straight-chain or branched alkyl having one to eight carbon atoms. Specific examples of alkyl are methyl, ethyl, n-propyl, n-butyl, n-pentyl, n-hexyl, n-heptyl, n-octyl, isopropyl, isobutyl, sec-butyl, tert-butyl, isopentyl and the like.

The cycloalkyl is cycloalkyl having three to eight carbon atoms. Specific examples of cycloalkyl are cyclopropyl, cyclobutyl, cyclopentyl, cyclohexyl, cycloheptyl, cyclooctyl and the like.

The aryl is a monocyclic or fused polycyclic aromatic hydrocarbon or a fused polycyclic hydrocarbon formed by condensation with a cycloalkane ring. Specific examples of aryl are phenyl and the like, which are the monocyclic aromatic hydrocarbons; naphthyl, anthryl, phenanthryl and the like, which are the fused polycyclic aromatic hydrocarbons; and indanyl, tetrahydronaphthyl, tetrahydroanthryl and the like, which are the fused polycyclic hydrocarbons.

The aryloxy is monocyclic or fused polycyclic aromatic hydrocarbon oxy having 6 to 14 carbon atoms or fused polycyclic hydrocarbon oxy formed by condensation with a cycloalkane ring. Specific examples of aryloxy are phenoxy and the like, which are the monocyclic aromatic hydrocarbon oxy; naphthoxy, anthroxy, phenanthroxy and the like, which are the fused polycyclic aromatic hydrocarbon oxy; and indanoxy, tetrahydronaphthoxy, tetrahydroanthroxy and the like, which are the fused polycyclic hydrocarbon oxy.

The heterocycle is a saturated or unsaturated monocyclic heterocycle or fused polycyclic heterocycle having one to four heteroatoms selected from a nitrogen atom, an oxygen atom and a sulfur atom in the ring.

Specific examples of saturated monocyclic heterocycles are pyrrolidine, piperidine, homopiperidine, piperazine and the like, which have nitrogen atom(s) in the ring; tetrahydrofuran, tetrahydropyrane, dioxane and the like, which have oxygen atom(s) in the ring; tetrahydrothiophene, tetrahydrothiopyrane having a sulfur atom in the ring; morpholine and the like, which have a nitrogen atom and an oxygen atom in the ring; and thiomorpholine and the like, which have a nitrogen atom and a sulfur atom in the ring. They can be fused with a benzene ring and the like to form fused polycyclic heterocycles such as 2,3-dihydroindole, benzodioxane, 1,3-dihydroisobenzofuran, tetrahydroquinoline and tetrahydroisoquinoline.

Specific examples of unsaturated monocyclic heterocycles are pyridine, pyrimidine, pyrrole, imidazole, pyrazole, triazine and the like, which have nitrogen atom(s) in the ring; furan and the like, which have an oxygen atom in the ring; thiophene and the like, which have a sulfur atom in the ring;

oxazole and the like, which have a nitrogen atom and an oxygen atom in the ring; and thiazole and the like, which have a nitrogen atom and a sulfur atom in the ring. They can be fused with a benzene ring and the like to form fused polycyclic heterocycles such as indole, indazole, quinoline, isoquinoline, phenanthridine, benzofuran, benzimidazole, benzotriazole, benzoxazole, benzisoxazole and benzothiazole.

The alkylamino is mono- or di-alkylamino. Specific examples of alkylamino are methylamino, ethylamino and the like, which are monoalkylamino; and dimethylamino, diethylamino, ethylmethylamino and the like, which are dialkylamino.

The arylamino is mono- or di-arylamino. Specific examples of arylamino are phenylamino, naphthylamino, methylphenylamino and the like, which are monoarylamino; and diphenylamino, naphthylphenylamino and the like, which are diarylamino.

The acyl is hydrocarbonyl, alkylcarbonyl, cycloalkylcarbonyl, arylcarbonyl or heterocyclecarbonyl. Specific examples of acyl are formyl, which is hydrocarbonyl; acetyl, propionyl, butyryl, isobutyryl, valeryl, isovaleryl, pivaloyl, monochloroacetyl, trifluoroacetyl and the like, which are alkylcarbonyl; cyclopentylcarbonyl, cyclohexylcarbonyl and the like, which are cycloalkylcarbonyl; benzoyl, naphthoyl, toluoyl and the like, which are arylcarbonyl; and furoyl, thenoyl, picolinoyl, nicotinoyl, isonicotinoyl and the like, which are heterocyclecarbonyl.

The halogen is fluorine, chlorine, bromine or iodine.

The alkylthio is straight-chain or branched alkylthio having one to eight carbon atoms. Specific examples of alkylthio are methylthio, ethylthio, n-propylthio, n-butylthio, n-pentylthio, n-hexylthio, n-heptylthio, n-octylthio, isopropylthio, isobutylthio, sec-butylthio, tert-butylthio, isopentylthio and the like.

Arylthio is monocyclic or fused polycyclic aromatic hydrocarbonthio having 6 to 14 carbon atoms or fused polycyclic hydrocarbonthio formed by condensation with a cycloalkane ring. Specific examples of arylthio are phenylthio and the like, which are monocyclic aromatic hydrocarbonthio; naphthylthio, anthrylthio, phenanthrylthio and the like, which are fused polycyclic aromatic hydrocarbonthio; and indanylthio, tetrahydronaphthylthio, tetrahydroanthrylthio and the like, which are fused polycyclic hydrocarbonthio.

Alkenyl is straight-chain or branched alkenyl having 2 to 8 carbon atoms. Specific examples of alkenyl are vinyl, allyl, propenyl, butenyl, pentenyl, hexenyl, heptenyl, octenyl, sec-butenyl, tert-pentenyl and the like.

Alkynyl is straight-chain or branched alkynyl having 2 to 8 carbon atoms. Specific examples of alkynyl are ethynyl, propynyl, butynyl, pentynyl, hexynyl, heptynyl, octynyl, sec-butynyl, tert-pentynyl and the like.

The ester of carboxyl is an ester with alkyl alcohol, aryl alcohol or the like.

Specific examples of alkyl alcohol are methanol, ethanol, propanol, butanol, benzyl alcohol, phenethyl alcohol and the like, and specific examples of aryl alcohol are phenol, naphthol, anthrol, cresol, xylenol and the like.

The amide of carboxyl is amide with alkylamine, cycloalkylamine, arylamine, heterocycleamine or the like.

Specific examples of alkylamine are methylamine, ethylamine, ethylmethyamine, dimethylamine, diethylamine, benzylamine and the like, specific examples of cycloalkylamine are cyclohexylamine, cyclohexylmethylamine and the like, specific examples of arylamine are aniline, naphthylamine, diphenylamine, ethylphenylamine, anisidine, toluidine and the like, and specific examples of heterocycleamine are benzofuranylamine, quinolylamine and the like.

Sulfonyl is alkylsulfonyl or arylsulfonyl. Specific examples of sulfonyl are methanesulfonyl, ethanesulfonyl and the like, which are alkylsulfonyl; and benzenesulfonyl, toluenesulfonyl and the like, which are arylsulfonyl.

The substituted alkoxy is alkoxy having one or plural groups as substituent(s) selected from halogen, hydroxy, alkoxy, alkoxy substituted by aryl, aryloxy, cycloalkyl, aryl, aryl substituted by alkoxy, heterocycles, amino, alkylamino, arylamino, mercapto, alkylthio, arylthio, carboxyl or ester thereof or amide thereof, cyano and nitro.

The substituted aryloxy is aryloxy having one or plural groups as substituent(s) selected from halogen, hydroxy, alkoxy, aryloxy, alkyl, cycloalkyl, aryl, heterocycles, amino, alkylamino, arylamino, mercapto, alkylthio, arylthio, carboxyl or ester thereof or amide thereof, formyl, alkylcarbonyl, arylcarbonyl, cyano and nitro.

The substituted alkyl is alkyl having one or plural groups as substituent(s) selected from halogen, hydroxy, alkoxy, aryloxy, cycloalkyl, alkenyl, aryl, aryl substituted by halogen, aryl substituted by alkoxy, heterocycles, amino, alkylamino, arylamino, mercapto, alkylthio, arylthio, carboxyl or ester thereof or amide thereof, formyl, alkylcarbonyl, arylcarbonyl, cyano and nitro.

The substituted cycloalkyl is cycloalkyl having one or plural groups as substituent(s) selected from halogen, hydroxy, alkoxy, aryloxy, alkyl, cycloalkyl, aryl, heterocycles, amino, alkylamino, arylamino, mercapto, alkylthio, arylthio, carboxyl or ester thereof or amide thereof, formyl, alkylcarbonyl, arylcarbonyl, cyano and nitro.

The substituted aryl is aryl having one or plural groups as substituent(s) selected from halogen, hydroxy, alkoxy, alkoxy substituted by halogen, alkoxy substituted by aryl, aryloxy, alkyl, alkyl substituted by halogen, alkyl substituted by hydroxy, alkyl substituted by ester of carboxyl, alkyl substituted by cyano, cycloalkyl, alkenyl, alkynyl, aryl, heterocycles, amino, alkylamino, arylamino, amino substituted by alkylsulfonyl, amino substituted by acyl, mercapto, alkylthio, alkylthio substituted by halogen, arylthio, carboxyl or ester thereof or amide thereof, carbonyl (i.e. oxo), formyl, alkylcarbonyl, arylcarbonyl, thiocarbonyl (i.e. thioxo), cyano, nitro, sulfonic group, alkylsulfonyl, alkylsulfonyl substituted by halogen and arylsulfonyl.

The substituted heterocycle is a heterocycle having one or plural groups as substituent(s) selected from halogen, hydroxy, alkoxy, alkoxy substituted by halogen, aryloxy, alkyl, alkyl substituted by halogen, alkyl substituted by hydroxy, alkyl substituted by carboxyl or ester thereof, cycloalkyl, aryl, heterocycles, amino, alkylamino, arylamino, amino substituted by acyl, mercapto, alkylthio, arylthio, carboxyl or ester thereof or amide thereof, carbonyl (i.e. oxo), formyl, alkylcarbonyl, arylcarbonyl, thiocarbonyl (i.e. thioxo), cyano and nitro.

The substituted alkylamino is amino having one or plural groups in its alkyl moiety as substituent(s) selected from halogen, hydroxy, alkoxy, aryloxy, cycloalkyl, aryl, heterocycles, amino, alkylamino, arylamino, mercapto, alkylthio, arylthio, carboxy or ester thereof or amide thereof, alkylcarbonyl, arylcarbonyl, cyano and nitro.

The substituted arylamino is amino having one or plural groups in its aryl moiety as substituent(s) selected from halogen, hydroxy, alkoxy, aryloxy, alkyl, cycloalkyl, aryl, heterocycles, amino, alkylamino, arylamino, mercapto, alkylthio, arylthio, carboxyl or ester thereof or amide thereof, alkylcarbonyl, arylcarbonyl, cyano and nitro.

The substituted acyl is acyl having one or plural groups as substituent(s) selected from halogen, hydroxy, alkoxy, aryloxy, cycloalkyl, aryl, heterocycles, amino, alkylamino, arylamino, mercapto, alkylthio, arylthio, carboxy or ester thereof or amide thereof, alkylcarbonyl, arylcarbonyl, cyano and nitro.

The substituted alkylthio is alkylthio having one or plural groups as substituent(s) selected from halogen, hydroxy, alkoxy, aryloxy, cycloalkyl, aryl, heterocycles, amino, alkylamino, arylamino, carboxyl or ester thereof or amide thereof, alkylcarbonyl, arylcarbonyl, cyano and nitro.

The substituted arylthio is arylthio having one or plural groups as substituent(s) selected from halogen, hydroxy, alkoxy, aryloxy, alkyl, cycloalkyl, aryl, heterocycles, amino, alkylamino, arylamino, carboxyl or ester thereof or amide thereof, alkylcarbonyl, arylcarbonyl, cyano and nitro.

When the present compound has free hydroxy, amino, alkylamino, arylamino or mercapto as a substituent, these substituents can be protected with a protecting group. When the heterocycle has a nitrogen atom, the nitrogen atom can be protected with a protecting group, too.

The protecting group of hydroxy is exemplified by widely-used protecting groups such as unsubstituted alkenyl such as allyl; unsubstituted heterocycles such as tetrahydropyranyl and tetrahydrofuranyl; esters such as methoxycarbonyl, ethoxycarbonyl, isobutoxycarbonyl, tert-butoxycarbonyl, vinyloxycarbonyl, allyloxycarbonyl, benzyloxycarbonyl and p-methoxybenzyloxycarbonyl; and substituted silyl such as trimethylsilyl, triethylsilyl, triisopropylsilyl, tert-butyldimethylsilyl or tert-butyldiphenylsilyl.

The protecting group of a nitrogen atom of amino, alkylamino, arylamino and heterocycles having a nitrogen atom in the ring is exemplified by widely-used protecting groups such as unsubstituted alkenyl such as allyl; substituted acyl such as trichloroacetyl or trifluoroacetyl; unsubstituted acyl such as formyl, acetyl, benzoyl or picolinoyl; esters such as methoxycarbonyl, isobutoxycarbonyl, tert-butoxycarbonyl, 2,2,2-trichloroethoxycarbonyl, benzyloxycarbonyl, diphenylmethoxycarbonyl and phenoxycarbonyl; substituted sulfonyl such as toluenesulfonyl or 2,4,6-trimethylbenzenesulfonyl; and unsubstituted sulfonyl such as methanesulfonyl or benzenesulfonyl.

The protecting group of mercapto is exemplified by widely-used protecting groups such as unsubstituted alkenyl such as allyl; unsubstituted heterocycles such as tetrahydropyranyl and tetrahydrofuranyl; and esters such as methoxycarbonyl, ethoxycarbonyl, isobutoxycarbonyl, tert-butoxycarbonyl, vinyloxycarbonyl, allyloxycarbonyl, benzyloxycarbonyl and p-methoxybenzyloxycarbonyl.

The "salts" in the present compound can be any pharmaceutically acceptable salts and are exemplified by salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, lactic acid, methanesulfonic acid, trifluoromethanesulfonic acid or p-toluenesulfonic acid; salts with an alkali metal such as lithium, sodium or potassium; salts with an alkaline earth metal such as calcium or magnesium; and quaternary salts with ammonia, methyl iodide or the like.

When there are geometrical isomers or optical isomers in the present compound, these isomers are also included in the present invention.

Further, the present compound can be in the form of a hydrate or a solvate.

(1) Preferred examples of the present compound are the following i) to iii).
i) Compounds wherein the ring "A" is a benzene ring in the general formula [I].
ii) Compounds wherein the ring "A" is selected from a pyrrole ring, a pyrazole ring, an imidazole ring, a [1,2,3]triazole ring, a furan ring, a thiophene ring, an oxazole ring, an isoxazole ring, a thiazole ring, an isothiazole ring, a tetrahydroindole ring, a tetrahydrobenzofuran ring and a tetrahydrobenzo[b]thiophene ring in the general formula [I]. The ring "A" is more preferably a pyrazole ring, a furan ring, a thiophene ring or tetrahydrobenzo[b]thiophene, particularly a thiophene ring.
iii) Compounds wherein the ring "A" is selected from a pyridine ring, a pyridazine ring, a pyrimidine ring, a pyrazine ring, a [1,2,3]triazine ring, a [1,2,4]triazine ring, a [1,2,3,4]tetrazine ring, a tetrahydroquinoline ring, a tetrahydroisoquinoline ring, a tetrahydroquinoxaline ring and a tetrahydrocinnoline ring in the general formula [I]. The ring "A" is more preferably a pyridine ring or a pyrazine ring, particularly preferably a pyridine ring.
(2) More preferred examples of the present compounds are compounds which satisfy the above-mentioned definitions (1) i) to iii) and wherein a partial structure [C]

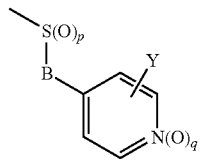

and a partial structure [D] in the general formula [I]

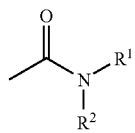

are bonded to adjacent carbon atoms on the ring "A".
(3) Further preferred examples of the present compound are compounds which satisfy the above-mentioned definitions (1) ii) and iii) and (2) and wherein the partial structure [C] or the partial structure [D] is bonded to a carbon atom existing at the α-position of a heteroatom of the ring "A".
(4) Preferred examples of respective substituents in the present compound are as follows;
in the general formula [I],
a) $R^1$ and $R^2$, the same or different, are hydrogen, substituted or unsubstituted alkoxy, substituted or unsubstituted alkyl, substituted or unsubstituted cycloalkyl, substituted or unsubstituted aryl, substituted or unsubstituted heterocycles, substituted or unsubstituted alkylamino or substituted or unsubstituted arylamino,
b) alternatively, $R^1$ and $R^2$ join together to form a substituted or unsubstituted heterocycle,
c) X and Y are one or plural groups selected from hydrogen, halogen, substituted or unsubstituted alkoxy, substituted or unsubstituted alkyl, substituted or unsubstituted alkylthio, carboxyl or ester thereof or amide thereof and cyano,
d) p is 0 or 1.
Of course, the above-mentioned choices defined in a) to d) can be arbitrarily combined.

(5) More preferred examples of respective substituents in the present compound are as follows;

in the general formula [I], a) $R^1$ is hydrogen, substituted alkoxy, substituted or unsubstituted alkyl, unsubstituted cycloalkyl, substituted or unsubstituted aryl, a substituted or unsubstituted heterocycle, unsubstituted alkylamino or substituted arylamino, b) $R^2$ is hydrogen or substituted or unsubstituted alkyl, c) alternatively, $R^1$ and $R^2$ join together to form a substituted or unsubstituted heterocycle, d) X is one or plural groups selected from hydrogen, halogen and substituted alkyl, e) Y is one or plural groups selected from hydrogen, halogen, substituted or unsubstituted alkoxy, unsubstituted alkyl, unsubstituted alkylthio, carboxyl or ester thereof or amide thereof and cyano.

Of course, the above-mentioned choices defined in a) to e) can be arbitrarily combined.

Particularly preferred specific examples in the present invention are shown below.

N-(4-Chlorophenyl)-2-(4-pyridylmethylthio)pyridine-3-carboxamide

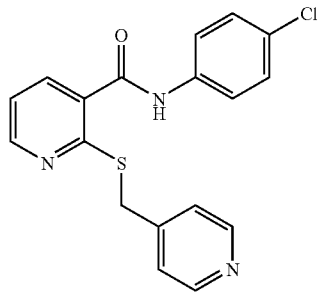

2-(4-Pyridylmethylthio)-N-(3-quinolyl)pyridine-3-carboxamide

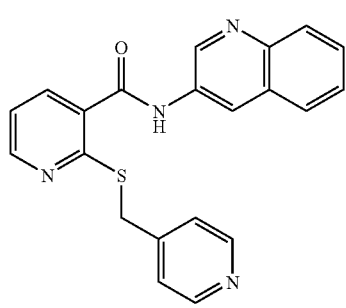

2-(4-Pyridylmethylthio)-N-(6-quinolyl)pyridine-3-carboxamide

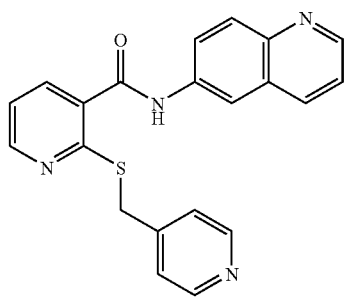

N-(3-Isoquinolyl)-2-(4-pyridylmethylthio)pyridine-3-carboxamide

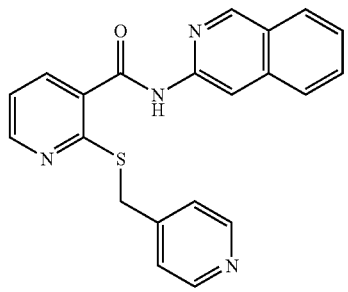

N-(Indazol-5-yl)-2-(4-pyridylmethylthio)pyridine-3-carboxamide

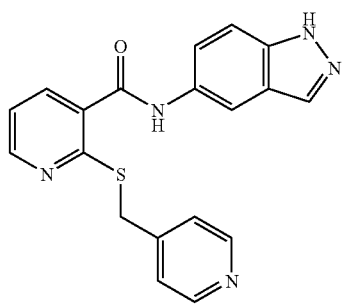

N-Phenyl-2-(4-pyridylmethylthio)pyridine-3-carboxamide

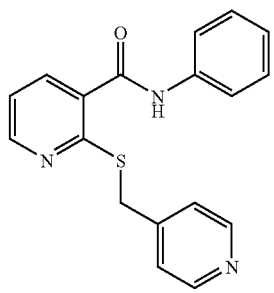

N-(3-Isopropylphenyl)-2-(4-pyridylmethylthio)pyridine-3-carboxamide

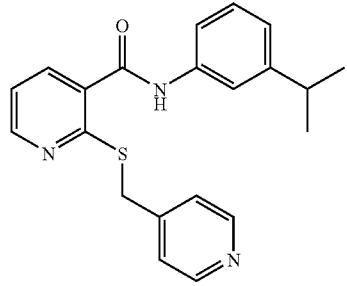

N-(3-Chlorophenyl)-2-(4-pyridylmethylthio)pyridine 3-carboxamide

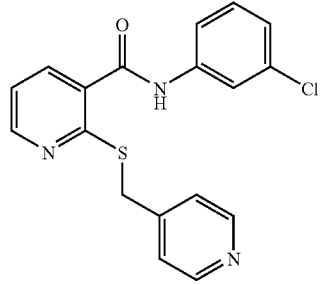

2-(4-Pyridylmethylthio)-N-(3-trifluoromethoxyphenyl)pyridine-3-carboxamide

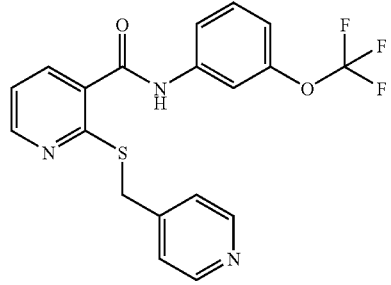

N-(4-Methylphenyl)-2-(4-pyridylmethylthio)pyridine-3-carboxamide

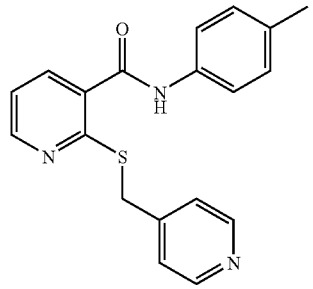

2-(4-Pyridylmethylthio)-N-(4-trifluoromethylphenyl)pyridine-3-carboxamide

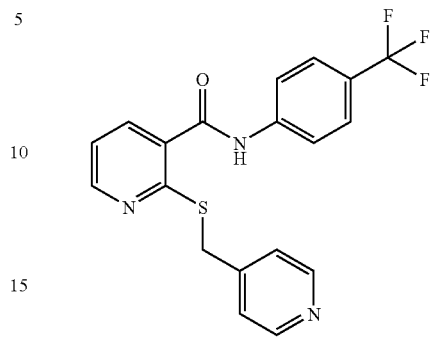

N-(4-n-Propylphenyl)-2-(4-pyridylmethylthio)pyridine-3-carboxamide

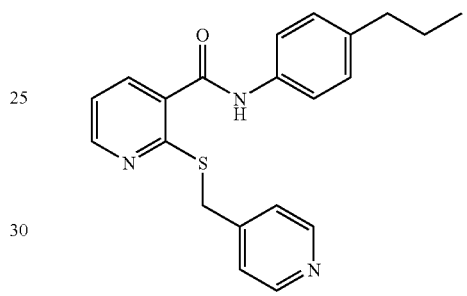

N-(4-n-Butylphenyl)-2-(4-pyridylmethylthio)pyridine-3-carboxamide

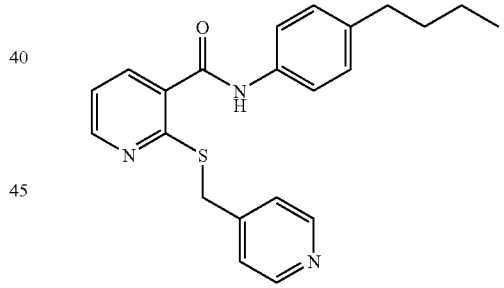

N-(4-tert-Butylphenyl)-2-(4-pyridylmethylthio)pyridine-3-carboxamide

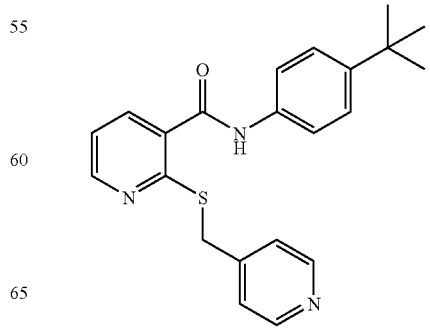

2-(4-Pyridylmethylthio)-N-(4-trifluoromethoxyphenyl)pyridine-3-carboxamide

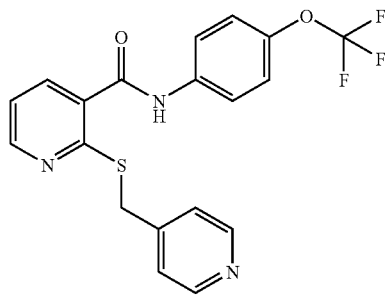

N-(4-Isopropoxyphenyl)-2-(4-pyridylmethylthio)pyridine-3-carboxamide

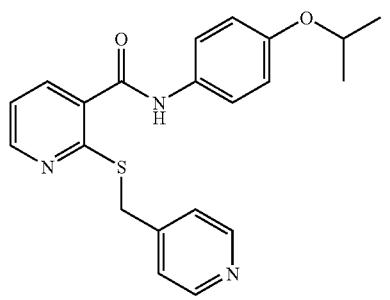

N-(4-Ethoxycarbonylmethylphenyl)-2-(4-pyridylmethylthio)pyridine-3-carboxamide

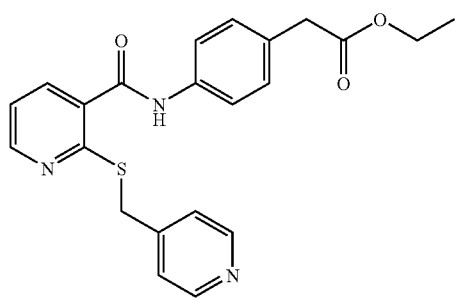

N-(4-Dimethylaminophenyl)-2-(4-pyridylmethylthio)pyridine-3-carboxamide

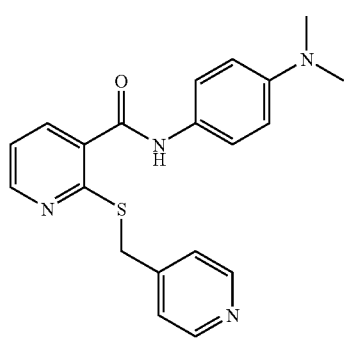

N-(3-Methylphenyl)-2-(4-pyridylmethylthio)pyridine-3-carboxamide

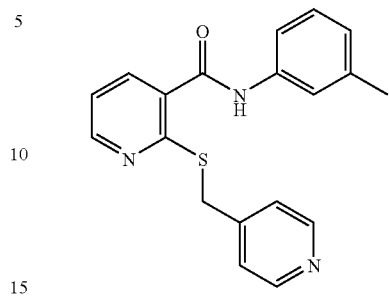

N-(4-Chloro-2-fluorophenyl)-2-(4-pyridylmethylthio)pyridine-3-carboxamide

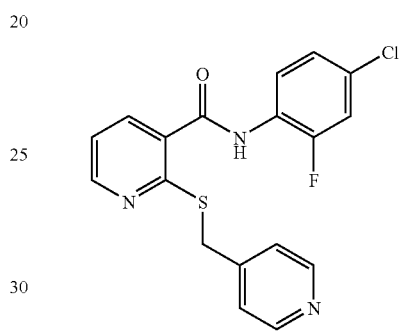

N-(2,4-Difluorophenyl)-2-(4-pyridylmethylthio)pyridine-3-carboxamide

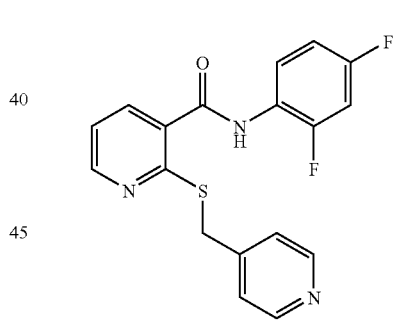

N-(3,4-Dimethoxyphenyl)-2-(4-pyridylmethylthio)pyridine-3-carboxamide

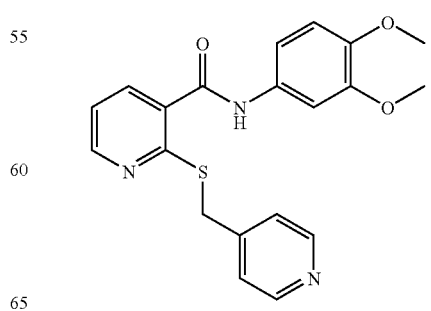

N-(4-Chloro-3-trifluoromethylphenyl)-2-(4-pyridylmethylthio)pyridine-3-carboxamide

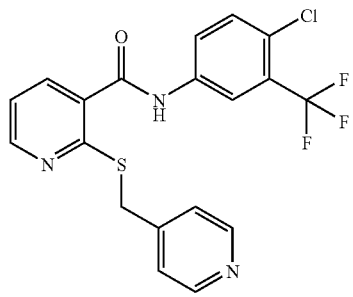

N-(3-Chloro-4-fluorophenyl)-2-(4-pyridylmethylthio)pyridine-3-carboxamide

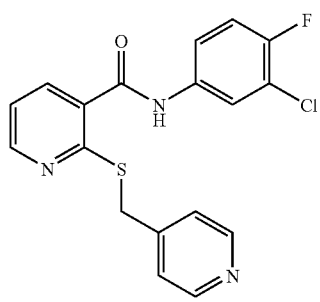

N-(4-Fluoro-3-trifluoromethylphenyl)-2-(4-pyridylmethylthio)pyridine-3-carboxamide

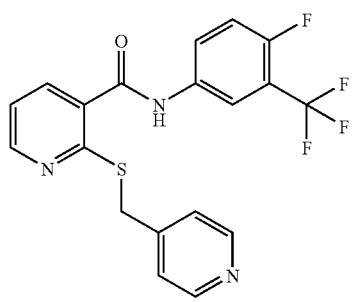

N-(3-Chloro-4-methylphenyl)-2-(4-pyridylmethylthio)pyridine-3-carboxamide

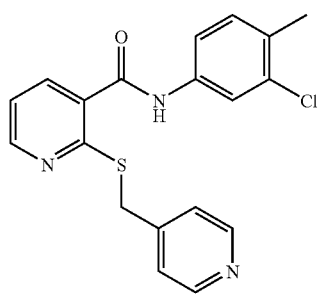

N-(4-Chloro-3-methylphenyl)-2-(4-pyridylmethylthio)pyridine-3-carboxamide

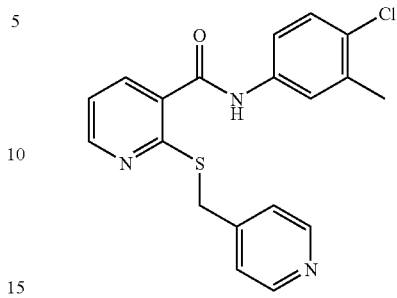

N-(3,4-Dimethylphenyl)-2-(4-pyridylmethylthio)pyridine-3-carboxamide

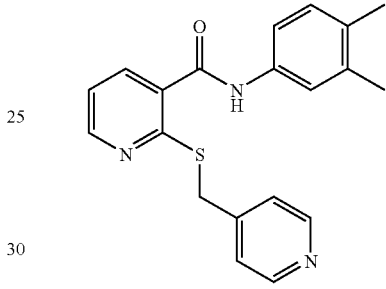

N-(3-Fluoro-5-trifluoromethylphenyl)-2-(4-pyridylmethylthio)pyridine-3-carboxamide

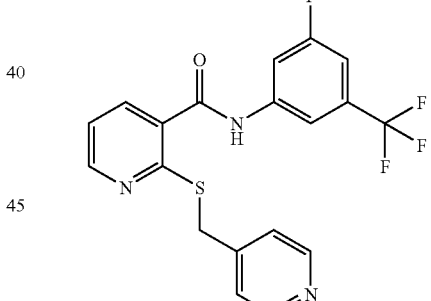

N-(3,5-Dichlorophenyl)-2-(4-pyridylmethylthio)pyridine-3-carboxamide

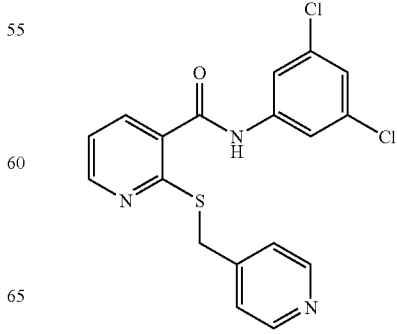

N-(5-Chloro-2,4-dimethoxyphenyl)-2-(4-pyridylmethylthio)pyridine-3-carboxamide

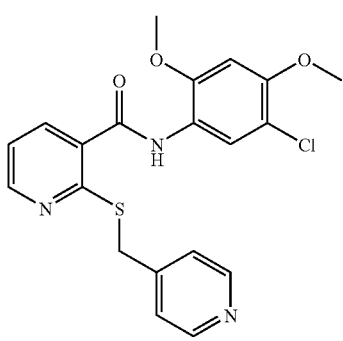

N-(4-Chlorophenyl)-2-(4-pyridylmethylthio)benzamide

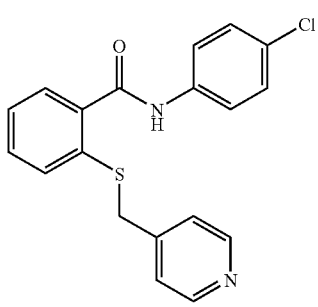

N-(3-Chlorophenyl)-2-(4-pyridylmethylthio)benzamide

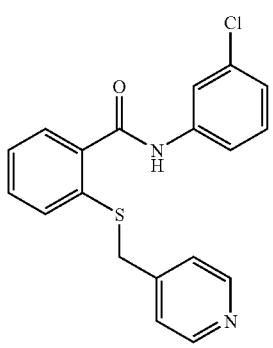

N-(4-Dimethylaminophenyl)-2-(4-pyridylmethylthio)benzamide

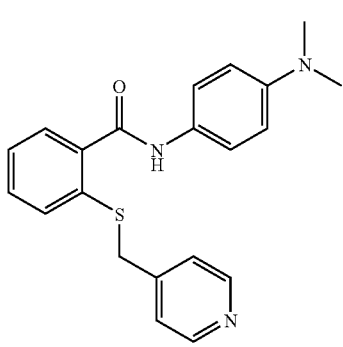

N-(3-Isopropylphenyl)-2-(4-pyridylmethylthio)benzamide

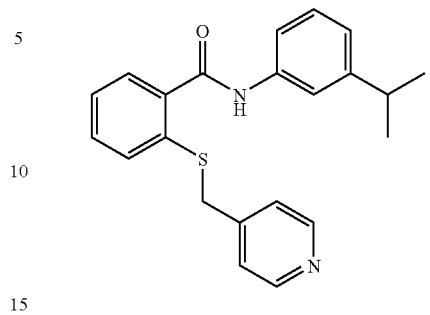

N-(3,4-Dimethoxyphenyl)-2-(4-pyridylmethylthio)benzamide

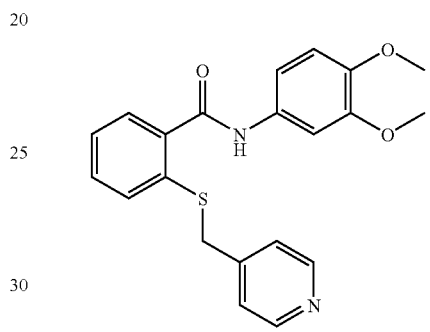

2-(4-Pyridylmethylthio)-N-(3-quinolyl)benzamide

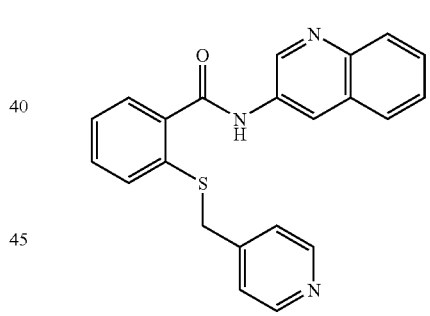

N-(4-Chlorophenyl)-5-fluoro-2-(4-pyridylmethylthio)benzamide

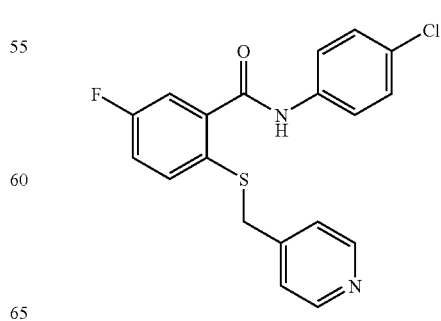

N-(4-Chloro-3-methylphenyl)-2-(4-pyridylmethylthio)benzamide

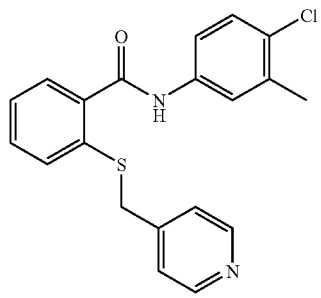

N-(5-Chloro-2,4-dimethoxyphenyl)-2-(4-pyridylmethylthio)benzamide

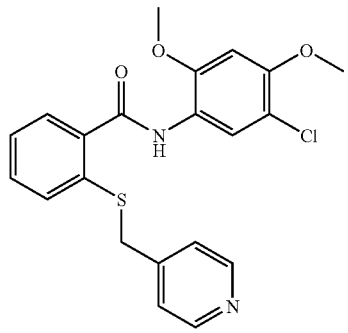

N-(3,5-Dimethylphenyl)-2-(4-pyridylmethylthio)benzamide

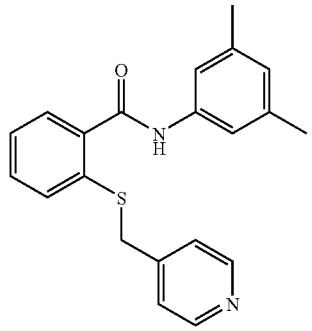

N-(3,5-Dimethylphenyl)-2-(4-pyridylmethylthio)pyridine-3-carboxamide

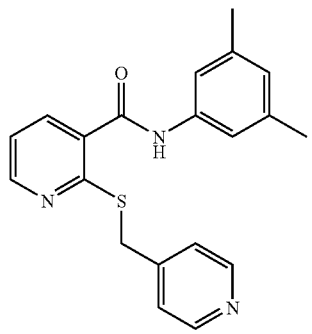

N-(4-Bromo-3-methylphenyl)-2-(4-pyridylmethylthio)benzamide

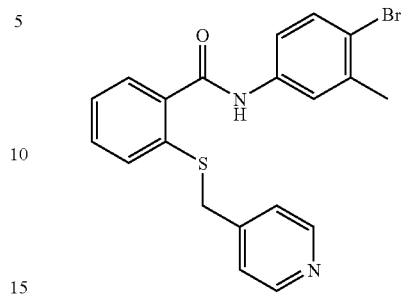

N-(5-Indanyl)-2-(4-pyridylmethylthio)pyridine-3-carboxamide

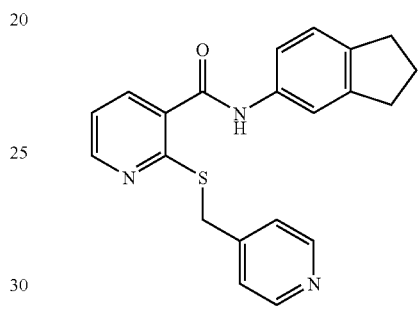

N-(3-Chloro-4-trifluoromethoxyphenyl)-2-(4-pyridylmethylthio)pyridine-3-carboxamide

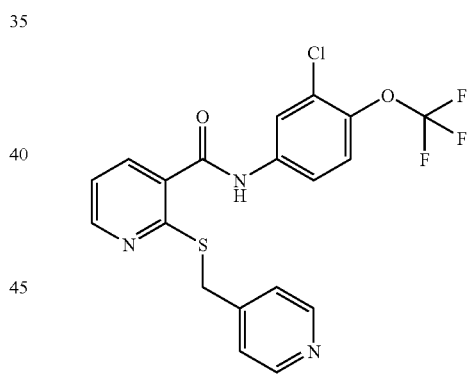

2-(4-Pyridylmethylthio)-N-(4-trifluoromethylthiophenol)pyridine-3-carboxamide

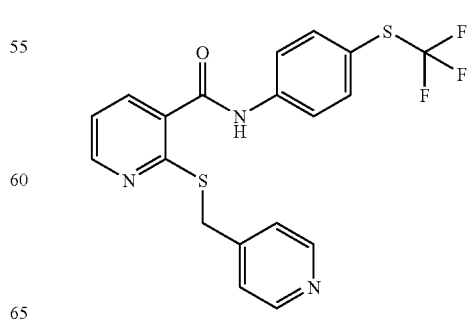

N-(3-Methyl-4-trifluoromethoxyphenyl)-2-(4-pyridylmethylthio)pyridine-3-carboxamide

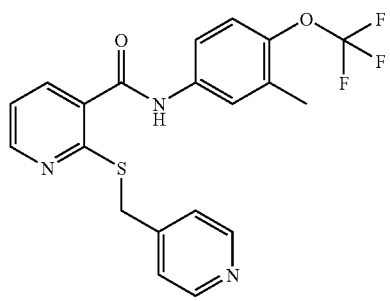

N-(3-Isoquinolyl)-2-(4-pyridylmethylthio)benzamide

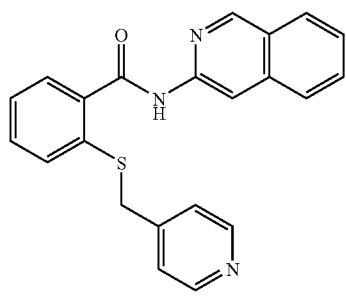

N-(3,5-Dimethylphenyl)-2-(2-fluoropyridin-4-ylmethylthio)pyridine-3-carboxamide

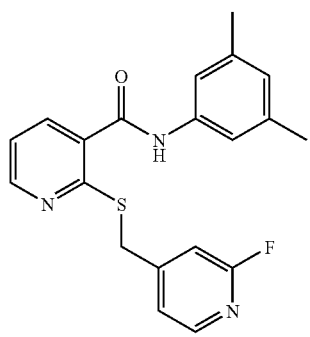

2-(2-Fluoropyridin-4-ylmethylthio)-N-(4-trifluoromethoxyphenyl)-pyridine-3-carboxamide

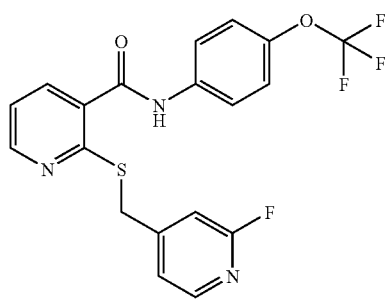

2-(2-Fluoropyridin-4-ylmethylthio)-N-(5-indanyl)pyridine-3-carboxamide

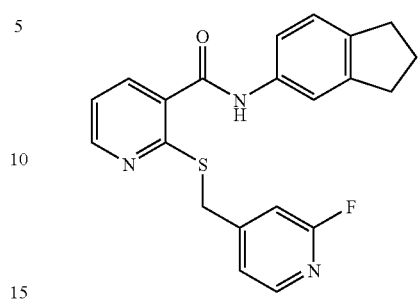

2-(2-Chloropyridin-4-ylmethylthio)-N-(5-indanyl)pyridine-3-carboxamide

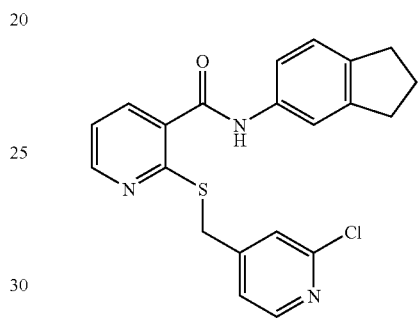

2-(2-Chloropyridin-4-ylmethylthio)-N-(3,5-dimethylphenyl)pyridine-3-carboxamide

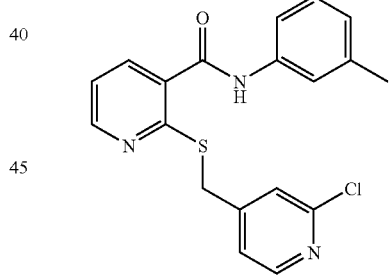

2-(2-Chloropyridin-4-ylmethylthio)-N-(4-trifluoromethoxyphenyl)-pyridine-3-carboxamide

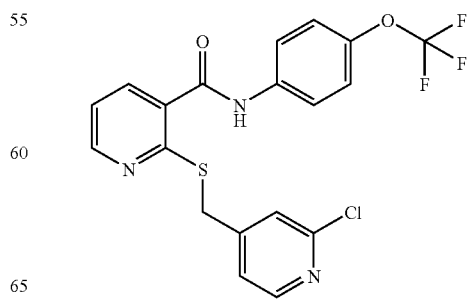

2-(3-Chloropyridin-4-ylmethylthio)-N-(3,5-dimethylphenyl)pyridine-3-carboxamide

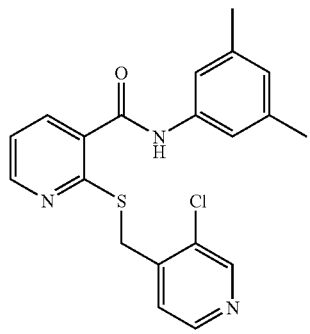

(2-Bromopyridin-4-ylmethylthio)-N-(3,5-dimethylphenyl)pyridine-3-carboxamide

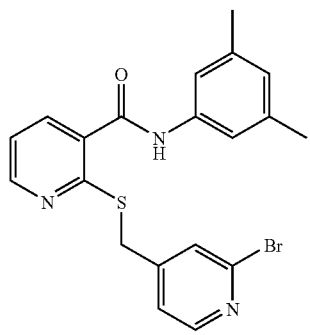

N-(3,5-Dimethylphenyl)-2-(2-methylthiopyridin-4-ylmethylthio)pyridine-3-carboxamide

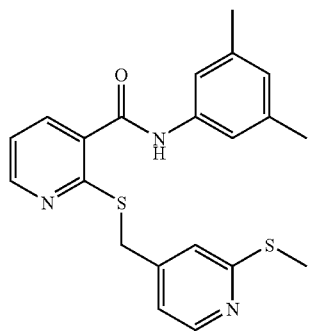

N-(4-Chlorophenyl)-2-(2-methylthiopyridin-4-ylmethylthio)pyridine-3-carboxamide

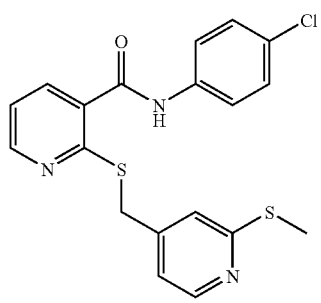

2-(2-Cyanopyridin-4-ylmethylthio)-N-(3,5-dimethylphenyl)pyridine-3-carboxamide

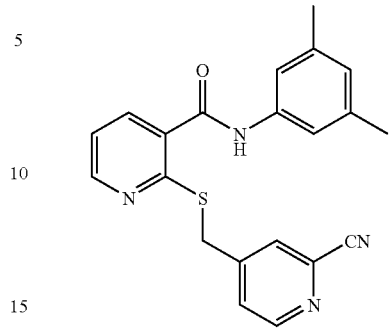

2-(2-Ethoxycarbonylpyridin-4-ylmethylthio)-N-(3,5-dimethylphenyl)-pyridine-3-carboxamide

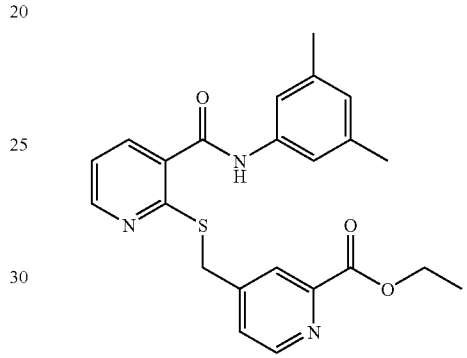

N-(4-Isopropoxyphenyl)-3-(4-pyridylmethylthio)thiophene-2-carboxamide

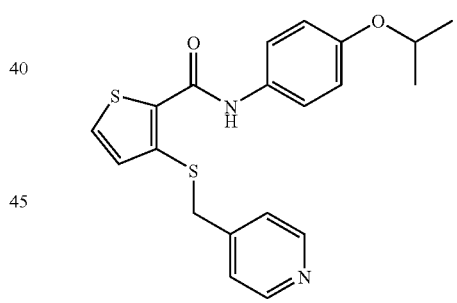

N-(3-Fluoro-4-methylphenyl)-3-(4-pyridylmethylthio)thiophene-2-carboxamide

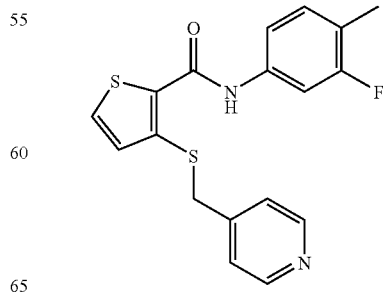

N-(3-Chlorophenyl)-3-(4-pyridylmethylthio)thiophene-2-carboxamide

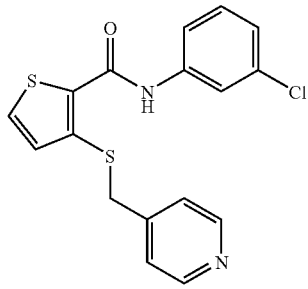

N-(4-Chlorophenyl)-3-(4-pyridylmethylthio)thiophene-2-carboxamide

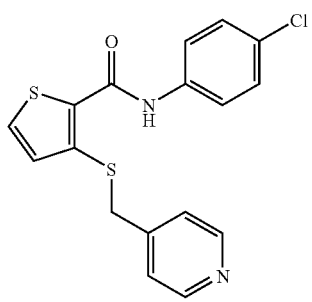

3-(2-Chloropyridin-4-ylmethylthio)-N-(3,5-dimethylphenyl)thiophene-2-carboxamide

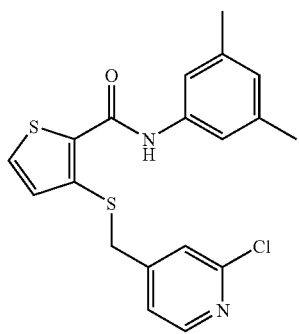

N-(4-Fluoro-3-methylphenyl)-3-(4-pyridylmethylthio)thiophene-2-carboxamide

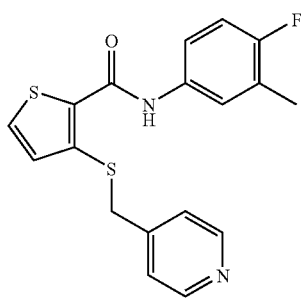

N-(3,4-Dimethylphenyl)-3-(4-pyridylmethylthio)thiophene-2-carboxamide

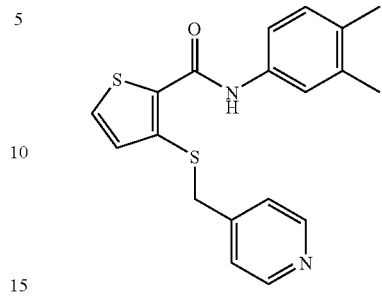

3-(4-Pyridylmethylthio)-N-(4-trifluoromethylphenyl)thiophene-2-carboxamide

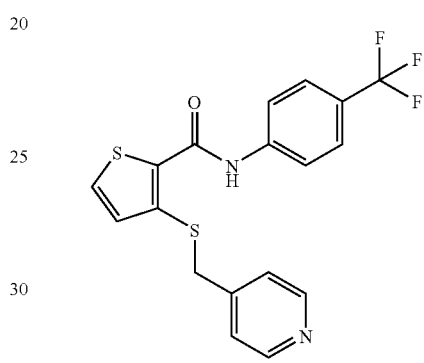

N-(4-tert-Butylphenyl)-3-(4-pyridylmethylthio)thiophene-2-carboxamide

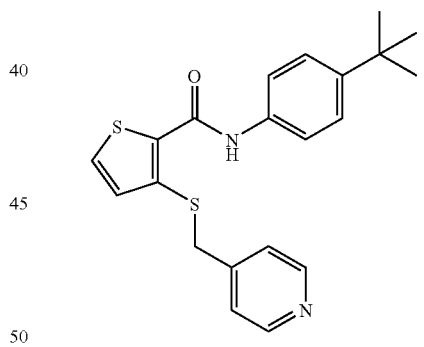

N-(3-Methylphenyl)-3-(4-pyridylmethylthio)thiophene-2-carboxamide

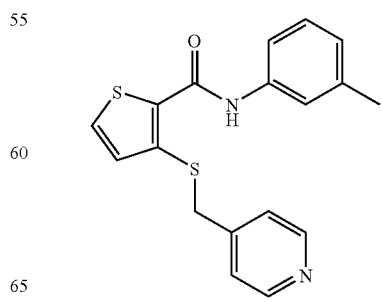

N-(3,4-Difluorophenyl)-3-(4-pyridylmethylthio)thiophene-2-carboxamide

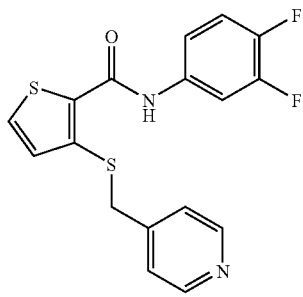

N-(4-n-Propylphenyl)-3-(4-pyridylmethylthio)thiophene-2-carboxamide

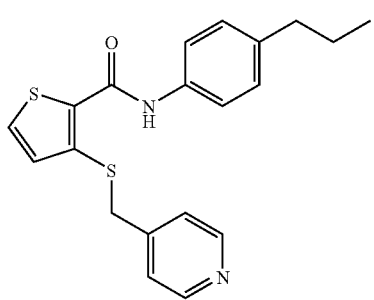

3-(4-Pyridylmethylthio)-N-(4-trifluoromethoxyphenyl)thiophene-2-carboxamide

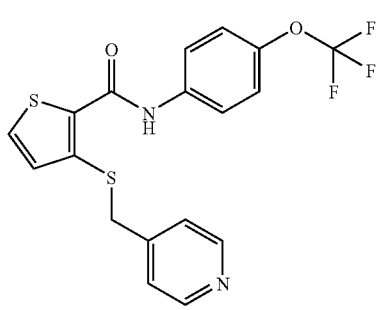

N-(3-Isoquinolyl)-3-(4-pyridylmethylthio)thiophene-2-carboxamide

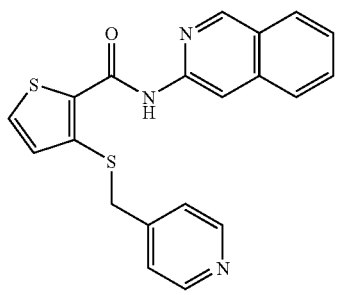

N-(3,5-Dimethylphenyl)-3-(4-pyridylmethylthio)thiophene-2-carboxamide

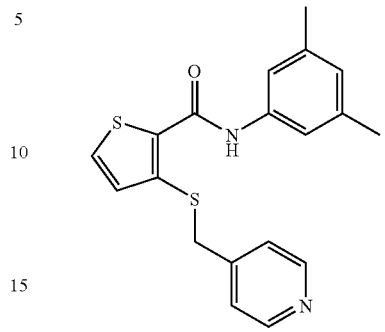

3-(4-Pyridylmethylthio)-N-(3-trifluoromethylphenyl)thiophene-2-carboxamide

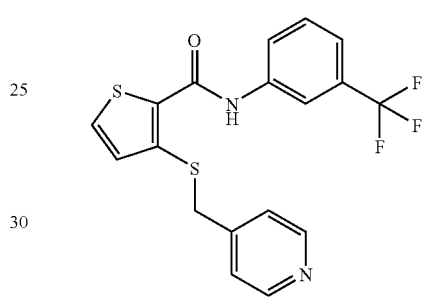

N-(5-Indanyl)-3-(4-pyridylmethylthio)thiophene-2-carboxamide

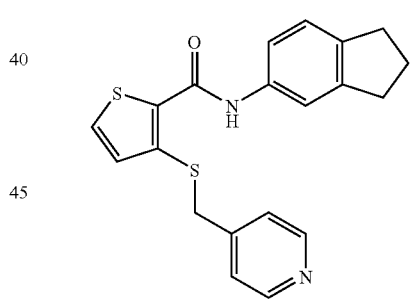

N-(4-Chlorophenyl)-2-(4-pyridylmethylthio)thiophene-3-carboxamide

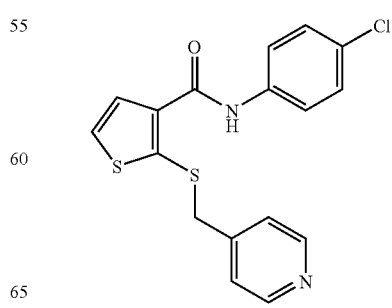

N-(3-Methylphenyl)-2-(4-pyridylmethylthio)thiophene-3-carboxamide

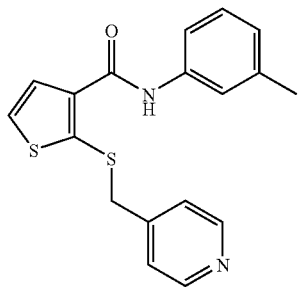

N-(5-Indanyl)-2-(4-pyridylmethylthio)thiophene-3-carboxamide

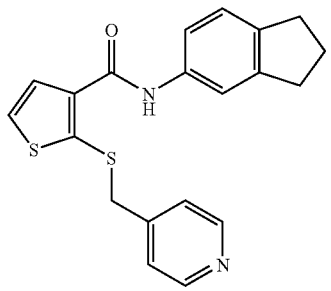

N-(4-Bromo-3-methylphenyl)-2-(4-pyridylmethylthio)thiophene-3-carboxamide

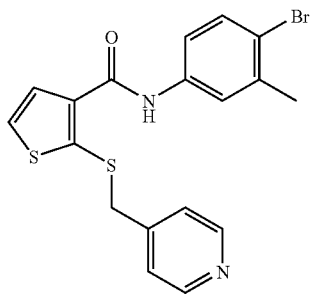

2-(4-Pyridylmethylthio)-N-(4-trifluoromethylphenyl)thiophene-3-carboxamide

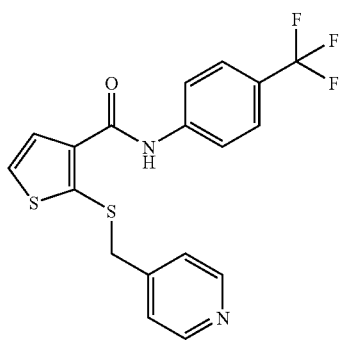

N-(3,5-Dimethylphenyl)-2-(4-pyridylmethylthio)thiophene-3-carboxamide

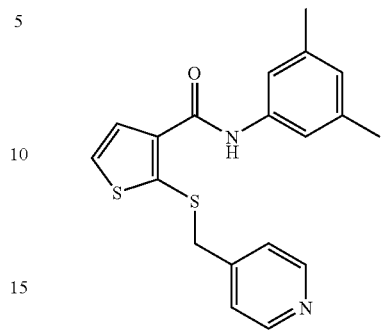

N-(3-Methylphenyl)-4-(4-pyridylmethylthio)thiophene-3-carboxamide

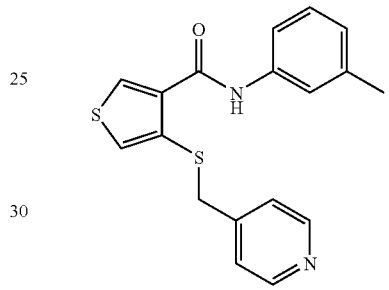

N-(Indazol-6-yl)-2-(4-pyridylmethylthio)pyridine-3-carboxamide

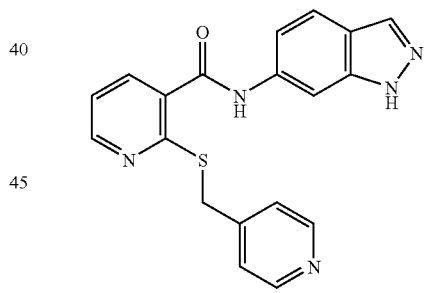

2-(2-Bromopyridin-4-ylmethylthio)-N-(4-trifluoromethoxyphenyl)-pyridine-3-carboxamide

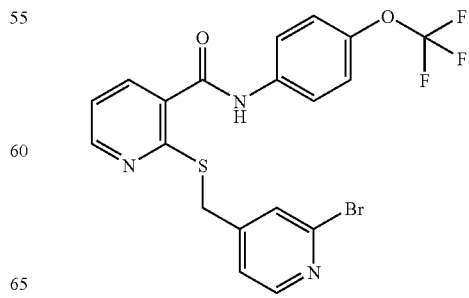

N-(3,5-Dimethylphenyl)-2-(2-methoxypyridin-4-ylmeth-ylthio)pyridine-3-carboxamide

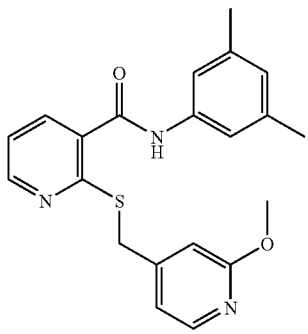

N-(3,5-Dimethylphenyl)-2-(2-methylpyridin-4-ylmeth-ylthio)pyridine-3-carboxamide

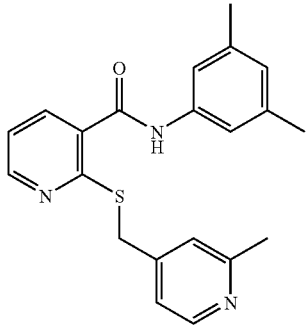

2-(2-Methylpyridin-4-ylmethylthio)-N-(4-trifluoromethox-yphenyl)-pyridine-3-carboxamide

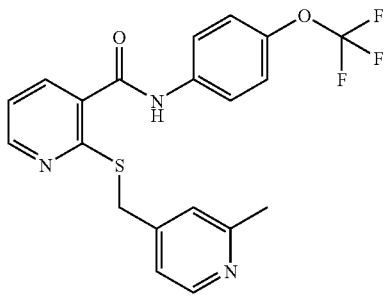

N-(4-Chlorophenyl)-2-(1-oxopyridin-4-ylmethylthio)pyri-dine-3-carboxamide

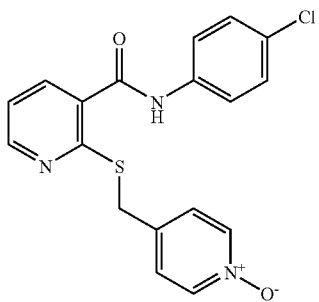

N-(3-Methylphenyl)-2-(1-oxopyridin-4-ylmethylthio)pyri-dine-3-carboxamide

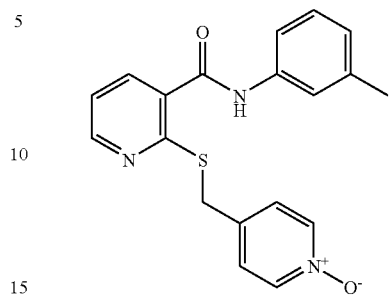

N-(3,5-Dimethylphenyl)-2-(1-oxopyridin-4-ylmethylthio)pyridine-3-carboxamide

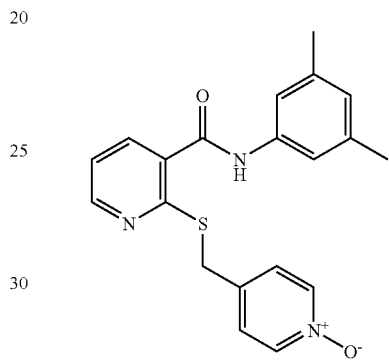

N-(3,4-Dimethylphenyl)-2-(1-oxopyridin-4-ylmethylthio)pyridine-3-carboxamide

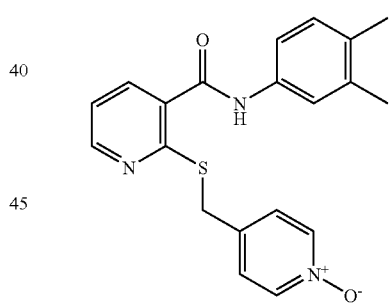

N-(3-Isopropylphenyl)-2-(1-oxopyridin-4-ylmethylthio)py-ridine-3-carboxamide

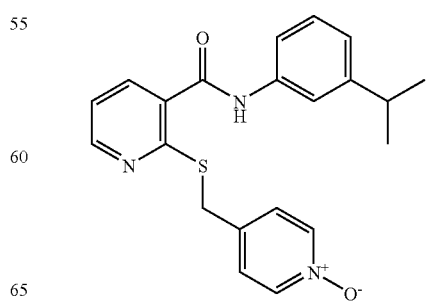

33

N-(4-Fluoro-3-methylphenyl)-2-(1-oxopyridin-4-ylmethylthio)pyridine-3-carboxamide

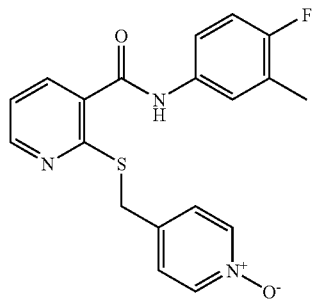

N-(5-Indanyl)-2-(1-oxopyridin-4-ylmethylthio)pyridine-3-carboxamide

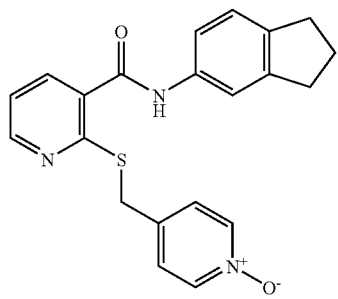

2-(1-Oxopyridin-4-ylmethylthio)-N-(4-trifluoromethoxyphenyl)pyridine-3-carboxamide

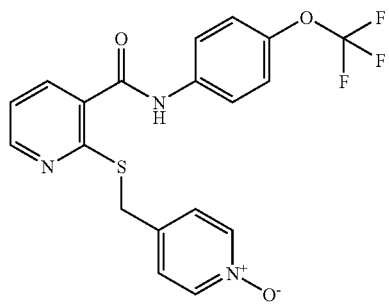

N-(4-tert-Butylphenyl)-2-(1-oxopyridin-4-ylmethylthio)pyridine-3-carboxamide

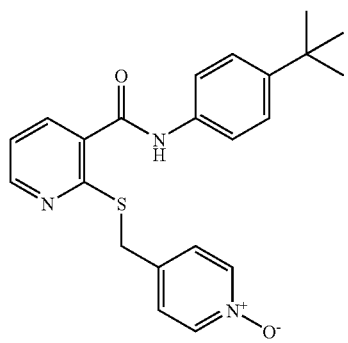

34

N-(3-Chloro-4-trifluoromethoxyphenyl)-2-(1-oxopyridin-4-ylmethylthio)-pyridine-3-carboxamide

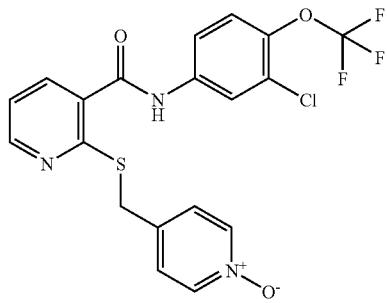

N-(3-Chlorophenyl)-2-[1-(4-pyridyl)ethylthio]pyridine-3-carboxamide

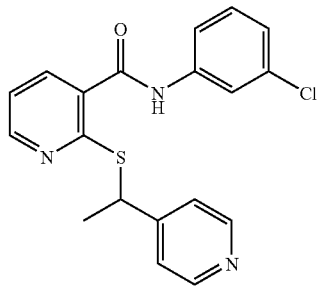

2-(2-Carboxypyridin-4-ylmethylthio)-N-(3,5-dimethylphenyl)pyridine-3-carboxamide

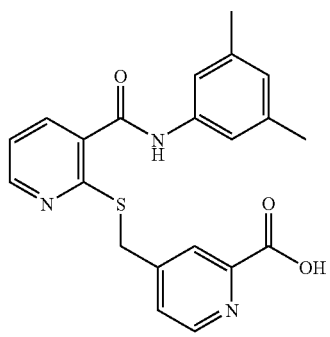

N-(3,5-Dimethylphenyl)-2-(2-n-propylaminocarbonylpyridin-4-yl-methylthio)pyridine-3-carboxamide

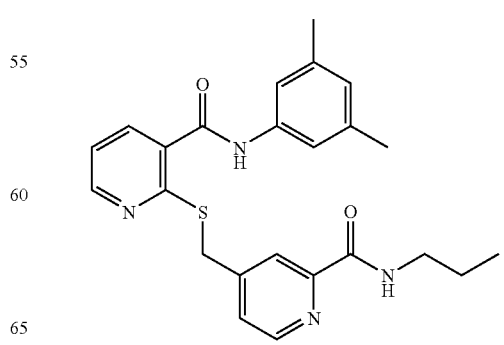

2-[2-(4-Chlorophenylaminocarbonyl)pyridin-4-ylmethylthio]-N-(3,5-dimethylphenyl)pyridine-3-carboxamide

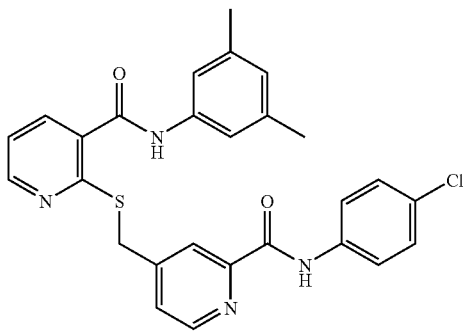

N-(3,5-Dimethylphenyl)-2-(2-methylaminocarbonylpyridin-4-yl-methylthio)pyridine-3-carboxamide

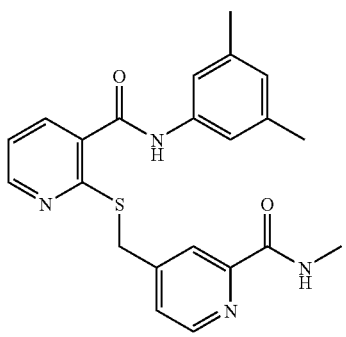

N-(3,5-Dimethylphenyl)-2-[2-(2-methoxyethylaminocarbonyl)pyridine-4-ylmethylthio]pyridine-3-carboxamide

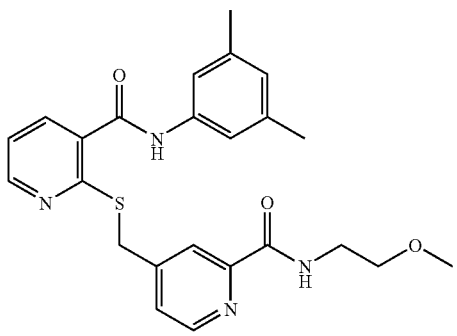

2-(2-Carbamoylpyridin-4-ylmethylthio)-N-(3,5-dimethylphenyl)pyridine-3-carboxamide

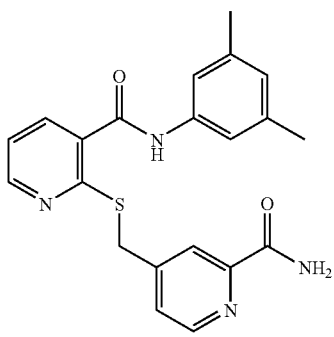

The compounds of the present invention can be prepared according to the following methods. Each specific process for preparing the present compounds will be described in detail in later Examples (section of Preparation). The term "Hal" used in the following synthetic routes represents a halogen atom.

The processes for preparing the compounds of the present invention are divided roughly into the methods 1~4) described below, and the suitable method can be chosen according to the kind of substituent.

1) The compound of the present invention (Ia, p=0) can be synthesized according to Synthetic route 1. Namely, the compound of this invention (Ia) can be given by the reaction of compound (II) with amine (III) in an organic solvent such as methylene chloride or N,N-dimethylformamide (DMF) in the presence of a condensing agent such as N,N'-dicyclohexylcarbodiimide (DCC) or O-(7-azabenzotriazol-1-yl)-1,1,3,3-tetramethyluronium hexafluoro-phosphate (HATU) or N-benzyl-N'-cyclohexylcarbodiimide polymer-bound, and in the presence of a base such as N,N-diisopropylethylamine at room temperature to 50° C. for 1 hour to 12 hours.

Synthetic route 1

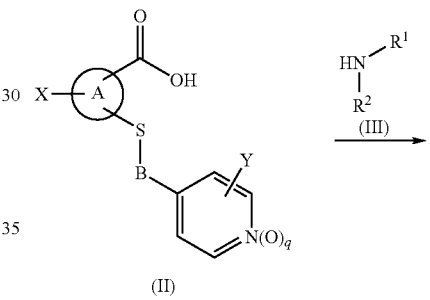

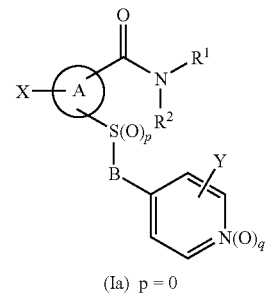

(Ia) p = 0

Compound (II) can be synthesized according to Synthetic route 1-1. Namely, compound (II) can be given by the reaction of compound (IV) with compound (Va) or compound (Vb) in an organic solvent such as DMF in the presence of a base such as triethylamine at 0° C. to room temperature for 1 hour to 12 hours.

Synthetic route 1-1

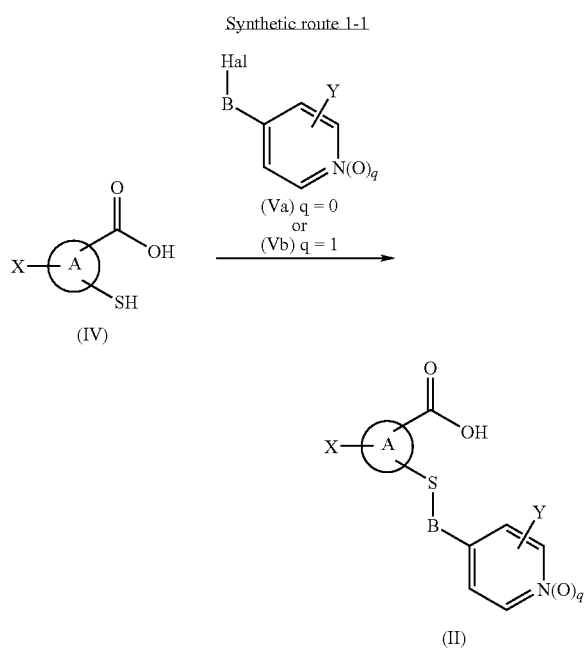

Compound (II) can also be synthesized according to Synthetic route 1-2. Namely, compound (II) can be given by the treatment of compound (VI) in an organic solvent such as methanol in the presence of a 1N aqueous sodium hydroxide solution at room temperature to 50° C. for 1 hour to 12 hours.

Synthetic route 1-2

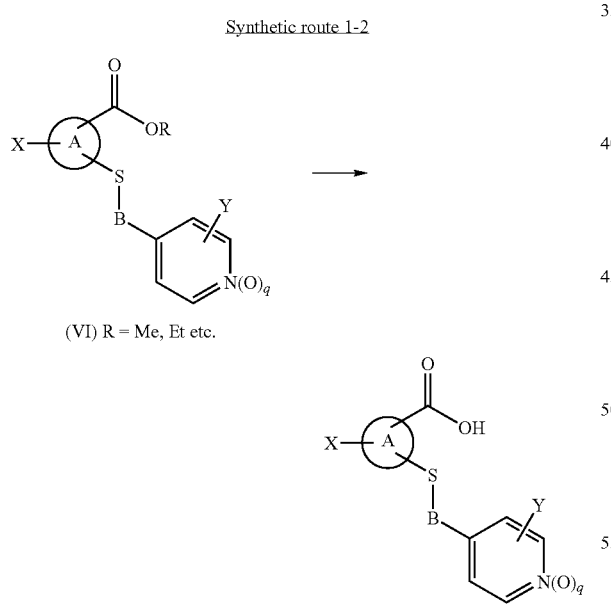

Compound (Va, q=0) can be synthesized according to Synthetic route 1-3. Namely, compound (Va) can be given by the treatment of compound (VII) in an organic solvent such as methylene chloride in the presence of a halogenating agent such as carbon tetrabromide-triphenylphosphine at 0° C. to room temperature for 1 hour to 4 hours.

Synthetic route 1-3

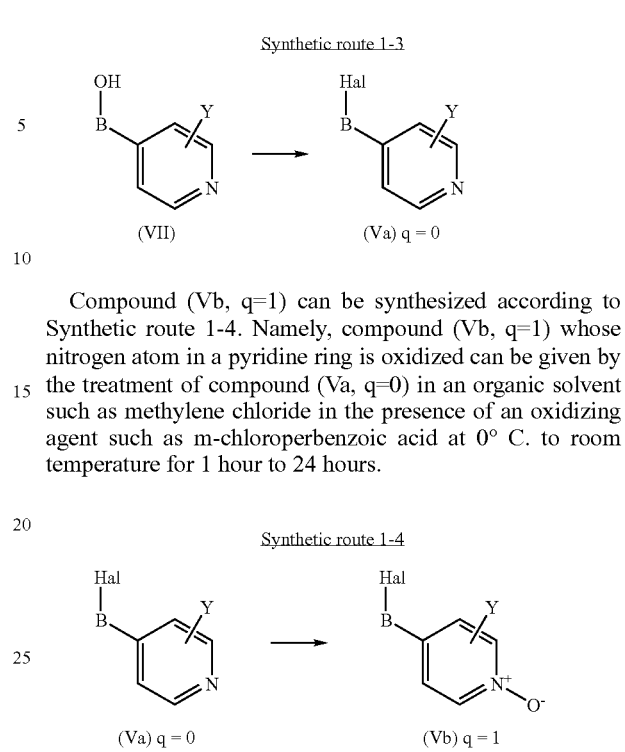

Compound (Vb, q=1) can be synthesized according to Synthetic route 1-4. Namely, compound (Vb, q=1) whose nitrogen atom in a pyridine ring is oxidized can be given by the treatment of compound (Va, q=0) in an organic solvent such as methylene chloride in the presence of an oxidizing agent such as m-chloroperbenzoic acid at 0° C. to room temperature for 1 hour to 24 hours.

Synthetic route 1-4

Compound (VI) can be synthesized according to Synthetic route 1-5. Namely, compound (VI) can be given by the reaction of compound (VIII) with compound (IX) in an organic solvent such as N,N-dimethylacetamide in the presence of a transition metal catalyst such as palladium, and in the presence of a catalytic ligand such as triphenylphosphine and a base such as N,N-diisopropylethylamine at 60° C. to 100° C. for 2 hours to 24 hours.

Synthetic route 1-5

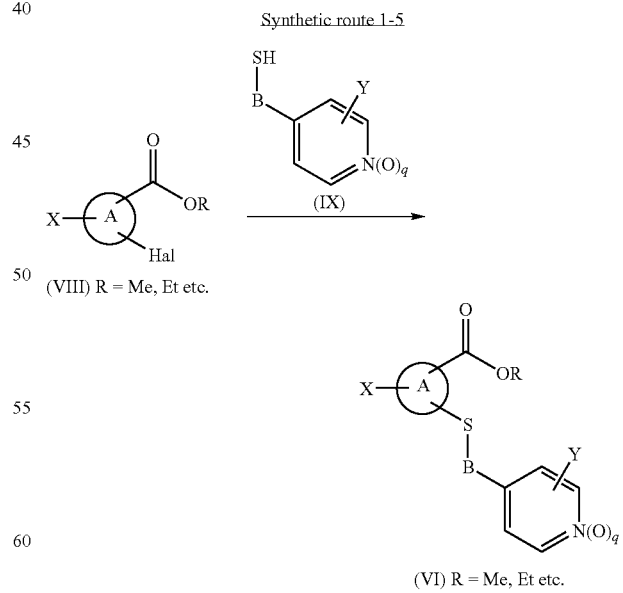

2) The compound of the present invention (Ib, p=0) can be synthesized according to Synthetic route 2. Namely, the compound of this invention (Ib) can be given by the reaction of compound (X) with compound (Va) or (Vb) in an organic solvent such as DMF in the presence of a base such as triethylamine at room temperature to 80° C. for 1 hour to 24 hours.

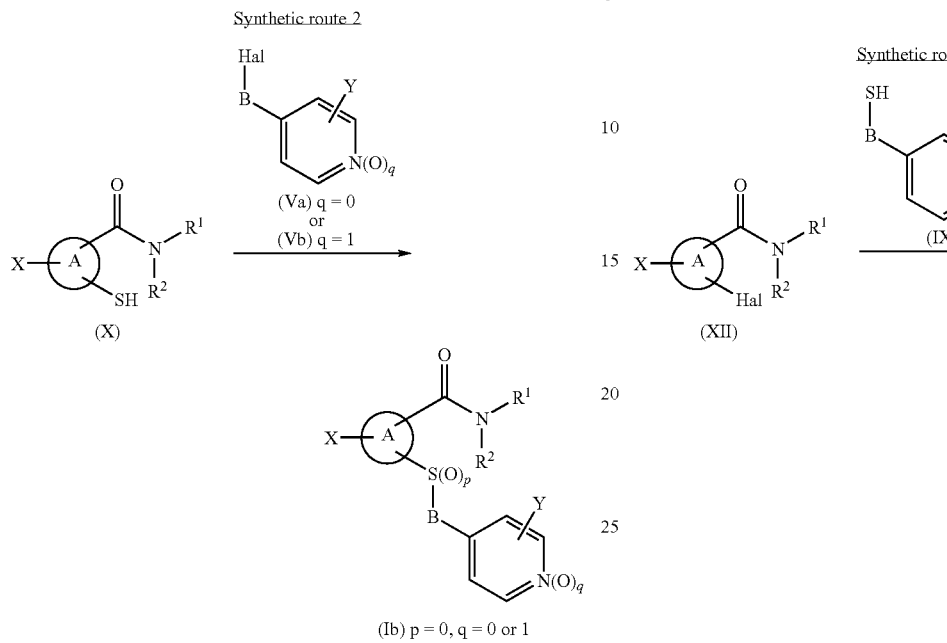

Compound (X) can be synthesized according to Synthetic route 2-1. Namely, compound (IV) is reacted with a halogenating agent such as thionyl chloride, in an organic solvent such as methylene chloride, and in the presence of a base such as pyridine at room temperature for 15 minutes to 3 hours. The resulting acid chloride (XI) is reacted with amine (III) in an organic solvent such as chloroform in the presence of a base such as pyridine at room temperature to 80° C. for 1 hour to 24 hours to give compound (X).

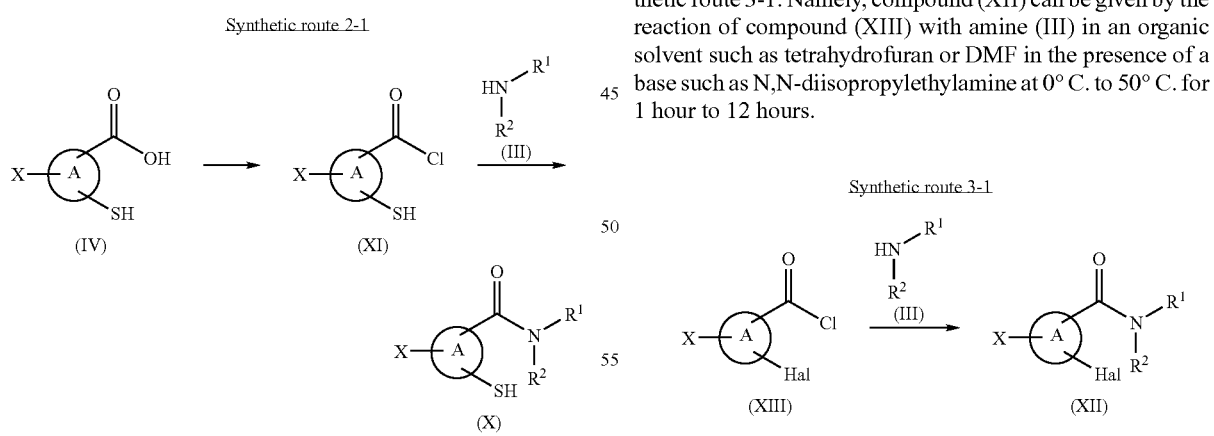

3) The compound of this invention (Ic, p=0) can be synthesized according to Synthetic route 3. Namely, the compound of this invention (Ic) can be also given by the reaction of compound (XII) with compound (IX) in an organic solvent such as DMF in the presence of a base such as potassium carbonate at 40° C. to 80° C. for 1 hour to 12 hours. It is also given by the reaction of compound (XII) with compound (IX) in an organic solvent such as N,N-dimethylacetamide in the presence of a transition metal catalyst such as palladium, a catalytic ligand such as triphenylphosphine and a base such as N,N-diisopropylethylamine at 60° C. to 100° C. for 2 hours to 24 hours.

Compound (XII) can be synthesized according to Synthetic route 3-1. Namely, compound (XII) can be given by the reaction of compound (XIII) with amine (III) in an organic solvent such as tetrahydrofuran or DMF in the presence of a base such as N,N-diisopropylethylamine at 0° C. to 50° C. for 1 hour to 12 hours.

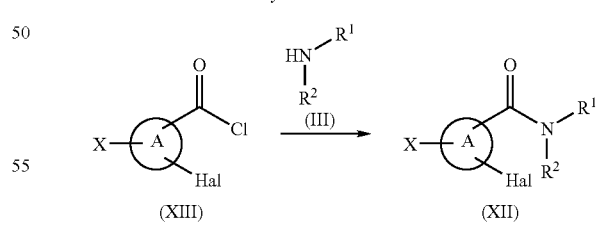

4) The compound of the present invention (Id, p=1 or 2) can also be synthesized according to Synthetic route 4. Namely, the compound of this invention (Id), wherein the sulfur atom of compound (Ia, Ib or Ic) is oxidized, can be given by the treatment of this compound (Ia, Ib or Ic) in an organic solvent such as chloroform in the presence of an oxidizing agent such as m-chloroperbenzoic acid or hydrogen peroxide at 0° C. to room temperature for 1 hour to 12 hours.

Synthetic route 4

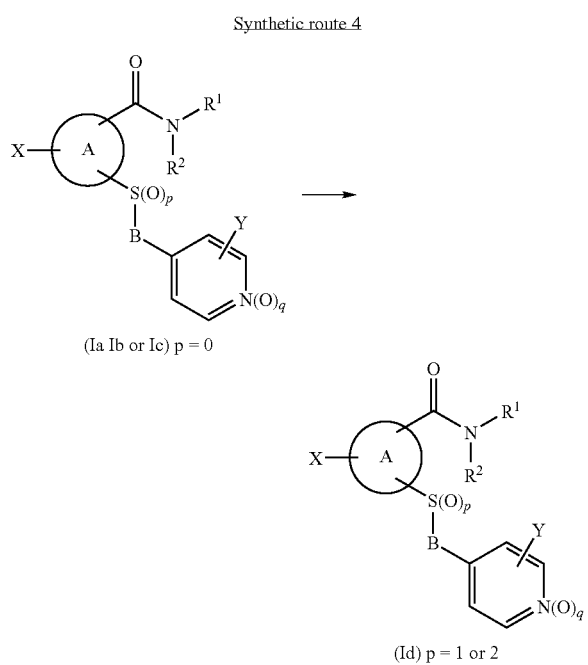

(Ia Ib or Ic) p = 0

(Id) p = 1 or 2

The compound of the present invention prepared by the above synthetic routes can be converted into the above-mentioned salts, hydrates or solvates using widely-used techniques.

The present invention also relates to pharmaceutical compositions comprising the present compound or the salt thereof and a pharmaceutical carrier.

The present invention further relates to a method of treating diseases in which angiogenesis or augmentation of vascular permeability is involved comprising administering to patients a pharmaceutically effective amount of the present compound or the salt thereof for the treatment.

The following pharmacological tests 1 to 4 were carried out, and pharmacological effects of the present compounds were evaluated in order to find utility of the present compounds. Details will be mentioned in Examples (under the item of pharmacological tests) later. The present compounds demonstrated excellent cell growth inhibitory actions in the pharmacological test 1 (in vitro), angiogenesis inhibitory effects were found, and inhibition of augmentation of vascular permeability was suggested. Further, the present compounds demonstrated excellent tumor growth inhibitory actions, paw edema inhibitory actions and choroidal neovascularization inhibitory effects in pharmacological tests 2 to 4 (in vivo) using specific disease model animals, and it was found that the present compounds are useful as therapeutic agents for specific diseases in which angiogenesis or augmentation of vascular permeability is involved.

1. Evaluation Tests of Angiogenesis Inhibitory Effects

Cell growth inhibitory action tests were carried out using a VEGF-induced HUVEC growth reaction evaluation system (HUVEC stands for human umbilical vein endothelial cells), which is one of widely-used methods of evaluating in vitro angiogenesis inhibitory effects of drugs.

2. Evaluation Tests of Anticancer Effects

Tumor proliferation inhibitory action tests of the present compounds were carried out using a mouse cancer model, which is one of widely-used methods of evaluating in vivo anticancer effects of drugs.

3. Evaluation Tests of Antiarthritis Effects

Paw edema inhibitory action tests of the present compounds were carried out using a rat adjuvant arthritis model, which is one of widely-used methods of evaluating in vivo antiarthritis effects of drugs.

4. Evaluation Tests of Choroidal Neovascularization Inhibitory Effects

Neovascularization incidence tests of the present compounds were carried out using a rat choroidal neovascularization model, which is one of widely-used methods of evaluating in vivo choroidal neovascularization inhibitory effects of drugs.

As shown in the tests 1 to 4, the present compounds are useful as a therapeutic agents for the diseases in which angiogenesis or augmentation of vascular permeability is involved, specifically cancer, rheumatoid arthritis, age-related macular degeneration, diabetic retinopathy, retinopathy of prematurity, retinal vein occlusion, polyploid choroidal angiopathy, diabetic macular edema, psoriasis vulgaris and pultaceous arteriosclerosis.

The present compound can be administered orally or parenterally. Examples of dosage forms are a tablet, a capsule, granule, powder, an injection, an ophthalmic solution and the like. The preparations can be prepared by the usual methods.

For example, oral preparations such as a tablet, a capsule, granule and powder can be prepared by optionally adding an excipient such as lactose, mannitol, starch, crystalline cellulose, light silicic anhydride, calcium carbonate or calcium hydrogenphosphate, a lubricant such as stearic acid, magnesium stearate or talc, a binder such as starch, hydroxypropylcellulose, hydroxypropylmethylcellulose or polyvinylpyrrolidone, a disintegrator such as carboxymethylcellulose, low-substituted hydroxypropylmethylcellulose or calcium citrate, a coating agent such as hydroxypropylmethylcellulose, macrogol or a silicone resin, a stabilizer such as ethyl p-hydroxybenzoate or benzyl alcohol, or corrigent such as a sweetening agent, a sour agent or a perfume.

Parenteral preparations such as an injection and an ophthalmic solution can be prepared by optionally adding a tonicity agent such as sodium chloride, concentrated glycerin, propylene glycol, polyethylene glycol, potassium chloride, sorbitol or mannitol, a buffer such as sodium phosphate, sodium hydrogenphosphate, sodium acetate, citric acid, glacial acetic acid or trometamol, a surfactant such as polyoxyethylene sorbitan monoolate, polyoxyl 40 stearate or polyoxyethylene hydrogenated castor oil, a stabilizer such as sodium citrate or disodium edetate, a preservative such as benzalkonium chloride, paraben, benzethonium chloride, p-hydroxybenzoate, sodium benzoate or chlorobutanol, a pH adjusting agent such as hydrochloric acid, citric acid, phosphoric acid, acetic acid, sodium hydroxide, sodium carbonate or sodium hydrogencarbonate or a soothing agent such as benzyl alcohol.

The dosage of the present compound can be appropriately selected depending on symptoms, age of patients, dosage form and the like. For example, in the case of oral preparations, the usually daily dosage is 0.01 to 1,000 mg, preferably 1 to 100 mg of the present compound, which can be given in a single dose or several divided doses.

In the case of ophthalmic solutions, they can be instilled once to several times per day with a concentration of 0.0001 to 10% (w/v), preferably 0.01 to 5% (w/v).

Examples of preparations and formulations of the present compounds and results of pharmacological tests are shown below. These examples do not limit the scope of the present invention, but are intended to make the present invention more clearly understandable.

Preparation Examples

Reference Example 1

2-(4-Pyridylmethylthio)pyridine-3-carboxylic acid

Reference Compound No. 1-1

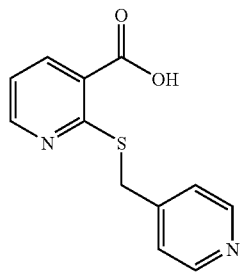

2-Mercaptonicotinic acid (7.8 g, 50 mmol) and 4-(bromomethyl)pyridine hydrobromide (12.6 g, 50 mmol) were suspended in N,N-dimethylformamide (100 mL) under ice-cooling. Triethylamine (21 ml, 150 mmol) was added dropwise to the suspension, and the whole was stirred at room temperature for 6 hours. Water (300 mL) was added to the reaction mixture, then the aqueous layer was washed with ethyl acetate (100 mL). 2 N hydrochloric acid was added to the aqueous layer to adjust to pH 7, and the precipitated solid was filtered off. The solid was washed with water and diethyl ether, and dried at 50° C. under reduced pressure to give 7.5 g of the title reference compound as a gray solid. (Yield 61%)

$^1$H-NMR (400 MHz, DMSO-$d_6$)

δ 4.38 (s, 2H), 7.27 (dd, J=8.1, 4.8 Hz, 1H), 7.42 (dd, J=4.4, 1.5 Hz, 2H), 8.22 (dd, J=8.1, 1.8 Hz, 1H), 8.46 (dd, J=4.4, 1.5 Hz, 2H), 8.63 (dd, J=4.8, 1.8 Hz, 1H), 13.70 (br s, 1H)

As described below, Reference compounds (No. 1-2~11) were obtained by a method similar to Reference Example 1.

2-(4-Pyridylmethylthio)benzoic acid

Reference Compound No. 1-2

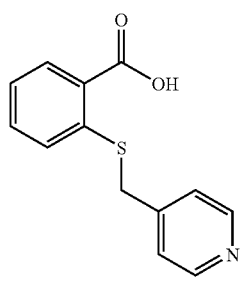

$^1$H-NMR (400 MHz, DMSO-$d_6$)

δ 4.25 (s, 2H), 7.21 (td, J=7.5, 1.2 Hz, 1H), 7.40-7.51 (m, 4H), 7.88 (dd, J=7.8, 1.8 Hz, 1H), 8.50 (dd, J=4.3, 1.5 Hz, 2H), 13.12 (br s, 1H)

5-Fluoro-2-(4-pyridylmethylthio)benzoic acid

Reference Compound No. 1-3

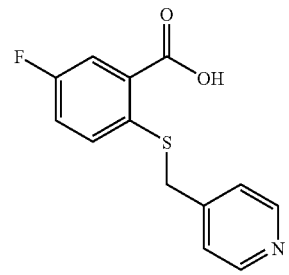

$^1$H-NMR (400 MHz, DMSO-$d_6$)

δ 4.55 (s, 2H), 7.39 (td, J=8.0, 2.9 Hz, 1H), 7.49 (dd, J=9.0, 5.1 Hz, 1H), 7.62 (dd, J=9.3, 2.9 Hz, 1H), 8.00 (d, J=6.6 Hz, 2H), 8.81 (d, J=6.6 Hz, 2H)

4-(4-Pyridylmethylthio)pyridine-3-carboxylic acid

Reference Compound No. 1-4

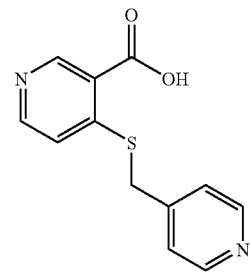

$^1$H-NMR (400 MHz, DMSO-$d_6$)

δ 4.35 (s, 2H), 7.45 (d, J=5.6 Hz, 1H), 7.49 (d, J=6.1 Hz, 2H), 8.50 (d, J=5.6 Hz, 1H), 8.54 (d, J=6.1 Hz, 2H), 8.92 (s, 1H), 13.70 (br s, 1H)

3-(4-Pyridylmethylthio)pyridine-2-carboxylic acid

Reference Compound No. 1-5

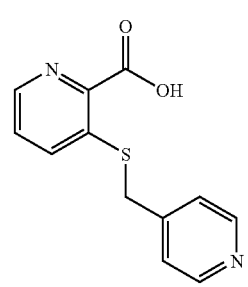

$^1$H-NMR (400 MHz, DMSO-$d_6$)

δ 4.30 (s, 2H), 7.42 (dd, J=4.4, 1.6 Hz, 2H), 7.50 (m, 1H), 7.92 (dd, J=8.3, 1.2 Hz, 1H), 8.40 (dd, J=4.6, 1.2 Hz, 1H), 8.50 (dd, J=4.4, 1.6 Hz, 2H), 13.26 (br s, 1H)

2-(2,6-Dichloropyridin-4-ylmethylthio)pyridine-3-carboxylic acid

Reference Compound No. 1-6

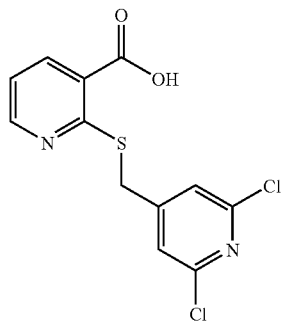

¹H-NMR (400 MHz, DMSO-d₆)

δ 4.40 (s, 2H), 7.29 (dd, J=7.8, 4.7 Hz, 1H), 7.62 (s, 2H), 8.25 (dd, J=7.8, 1.7 Hz, 1H), 8.64 (dd, J=4.7, 1.7 Hz, 1H), 13.58 (s, 1H)

2-(2-Fluoropyridin-4-ylmethylthio)pyridine-3-carboxylic acid

Reference Compound No. 1-7

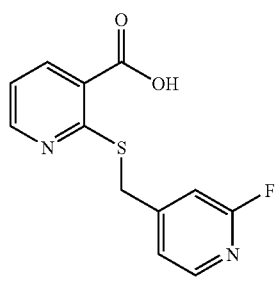

¹H-NMR (500 MHz, DMSO-d₆)

δ 4.43 (s, 2H), 7.20 (s, 1H), 7.27 (dd, J=7.6, 4.7 Hz, 1H), 7.40 (m, 1H), 8.13 (d, J=5.2 Hz, 1H), 8.23 (dd, J=7.6, 1.8 Hz, 1H), 8.64 (dd, J=4.7, 1.8 Hz, 1H), 13.49 (s, 1H)

2-(2-Bromopyridin-4-ylmethylthio)pyridine-3-carboxylic acid

Reference Compound No. 1-8

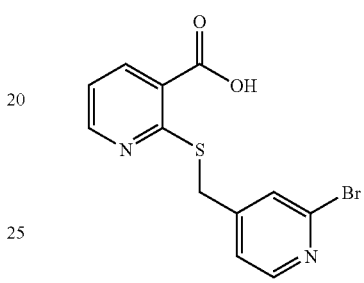

¹H-NMR (500 MHz, DMSO-d₆)

δ 4.37 (s, 2H), 7.28 (dd, J=7.8, 4.7 Hz, 1H), 7.48 (dd, J=4.9, 1.4 Hz, 1H), 7.69 (dd, J=1.4, 0.4 Hz, 1H), 8.23 (dd, J=7.8, 1.8 Hz, 1H), 8.27 (dd, J=4.9, 0.4 Hz, 1H), 8.63 (dd, J=4.7, 1.8 Hz, 1H), 13.55 (s, 1H)

3-(4-Pyridylmethylthio)thiophene-2-carboxylic acid

Reference Compound No. 1-9

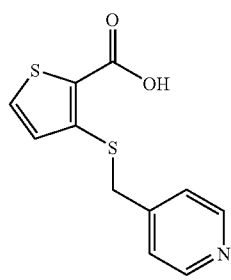

¹H-NMR (500 MHz, DMSO-d₆)

δ 4.35 (s, 2H), 7.19 (d, J=5.2 Hz, 1H), 7.45 (d, J=5.8 Hz, 2H), 7.84 (d, J=5.2 Hz, 1H), 8.51 (d, J=5.8 Hz, 2H), 13.06 (s, 1H)

3-(4-Pyridylmethylthio)benzoic acid

Reference Compound No. 1-10

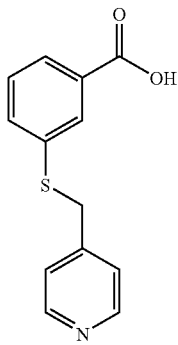

$^1$H-NMR (400 MHz, DMSO-$d_6$)
δ 4.33 (s, 2H), 7.35 (dd, J=4.3, 1.5 Hz, 2H), 7.42 (m, 1H), 7.58 (ddd, J=7.8, 2.0, 1.0 Hz, 1H), 7.74 (m, 1H), 7.82 (t, J=7.8 Hz, 1H), 8.47 (dd, J=4.4, 1.7 Hz, 2H), 13.12 (s, 1H)

4-(4-Pyridylmethylthio)benzoic acid

Reference Compound No. 1-11

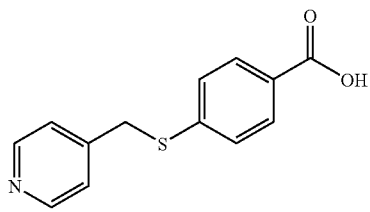

$^1$H-NMR (500 MHz, DMSO-$d_6$)
δ 4.38 (s, 2H), 7.42 (m, 4H), 7.82 (dt, J=8.6, 1.8 Hz, 2H), 8.50 (dd, J=4.4, 1.7 Hz, 2H), 12.92 (s, 1H)

Reference Example 2

2-Chloro-N-(4-chlorophenyl)pyridine-3-carboxamide

Reference Compound No. 2-1

2-Chloronicotinoyl chloride (4.0 g, 23 mmol) was added to a solution of 4-chloroaniline (3.2 g, 25 mmol) and N,N-diisopropylethylamine (7.7 mL, 46 mmol) in tetrahydrofuran (40 mL), and then the mixture was stirred at room temperature for 3 hours. Ethyl acetate (150 mL) was added to the reaction mixture, and the ethyl acetate layer was washed with a saturated aqueous sodium hydrogencarbonate solution (100 mL) twice and brine (100 mL) twice. The ethyl acetate layer was dried over anhydrous magnesium sulfate, the solvent was evaporated under reduced pressure, and the precipitated solid was filtered off. The solid was washed with diethyl ether:ethyl acetate (3:1), and then dried under reduced pressure to give 4.2 g of the title reference compound as a white solid. (Yield 82%).

$^1$H-NMR (400 MHz, CDCl$_3$)
δ 7.36 (d, J=8.9 Hz, 2H), 7.42 (dd, J=7.7, 4.8 Hz, 1H), 7.61 (d, J=8.9 Hz, 2H), 8.22 (s, 1H), 8.23 (dd, J=7.7, 1.9 Hz, 1H), 8.53 (dd, J=4.8, 1.9 Hz, 1H)

As described below, Reference compounds (No. 2-2~7) were obtained by the method similar to Reference Example 2.

2-Chloro-N-(4-trifluoromethylsulfonylphenyl)pyridine-3-carboxamide

Reference Compound No. 2-2

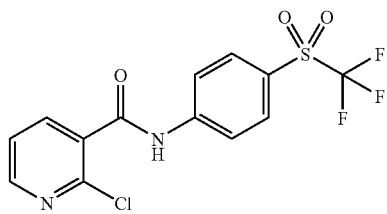

$^1$H-NMR (400 MHz, DMSO-$d_6$)
δ 7.62 (dd, J=7.6, 4.9 Hz, 1H), 8.11-8.18 (m, 5H), 8.59 (dd, J=4.9, 2.0 Hz, 1H), 11.41 (s, 1H)

N-(3-Fluoro-5-trifluoromethylphenyl)-2-iodobenzamide

Reference Compound No. 2-3

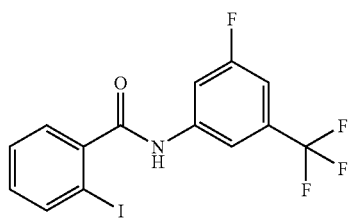

$^1$H-NMR (500 MHz, DMSO-$d_6$)

δ 7.27 (m, 1H), 7.52 (dd, J=9.7, 1.7 Hz, 1H), 7.53-7.55 (m, 2H), 7.87 (d, J=1.0 Hz, 1H), 7.96 (s, 1H), 7.97 (d, J=7.8 Hz, 1H), 10.96 (s, 1H)

5-Bromo-N-(4-chlorophenyl)furan-2-carboxamide

Reference Compound No. 2-4

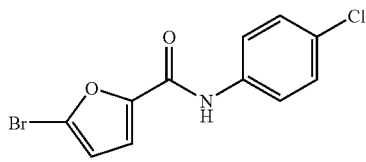

$^1$H-NMR (500 MHz, DMSO-$d_6$)

δ 6.84 (d, J=3.7 Hz, 1H), 7.38 (d, J=3.7 Hz, 1H), 7.41 (d, J=7.0 Hz, 2H), 7.76 (d, J=7.0 Hz, 2H), 10.33 (s, 1H)

5-Bromo-N-(4-chlorophenyl)thiophene-2-carboxamide

Reference Compound No. 2-5

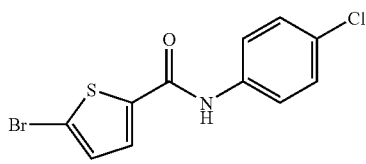

$^1$H-NMR (500 MHz, DMSO-$d_6$)

δ 7.38 (d, J=4.0 Hz, 1H), 7.42 (d, J=8.9 Hz, 2H), 7.73 (d, J=8.9 Hz, 2H), 7.85 (d, J=4.0 Hz, 1H), 10.38 (s, 1H)

5-Bromo-N-(3,5-dimethylphenyl)furan-2-carboxamide

Reference Compound No. 2-6

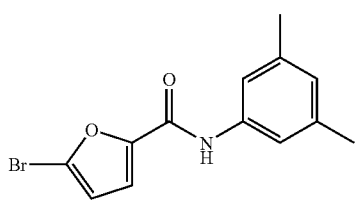

$^1$H-NMR (500 MHz, DMSO-$d_6$)

δ 2.26 (s, 6H), 6.75 (d, J=0.7 Hz, 1H), 6.82 (d, J=3.7 Hz, 1H), 7.35 (d, J=0.7 Hz, 2H), 7.35 (d, J=3.7 Hz, 1H), 10.02 (s, 1H)

5-Bromo-N-(3,5-dimethylphenyl)thiophene-2-carboxamide

Reference Compound No. 2-7

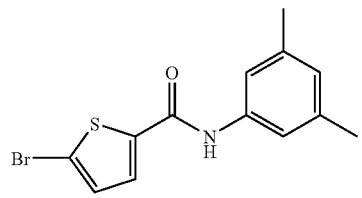

$^1$H-NMR (500 MHz, DMSO-$d_6$)

δ 2.26 (s, 6H), 6.76 (s, 1H), 7.33 (s, 2H), 7.36 (d, J=4.0 Hz, 1H), 7.85 (d, J=4.0 Hz, 1H), 10.12 (s, 1H)

Reference Example 3

4-(Chloromethyl)pyridine-N-oxide

Reference Compound No. 3-1

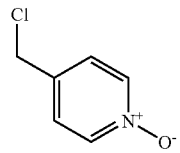

A 2 N aqueous sodium hydroxide solution (10 mL) and water (20 mL) were added to 4-(chloromethyl)pyridine hydrochloride (1.6 g, 10 mmol), and the reaction mixture was extracted with chloroform (20 mL) twice. The chloroform layer was dried over anhydrous magnesium sulfate, and then the solvent was evaporated under reduced pressure. m-Chloroperoxybenzoic acid (65%, 5.3 g, 20 mmol) was added to a solution of the resulting residue in dichloromethane (20 mL), and then the mixture was stirred at room temperature for 17 hours. Chloroform (100 mL) and a saturated aqueous sodium hydrogencarbonate solution (120 mL) were added to the reaction mixture, and then the chloroform layer was washed with a saturated aqueous sodium hydrogencarbonate solution (80 ml) and brine (100 mL). The chloroform layer was dried over anhydrous magnesium sulfate, and then the solvent was evaporated under reduced pressure. The resulting residue was purified by silica gel column chromatography to give 300 mg of the title reference compound as a brown solid. (Yield 21%)

$^1$H-NMR (400 MHz, DMSO-$d_6$)

δ 4.77 (s, 2H), 7.47 (d, J=7.1 Hz, 2H), 8.22 (d, J=7.1 Hz, 2H)

Reference Example 4

2-(1-Oxopyridin-4-ylmethylthio)pyridine-3-carboxylic acid

Reference Compound No. 4-1

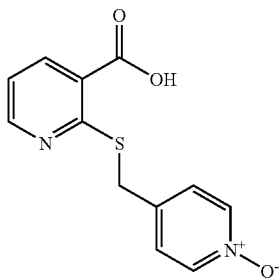

2-Mercaptonicotinic acid (270 mg, 1.7 mmol) and 4-(chloromethyl)pyridine-N-oxide (260 mg, 1.7 mmol, Reference compound No. 3-1) were suspended in N,N-dimethylformamide (100 mL). Triethylamine (0.75 ml, 5.4 mmol) was added dropwise thereto, and the mixture was stirred at room temperature for 7.5 hours. Water (30 mL) was added to the reaction mixture, and the whole was washed with ethyl acetate (50 mL). 1 N hydrochloric acid (5.0 ml) was added to the aqueous layer to adjust to pH 7, the precipitated solid was filtered off. The solid was washed with water and diethyl ether, and then dried under reduced pressure to give 200 mg of the title reference compound as a pale red solid. (Yield 47%)

$^1$H-NMR (400 MHz, DMSO-$d_6$)

δ 4.35 (s, 2H), 7.28 (dd, J=7.8, 4.8 Hz, 1H), 7.43 (d, J=7.1 Hz, 2H), 8.11 (dd, J=5.1, 2.0 Hz, 2H), 8.23 (dd, J=7.8, 1.9 Hz, 1H), 8.64 (dd, J=4.8, 1.9 Hz, 1H), 13.50 (br, 1H)

Reference Example 5

2-[1-(4-Pyridyl)ethylthio]pyridine-3-carboxylic acid

Reference Compound No. 5-1

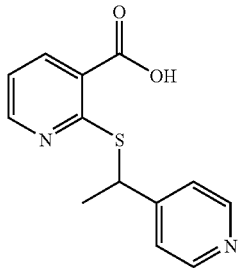

Triphenylphosphine (4.8 g, 18 mmol) and carbon tetrabromide (7.4 g, 22 mmol) were added to a solution of (±)-1-(4-pyridyl)ethanol (1.9 g, 15 mmol) in methylene chloride (75 mL) under ice-cooling, and then the mixture was stirred at room temperature for 1 hour. A saturated aqueous sodium hydrogencarbonate solution (100 mL) was added to the reaction mixture, the whole was extracted with chloroform (60 mL), and then the chloroform layer was washed with brine (80 mL). The chloroform layer was dried over anhydrous magnesium sulfate, and then the solvent was evaporated under reduced pressure. The resulting residue was purified by silica gel column chromatography to give (±)-1-(1-bromoethyl)pyridine (2.0 g, 72%).

Immediately, triethylamine (3.1 mL, 22 mmol) was added dropwise to a solution of this bromo intermediate (2.0 g) 11 mmol) and 2-mercaptonicotinic acid (1.2 g, 7.8 mmol) in N,N-dimethylformamide (100 mL) at room temperature, and the reaction mixture was stirred for 15 hours. Water (50 mL) was added to the reaction mixture, the whole was washed with ethyl acetate (50 mL), then the aqueous layer was adjusted to pH 7 with 1N hydrochloric acid and extracted with chloroform (50 mL). The chloroform layer was dried over anhydrous magnesium sulfate, and then the solvent was evaporated under reduced pressure to give the title reference compound including N,N-dimethylformamide.

$^1$H-NMR (400 MHz, DMSO-$d_6$)

δ 1.64 (d, J=7.1 Hz, 3H), 5.14 (q, J=7.1 Hz, 1H), 7.23 (dd, J=7.6, 4.7 Hz, 1H), 7.48 (dd, J=4.5, 1.5 Hz, 2H), 8.19 (dd, J=7.6, 1.7 Hz, 1H), 8.48 (dd, J=4.5, 1.5 Hz, 2H), 8.60 (dd, J=4.7, 1.7 Hz, 1H), 13.50 (br s, 1H)

Reference Example 6

2-Methylthioisonicotinic acid methyl ester

Reference Compound No. 6-1

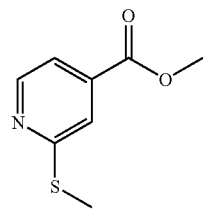

2-Chloroisonicotinic acid methyl ester (1.0 g, 60 mmol) and sodium thiomethoxide (0.42 g, 60 mmol) were suspended in methanol (10 mL); and the whole was refluxed under a nitrogen atmosphere for 3 hours. The reaction mixture was diluted with ethyl acetate (60 mL) and washed with a saturated aqueous sodium hydrogencarbonate solution (100 mL) and brine (100 mL). The ethyl acetate layer was dried over anhydrous magnesium sulfate, and then the solvent was evaporated under reduced pressure. The resulting residue was purified by silica gel column chromatography to give 0.20 g of the title reference compound as a colorless oil. (Yield 22%)

$^1$H-NMR (500 MHz, CDCl$_3$)

δ 2.60 (s, 3H), 3.94 (s, 3H), 7.49 (dd, J=5.2, 1.6 Hz, 1H), 7.73 (dd, J=1.6, 1.0 Hz, 1H), 8.56 (dd, J=5.2, 1.0 Hz, 1H)

Reference Example 7

2-Chloropyridine-4-methanol

Reference Compound No. 7-1

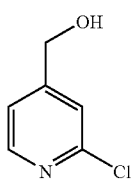

A 0.95 M solution of diisobutylaluminum hydride in hexane (200 mL, 190 mmol) was added dropwise to a solution of 2-chloroisonicotinic acid methyl ester (11 g, 62 mmol) in anhydrous tetrahydrofuran (300 mL) under a nitrogen atmosphere under ice-cooling, and then the mixture was stirred under ice-cooling for 2 hours. After that, 1 N hydrochloric acid (200 mL) was added thereto, the mixture was stirred at room temperature for 1 hour. A saturated aqueous sodium hydrogencarbonate solution (400 mL) was added to the reaction mixture, then the whole was extracted with ethyl acetate (100 mL) three times. The ethyl acetate layer was dried over anhydrous magnesium sulfate, and then the solvent was evaporated under reduced pressure to give 8.5 g of the title reference compound as a white solid. (Yield 95%)

$^1$H-NMR (500 MHz, DMSO-$d_6$)

δ 4.56 (d, J=5.8 Hz, 2H), 5.54 (t, J=5.8 Hz, 1H), 7.34 (d, J=4.9 Hz, 1H), 7.41 (s, 1H), 8.34 (d, J=4.9 Hz, 1H)

As described below, Reference compounds (No. 7-2~3) were obtained by a method similar to Reference Example 7.

2-Methylthiopyridine-4-methanol

Reference Compound No. 7-2

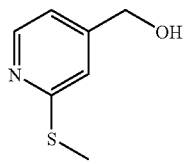

$^1$H-NMR (500 MHz, CDCl$_3$)

δ 2.16 (br s, 1H), 2.56 (s, 3H), 4.68 (s, 2H), 6.95 (dt, J=5.1, 0.7 Hz, 1H), 7.19 (dd, J=1.4, 0.7 Hz, 1H), 8.38 (d, J=5.1 Hz, 1H)

2-Methylpyridine-4-methanol

Reference Compound No. 7-3

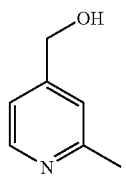

$^1$H-NMR (500 MHz, DMSO-$d_6$)

δ 2.44 (s, 3H), 4.49 (d, J=5.5 Hz, 2H), 5.36 (t, J=5.5 Hz, 1H), 7.10 (d, J=5.1 Hz, 1H), 7.17 (s, 1H), 8.35 (d, J=5.1 Hz, 1H)

Reference Example 8

2-Methoxypyridine-4-methyl methoxymethyl ether

Reference Compound No. 8-1

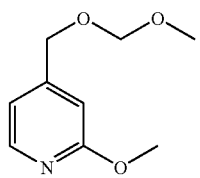

Methanol (0.46 mL, 11 mmol) was added to the suspension of potassium tert-butoxide (1.2 g, 11 mmol) in tetrahydrofuran (50 mL), then the mixture was refluxed for 3 hours. A solution of 2-chloropyridine-4-methyl methoxymethyl ether (1.0 g, 5.3 mmol) in tetrahydrofuran (10 mL) was added to the reaction mixture, and the mixture was refluxed for 3 hours. The mixture was allowed to stand and diluted with ethyl acetate (100 mL), and then the ethyl acetate layer was washed with water (200 mL) and brine (100 mL). The ethyl acetate was dried over anhydrous magnesium sulfate, and then the solvent was evaporated under reduced pressure. The resulting residue was purified by silica gel column chromatography to give 0.89 g of the title reference compound as a yellow oil. (Yield 91%)

$^1$H-NMR (500 MHz, CDCl$_3$)

δ 3.41 (s, 3H), 3.94 (s, 3H), 4.56 (s, 2H), 4.71 (s, 2H), 6.74 (s, 1H), 6.85 (dd, J=5.2, 0.6 Hz, 1H), 8.12 (d, J=5.2 Hz, 1H)

As described below, Reference compounds (No. 8-2~4) were obtained by a method similar to Reference Example 8.

2-Ethoxypyridine-4-methyl methoxymethyl ether

Reference Compound No. 8-2

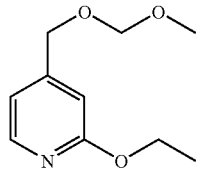

¹H-NMR (500 MHz, CDCl₃)

δ 1.39 (t, J=7.0 Hz, 3H), 3.41 (s, 3H), 4.35 (q, J=7.0 Hz, 2H), 4.56 (s, 2H), 4.71 (s, 2H), 6.73 (s, 1H), 6.82 (dd, J=5.2, 1.2 Hz, 1H), 8.10 (d, J=5.2 Hz, 1H)

2-Isopropoxypyridine-4-methyl-methoxymethyl ether

Reference Compound No. 8-3

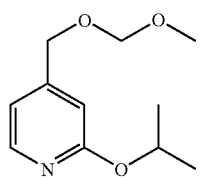

¹H-NMR (500 MHz, CDCl₃)

δ 1.34 (d, J=6.1 Hz, 6H), 3.41 (s, 3H), 4.54 (s, 2H), 4.71 (s, 2H), 5.30 (m, 1H), 6.68 (s, 1H), 6.80 (dd, J=5.2, 1.2 Hz, 1H), 8.09 (d, J=5.2 Hz, 1H)

2-Benzyloxypyridine-4-methyl methoxymethyl ether

Reference Compound No. 8-4

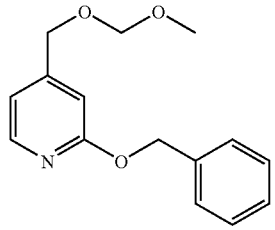

¹H-NMR (400 MHz, CDCl₃)

δ 3.41 (s, 3H), 4.57 (s, 2H), 4.71 (s, 2H), 5.38 (s, 2H), 6.62 (dd, J=1.6, 1.0 Hz, 1H), 6.87 (dd, J=5.2, 0.6 Hz, 1H), 7.32 (d, J=7.3 Hz, 1H), 7.37 (t, J=7.6 Hz, 2H), 7.45 (dd, J=7.6, 0.6 Hz, 2H), 8.13 (dd, J=5.2, 0.6 Hz, 1H)

Reference Example 9

2-Methoxypyridine-4-methanol

Reference Compound No. 9-1

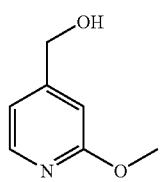

A solution of 4 N hydrogen chloride in ethyl acetate (11 mL, 44 mmol) was added to 2-methoxypyridine-4-methyl methoxymethyl ether (0.77 g, 4.2 mmol, Reference compound No. 8-1) under ice-cooling, then the mixture was stirred for 30 minutes. The mixture was diluted with chloroform (100 mL) and washed with a saturated aqueous sodium hydrogencarbonate solution (50 mL) twice. The chloroform layer was dried over anhydrous magnesium sulfate, then the solvent was evaporated under reduced pressure to give 0.69 g of the title reference compound as a yellow oil. (Yield 99%)

¹H-NMR (500 MHz, CDCl₃)

δ 1.89 (s, 1H), 3.94 (s, 3H), 4.69 (d, J=4.3 Hz, 2H), 6.75 (s, 1H), 6.85 (d, J=5.2 Hz, 1H), 8.12 (d, J=5.2 Hz, 1H)

As described below, Reference compounds (No. 9-24) were obtained by a method similar to Reference Example 9.

2-Ethoxypyridine-4-methanol

Reference Compound No. 9-2

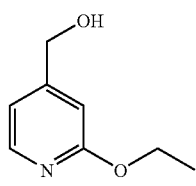

¹H-NMR (400 MHz, CDCl₃)

δ 1.39 (t, J=7.1 Hz, 3H), 2.32 (br s, 1H) 4.34 (q, J=7.1 Hz, 2H), 4.67 (s, 2H), 6.73 (dd, J=1.5, 1.0 Hz, 1H), 6.82 (dd, J=5.4, 1.0 Hz, 1H), 8.08 (d, J=5.4 Hz, 1H)

2-Isopropoxypyridine-4-methanol

Reference Compound No. 9-3

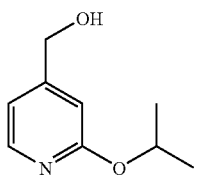

$^1$H-NMR (400 MHz, CDCl$_3$)
δ 1.34 (d, J=6.5 Hz, 6H), 1.78 (br s, 1H), 4.71 (s, 2H), 5.30 (m, 1H), 6.69 (s, 1H), 6.81 (d, J=5.2 Hz, 1H), 8.10 (d, J=5.2 Hz, 1H)

2-Benzyloxypyridine-4-methanol hydrochloride

Reference Compound 9-4

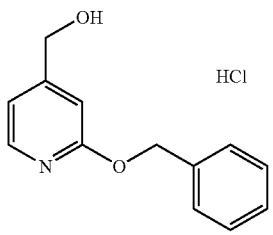

$^1$H-NMR (400 MHz, DMSO-d$_6$)
δ 4.52 (s, 2H), 5.36 (s, 2H), 6.89 (m, 1H), 6.98 (m, 1H), 7.32 (d, J=7.0 Hz, 1H), 7.37 (t, J=7.0 Hz, 2H), 7.43 (d, J=7.0 Hz, 2H), 8.10 (d, J=5.5 Hz, 1H), 7.00-8.20 (br s, 1H)

Reference Example 10

2-Cyano-4-(trimethylsilyloxymethyl)pyridine

Reference Compound No. 10-1

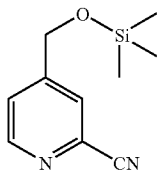

Trimethylsilylnitrile (8.0 mL, 60 mmol) and dimethylcarbamoyl chloride (4.1 mL, 45 mmol) were added to a solution of 4-pyridylcarbinol-N-oxide (5.1 g, 41 mmol) in methylene chloride (200 mL) at room temperature, then the mixture was stirred for 4 days. The solvent was evaporated under reduced pressure, then diethyl ether (40 mL) was added to the residue, and the resulting insoluble matter was filtered out. The filtrate was evaporated under reduced pressure, and then the resulting residue was purified by silica gel column chromatography to give 5.8 g of the title reference compound as a pale yellow solid. (Yield 68%)
$^1$H-NMR (400 MHz, DMSO-d$_6$)
δ 0.16 (s, 9H), 4.79 (s, 2H), 7.66 (m, 1H), 7.92 (dd, J=1.6, 0.7 Hz, 1H), 8.71 (dd, J=5.1, 0.7 Hz, 1H)

Reference Example 11

2-Cyanopyridine-4-methanol

Reference Compound No. 11-1

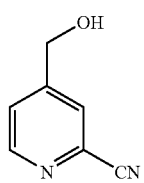

Tetra-n-butylammonium fluoride trihydrate (1.1 g, 3.5 mmol) was added to a solution of 2-cyano-4-(trimethylsilyloxymethyl)pyridine (600 mg, 2.9 mmol, Reference compound No. 10-1) in tetrahydrofuran (15 mL) at room temperature, then the mixture was stirred for 3 hours. The solvent was evaporated under reduced pressure, and then the resulting residue was purified by silica gel column chromatography to give 120 mg of the title reference compound as a yellow solid. (Yield 32%)
$^1$H-NMR (500 MHz, DMSO-d$_6$)
δ 4.61 (d, J=5.8 Hz, 2H), 5.64 (t, J=5.8 Hz, 1H), 7.67 (ddd, J=4.0, 1.5, 0.6 Hz, 1H), 7.92 (dd, J=1.5, 0.9 Hz, 1H), 8.69 (dd, J=5.0, 0.6 Hz, 1H)

Reference Example 12

2-Ethoxycarbonylpyridine-4-methanol

Reference Compound No. 12-1

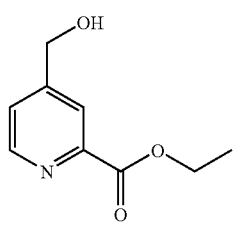

Trimethylsilyl chloride (0.4 mL, 3.0 mmol) was added to a solution of 2-cyanopyridine-4-methanol (200 mg, 1.5 mmol, Reference compound No. 11-1) in ethanol (3 mL) at 50° C. under a nitrogen atmosphere, then the mixture was stirred for 12 hours. The mixture was allowed to stand, and a little water and sodium carbonate (160 mg, 1.5 mmol) were added thereto. The solution was dried over anhydrous magnesium sulfate, then the solvent was evaporated under reduced pressure. The resulting residue was purified by silica gel column chromatography to give 43 mg of the title reference compound as a white solid. (Yield 16%)
$^1$H-NMR (500 MHz, DMSO-d$_6$)

δ 1.33 (t, J=7.0 Hz, 3H), 4.35 (q, J=7.0 Hz, 2H), 4.62 (d, J=5.8 Hz, 2H), 5.56 (t, J=5.8 Hz, 1H), 7.55 (m, 1H), 8.01 (dd, J=1.6, 0.6 Hz, 1H), 8.63 (dd, J=4.6, 0.6 Hz, 1H)

As described below, Reference compound (No. 12-2) was obtained by a method similar to Reference Example 12.

2-Methoxycarbonylpyridine-4-methanol

Reference Compound No. 12-2

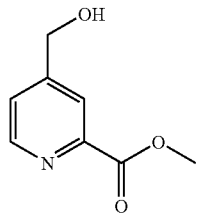

¹H-NMR (500 MHz, DMSO-d₆)

δ 3.88 (s, 3H), 4.62 (d, J=5.8 Hz, 2H), 5.57 (t, J=5.8 Hz, 1H), 7.56 (dt, J=4.9, 0.9 Hz, 1H), 8.02 (dd, J=1.5, 0.6 Hz, 1H), 8.64 (dd, J=4.9, 0.6 Hz, 1H)

Reference Example 13

2-Carbamoylpyridine-4-methanol

Reference Compound No. 13-1

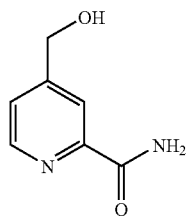

Trimethylsilyl chloride (27 mL) and a suspension of 2-cyanopyridine-4-methanol (1.6 g, 11 mmol, Reference compound II-1) in ethanol (20 mL) were added to ethanol (14 mL) at room temperature under a nitrogen atmosphere, and then the mixture was stirred at 50° C. for 5.5 hours. The mixture was allowed to stand, and water (27 mL) and sodium carbonate (2.3 g 22 mmol) were added thereto. The solvent was evaporated under reduced pressure, ethanol (100 mL) was added thereto, and the resulting insoluble matter was filtered out. The filtrate was evaporated under reduced pressure, then the resulting residue was dried at 50° C. under reduced pressure to the title reference compound including inorganic salt.

¹H-NMR (500 MHz, DMSO-d₆)

δ 4.61 (d, J=6.1 Hz, 2H), 5.52 (t, J=6.1 Hz, 1H), 7.50 (dt, J=4.9, 0.9 Hz, 1H), 7.60 (s, 1H), 8.01 (d, J=0.9 Hz, 1H), 8.08 (s, 1H), 8.55 (d, J=4.9 Hz, 1H)

Reference Example 14

2-(2-Chloropyridin-4-ylmethylthio)pyridine-3-carboxylic acid

Reference Compound No. 14-1

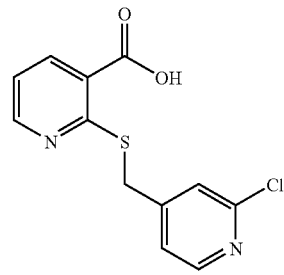

Triphenylphosphine (19 g, 71 mmol) and carbon tetrabromide (29 g, 88 mmol) were added to a solution of 2-chloropyridine-4-methanol (8.5 g, 59 mmol, Reference compound No. 7-1) in methylene chloride (250 mL), then the mixture was stirred at room temperature for 1 hour. The solvent was evaporated under reduced pressure, and then the resulting residue was purified by silica gel column chromatography to give 4-bromomethyl-2-chloropyridine. Immediately, 2-mercaptonicotinic acid (9.1 g, 59 mmol) was added to a solution of this bromo intermediate in N,N-dimethylformamide (100 mL) under ice-cooling, then triethylamine (25 mL, 180 mmol) was added dropwise thereto. The reaction mixture was stirred at room temperature for 15 hours, then diethyl ether (100 mL) and water (600 mL) were added thereto, and the organic layer and the aqueous layer were separated. The aqueous layer was adjusted to pH 6 with 2N hydrochloric acid, the precipitated solid was filtered off. The solid was washed with water and diethyl ether, and dried at 50° C. under reduced pressure to give 12 g of the title reference compound as a yellow solid. (Yield 73%)

¹H-NMR (500 MHz, DMSO-d₆)

δ 4.40 (s, 2H), 7.27 (dd, J=7.7, 4.7 Hz, 1H), 7.45 (dd, J=5.2, 1.5 Hz, 1H), 7.55 (d, J=0.6 Hz, 1H), 8.24 (dd, J=7.7, 1.9 Hz, 1H), 8.30 (dd, J=5.2, 0.6 Hz, 1H), 8.64 (dd, J=4.7, 1.9 Hz, 1H), 13.52 (s, 1H)

As described below, Reference compounds (No. 14-2~10) were obtained by a method similar to Reference Example 14.

2-(2-Methylthiopyridin-4-ylmethylthio)pyridine-3-carboxylic acid

Reference Compound No. 14-2

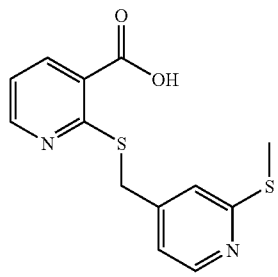

¹H-NMR (500 MHz, DMSO-d₆)
δ 2.47 (s, 3H), 4.32 (s, 2H), 7.13 (dd, J=5.1, 1.4 Hz, 1H), 7.27 (dd, J=7.7, 4.8 Hz, 1H), 7.32 (s, 1H), 8.22 (dd, J=7.7, 1.8 Hz, 1H), 8.31 (dd, J=5.1, 0.7 Hz, 1H), 8.63 (dd, J=4.8, 1.8 Hz, 1H), 13.50 (s, 1H)

2-(2-Methoxypyridin-4-ylmethylthio)pyridine-3-carboxylic acid

Reference Compound No. 14-3

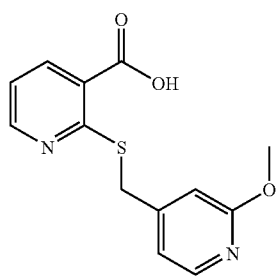

¹H-NMR (400 MHz, DMSO-d₆)
δ 3.80 (s, 3H), 4.33 (s, 2H), 6.82 (s, 1H), 7.00 (dd, J=5.1, 1.4 Hz, 1H), 7.26 (dd, J=8.1, 4.7 Hz, 1H), 8.05 (d, J=5.1 Hz, 1H), 8.21 (dd, J=8.1, 1.8 Hz, 1H), 8.63 (dd, J=4.7, 1.8 Hz, 1H), 13.48 (s, 1H)

2-(2-Ethoxypyridin-4-ylmethylthio)pyridine-3-carbooxylic acid

Reference Compound No. 14-4

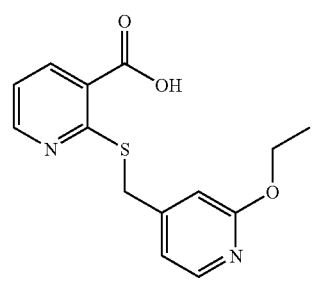

¹H-NMR (500 MHz, DMSO-d₆)
δ1.28 (t, J=7.0 Hz, 3H), 4.22-4.30 (m, 2H), 4.33 (s, 2H), 6.79 (s, 1H), 6.98 (dd, J=5.3, 1.4 Hz, 1H), 7.27 (dd, J=7.7, 4.7 Hz, 1H), 8.03 (d, J=5.3 Hz, 1H), 8.23 (dd, J=7.7, 1.8 Hz, 1H), 8.64 (dd, J=4.7, 1.8 Hz, 1H), 13.50 (br s, 1H)

2-(2-Isopropoxypyridine-4-ylmethylthio)pyridine-3-carboxylic acid

Reference Compound No. 14-5

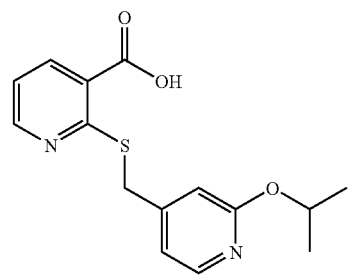

¹H-NMR (500 MHz, DMSO-d₆)

δ 1.25 (d, J=6.1 Hz, 6H), 4.30 (s, 2H), 5.21 (m, 1H), 6.72 (s, 1H), 6.95 (d, J=5.3 Hz, 1H), 7.25 (dd, J=7.6, 4.6 Hz, 1H), 8.02 (d, J=5.3 Hz, 1H), 8.21 (d, J=7.6 Hz, 1H), 8.61 (m, 1H), 13.50 (br s, 1H)

2-(2-Cyanopyridin-4-ylmethylthio)pyridine-3-carboxylic acid

Reference Compound No. 14-6

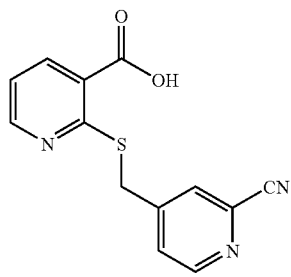

¹H-NMR (500 MHz, DMSO-d₆)

δ 4.44 (s, 2H), 7.28 (dd, J=7.9, 4.7 Hz, 1H), 7.78 (dd, J=5.2, 1.8 Hz, 1H), 8.08 (s, 1H), 8.24 (dd, J=7.9, 1.8 Hz, 1H), 8.63-8.64 (m, 2H), 13.55 (s, 1H)

2-(2-Ethoxycarbonylpyridine-4-ylmethylthio)pyridine-3-carboxylic acid

Reference Compound No. 14-7

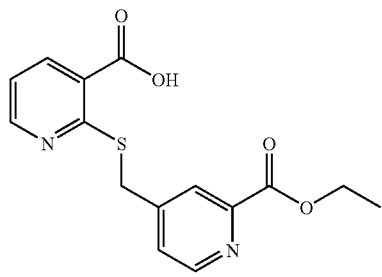

¹H-NMR (400 MHz, DMSO-d₆)

δ 1.32 (t, J=7.1 Hz, 3H), 4.33 (q, J=7.1 Hz, 2H), 4.47 (s, 2H), 7.27 (dd, J=7.6, 4.6 Hz, 1H), 7.67 (dd, J=4.9, 1.7 Hz, 1H), 8.10 (m, 1H), 8.23 (dd, J=7.6, 2.0 Hz, 1H), 8.59 (dd, J=4.9, 0.7 Hz, 1H), 8.62 (dd, J=4.6, 2.0 Hz, 1H), 13.53 (s, 1H)

3-(2-Chloropyridin-4-ylmethylthio)thiophene-2-carboxylic acid

Reference Compound No. 14-8

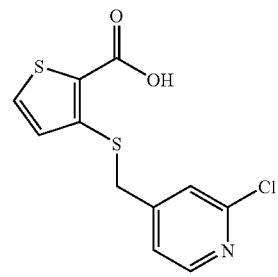

¹H-NMR (500 MHz, DMSO-d₆)

δ 4.38 (s, 2H), 7.19 (d, J=5.2 Hz, 1H), 7.49 (dd, J=5.2, 1.5 Hz, 1H), 7.59 (d, J=0.9 Hz, 1H), 7.86 (d, J=5.2 Hz, 1H), 8.36 (dd, J=5.2, 0.9 Hz, 1H), 13.11 (s, 1H)

2-(2-Methoxycarbonylpyridin-4-ylmethylthio)pyridine-3-carboxylic acid

Reference Compound No. 14-9

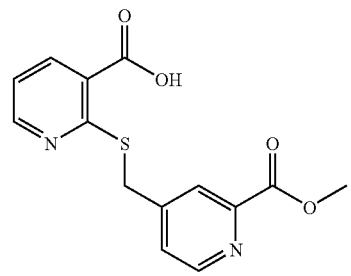

¹H-NMR (400 MHz, DMSO-d₆)

δ 3.86 (s, 3H), 4.46 (s, 2H), 7.26 (dd, J=7.7, 4.8 Hz, 1H), 7.67 (dd, J=4.8, 1.4 Hz, 1H), 8.10 (d, J=1.4 Hz, 1H), 8.22 (dd, J=7.7, 1.8 Hz, 1H), 8.58 (d, J=4.8 Hz, 1H), 8.61 (dd, J=4.8, 1.8 Hz, 1H), 13.52 (br s, 1H)

2-(2-Methylpyridin-4-ylmethylthio)pyridine-3-carboxylic acid

Reference Compound No. 14-10

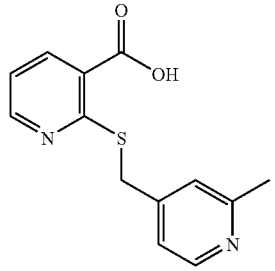

¹H-NMR (400 MHz, DMSO-d₆)

δ 2.65 (s, 3H), 4.53 (s, 2H), 7.28 (dd, J=7.7, 4.8 Hz, 1H), 7.84-7.90 (m, 2H), 8.24 (dd, J=7.7, 1.8 Hz, 1H), 8.59-8.62 (m, 2H), 13.50-13.65 (br s, 1H)

Reference Example 15

3-Iodopyrazine-2-carboxylic acid methyl ester

Reference Compound No. 15-1

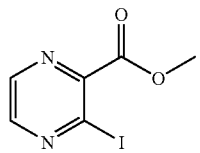

Isoamyl nitrite (5.2 mL, 39 mmol) was added to a suspension of 3-aminopyrazine-2-carboxylic acid methyl ester (1.9 g, 12 mmol) in diiodomethane (20 mL) at 85° C., then the mixture was stirred at 100° C. for 15 hours. The reaction mixture was allowed to stand and purified by silica gel column chromatography to give 1.4 g of the title reference compound as a pale yellow solid. (Yield 44%)

¹H-NMR (500 MHz, CDCl₃)

δ 4.04 (s, 3H), 8.47 (d, J=2.1 Hz, 1H), 8.56 (d, J=2.1 Hz, 1H)

As described below, Reference compounds (No. 15-2~4) were obtained by a method similar to Reference Example 15.

5-Iodo-1-methylpyrazole-4-carboxylic acid ethyl ester

Reference Compound No. 15-2

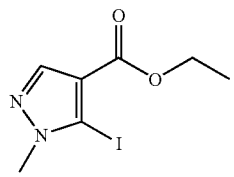

¹H-NMR (40 MHz, DMSO-d₆)

δ 1.28 (t, J=7.1 Hz, 3H), 3.92 (s, 3H), 4.23 (q, J=7.1 Hz, 2H), 7.92 (s, 1H)

2-Iodothiophene-3-carboxylic acid methyl ester

Reference Compound No. 15-3

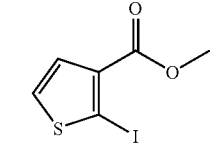

¹H-NMR (500 MHz, CDCl₃)

δ 3.89 (s, 3H), 7.32 (d, J=5.7 Hz, 1H), 7.41 (d, J=5.7 Hz, 1H)

4-Iodothiophene-3-carboxylic acid methyl ester

Reference Compound No. 15-4

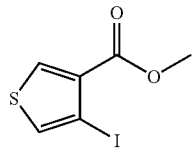

¹H-NMR (400 MHz, CDCl₃)

δ 3.89 (s, 3H), 7.51 (d, J=3.5 Hz, 1H), 8.07 (d, J=3.5 Hz, 1H)

Reference Example 16

3-(4-Pyridylmethylthio)pyrazine-2-carboxylic acid methyl ester

Reference Compound No. 16-1

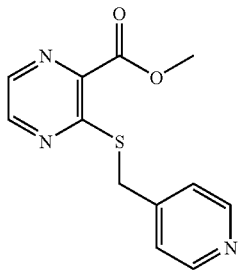

3-Iodopyrazine-2-carboxylic acid methyl ester (0.37 g, 1.4 mmol, Reference compound No. 15-1), 4-pyridinemethanethiol hydrochloride (0.24 g, 1.5 mmol) and potassium carbonate (0.41 g, 3.0 mmol) were suspended in N,N-dimethylformamide (10 mL), then the mixture was stirred at 60° C. for 1 hour. The reaction mixture was diluted with ethyl acetate (70 mL), and washed with water (100 mL) twice and brine (70 mL) twice. The ethyl acetate layer was dried over anhydrous magnesium sulfate, and then the solvent was evaporated under reduced pressure. The resulting residue was filtered off with diisopropyl ether to give 0.25 g of the title reference compound as a pale cinnabar solid. (Yield 69%)

$^1$H-NMR (500 MHz, CDCl$_3$)

δ 4.03 (s, 3H), 4.37 (s, 2H), 7.35 (dd, J=4.3, 1.5 Hz, 2H), 8.39 (d, J=2.1 Hz, 1H), 8.52 (dd, J=4.3, 1.5 Hz, 2H), 8.53 (d, J=2.1 Hz, 1H)

As described below, Reference compounds (No. 16-2~5) were obtained by a method similar to Reference Example 16.

1-Methyl-5-(4-pyridylmethylthio)pyrazole-4-carboxylic acid ethyl ester

Reference Compound No. 16-2

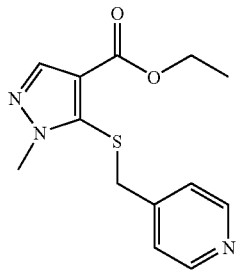

$^1$H-NMR (400 MHz, CDCl$_3$)

δ 1.40 (t, J=7.1 Hz, 3H), 3.56 (s, 3H), 4.11 (s, 2H), 4.36 (q, J=7.1 Hz, 2H), 6.99 (dd, J=4.6, 1.5 Hz, 2H), 7.95 (s, 1H), 8.48 (dd, J=4.6, 1.5 Hz, 2H)

2-(4-Pyridylmethylthio)thiophene-3-carboxylic acid methyl ester

Reference Compound No. 16-3

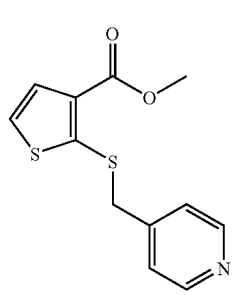

$^1$H-NMR (400 MHz, CDCl$_3$)

δ 3.87 (s, 3H), 4.20 (s, 2H), 7.09 (d, J=5.5 Hz, 1H), 7.30 (dd, J=4.4, 1.5 Hz, 2H), 7.41 (d, J=5.5 Hz, 1H), 8.55 (dd, J=4.4, 1.5 Hz, 2H)

4-(4-Pyridylmethylthio)thiophene-3-carboxylic acid methyl ester

Reference Compound No. 16-4

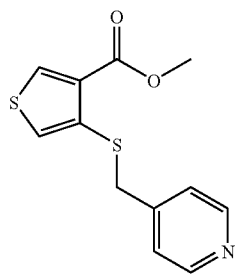

$^1$H-NMR (400 MHz, CDCl$_3$)

δ 3.88 (s, 3H), 4.10 (s, 2H), 6.77 (d, J=3.3 Hz, 1H), 7.33-7.35 (m, 2H), 8.16 (d, J=3.3 Hz, 1H), 8.67 (br s, 2H)

3-(4-Pyridylmethylthio)thiophene-2-carboxylic acid methyl ester

Reference Compound No. 16-5

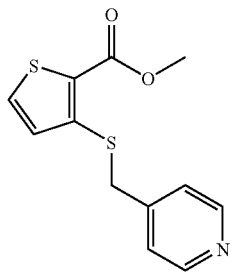

$^1$H-NMR (500 MHz, DMSO-$d_6$)

δ 3.85 (s, 3H), 4.75 (s, 2H), 7.17 (d, J=5.3 Hz, 1H), 7.45 (dd, J=4.3, 1.5 Hz, 2H), 7.88 (d, J=5.3 Hz, 1H), 8.50 (dd, J=4.3, 1.5 Hz, 2H)

Reference Example 17

3-(4-Pyridylmethylthio)pyrazine-2-carboxylic acid

Reference Compound No. 17-1

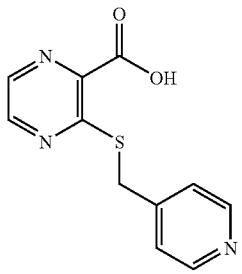

3-(4-Pyridylmethylthio)pyrazine-2-carboxylic acid methyl ester (0.21 g, 0.80 mmol, Reference compound No. 16-1) was dissolved in methanol (4.0 mL), a 1 N aqueous sodium hydroxide solution (4.0 mL) was added thereto, and then the mixture was stirred at room temperature for 7 hours. The solvent was evaporated under reduced pressure, water was added to the resulting residue, and then the mixture was adjusted to approximately pH 5 with 1N hydrochloric acid under ice-cooling. The precipitated solid was filtered off to give 0.17 g of the title reference compound as a red solid. (Yield 85%)

$^1$H-NMR (400 MHz, DMSO-$d_6$)

δ 4.38 (s, 2H), 7.43 (dd, J=4.6, 1.5 Hz, 2H), 8.47 (d, J=2.4 Hz, 1H), 8.48 (dd, J=4.6, 1.5 Hz, 2H), 8.70 (d, J=2.4 Hz, 1H), 13.74 (br s, 1H)

As described below, Reference compounds (No. 17-2~4) were obtained by a method similar to Reference Example 17.

1-Methyl-5-(4-pyridylmethylthio)pyrazole-4-carboxylic acid

Reference Compound No. 17-2

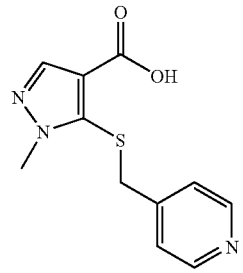

$^1$H-NMR (500 MHz, DMSO-$d_6$)

δ 3.48 (s, 3H), 4.27 (s, 2H), 7.07 (d, J=4.6, 1.5 Hz, 2H), 7.73 (s, 1H), 8.40 (dd, J=4.6, 1.5 Hz, 2H)

2-(4-Pyridylmethylthio)thiophene-3-carboxylic acid

Reference Compound No. 17-3

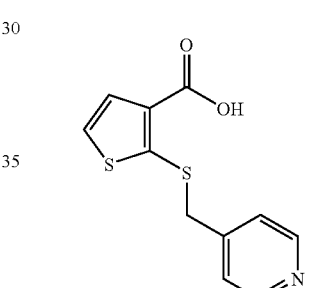

$^1$H-NMR (400 MHz, DMSO-$d_6$)

δ 4.32 (s, 2H), 7.31 (d, J=5.4 Hz, 1H), 7.41 (d, J=5.4 Hz, 1H), 7.43 (dd, J=4.4, 1.7 Hz, 2H), 8.52 (dd, J=4.4, 1.7 Hz, 2H), 12.83 (s, 1H)

4-(4-Pyridylmethylthio)thiophene-3-carboxylic acid

Reference Compound No. 17-4

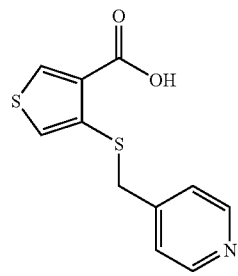

$^1$H-NMR (400 MHz, DMSO-$d_6$)

δ

4.20 (s, 2H), 7.20 (m, 1H), 7.44-7.45 (m, 2H), 8.36 (m, 1H), 8.50-8.51 (m, 2H), 12.86 (s, 1H)

Reference Example 18

N-(3,5-Dimethylphenyl)-2-thiopyridone-3-carboxamide

Reference Compound No. 18-1

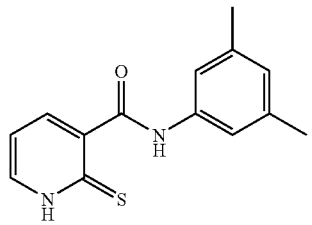

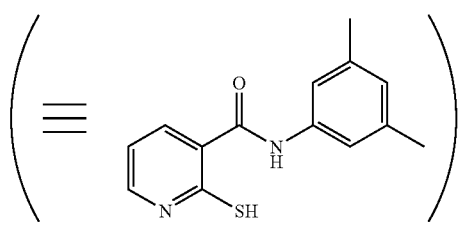

Pyridine (30 mL, 0.37 mol) and thionyl chloride (20 mL, 0.23 mol) were added to a solution of 2-mercaptonicotinic acid (10 g, 64 mmol) in methylene chloride (80 mL) under ice-cooling, then the mixture was stirred for 1 hour. The reaction mixture was concentrated under reduced pressure, then the resulting residue was suspended in chloroform (80 mL) and pyridine (20 mL, 0.26 mmol). 3,5-Xylidine (8.0 mL, 64 mmol) was added to the suspension, and the mixture was stirred at room temperature for 4 hours. The reaction mixture was concentrated under reduced pressure, ethyl acetate and ethanol were added to the precipitated solid, then the solid was filtered off. The solid was dried under reduced pressure to give 1.9 g of the title reference compound as a pink solid. (Yield 11%).

$^1$H-NMR (500 MHz, DMSO-d$_6$)

δ 2.27 (s, 6H), 6.77 (d, J=0.6 Hz, 1H), 7.10 (dd, J=7.6, 6.0 Hz, 1H), 7.34 (s, 2H), 8.03 (dd, J=6.0, 1.8 Hz, 1H), 8.55 (dd, J=7.6, 1.8 Hz, 1H), 12.90 (s, 1H), 14.18 (s, 1H)

Example 1

N-(4-Chlorophenyl)-2-(4-pyridylmethylthio)pyridine-3-carboxamide

Compound No. 1-1

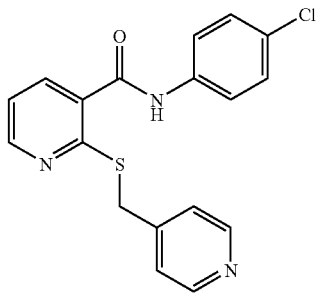

N,N-Diisopropylethylamine (1.6 mL, 8.9 mmol) and o-(7-azabenzotriazol-1-yl)-N,N,N',N'-tetramethyluronium hexafluorophosphate (1.6 g, 4.3 mmol) were added to a solution of 2-(4-pyridylmethylthio)pyridine-3-carboxylic acid (1.0 g, 4.1 mmol, Reference compound No. 1-1) and 4-chloroaniline (0.54 g, 4.3 mmol) in N,N-dimethylformamide (20 mL), then the mixture was stirred for 3 hours. A saturated aqueous sodium hydrogencarbonate solution (150 mL) was added to the reaction mixture, then the whole was extracted with ethyl acetate (150 mL). The ethyl acetate layer was washed with a saturated aqueous sodium hydrogencarbonate solution (150 mL) twice and saturated brine (150 mL) twice, and was dried over anhydrous magnesium sulfate. The solvent was evaporated under reduced pressure. The precipitated solid was filtered off, was washed with diethyl ether:ethyl acetate (10:1), and was dried under reduced pressure to give 1.3 g of the target compound as a white solid. (Yield 91%)

$^1$H-NMR (400 MHz, DMSO-d$_6$)

δ 4.42 (s, 2H), 7.30 (dd, J=7.6, 4.7 Hz, 1H), 7.37-7.43 (m, 4H), 7.72 (d, J=7.6 Hz, 2H), 7.98 (dd, J=7.6, 1.7 Hz, 1H), 8.45 (dd, J=4.5, 1.8 Hz, 2H), 8.59 (dd, J=4.7, 1.7 Hz, 1H), 10.60 (s, 1H)

$^{13}$C-NMR (100 MHz, DMSO-d$_6$)

δc 32.0, 119.3, 121.3, 124.0, 127.5, 128.5, 129.8, 135.8, 137.6, 147.7, 149.3, 150.2, 155.9, 164.6

Below compounds (No. 1-2~308) were obtained by a method similar to Example 1.

N-(2,2-Dimethylpropyl)-2-(4-pyridylmethylthio)pyridine-3-carboxamide

Compound No. 1-2

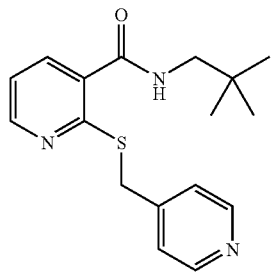

¹H-NMR (400 MHz, CDCl₃)

δ 1.00 (s, 9H), 3.27 (d, J=6.4 Hz, 2H), 4.44 (s, 2H), 6.23 (br s, 1H), 7.10 (dd, J=7.6, 4.4 Hz, 1H), 7.34 (dd, J=4.4, 1.6 Hz, 2H), 7.81 (dd, J=7.6, 1.8 Hz, 1H), 8.48-8.51 (m, 3H)

N-Cyclohexyl-2-(4-pyridylmethylthio)pyridine-3-carboxamide

Compound No. 1-3

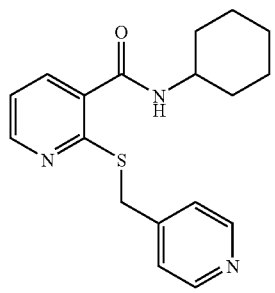

¹H-NMR (400 MHz, DMSO-d₆)

δ 1.00-1.35 (m, 5H), 1.50-1.85 (m, 5H), 3.67 (m, 1H), 4.37 (s, 2H), 7.20 (dd, J=7.6, 4.9 Hz, 1H), 7.39 (dd, J=4.4, 1.7 Hz, 2H), 7.76 (dd, J=7.6, 1.7 Hz, 1H), 8.35 (d, J=7.8 Hz, 1H), 8.45 (dd, J=4.4, 1.7 Hz, 2H), 8.50 (dd, J=4.9, 1.7 Hz, 1H)

3-Morpholinocarbonyl-2-(4-pyridylmethylthio)pyridine

Compound No. 1-4

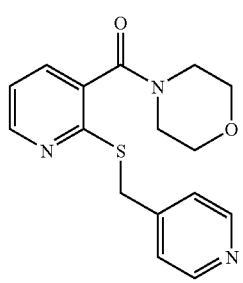

¹H-NMR (400 MHz, DMSO-d₆)

δ 3.06 (br s, 2H), 3.47 (br s, 2H), 3.62 (br s, 4H), 4.47 (s, 2H), 7.25 (dd, J=7.6, 4.9 Hz, 1H), 7.37 (dd, J=4.4, 1.7 Hz, 2H), 7.65 (dd, J=7.6, 1.9 Hz, 1H), 8.46 (dd, J=4.4, 1.7 Hz, 2H), 8.53 (dd, J=4.9, 1.9 Hz, 1H)

N'-(4-Chlorophenyl)-2-(4-pyridylmethylthio)pyridine-3-carbohydrazide

Compound No. 1-5

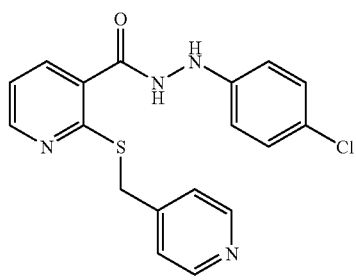

¹H-NMR (400 MHz, DMSO-d₆)

δ 4.40 (s, 2H), 6.82 (d, J=8.9 Hz, 2H), 7.19 (d, J=8.9 Hz, 2H), 7.28 (dd, J=7.6, 4.9 Hz, 1H), 7.40 (dd, J=4.6, 1.5 Hz,

2H), 7.98 (dd, J=7.6, 1.8 Hz, 1H), 8.19 (d, J=2.5 Hz, 1H), 8.47 (dd, J=4.6, 1.5 Hz, 2H), 8.59 (dd, J=4.5, 1.8 Hz, 1H), 10.37 (s, 1H)

N'-tert-Butyl-2-(4-pyridylmethylthio)pyridine-3-carbohydrazide

Compound No. 1-6

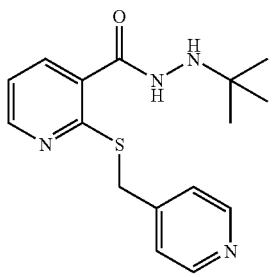

$^1$H-NMR (500 MHz, DMSO-d$_6$)

δ 1.07 (s, 9H), 4.40 (s, 2H), 4.92 (br s, 1H), 7.22 (dd, J=7.5, 4.8 Hz, 1H), 7.39 (dd, J=4.4, 1.6 Hz, 2H), 7.78 (dd, J=7.5, 1.8 Hz, 1H), 8.45 (dd, J=4.4, 1.6 Hz, 2H), 8.53 (dd, J=4.8, 1.8 Hz, 1H), 9.85 (s, 1H)

N-(4-Chlorobenzyl)-2-(4-pyridylmethylthio)pyridine-3-carboxamide

Compound No. 1-7

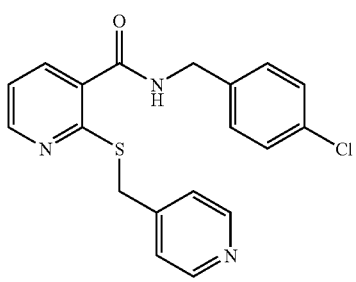

$^1$H-NMR (400 MHz, DMSO-d$_6$)

δ 4.37 (s, 2H), 4.42 (d, J=5.8 Hz, 2H), 7.23 (dd, J=7.6, 4.4 Hz, 1H), 7.36 (dd, J=4.4, 1.9 Hz, 2H), 7.37-7.42 (m, 4H), 7.88 (dd, J=7.6, 1.7 Hz, 1H), 8.45 (dd, J=4.5, 1.7 Hz, 2H), 8.55 (dd, J=4.4, 1.7 Hz, 1H), 9.10 (t, J=5.8 Hz, 1H)

N-[2-(4-Chlorophenyl)ethyl]-2-(4-pyridylmethylthio)pyridine-3-carboxamide

Compound No. 1-8

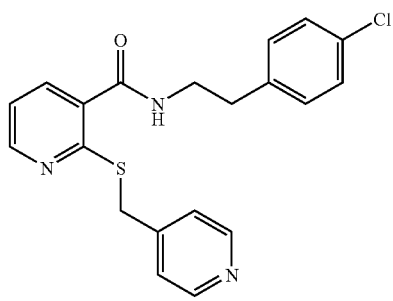

$^1$H-NMR (500 MHz, DMSO-d$_6$)

δ 2.82 (t, J=7.0 Hz, 2H), 3.43 (td, J=7.0, 5.8 Hz, 2H), 4.36 (s, 2H), 7.20 (dd, J=7.6, 4.6 Hz, 1H), 7.27 (d, J=8.6 Hz, 2H), 7.32 (d, J=8.6 Hz, 2H), 7.38 (dd, J=4.3, 1.5 Hz, 2H), 7.71 (dd, J=7.6, 1.5 Hz, 1H), 8.45 (dd, J=4.3, 1.5 Hz, 2H), 8.52 (dd, J=4.6, 1.5 Hz, 1H), 8.59 (t, J=5.8 Hz, 1H)

N-[2-(4-Methoxyphenyl)ethyl]-2-(4-pyridylmethylthio)pyridine-3-carboxamide

Compound No. 1-9

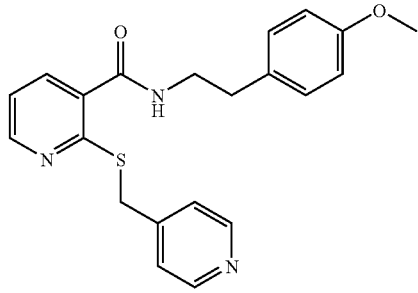

1H-NMR (400 MHz, DMSO-d$_6$)

δ 2.75 (t, J=7.2 Hz, 2H), 3.39 (td, J=7.2, 5.5 Hz, 2H), 3.71 (s, 3H), 4.37 (s, 2H), 6.84 (dd, J=6.5, 2.2 Hz, 2H), 7.15 (d, J=8.6 Hz, 2H), 7.21 (dd, J=7.5, 4.8 Hz, 1H), 7.39 (dd, J=4.4, 1.6 Hz, 2H), 7.74 (dd, J=7.5, 1.8 Hz, 1H), 8.45 (dd, J=4.4, 1.6 Hz, 2H), 8.52 (dd, J=4.8, 1.8 Hz, 1H), 8.59 (t, J=5.5 Hz, 1H)

O-Benzyl-2-(4-pyridylmethylthio)pyridine-3-carbohydroxamate

Compound No. 1-10

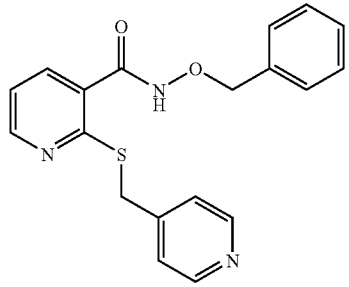

¹H-NMR (500 MHz, DMSO-d₆)

δ 4.40 (s, 2H), 4.93 (s, 2H), 7.21 (dd, J=7.6, 4.9 Hz, 1H), 7.30-7.50 (m, 7H), 7.70 (d, J=6.4 Hz, 1H), 8.46 (d, J=4.6 Hz, 2H), 8.55 (dd, J=4.9, 1.5 Hz, 1H), 11.73 (s, 1H)

N-(1H-Benzimidazol-2-yl)methyl-2-(4-pyridylmethylthio)pyridine-3-carboxamide

Compound No. 1-11

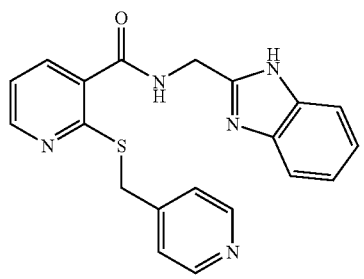

¹H-NMR (500 MHz, DMSO-d₆)

δ 4.36 (s, 2H), 4.66 (d, J=5.8 Hz, 2H), 7.12-7.16 (m, 2H), 7.27 (dd, J=7.6, 4.9 Hz, 1H), 7.39 (dd, J=4.3, 1.5 Hz, 2H), 7.49-7.54 (m, 2H), 8.06 (dd, J=7.6, 1.8 Hz, 1H), 8.45 (dd, J=4.3, 1.5 Hz, 2H), 8.57 (dd, J=4.9, 1.8 Hz, 1H), 9.24 (t, J=5.8 Hz, 1H), 12.40 (br s, 1H)

N-[2-(Indol-3-yl)ethyl]-2-(4-pyridylmethylthio)pyridine-3-carboxamide

Compound No. 1-12

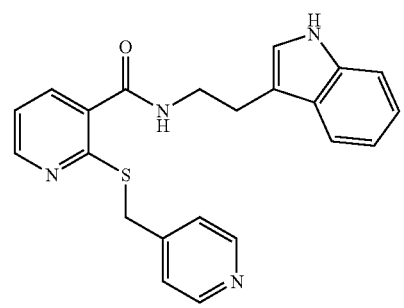

¹H-NMR (400 MHz, DMSO-d₆)

δ 2.89-2.98 (m, 2H), 3.46-3.55 (m, 2H), 4.37 (s, 2H), 6.97 (m, 1H), 7.07 (m, 1H), 7.18-7.24 (m, 2H), 7.34 (d, J=8.1 Hz, 1H), 7.39 (dd, J=4.4, 1.7 Hz, 2H), 7.56 (d, J=7.8 Hz, 1H), 7.76 (m, 1H), 8.45 (dd, J=4.4, 1.7 Hz, 2H), 8.52 (dd, J=4.6, 1.7 Hz, 1H), 8.66 (t, J=5.6 Hz, 1H), 10.83 (br s, 1H)

N-(2-Phenoxyethyl)-2-(4-pyridylmethylthio)pyridine-3-carboxamide

Compound No. 1-13

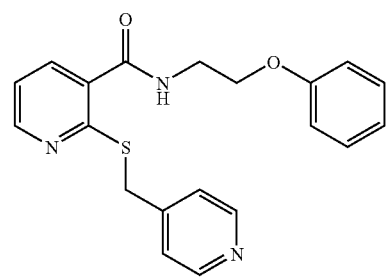

¹H-NMR (500 MHz, DMSO-d₆)

δ 3.59 (td, J=5.8, 5.5 Hz, 2H), 4.09 (t, J=5.8 Hz, 2H), 4.36 (s, 2H), 6.90-7.00 (m, 3H), 7.22 (dd, J=7.6, 4.6 Hz, 1H), 7.25-7.32 (m, 2H), 7.37 (dd, J=4.6, 1.5 Hz, 2H), 7.82 (dd, J=7.6, 1.8 Hz, 1H), 8.44 (dd, J=4.6, 1.5 Hz, 2H), 8.53 (m, 1H), 8.78 (dd, J=4.6, 1.8 Hz, 1H)

N-(4-Chlorophenyl)-N-methyl-2-(4-pyridylmethylthio)pyridine-3-carboxamide

Compound No. 1-14

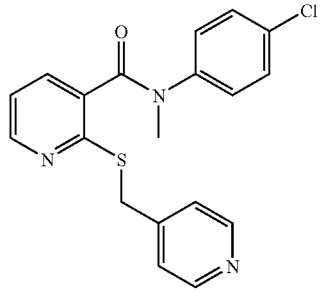

$^1$H-NMR (500 MHz, DMSO-d$_6$).

δ3.30 (br s, 3H), 4.42 (s, 2H), 7.03 (br s, 1H), 7.08-7.25 (m, 4H), 7.32 (d, J=4.5 Hz, 2H), 7.50 (br s, 1H), 8.36 (br s, 1H), 8.47 (d, J=4.5 Hz, 2H)

N-(4-Chlorophenyl)-N-ethyl-2-(4-pyridylmethylthio)pyridine-3-carboxamide

Compound No. 1-15

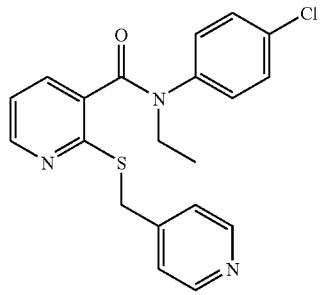

$^1$H-NMR (400 MHz, CDCl$_3$)

δ 1.15-1.28 (m, 3H), 3.80-4.00 (m, 2H), 4.41 (s, 2H), 6.82 (m, 1H), 6.88-7.20 (m, 5H), 7.28 (d, J=4.5 Hz, 2H), 8.29 (br s, 1H), 8.51 (d, J=4.5 Hz, 2H)

N-(5-Methylpyridin-2-yl)-2-(4-pyridylmethylthio)pyridine-3-carboxamide

Compound No. 1-16

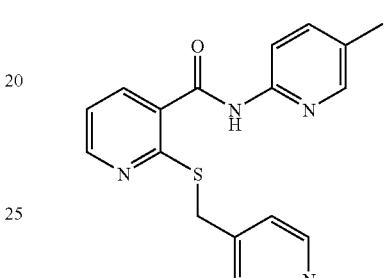

$^1$H-NMR (400 MHz, DMSO-d$_6$)

δ 2.28 (s, 3H), 4.41 (s, 2H), 7.25 (dd, J=7.5, 4.9 Hz, 1H), 7.40 (dd, J=4.4, 1.7 Hz, 2H), 7.66 (dd, J=8.8, 2.2 Hz, 1H), 7.98 (dd, J=7.5, 1.7 Hz, 1H), 8.03 (d, J=8.8 Hz, 1H), 8.20 (d, J=2.2 Hz, 1H), 8.45 (dd, J=4.4, 1.7 Hz, 2H), 8.57 (dd, J=4.9, 1.7 Hz, 1H), 10.94 (s, 1H)

N-(3-Pyridyl)-2-(4-pyridylmethylthio)pyridine-3-carboxamide

Compound No. 1-17

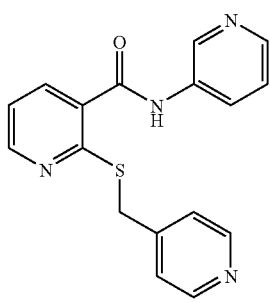

$^1$H-NMR (500 MHz, DMSO-d$_6$)

δ 4.43 (s, 2H), 7.32 (dd, J=7.6, 4.9 Hz, 1H), 7.40 (dd, J=4.9, 1.5 Hz, 2H), 8.03 (dd, J=7.6, 1.8 Hz, 1H), 8.13 (d, J=8.3 Hz,

1H), 8.33 (dd, J=4.9, 1.5 Hz, 1H), 8.46 (dd, J=4.9, 1.5 Hz, 2H), 8.60 (m, 1H), 8.64 (d, J=2.4 Hz, 1H), 8.84 (d, J=4.9, 1.5 Hz, 1H), 10.69 (s, 1H)

N-(2-Chloropyridin-5-yl)-2-(4-pyridylmethylthio)pyridine-3-carboxamide

Compound No. 1-18

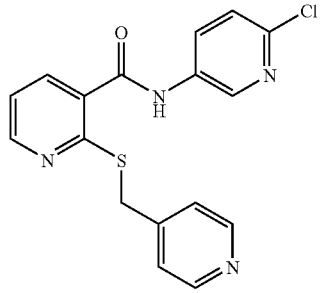

¹H-NMR (500 MHz, DMSO-d₆)

δ 4.42 (s, 2H), 7.32 (dd, J=7.6, 4.9 Hz, 1H), 7.40 (dd, J=4.3, 1.5 Hz, 2H), 7.54 (d, J=8.9 Hz, 1H), 8.04 (dd, J=7.6, 1.8 Hz, 1H), 8.17 (dd, J=8.9, 2.7 Hz, 1H), 8.45 (dd, J=4.3, 1.5 Hz, 2H), 8.61 (dd, J=4.9, 1.8 Hz, 1H), 8.70 (d, J=2.7 Hz, 1H), 10.83 (s, 1H)

N-(4-Pyridyl)-2-(4-pyridylmethylthio)pyridine-3-carboxamide

Compound No. 1-19

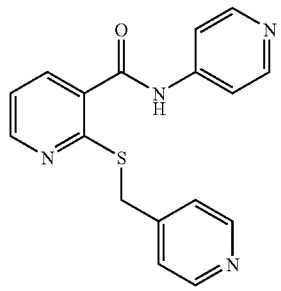

¹H-NMR (400 MHz, DMSO-d₆)

δ 4.43 (s, 2H), 7.32 (dd, J=7.6, 4.8 Hz, 1H), 7.40 (dd, J=4.5, 1.7 Hz, 2H), 7.67 (dd, J=4.6, 1.6 Hz, 2H), 8.02 (dd, J=7.6, 1.8 Hz, 1H), 8.45 (dd, J=4.5, 1.7 Hz, 2H), 8.48 (dd, J=4.6, 1.6 Hz, 2H), 8.61 (dd, J=4.8, 1.8 Hz, 1H), 10.84 (s, 1H)

2-(4-Pyridylmethylthio)-N-(3-quinolyl)pyridine-3-carboxamide

Compound No. 1-20

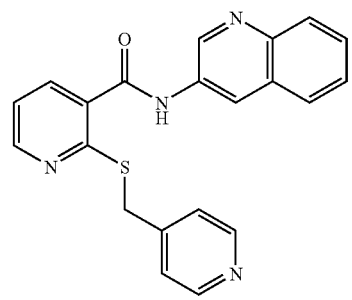

¹H-NMR (500 MHz, DMSO-d₆)

δ 4.44 (s, 2H), 7.34 (dd, J=7.6, 4.8 Hz, 1H), 7.42 (dd, J=4.5, 1.6 Hz, 2H), 7.60 (m, 1H), 7.68 (m, 1H), 7.98 (d, J=8.6 Hz, 2H), 8.11 (dd, J=7.6, 1.5 Hz, 1H), 8.46 (dd, J=4.5, 1.6 Hz, 2H), 8.64 (dd, J=4.8, 1.8 Hz, 1H), 8.83 (d, J=2.1 Hz, 1H), 9.02 (d, J=2.5 Hz, 1H), 10.96 (s, 1H)

2-(4-Pyridylmethylthio)-N-(6-quinolyl)pyridine-3-carboxamide

Compound No. 1-21

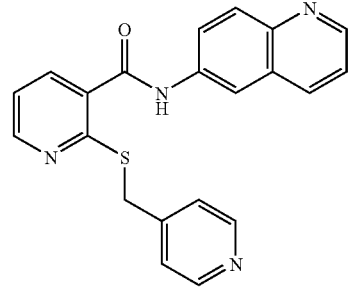

¹H-NMR (400 MHz, DMSO-d₆)

δ 4.43 (s, 2H), 7.33 (dd, J=7.6, 4.7 Hz, 1H), 7.40-7.45 (m, 2H), 7.51 (dd, J=8.3, 4.4 Hz, 1H), 7.89 (dd, J=9.0, 2.2 Hz, 1H), 8.00-8.10 (m, 2H), 8.35 (d, J=8.0 Hz, 1H), 8.45-8.50 (m,

2H), 8.53 (m, 1H), 8.62 (dd, J=4.9, 1.7 Hz, 1H), 8.82 (dd, J=4.2, 1.7 Hz, 1H), 10.82 (s, 1H)

N-(3-Isoquinolyl)-2-(4-pyridylmethylthio)pyridine-3-carboxamide

Compound No. 1-22

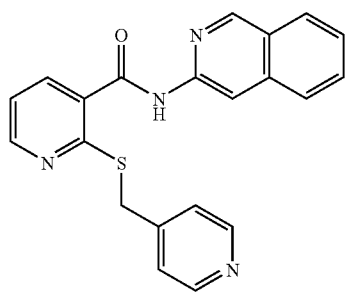

¹H-NMR (400 MHz, DMSO-d₆)

δ 4.43 (s, 2H), 7.28 (dd, J=7.6, 4.9 Hz, 1H), 7.40 (d, J=6.1 Hz, 2H), 7.58 (t, J=7.3 Hz, 1H), 7.75 (dt, J=7.3, 0.9 Hz, 1H), 7.97 (d, J=7.9 Hz, 1H), 8.05 (dd, J=7.6, 1.8 Hz, 1H), 8.09 (d, J=8.2 Hz, 1H), 8.45 (dd, J=4.6, 1.5 Hz, 2H), 8.59 (dd, J=4.6, 1.8 Hz, 2H), 9.19 (s, 1H), 11.20 (s, 1H)

N-(Indazol-5-yl)-2-(4-pyridylmethylthio)pyridine-3-carboxamide

Compound No. 1-23

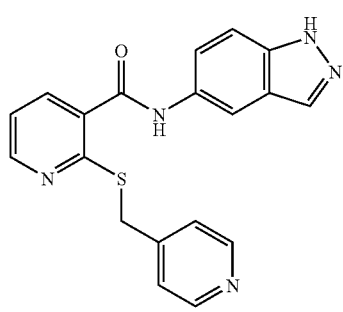

¹H-NMR (500 MHz, DMSO-d₆)

δ 4.42 (s, 2H), 7.30 (dd, J=7.6, 4.9 Hz, 1H), 7.41 (dd, J=4.6, 1.5 Hz, 2H), 7.50-7.60 (m, 2H), 7.99 (dd, J=7.6, 1.5 Hz, 1H), 8.07 (s, 1H), 8.23 (s, 1H), 8.46 (dd, J=4.6, 1.5 Hz, 2H), 8.59 (dd, J=4.9, 1.5 Hz, 1H), 10.48 (br, 1H), 13.04 (br s, 1H)

N-(1-Naphthyl)-2-(4-pyridylmethylthio)pyridine-3-carboxamide

Compound No. 1-24

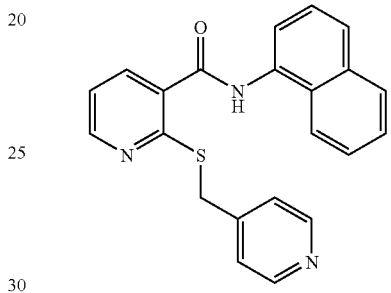

¹H-NMR (500 MHz, DMSO-d₆)

δ 4.45 (s, 2H), 7.36 (m, 1H), 7.43 (d, J=5.8 Hz, 2H), 7.50-7.60 (m, 3H), 7.70 (m, 1H), 7.85 (d, J=8.2 Hz, 1H), 7.98 (m, 1H), 8.06-8.20 (m, 2H), 8.45-8.50 (m, 2H), 8.62 (d, J=3.7 Hz, 1H), 10.57 (s, 1H)

N-(5-Methylisoxazol-3-yl)-2-(4-pyridylmethylthio)pyridine-3-carboxamide

Compound No. 1-25

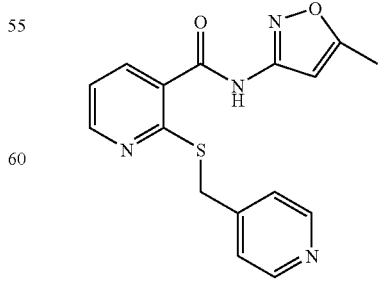

¹H-NMR (500 MHz, CDCl₃).

δ 2.43 (s, 3H), 4.43 (s, 2H), 6.85 (s, 1H), 7.16 (dd, J=7.6, 4.9 Hz, 1H), 7.34 (dd, J=4.6, 1.5 Hz, 2H), 7.95 (dd, J=7.6, 1.7 Hz, 1H), 8.46 (dd, J=4.6, 1.5 Hz, 2H), 8.57 (dd, J=4.9, 1.7 Hz, 1H), 9.25 (br s, 1H)

2-(4-Pyridylmethylthio)-N-(2-thiazolyl)pyridine-3-carboxamide

Compound No. 1-26

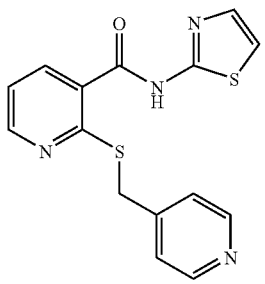

$^1$H-NMR (500 MHz, DMSO-d$_6$)

δ 4.42 (s, 2H), 7.26-8.02 (m, 2H), 7.43 (d, J=5.8 Hz, 2H), 7.56 (d, J=3.4 Hz, 1H), 8.15 (d, J=7.3 Hz, 1H), 8.47 (d, J=5.8 Hz, 2H), 8.61 (dd, J=4.7, 1.4 Hz, 1H), 12.78 (s, 1H)

N-(6-Chlorobenzothiazol-2-yl)-2-(4-pyridylmethylthio)pyridine-3-carboxamide

Compound No. 1-27

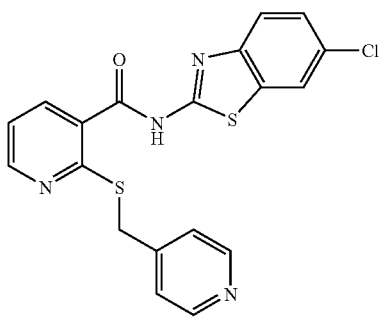

$^1$H-NMR (500 MHz, DMSO-d$_6$)

δ 4.44 (s, 2H), 7.33 (dd, J=7.6, 4.8 Hz, 1H), 7.42 (dd, J=4.5, 1.5 Hz, 2H), 7.48 (dd, J=8.6, 2.1 Hz, 1H), 7.77 (d, J=8.6 Hz, 1H), 8.17 (d, J=2.1 Hz, 1H), 8.23 (dd, J=7.6, 1.5 Hz, 1H), 8.46 (dd, J=4.5, 1.5 Hz, 2H), 8.64 (dd, J=4.8, 1.5 Hz, 1H)

N-(4-Chlorophenyl)-2-(2,6-dichloropyridin-4-ylmethylthio)pyridine-3-carboxamide

Compound No. 1-28

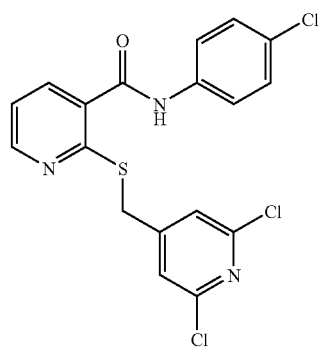

$^1$H-NMR (400 MHz, DMSO-d$_6$)

δ 4.43 (s, 2H), 7.33 (dd, J=7.6, 4.9 Hz, 1H), 7.43 (d, J=9.0 Hz, 2H), 7.60 (s, 2H), 7.73 (d, J=9.0 Hz, 2H), 8.02 (dd, J=7.6, 1.7 Hz, 1H), 8.61 (dd, J=4.9, 1.7 Hz, 1H), 10.60 (s, 1H)

N-(3-Chlorophenyl)-2-(2,6-dichloropyridin-4-ylmethylthio)pyridine-3-carboxamide

Compound No. 1-29

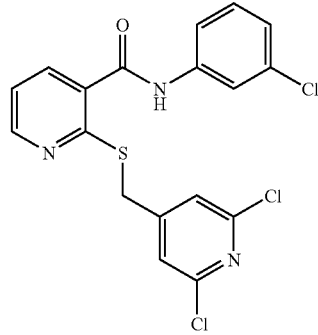

$^1$H-NMR (400 MHz, DMSO-d$_6$)

δ 4.43 (s, 2H), 7.19 (ddd, J=8.0, 2.0, 0.9 Hz, 1H), 7.34 (dd, J=7.6, 4.9 Hz, 1H), 7.40 (t, J=8.1 Hz, 1H), 7.58-7.63 (m, 3H), 7.89 (s, 1H), 8.03 (dd, J=7.6, 1.7 Hz, 1H), 8.61 (dd, J=4.9 Hz, 1.7 Hz, 1H), 10.70 (s, 1H)

N-Phenyl-2-(4-pyridylmethylthio)pyridine-3-carboxamide

Compound No. 1-30

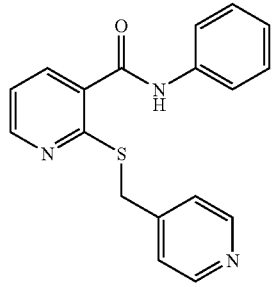

$^1$H-NMR (500 MHz, CDCl$_3$)

δ 4.45 (s, 2H), 7.13 (dd, J=7.6, 4.6 Hz, 1H), 7.18 (m, 1H), 7.33 (dd, J=4.6, 1.2 Hz, 2H), 7.37 (t, J=7.6 Hz, 2H), 7.61 (d, J=7.6 Hz, 2H), 7.90 (d, J=7.6 Hz, 1H), 8.02 (br s, 1H), 8.47 (dd, J=4.6, 1.2 Hz, 2H), 8.53 (dd, J=4.6, 1.5 Hz, 1H)

N-(2-Chlorophenyl)-2-(4-pyridylmethylthio)pyridine-3-carboxamide

Compound No. 1-31

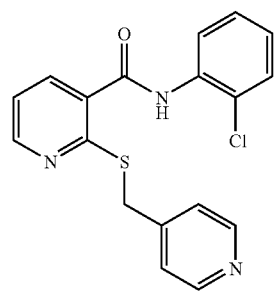

$^1$H-NMR (400 MHz, CDCl$_3$)

δ 4.46 (s, 2H), 7.11 (td, J=7.7, 1.5 Hz, 1H), 7.17 (dd, J=7.6, 4.8 Hz, 1H), 7.32 (dd, J=7.6, 1.6 Hz, 1H), 7.35 (dd, J=5.9, 1.5 Hz, 2H), 7.41 (dd, J=7.7, 1.5 Hz, 1H), 7.93 (dd, J=7.7, 1.5 Hz, 1H), 8.40 (s, 1H), 8.48-8.60 (m, 4H)

N-(2-Hydroxymethylphenyl)-2-(4-pyridylmethylthio)pyridine-3-carboxamide

Compound No. 1-32

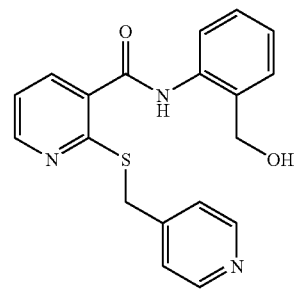

$^1$H-NMR (500 MHz, CDCl$_3$)

δ 4.42 (s, 2H), 4.78 (s, 2H), 6.73 (m, 1H), 7.05-7.16 (m, 2H), 7.19 (m, 1H), 7.36 (dd, J=4.6, 1.5 Hz, 2H), 7.37 (m, 1H), 7.88 (dd, J=7.6, 1.7 Hz, 1H), 8.27 (m 1H), 8.43 (dd, J=4.6, 1.5 Hz, 2H), 8.52 (dd, J=4.9, 1.7 Hz, 1H), 9.49 (s, 1H)

N-(2-Methoxyphenyl)-2-(4-pyridylmethylthio)pyridine-3-carboxamide

Compound No. 1-33

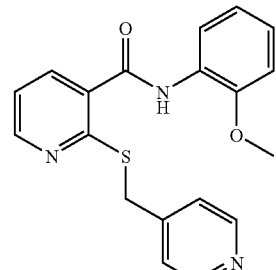

$^1$H-NMR (500 MHz, CDCl$_3$)

δ 3.87 (s, 3H), 4.45 (s, 2H), 6.92 (dd, J=7.9, 1.2 Hz, 1H), 7.02 (td, J=7.6, 0.9 Hz, 1H), 7.10 (dd, J=7.9, 1.2 Hz, 1H), 7.14

(dd, J=7.6, 4.9 Hz, 1H), 7.40 (d, J=5.8 Hz, 2H), 7.42 (d, J=6.1 Hz, 1H), 7.88 (dd, J=7.6, 1.5 Hz, 1H), 8.41-8.55 (m, 4H)

N-(2-Ethoxyphenyl)-2-(4-pyridylmethylthio)pyridine-3-carboxamide

Compound No. 1-34

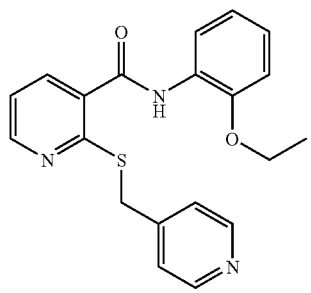

¹H-NMR (500 MHz, CDCl₃)

δ 1.39 (t, J=7.0 Hz, 3H), 4.11 (q, J=7.0 Hz, 2H), 4.46 (s, 2H), 6.90 (dd, J=7.9, 1.2 Hz, 1H), 7.00 (td, J=7.6, 1.2 Hz, 1H), 7.07 (dd, J=7.9, 1.5 Hz, 1H), 7.15 (dd, J=7.6, 4.9 Hz, 1H), 7.38 (dd, J=4.6, 1.8 Hz, 2H), 7.91 (dd, J=7.6, 1.5 Hz, 1H), 8.51 (m, 2H), 8.53 (dd, J=4.6, 1.8 Hz, 2H), 8.56 (m, 1H)

N-(3-Isopropylphenyl)-2-(4-pyridylmethylthio)pyridine-3-carboxamide

Compound No. 1-35

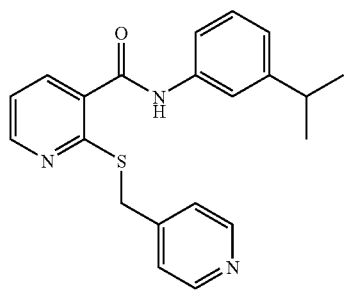

¹H-NMR (400 MHz, DMSO-d₆)

δ 1.20 (d, J=6.8 Hz, 6H), 2.85 (m, 1H), 4.41 (s, 2H), 7.00 (d, J=7.8 Hz, 1H), 7.20-7.30 (m, 2H), 7.40 (dd, J=4.4, 1.5 Hz, 2H), 7.51 (d, J=8.1 Hz, 1H), 7.60 (s, 1H), 7.96 (dd, J=7.6, 1.5 Hz, 1H), 8.45 (dd, J=4.4, 1.5 Hz, 2H), 8.58 (dd, J=4.6, 1.5 Hz, 1H), 10.41 (s, 1H)

N-(3-Methoxyphenyl)-2-(4-pyridylmethylthio)pyridine-3-carboxamide

Compound No. 1-36

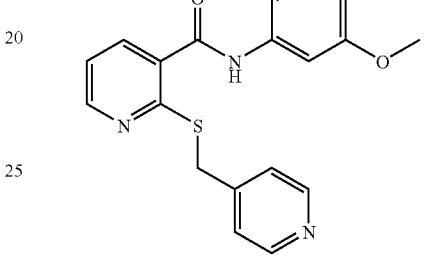

¹H-NMR (500 MHz, CDCl₃)

δ 3.83 (s, 3H), 4.46 (s, 2H), 6.74 (m, 1H), 7.05 (m, 1H), 7.14 (dd, J=7.6, 4.9 Hz, 1H), 7.26 (m, 1H), 7.37 (dd, J=4.6, 1.5 Hz, 2H), 7.39 (m, 1H), 7.88-8.03 (m, 2H), 8.50 (dd, J=4.6, 1.5 Hz, 2H), 8.53 (dd, J=4.6, 1.8 Hz, 1H)

N-(3-Fluorophenyl)-2-(4-pyridylmethylthio)pyridine-3-carboxamide

Compound No. 1-37

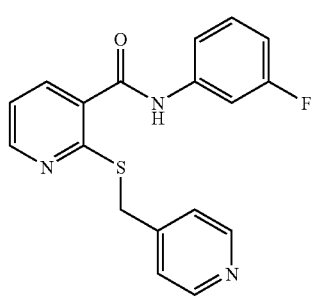

¹H-NMR (400 MHz, DMSO-d₆)

δ 4.42 (s, 2H), 6.95 (m, 1H), 7.30 (dd, J=7.6, 4.9 Hz, 1H), 7.35-7.50 (m, 4H), 7.65 (m, 1H), 7.98 (dd, J=7.8, 1.7 Hz, 1H), 8.43-8.50 (m, 2H), 8.60 (dd, J=4.9, 1.7 Hz, 1H), 10.68 (s, 1H)

N-(3-Chlorophenyl)-2-(4-pyridylmethylthio)pyridine-3-carboxamide

Compound No. 1-38

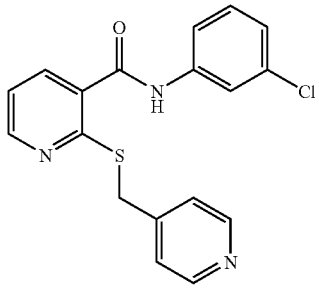

$^1$H-NMR (500 MHz, DMSO-d$_6$)

δ 4.42 (s, 2H), 7.19 (dd, J=7.9, 1.7 Hz, 1H), 7.29 (dd, J=7.3, 4.8 Hz, 1H), 7.37-7.43 (m, 3H), 7.58 (d, J=9.1 Hz, 1H), 7.89 (d+J=1.7 Hz, 1H), 7.99 (dd, J=7.3, 1.7 Hz, 1H), 8.45 (dd, J=4.5, 1.5 Hz, 2H), 8.60 (dd, J=4.8, 1.7 Hz, 1H), 10.65 (s, 1H)

N-(3-Bromophenyl)-2-(4-pyridylmethylthio)pyridine-3-carboxamide

Compound No. 1-39

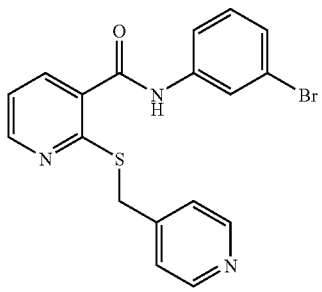

$^1$H-NMR (500 MHz, DMSO-d$_6$)

δ 4.42 (s, 2H), 7.28-7.35 (m, 2H), 7.40 (dd, J=4.6, 1.5 Hz, 2H), 7.63 (m, 1H), 7.99 (dd, J=7.6, 1.5 Hz, 1H), 8.03 (s, 1H), 8.46 (dd, J=4.6, 1.5 Hz, 2H), 8.56-8.64 (m, 2H), 10.64 (s, 1H)

N-(3-Hydroxymethylphenyl)-2-(4-pyridylmethylthio)pyridine-3-carboxamide

Compound No. 1-40

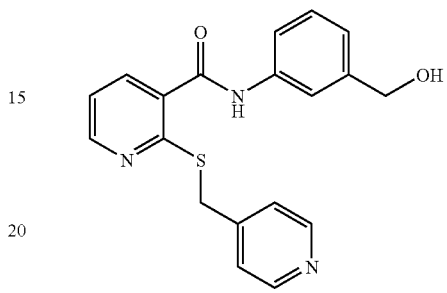

$^1$H-NMR (500 MHz, CDCl$_3$)

δ 3.49 (br s, 1H), 4.46 (s, 2H), 4.72 (s, 2H), 7.15 (dd, J=7.6, 4.5 Hz, 1H), 7.18 (dd, J=7.6, 0.6 Hz, 1H), 7.34 (dd, J=4.5, 1.7 Hz, 2H), 7.37 (d, J=7.6 Hz, 1H), 7.51 (d, J=7.6 Hz, 1H), 7.66 (s, 1H), 7.89-7.97 (M, 2H), 8.49 (dd, J=4.5, 1.7 Hz, 2H), 8.55 (dd, J=4.9, 1.8 Hz, 1H)

N-(3-Isopropoxyphenyl)-2-(4-pyridylmethylthio)pyridine-3-carboxamide

Compound No. 1-41

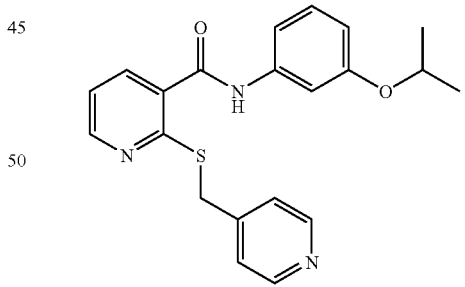

$^1$H-NMR (500 MHz, CDCl$_3$)

δ 1.34 (d, J=6.1 Hz, 6H), 4.46 (s, 2H), 4.58 (m, 1H), 6.71 (dd, J=7.9, 2.1 Hz, 1H), 7.04 (d, J=7.6 Hz, 1H), 7.14 (dd, J=7.6, 4.8 Hz, 1H), 7.24 (m, 1H), 7.35 (m, 1H), 7.37 (dd,

J=4.6, 1.5 Hz, 2H), 7.70-7.94 (m, 2H), 8.50 (dd, J=4.6, 1.5 Hz, 2H), 8.53 (dd, J=4.8, 1.5 Hz, 1H)

2-(4-Pyridylmethylthio)-N-(3-trifluoromethoxyphenyl)pyridine-3-carboxamide

Compound No. 1-42

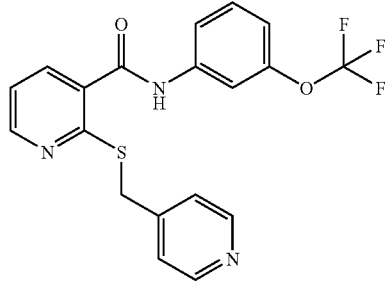

¹H-NMR (400 MHz, DMSO-d₆)

δ 4.43 (s, 2H), 7.12 (dt, J=8.3, 1.2 Hz, 1H), 7.31 (dd, J=7.6, 4.9 Hz, 1H), 7.41 (dd, J=4.4, 1.6 Hz, 2H), 7.49 (t, J=8.1 Hz, 1H), 7.64 (d, J=8.3 Hz, 1H), 7.86 (s, 1H), 8.01 (dd, J=7.6, 1.7 Hz, 1H), 8.46 (dd, J=4.4, 1.6 Hz, 2H), 8.67 (dd, J=1.7 Hz, 1H), 10.75 (s, 1H)

N-(3-Ethoxycarbonylphenyl)-2-(4-pyridylmethylthio)pyridine-3-carboxamide

Compound No. 1-43

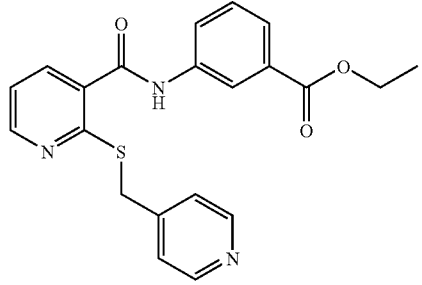

¹H-NMR (400 MHz, CDCl₃)

δ 1.39 (t, J=7.1 Hz, 3H), 4.38 (q, J=7.1 Hz, 2H), 4.46 (s, 2H), 7.15 (dd, J=7.6, 4.9 Hz, 1H), 7.34 (dd, J=4.6, 1.5 Hz, 2H), 7.46 (dd, J=7.8 Hz, 1H), 7.85 (dt, J=7.8, 1.5 Hz, 1H), 7.92 (dd, J=7.6, 1.7 Hz, 1H), 8.04 (dt, J=7.8, 1.5 Hz, 1H), 8.09 (t, J=1.5 Hz, 1H), 8.20 (s, 1H), 8.47 (dd, J=4.6, 1.5 Hz, 2H), 8.55 (dd, J=4.9, 1.7 Hz, 1H)

N-(4-Fluorophenyl)-2-(4-pyridylmethylthio)pyridine-3-carboxamide

Compound No. 1-44

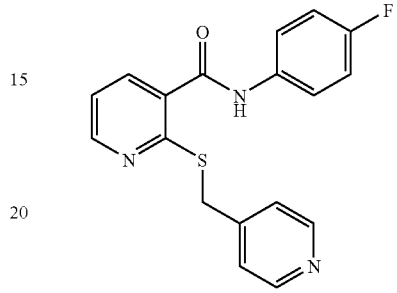

¹H-NMR (400 MHz, DMSO-d₆)

δ 4.42 (s, 2H), 7.20 (td, J=8.9, 1.7 Hz, 2H), 7.30 (dd, J=7.6, 4.9 Hz, 1H), 7.40 (dd, J=4.4, 1.5 Hz, 2H), 7.68-7.76 (m, 2H), 7.97 (dd, J=7.6, 1.7 Hz, 1H), 8.45 (dd, J=4.4, 1.5 Hz, 2H), 8.59 (dd, J=4.9, 1.7 Hz, 1H), 10.53 (s, 1H)

N-(4-Bromophenyl)-2-(4-pyridylmethylthio)pyridine-3-carboxamide

Compound No. 1-45

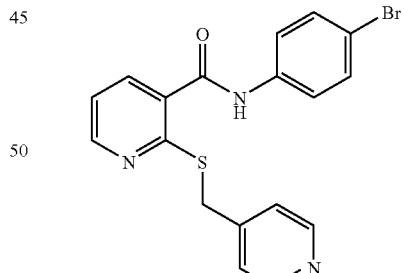

¹H-NMR (400 MHz, DMSO-d₆)

δ 4.42 (s, 2H), 7.30 (dd, J=7.6, 4.9 Hz, 1H), 7.40 (dd, J=4.5, 1.5 Hz, 2H), 7.54 (d, J=8.8 Hz, 2H), 7.67 (d, J=8.8 Hz, 2H), 7.98 (dd, J=7.5, 1.7 Hz, 1H), 8.45 (dd, J=4.5, 1.5 Hz, 2H), 8.60 (dd, J=4.9, 1.7 Hz, 1H), 10.60 (s, 1H)

N-(4-Iodophenyl)-2-(4-pyridylmethylthio)pyridine-3-carboxamide

Compound No. 1-46

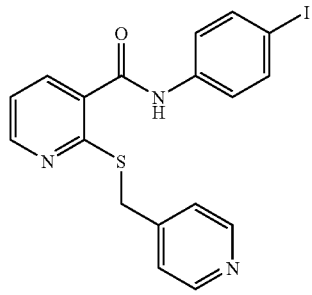

¹H-NMR (500 MHz, DMSO-d₆)

δ 4.42 (s, 2H), 7.29 (dd, J=7.6, 4.8 Hz, 1H), 7.40 (dd, J=4.4, 1.5 Hz, 2H), 7.53 (d, J=8.8 Hz, 2H), 7.69 (d, J=8.8 Hz, 2H), 7.97 (dd, J=7.6, 1.8 Hz, 1H), 8.45 (dd, J=4.4, 1.5 Hz, 2H), 8.59 (dd, J=4.8, 1.8 Hz, 1H), 10.57 (s, 1H)

N-(4-Methylphenyl)-2-(4-pyridylmethylthio)pyridine-3-carboxamide

Compound No. 1-47

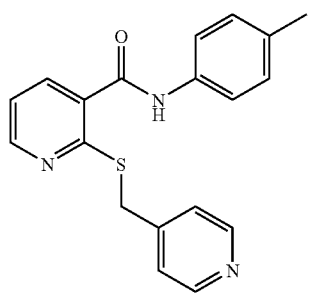

¹H-NMR (500 MHz, DMSO-d₆)

δ 2.27 (s, 3H), 4.41 (s, 2H), 7.15 (d, J=8.2 Hz, 2H), 7.28 (dd, J=7.6, 4.8 Hz, 1H), 7.40 (dd, J=4.6, 1.5 Hz, 2H), 7.57 (d,

J=8.2 Hz, 2H), 7.94 (dd, J=7.6, 1.5 Hz, 1H), 8.45 (dd, J=4.6, 1.5 Hz, 2H), 8.58 (dd, J=4.8, 1.5 Hz, 1H), 10.38 (s, 1H)

2-(4-Pyridylmethylthio)-N-(4-trifluoromethylphenyl)pyridine-3-carboxamide

Compound No. 1-48

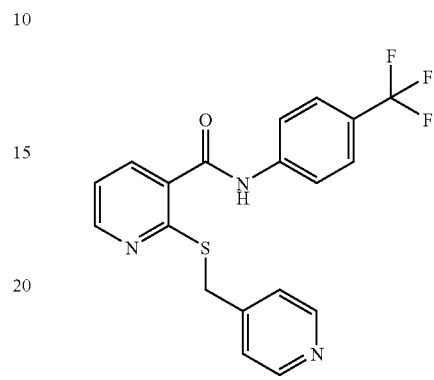

¹H-NMR (400 MHz, DMSO-d₆)

δ 4.43 (s, 2H), 7.32 (dd, J=7.6, 4.7 Hz, 1H), 7.40 (dd, J=4.4, 1.7 Hz, 2H), 7.73 (d, J=8.6 Hz, 2H), 7.91 (d, J=8.6 Hz, 2H), 8.02 (dd, J=7.6, 1.7 Hz, 1H), 8.45 (dd, J=4.4, 1.7 Hz, 2H), 8.61 (dd, J=4.7, 1.7 Hz, 1H), 10.83 (s, 1H)

N-(4-n-Propylphenyl)-2-(4-pyridylmethylthio)pyridine-3-carboxamide

Compound No. 1-49

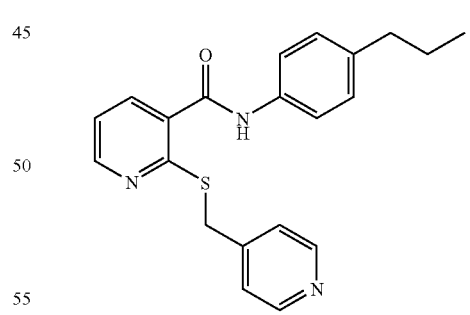

¹H-NMR (500 MHz, DMSO-d₆)

δ 0.88 (t, J=7.3 Hz, 3H), 1.53-1.62 (m, 2H), 2.52 (t, J=7.6 Hz, 2H), 4.41 (s, 2H), 7.16 (d, J=8.3 Hz, 2H), 7.28 (dd, J=7.6, 4.8 Hz, 1H), 7.40 (dd, J=4.5, 1.4 Hz, 2H), 7.59 (d, J=8.3 Hz,

2H), 7.94 (dd, J=7.6, 1.5 Hz, 1H), 8.45 (dd, J=4.5, 1.4 Hz, 2H), 8.58 (dd, J=4.8, 1.5 Hz, 1H), 10.39 (s, 1H)

N-(4-n-Butylphenyl)-2-(4-pyridylmethylthio)pyridine-3-carboxamide

Compound No. 1-50

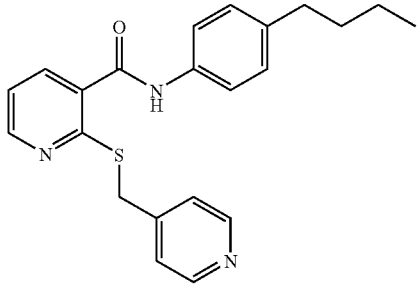

¹H-NMR (500 MHz, CDCl₃)

δ 0.92 (t, J=7.3 Hz, 3H), 1.30-1.39 (m, 2H), 1.50-1.62 (m, 2H), 2.60 (t, J=7.6 Hz, 2H), 4.44 (s, 2H), 7.12 (dd, J=7.6, 4.9 Hz, 1H), 7.17 (d, J=8.1 Hz, 2H), 7.35 (dd, J=4.6, 1.8 Hz, 2H), 7.51 (d, J=8.1 Hz, 2H), 7.88 (d, J=7.6 Hz, 1H), 8.00 (s, 1H), 8.49 (dd, J=4.6, 1.8 Hz, 2H), 8.51 (dd, J=4.9, 1.5 Hz, 1H)

N-(4-tert-Butylphenyl)-2-(4-pyridylmethylthio)pyridine-3-carboxamide

Compound No. 1-51

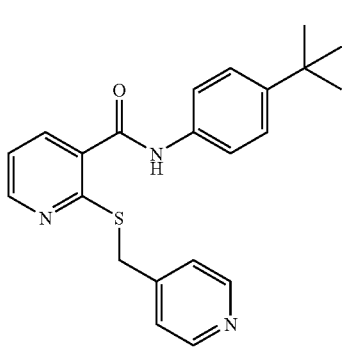

¹H-NMR (500 MHz, DMSO-d₆)

δ 1.27 (s, 9H), 4.41 (s, 2H), 7.28 (dd, J=7.6, 4.9 Hz, 1H), 7.36 (d, J=8.6 Hz, 2H), 7.40 (dd, J=4.3, 1.5 Hz, 2H), 7.60 (d,

J=8.6 Hz, 2H), 7.94 (dd, J=7.6, 1.5 Hz, 1H), 8.45 (dd, J=4.3, 1.5 Hz, 2H), 8.58 (dd, J=4.9, 1.5 Hz, 1H), 10.40 (s, 1H)

N-(4-n-Octylphenyl)-2-(4-pyridylmethylthio)pyridine-3-carboxamide

Compound No. 1-52

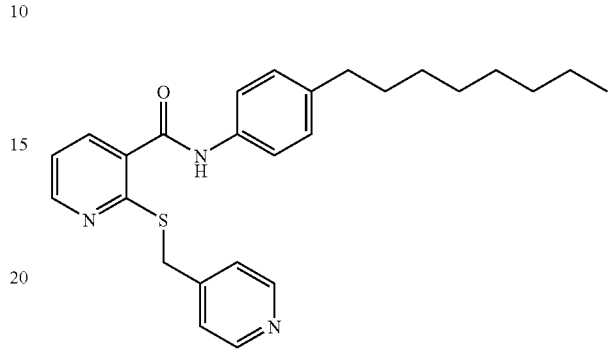

¹H-NMR (500 MHz, CDCl₃)

δ 0.88 (t, J=7.0 Hz, 3H), 1.20-1.35 (m, 10H), 1.50-1.65 (m, 2H), 2.58 (t, J=7.6 Hz, 2H), 4.45 (s, 2H), 7.13 (dd, J=7.6, 4.9 Hz, 1H), 7.18 (d, J=7.9 Hz, 2H), 7.34 (dd, J=4.3, 1.5 Hz, 2H), 7.51 (d, J=7.9 Hz, 2H), 7.85-7.92 (m, 2H), 8.48 (dd, J=4.3, 1.5 Hz, 2H), 8.53 (dd, J=4.9, 1.8 Hz, 1H)

N-(4-Methoxyphenyl)-2-(4-pyridylmethylthio)pyridine-3-carboxamide

Compound No. 1-53

¹H-NMR (400 MHz, DMSO-d₆)

δ 3.73 (s, 3H), 4.42 (s, 2H), 6.92 (d, J=9.0 Hz, 2H), 7.28 (dd, J=7.6, 4.8 Hz, 1H), 7.44 (d, J=6.1 Hz, 2H), 7.60 (d, J=9.0

Hz, 2H), 7.95 (dd, J=7.6, 1.5 Hz, 1H), 8.47 (d, J=6.1 Hz, 2H), 8.57 (dd, J=4.8, 1.5 Hz, 1H), 10.34 (s, 1H)

2-(4-Pyridylmethylthio)-N-(4-trifluoromethoxyphenyl)pyridine-3-carboxamide

Compound No. 1-54

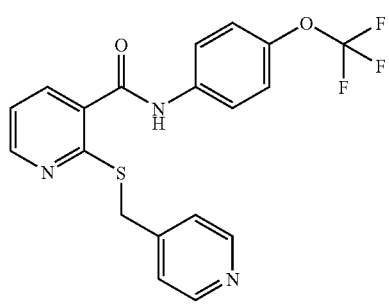

¹H-NMR (400 MHz, DMSO-d₆)

δ 4.42 (s, 2H), 7.30 (dd, J=7.6, 4.8 Hz, 1H), 7.37 (d, J=8.6 Hz, 2H), 7.40 (dd, J=4.5, 1.2 Hz, 2H), 7.80 (d, J=8.6 Hz, 2H), 7.98 (dd, J=7.6, 1.8 Hz, 1H), 8.45 (dd, J=4.5, 1.2 Hz, 2H), 8.60 (dd, J=4.8, 1.8 Hz, 1H), 10.67 (s, 1H)

N-(4-Isopropoxyphenyl)-2-(4-pyridylmethylthio)pyridine-3-carboxamide

Compound No. 1-55

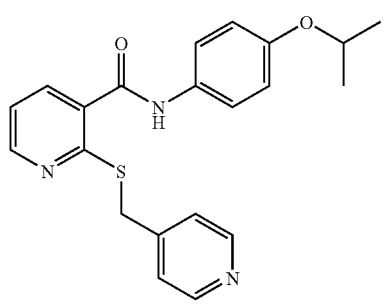

¹H-NMR (500 MHz, CDCl₃)

δ 1.33 (d, J=5.8 Hz, 6H), 4.45 (s, 2H), 4.52 (m, 1H), 6.89 (d, J=8.8 Hz, 2H), 7.13 (dd, J=7.6, 4.9 Hz, 1H), 7.36 (dd, J=4.6, 1.5 Hz, 2H), 7.50 (d J=8.8 Hz, 2H), 7.85 (s, 1H), 7.89 (d, J=7.0 Hz, 1H), 8.50 (dd, J=4.6, 1.5 Hz, 2H), 8.52 (dd, J=4.9, 1.5 Hz, 1H)

N-(4-n-Butoxyphenyl)-2-(4-pyridylmethylthio)pyridine-3-carboxamide

Compound No. 1-56

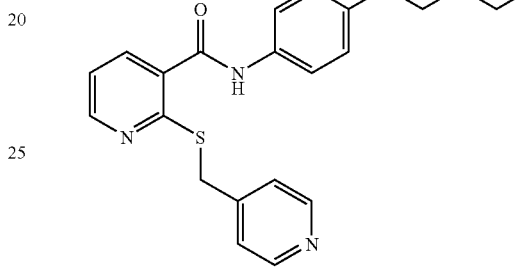

¹H-NMR (500 MHz, CDCl₃)

δ 0.98 (t, J=7.3 Hz, 3H), 1.45-1.54 (m, 2H), 1.73-1.80 (m, 2H), 3.96 (t, J=6.4 Hz, 2H), 4.45 (s, 2H), 6.89 (d, J=8.5 Hz, 2H), 7.13 (dd, J=7.3, 4.6 Hz, 1H), 7.34 (dd, J=4.3, 1.5 Hz, 2H), 7.50 (d, J=8.5 Hz, 2H), 7.85 (s, 1H), 7.89 (d, J=7.3 Hz, 1H), 8.48 (dd, J=4.3, 1.5 Hz, 2H), 8.52 (dd, J=4.6, 1.5 Hz, 1H)

N-(4-Phenoxyphenyl)-2-(4-pyridylmethylthio)pyridine-3-carboxamide

Compound No. 1-57

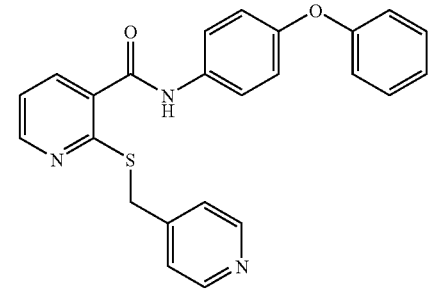

¹H-NMR (500 MHz, DMSO-d₆)

δ 4.42 (s, 2H), 6.95-7.00 (m, 2H), 7.00-7.10 (m, 2H), 7.13 (m, 1H), 7.29 (dd, J=7.3, 4.9 Hz, 1H), 7.35-7.45 (m, 4H), 7.71 (d, J=8.8 Hz, 2H), 7.98 (m, 1H), 8.46 (dd, J=4.3, 1.5 Hz, 2H), 8.59 (m, 1H), 10.51 (s, 1H)

N-(4-Hydroxyphenyl)-2-(4-pyridylmethylthio)pyridine-3-carboxamide

Compound No. 1-58

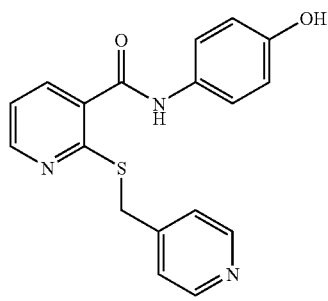

¹H-NMR (400 MHz, DMSO-d₆)

δ 4.40 (s, 2H), 6.73 (d, J=8.8 Hz, 2H), 7.27 (dd, J=7.8, 4.9 Hz, 1H), 7.39 (d, J=6.1 Hz, 2H), 7.47 (d, J=8.8. Hz, 2H), 7.91 (dd, J=7.6, 1.5 Hz, 1H), 8.42-8.50 (m, 2H), 8.56 (dd, J=4.9, 1.5 Hz, 1H), 9.29 (s, 1H), 10.22 (s, 1H)

N-[4-(2-Hydroxyethyl)phenyl]-2-(4-pyridylmethylthio)pyridine-3-carboxamide

Compound No. 1-59

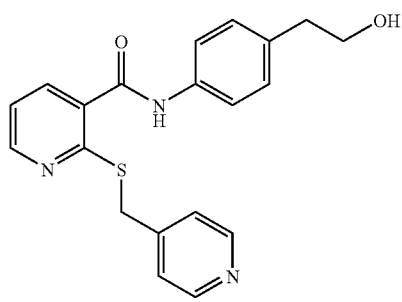

¹H-NMR (500 MHz, CDCl₃).

δ 2.86 (t, J=6.4 Hz, 2H), 3.85 (t, J=6.4 Hz, 2H), 4.45 (s, 2H), 7.13 (dd, J=7.5, 4.6 Hz, 1H), 7.23 (d, J=8.1 Hz, 2H), 7.33 (d, J=5.5 Hz, 2H), 7.55 (d, J=8.1 Hz, 2H), 7.89 (dd, J=7.5, 1.8 Hz, 1H), 8.01 (br s, 1H), 8.46 (br s, 2H) 8.53 (dd, J=4.6, 1.8 Hz, 1H)

N-(4-Isopropoxycarbonylphenyl)-2-(4-pyridylmethylthio)pyridine-3-carboxamide

Compound No. 1-60

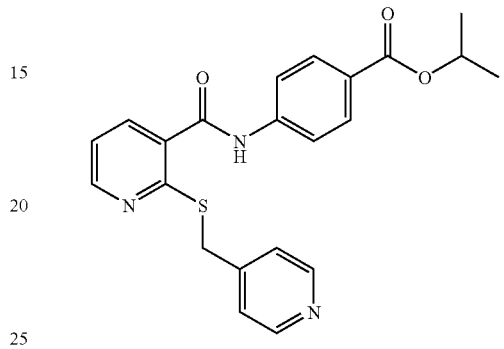

¹H-NMR (400 MHz, CDCl₃)

δ 1.37 (d, J=6.1 Hz, 6H), 4.46 (s, 2H), 5.25 (m, 1H), 7.16 (dd, J=7.6, 4.6 Hz, 1H), 7.34 (dd, J=4.6, 1.4 Hz, 2H), 7.69 (d, J=8.8 Hz, 2H), 7.83 (dd, J=7.6, 1.8 Hz, 1H), 8.04 (d, J=8.8 Hz, 2H), 8.18 (s, 1H), 8.47 (dd, J=4.6, 1.4 Hz, 2H), 8.56 (dd, J=4.6, 1.4 Hz, 1H)

N-(4-Ethoxycarbonylmethylphenyl)-2-(4-pyridylmethylthio)pyridine-3-carboxamide

Compound No. 1-61

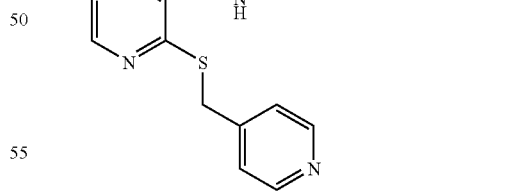

¹H-NMR (500 MHz, DMSO-d₆)

δ 1.18 (t, J=7.1 Hz, 3H), 3.62 (s, 2H), 4.07 (q, J=7.1 Hz, 2H), 4.41 (s, 2H), 7.24 (d, J=8.5 Hz, 2H), 7.29 (dd, J=7.6, 4.9 Hz, 1H), 7.40 (dd, J=4.2, 1.5 Hz, 2H), 7.63 (d, J=8.5 Hz, 2H), 7.95 (dd, J=7.6, 1.5 Hz, 1H), 8.45 (dd, J=4.2, 1.5 Hz, 2H), 8.59 (dd, J=4.9, 1.5 Hz, 1H), 10.47 (s, 1H)

N-(4-Benzoylphenyl)-2-(4-pyridylmethylthio)pyridine-3-carboxamide

Compound No. 1-62

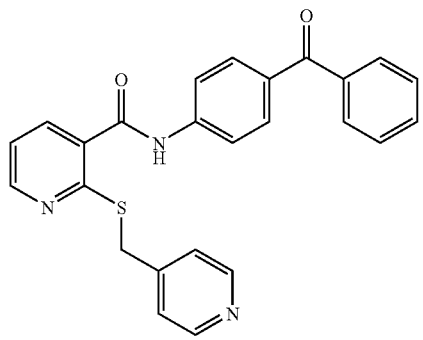

¹H-NMR (500 MHz, DMSO-d₆)

δ 4.44 (s, 2H), 7.32 (dd, J=7.6, 4.8 Hz, 1H), 7.41 (dd, J=7.4, 1.5 Hz, 2H), 7.55-7.60 (m, 2H), 7.68 (m, 1H), 7.73 (dd, J=8.2, 1.2 Hz, 2H), 7.79 (d, J=8.8 Hz, 2H), 7.89 (d, J=8.8 Hz, 2H), 8.02 (dd, J=7.6, 1.8 Hz, 1H), 8.46 (dd, J=4.2, 1.5 Hz, 2H), 8.62 (dd, J=4.8, 1.8 Hz, 1H), 10.86 (s, 1H)

N-(4-Aminophenyl)-2-(4-pyridylmethylthio)pyridine-3-carboxamide

Compound No. 1-63

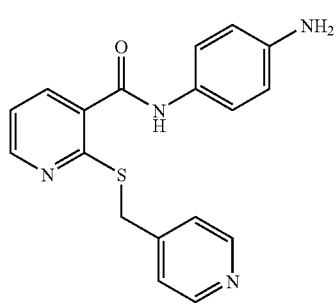

¹H-NMR (500 MHz, CDCl₃)

δ 3.65 (br s, 2H), 4.45 (s, 2H), 6.69 (d, J=8.6 Hz, 2H), 7.13 (dd, J=7.6, 4.9 Hz, 1H), 7.34 (d, J=4.6, 1.8 Hz, 2H), 7.38 (d, J=8.6 Hz, 2H), 7.70 (s, 1H), 7.89 (d, J=7.6 Hz, 1H), 8.49 (dd, J=4.6, 1.8 Hz, 2H), 8.52 (m, 1H)

N-(4-Dimethylaminophenyl)-2-(4-pyridylmethylthio)pyridine-3-carboxamide

Compound No. 1-64

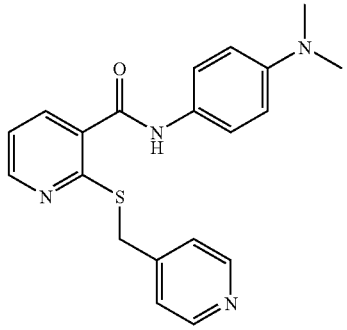

¹H-NMR (500 MHz, DMSO-d₆)

δ 2.86 (s, 6H), 4.40 (s, 2H), 6.71 (dd, J=7.0, 2.1 Hz, 2H), 7.27 (dd, J=7.6, 4.9 Hz, 1H), 7.40 (dd, J=4.6, 1.5 Hz, 2H), 7.51 (dd, J=7.0, 2.1 Hz, 2H), 7.92 (dd, J=7.6, 1.8 Hz, 1H), 8.45 (dd, J=4.6, 1.5 Hz, 2H), 8.56 (dd, J=4.9, 1.8 Hz, 1H), 10.17 (s, 1H)

N-(3-Methylphenyl)-2-(4-pyridylmethylthio)pyridine-3-carboxamide

Compound No. 1-65

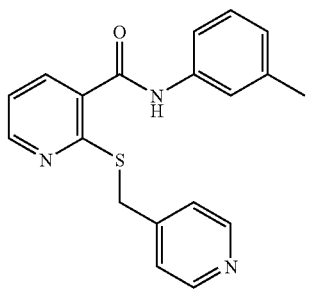

¹H-NMR (500 MHz, DMSO-d₆)

δ 2.30 (s, 3H), 4.42 (s, 2H), 6.93 (d, J=7.6 Hz, 1H), 7.23 (dd, J=8.1, 7.6 Hz, 1H), 7.28 (dd, J=7.6, 4.6 Hz, 1H), 7.40 (dd, J=4.4, 1.5 Hz, 2H), 7.46 (d, J=8.1 Hz, 1H), 7.56 (s, 1H), 7.94

(dd, J=7.6, 1.7 Hz, 1H), 8.45 (dd, J=4.4, 1.7 Hz, 2H), 8.58 (dd, J=4.6, 1.7 Hz, 1H), 10.40 (s, 1H)

N-(4-Acetylaminophenyl)-2-(4-pyridylmethylthio)pyridine-3-carboxamide

Compound No. 1-66

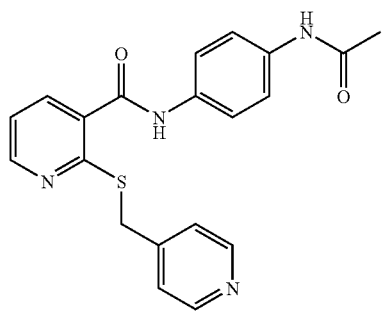

¹H-NMR (400 MHz, DMSO-d₆)

δ 2.03 (s, 3H), 4.41 (s, 2H), 7.28 (dd, J=7.6, 4.6 Hz, 1H), 7.40 (d, J=5.9 Hz, 2H), 7.54 (d, J=9.0 Hz, 2H), 7.60 (d, J=9.0 Hz, 2H), 7.95 (m, 1H), 8.43-8.50 (m, 2H), 8.58 (dd, J=4.6, 1.4 Hz, 1H), 9.93 (s, 1H), 10.41 (s, 1H)

N-(4-Morpholinophenyl)-2-(4-pyridylmethylthio)pyridine-3-carboxamide

Compound No. 1-67

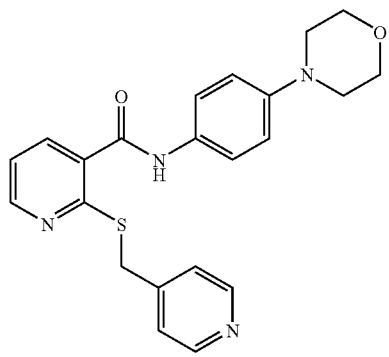

¹H-NMR (500 MHz, DMSO-d₆)

δ 3.06 (t, J=4.8 Hz, 4H), 3.74 (t, J=4.8 Hz, 4H), 4.41 (s, 2H), 6.93 (d, J=9.0 Hz, 2H), 7.27 (dd, J=7.6, 4.9 Hz, 1H), 7.40 (dd, J=4.7, 1.5 Hz, 2H), 7.56 (d, J=9.0 Hz, 2H), 7.93 (dd, J=7.6, 1.8 Hz, 1H), 8.45 (dd, J=4.7, 1.5 Hz, 2H), 8.57 (dd, J=4.9, 1.8 Hz, 1H), 10.27 (br, 1H)

N-(2,3-Dimethylphenyl)-2-(4-pyridylmethylthio)pyridine-3-carboxamide

Compound No. 1-68

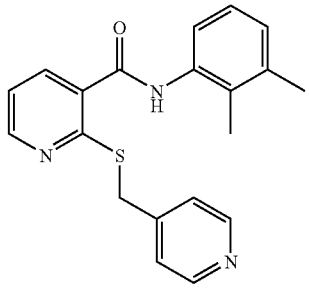

¹H-NMR (500 MHz, DMSO-d₆)

δ 2.13 (s, 3H), 2.27 (s, 3H), 4.42 (s, 2H), 7.05-7.20 (m, 3H), 7.30 (m, 1H), 7.41 (dd, J=4.3, 1.5 Hz, 2H), 8.01 (m, 1H), 8.46 (dd, J=4.3, 1.5 Hz, 2H), 8.59 (m, 1H), 10.03 (s, 1H)

N-(4-Chloro-2-fluorophenyl)-2-(4-pyridylmethylthio)pyridine-3-carboxamide

Compound No. 1-69

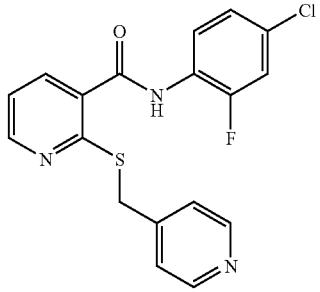

¹H-NMR (500 MHz, CDCl₃)

δ 4.46 (s, 2H), 7.15-7.20 (m, 3H), 7.34 (dd, J=4.6, 1.5 Hz, 2H), 7.93 (dd, J=7.6, 1.8 Hz, 1H), 8.18 (s, 1H), 8.43 (m, 1H), 8.49 (dd, J=4.6, 1.5 Hz, 2H), 8.56 (dd, J=4.6, 1.8 Hz, 1H)

N-(2,4-Difluorophenyl)-2-(4-pyridylmethylthio)pyridine-3-carboxamide

Compound No. 1-70

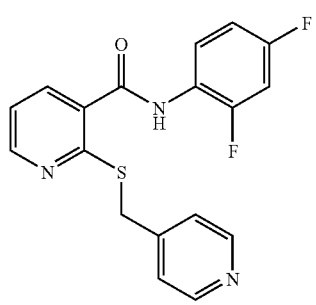

¹H-NMR (500 MHz, DMSO-d₆)
δ 4.41 (s, 2H), 7.13 (m, 1H), 7.30 (dd, J=7.7, 4.9 Hz, 1H), 7.35 (m, 1H), 7.41 (dd, J=4.5, 1.4 Hz, 2H), 7.68 (m, 1H), 8.02 (m, 1H), 8.46 (dd, J=4.5, 1.4 Hz, 2H), 8.60 (dd, J=4.9, 1.5 Hz, 1H), 10.33 (s, 1H)

N-(2,6-Diisopropylphenyl)-2-(4-pyridylmethylthio)pyridine-3-carboxamide

Compound No. 1-71

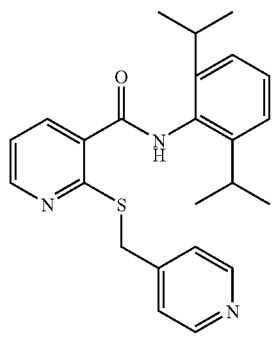

¹H-NMR (400 MHz, DMSO-d₆)

δ 1.14 (d, J=6.6 Hz, 12H), 3.18 (m, 2H), 4.43 (s, 2H), 7.19 (d, J=7.6 Hz, 2H), 7.25-7.35 (m, 2H), 7.41 (d, J=5.8 Hz, 2H), 7.95 (m, 1H), 8.47 (d, J=5.8 Hz, 2H), 8.60 (m, 1H), 9.86 (s, 1H)

N-(3,4-Dimethoxyphenyl)-2-(4-pyridylmethylthio)pyridine-3-carboxamide

Compound No. 1-72

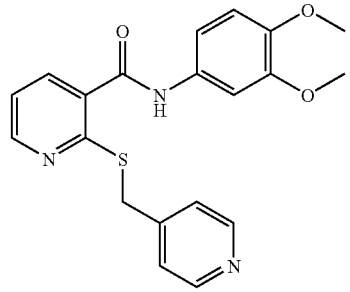

¹H-NMR (500 MHz, DMSO-d₆)
δ 3.73 (s, 6H), 4.41 (s, 2H), 6.93 (d, J=8.8 Hz, 1H), 7.22 (dd, J=8.8, 2.4 Hz, 1H), 7.28 (dd, J=7.3 4.8 Hz, 1H), 7.38-7.41 (m, 3H), 7.95 (dd, J=7.6, 1.5 Hz, 1H), 8.43-8.47 (m, 2H), 8.57 (dd, J=4.8, 1.5 Hz, 1H), 10.31 (s, 1H)

N-(3,4-Difluorophenyl)-2-(4-pyridylmethylthio)pyridine-3-carboxamide

Compound No. 1-73

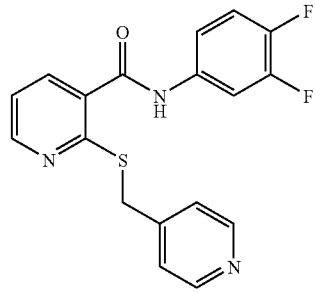

¹H-NMR (400 MHz, DMSO-d₆)

δ 4.42 (s, 2H), 7.31 (dd, J=7.8, 4.6 Hz, 1H), 7.40-7.50 (m, 4H), 7.85 (m, 1H), 7.99 (dd, J=7.8, 1.7 Hz, 1H), 8.45 (d, J=4.4, 1.7 Hz, 2H), 8.60 (dd, J=4.6, 1.7 Hz, 1H), 10.70 (s, 1H)

N-(4-Chloro-3-trifluoromethylphenyl)-2-(4-pyridyl-methylthio)pyridine-3-carboxamide Compound No. 1-74

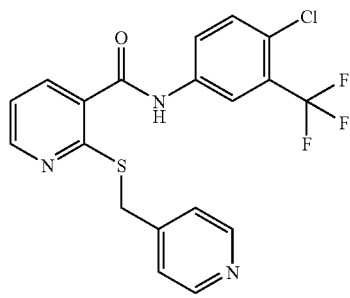

¹H-NMR (400 MHz, DMSO-d₆)

δ 4.43 (s, 2H), 7.32 (dd, J=7.6, 4.9 Hz, 1H), 7.40 (d, J=5.9 Hz, 2H), 7.73 (d, J=8.8 Hz, 1H), 7.97 (dd, J=8.8, 2.4 Hz, 1H), 8.04 (dd, J=7.6, 1.7 Hz, 1H), 8.28 (d, J=2.4 Hz, 1H), 8.45 (d, J=5.9 Hz, 2H), 8.62 (dd, J=4.9, 1.7 Hz, 1H), 10.89 (s, 1H)

N-(3-Chloro-4-fluorophenyl)-2-(4-pyridylmeth-ylthio)pyridine-3-carboxamide

Compound No. 1-75

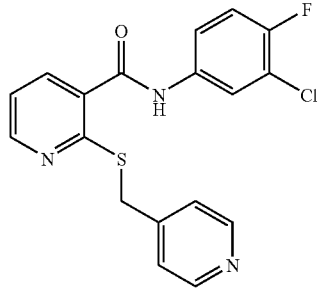

¹H-NMR (500 MHz, DMSO-d₆)

δ 4.42 (s, 2H), 7.31 (dd, J=7.7, 4.9 Hz, 1H), 7.40 (dd, J=4.3, 1.5 Hz, 2H), 7.44 (t, J=Hz, 1H), 7.61 (m, 1H), 7.96-8.04 (m, 2H), 8.46 (dd, J=4.3, 1.5 Hz, 2H), 8.61 (dd, J=4.9, 1.5 Hz, 1H), 10.68 (s, 1H)

N-(3,4-Dichlorophenyl)-2-(4-pyridylmethylthio)pyridine-3-carboxamide

Compound No. 1-76

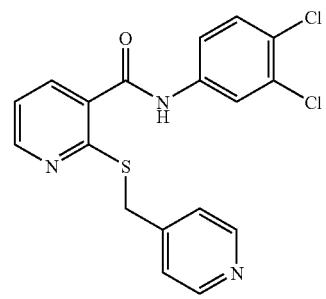

¹H-NMR (400 MHz, DMSO-d₆)

δ 4.42 (s, 2H), 7.31 (dd, J=7.6, 4.9 Hz, 1H), 7.40 (dd, J=4.4, 1.5 Hz, 2H), 7.62 (d, J=Hz, 2H), 8.00 (dd, J=7.6, 1.7 Hz, 1H), 8.07 (t, J=1.2 Hz, 1H), 8.45 (dd, J=4.4, 1.5 Hz, 2H), 8.61 (dd, J=4.9, 1.7 Hz, 1H), 10.70 (s, 1H)

N-(4-Fluoro-3-trifluoromethylphenyl)-2-(4-pyridyl-methylthio)pyridine-3-carboxamide Compound No. 1-77

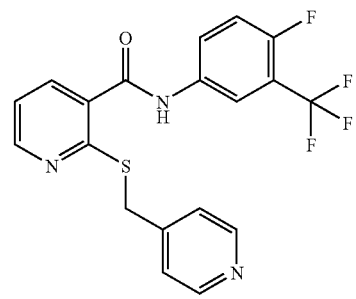

¹H-NMR (500 MHz, DMSO-d₆)

δ 4.42 (s, 2H), 7.32 (dd, J=7.6, 4.9 Hz, 1H), 7.40 (dd, J=4.4, 1.7 Hz, 2H), 7.54 (m, 1H), 7.97 (m, 1H), 8.03 (dd, J=7.6, 1.7

Hz, 1H), 8.19 (m, 1H), 8.46 (dd, J=4.4, 1.7 Hz, 2H), 8.62 (dd, J=4.9, 1.7 Hz, 1H), 10.81 (s, 1H)

N-(3-Chloro-4-methylphenyl)-2-(4-pyridylmethylthio)pyridine-3-carboxamide

Compound No. 1-78

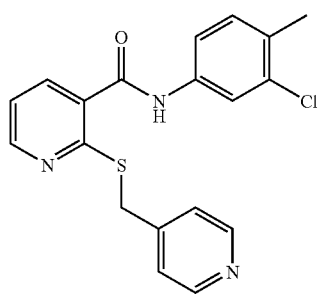

¹H-NMR (500 MHz, CDCl₃)

δ 2.35 (s, 3H), 4.46 (s, 2H), 7.14 (dd, J=7.6, 4.6 Hz, 1H), 7.20 (d, J=8.2 Hz, 1H), 7.35 (dd, J=4.5, 1.5 Hz, 2H), 7.37 (m, 1H), 7.72 (s, 1H), 7.89 (dd, J=7.6, 1.5 Hz, 1H), 8.02 (m, 1H), 8.48 (dd, J=4.5, 1.5 Hz, 2H), 8.54 (dd, J=4.9, 1.5 Hz, 1H)

N-(4-Chloro-3-methylphenyl)-2-(4-pyridylmethylthio)pyridine-3-carboxamide

Compound No. 1-79

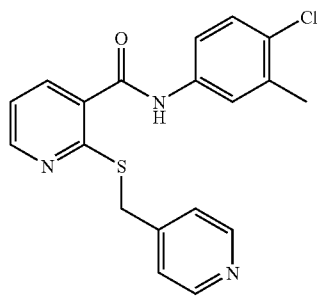

¹H-NMR (500 MHz, CDCl₃)

δ 2.39 (s, 3H), 4.46 (s, 2H), 7.15 (dd, J=7.6, 4.9 Hz, 1H), 7.33 (m, 1H), 7.35 (dd, J=4.5, 1.5 Hz, 2H), 7.37 (m, 1H), 7.56

(s, 1H), 7.90 (d, J=6.4 Hz, 1H), 8.01 (s, 1H), 8.50 (dd, J=4.5, 1.5 Hz, 2H), 8.55 (dd, J=4.9, 1.8 Hz, 1H)

N-(3,4-Dimethylphenyl)-2-(4-pyridylmethylthio)pyridine-3-carboxamide

Compound No. 1-80

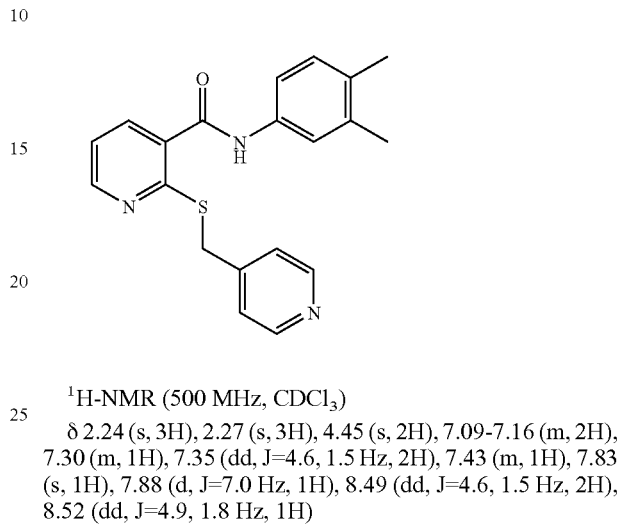

¹H-NMR (500 MHz, CDCl₃)

δ 2.24 (s, 3H), 2.27 (s, 3H), 4.45 (s, 2H), 7.09-7.16 (m, 2H), 7.30 (m, 1H), 7.35 (dd, J=4.6, 1.5 Hz, 2H), 7.43 (m, 1H), 7.83 (s, 1H), 7.88 (d, J=7.0 Hz, 1H), 8.49 (dd, J=4.6, 1.5 Hz, 2H), 8.52 (dd, J=4.9, 1.8 Hz, 1H)

N-(4-Bromo-3-methylphenyl)-2-(4-pyridylmethylthio)pyridine-3-carboxamide

Compound No. 1-81

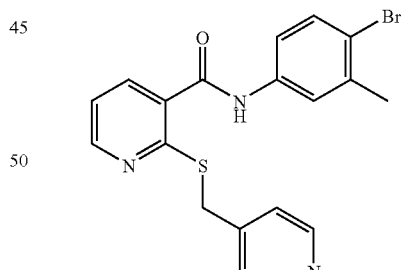

¹H-NMR (500 MHz, CDCl₃)

δ 2.41 (s, 3H), 4.46 (s, 2H), 7.15 (dd, J=7.6, 4.9 Hz, 1H), 7.29 (m, 1H), 7.35 (dd, J=4.3, 1.5 Hz, 2H), 7.50 (d, J=8.6 Hz,

1H), 7.57 (s, 1H), 7.88-7.94 (m, 2H), 8.50 (dd, J=4.3, 1.5 Hz, 2H), 8.55 (dd, J=4.9, 1.8 Hz, 1H)

N-(3-Hydroxy-4-methylphenyl)-2-(4-pyridylmethylthio)pyridine-3-carboxamide

Compound No. 1-82

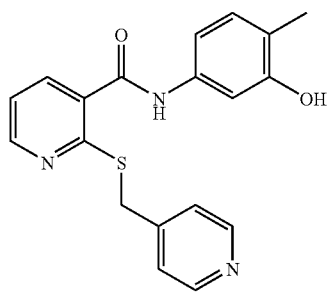

¹H-NMR (400 MHz, DMSO-d₆)

δ 2.07 (s, 3H), 4.41 (s, 2H), 6.94 (d, J=8.3 Hz, 1H), 6.98 (d, J=8.3 Hz, 1H), 7.27 (dd, J=7.8, 4.9 Hz, 1H), 7.35 (s, 1H), 7.40 (dd, J=4.4, 1.5 Hz, 2H), 7.91 (dd, J=7.8, 1.9 Hz, 1H), 8.45 (dd, J=4.4, 1.5 Hz, 2H), 8.57 (dd, J=4.9, 1.9 Hz, 1H), 9.36 (s, 1H), 10.27 (s, 1H)

N-(3-Fluoro-5-trifluoromethylphenyl)-2-(4-pyridylmethylthio)pyridine-3-carboxamide Compound No. 1-83

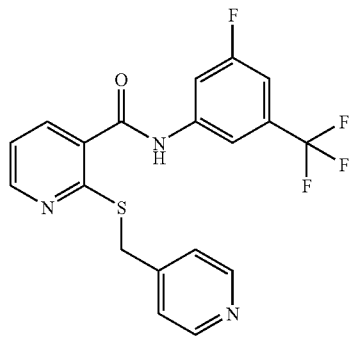

¹H-NMR (400 MHz, CDCl₃)

δ 4.48 (s, 2H), 7.10-7.20 (m, 2H), 7.33 (dd, J=4.6, 1.5 Hz, 2H), 7.55 (s, 1H), 7.83 (d, J=Hz, 1H), 7.92 (dd, J=7.6, 1.8 Hz, 1H), 8.38 (s, 1H), 8.45 (d, J=5.9 Hz, 2H), 8.57 (dd, J=5.9, 1.8 Hz, 1H)

N-(3,6-Dichlorophenyl)-2-(4-pyridylmethylthio)pyridine-3-carboxamide

Compound No. 1-84

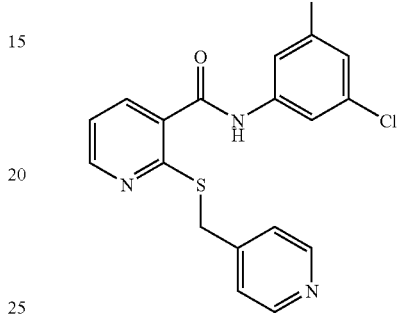

¹H-NMR (500 MHz, CDCl₃)

δ 4.47 (s, 2H), 7.14-7.18 (m, 2H), 7.33 (d, J=5.8 Hz, 2H), 7.59 (d, J=1.5 Hz, 2H), 7.89 (dd, J=7.6, 1.8 Hz, 1H), 8.14 (s, 1H), 8.47 (d, J=5.8 Hz, 2H), 8.55 (dd, J=4.9, 1.8 Hz, 1H)

N-(5-Chloro-2,4-dimethoxyphenyl)-2-(4-pyridylmethylthio)pyridine-3-carboxamide

Compound No. 1-85

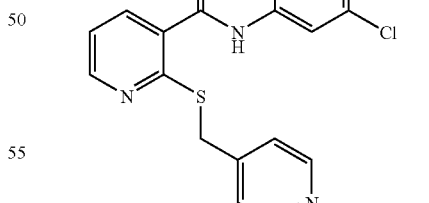

¹H-NMR (400 MHz, DMSO-d₆)

δ 3.86 (s, 3H), 3.90 (s, 3H), 4.40 (s, 2H), 6.87 (s, 1H), 7.26 (dd, J=7.1, 4.4 Hz, 1H), 7.40 (d, J=4.5, 1.7 Hz, 2H), 7.76 (s,

1H), 7.96 (d, J=7.1 Hz, 1H), 8.46 (dd, J=4.5, 1.7 Hz, 2H), 8.57 (d, J=2.9 Hz, 1H), 9.73 (s, 1H)

2-(4-Pyridylmethylthio)-N-(3,4,5-trimethoxyphenyl)pyridine-3-carboxamide

Compound No. 1-86

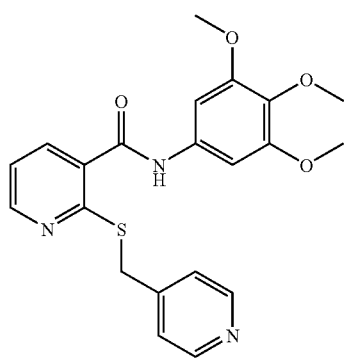

$^1$H-NMR (400 MHz, DMSO-d$_6$)

δ 3.63 (s, 3H), 3.75 (s, 6H), 4.41 (s, 2H), 7.12 (s, 2H), 7.29 (dd, J=7.6, 4.8 Hz, 1H), 7.39-7.41 (m, 2H), 7.95 (dd, J=7.6, 1.6 Hz, 1H), 8.44-8.47 (m, 2H), 8.59 (dd, J=4.8, 1.6 Hz, 1H), 10.39 (s, 1H)

N-(4-Chlorophenyl)-2-(4-pyridylmethylthio)benzamide

Compound No. 11-87

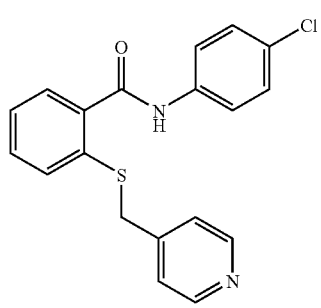

$^1$H-NMR (400 MHz, DMSO-d$_6$)

δ 4.26 (s, 2H), 7.29 (td, J=7.5, 1.2 Hz, 1H), 7.36 (dd, J=4.5, 1.6 Hz, 2H), 7.40-7.55 (m, 3H), 7.47 (dd, J=8.0, 0.9 Hz, 1H), 7.52 (dd, J=7.5, 1.2 Hz, 1H), 7.76 (d, J=8.7 Hz, 2H), 8.45 (dd, J=4.5, 1.6 Hz, 2H), 10.51 (s, 1H)

N-(4-Methoxyphenyl)-2-(4-pyridylmethylthio)benzamide

Compound No. 1-88

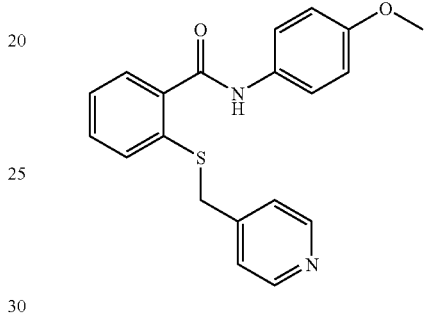

$^1$H-NMR (400 MHz, DMSO-d$_6$)

δ 3.74 (s, 3H), 4.25 (s, 2H), 6.92 (d, J=9.0 Hz, 2H), 7.28 (m, 1H), 7.30-7.50 (m, 5H), 7.63 (d, J=9.0 Hz, 2H), 8.40-8.50 (m, 2H), 10.22 (s, 1H)

N-(4-tert-Butylphenyl)-2-(4-pyridylmethylthio)benzamide

Compound No. 1-89

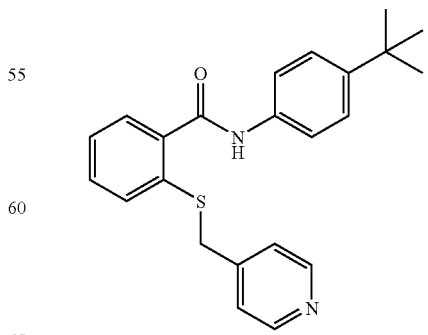

$^1$H-NMR (400 MHz, DMSO-d$_6$)

δ 1.27 (s, 9H), 4.25 (s, 2H), 7.26-7.52 (m, 8H), 7.63 (d, J=9.5 Hz, 2H), 8.45 (dd, J=4.4, 1.5 Hz, 2H), 10.28 (s, 1H)

N-(3-Chlorophenyl)-2-(4-pyridylmethylthio)benzamide

Compound No. 1-90

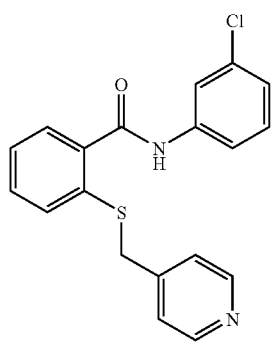

¹H-NMR (500 MHz, DMSO-d₆)

δ 4.26 (s, 2H), 7.16 (ddd, J=8.2, 2.1, 0.9 Hz, 1H), 7.30 (td, J=7.8, 1.2 Hz, 1H), 7.35 (d, J=4.3 Hz, 2H), 7.38 (d, J=8.2 Hz, 1H), 7.43 (td, J=7.8, 1.5 Hz, 1H), 7.47 (dd, J=7.8, 0.9 Hz, 1H), 7.53 (dd, J=7.8, 1.5 Hz, 1H), 7.60 (d, J=8.2 Hz, 1H), 7.92 (s, 1H), 8.45 (dd, J=4.3, 1.5 Hz, 2H), 10.54 (s, 1H)

N-(4-Dimethylaminophenyl)-2-(4-pyridylmethylthio)benzamide

Compound No. 1-91

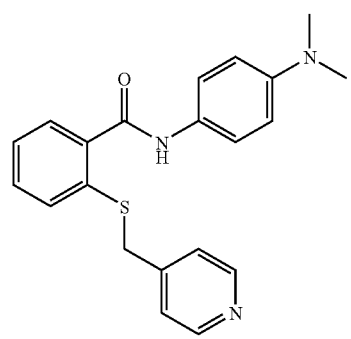

¹H-NMR (500 MHz, DMSO-d₆)

δ 2.86 (s, 6H), 4.24 (s, 2H), 6.71 (d, J=8.8 Hz, 2H), 7.27 (td, J=7.5, 1.2 Hz, 1H), 7.37 (m, 3H), 7.43 (d, J=7.5 Hz, 1H), 7.48 (dd, J=7.5, 1.9 Hz, 1H), 7.53 (d, J=8.8 Hz, 2H), 8.46 (dd, J=4.6, 1.5 Hz, 2H), 10.03 (s, 1H)

N-(3-Isopropylphenyl)-2-(4-pyridylmethylthio)benzamide

Compound No. 1-92

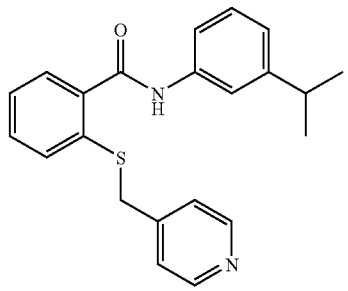

¹H-NMR (400 MHz, DMSO-d₆)

δ 1.20 (d, J=7.1 Hz, 6H), 2.85 (m, 1H), 4.25 (s, 2H), 6.98 (d, J=7.6 Hz, 1H), 7.21-7.33 (m, 2H), 7.36 (dd, J=4.4, 1.5 Hz, 2H), 7.37-7.48 (m, 2H), 7.49-7.57 (m, 2H), 7.63 (s, 1H), 8.45 (dd, J=4.4, 1.5 Hz, 2H), 10.28 (s, 1H)

N-(3,4-Dimethoxyphenyl)-2-(4-pyridylmethylthio)benzamide

Compound No. 1-93

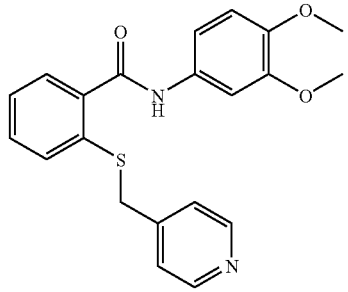

¹H-NMR (400 MHz, DMSO-d₆)

δ 3.73 (s, 6H), 4.25 (s, 2H), 6.92 (d, J=8.5 Hz, 1H), 7.20-7.30 (m, 2H), 7.30-7.55 (m, 6H), 8.46 (d, J=6.1 Hz, 2H), 10.21 (s, 1H)

2-(4-Pyridylmethylthio)-N-(3,4,5-trimethoxyphenyl)benzamide

Compound No. 1-94

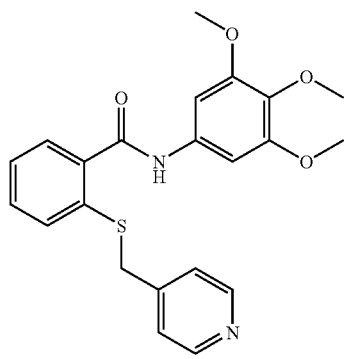

$^1$H-NMR (400 MHz, DMSO-$d_6$)

δ 3.63 (s, 3H), 3.75 (s, 6H), 4.26 (s, 2H), 7.16 (s, 2H), 7.29 (dd, J=7.3, 1.2 Hz, 1H), 7.34 (dd, J=4.4, 1.7 Hz, 2H), 7.35-7.55 (m, 3H), 8.46 (d, J=4.4, 1.7 Hz, 2H), 10.26 (s, 1H)

2-(4-Pyridylmethylthio)-N-(3-quinolyl)benzamide

Compound No. 1-95

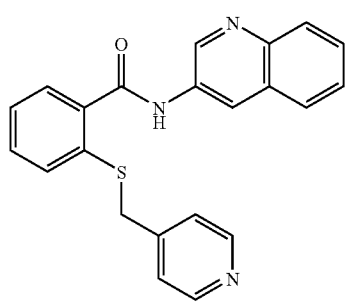

$^1$H-NMR (400 MHz, DMSO-$d_6$)

δ 4.29 (s, 2H), 7.30-7.70 (m, 8H), 7.98 (d, J=8.3 Hz, 2H), 8.46 (dd, J=4.4, 1.5 Hz, 2H), 8.86 (s, 1H), 9.02 (d, J=2.2 Hz, 1H), 10.86 (s, 1H)

N-(4-Chlorophenyl)-5-fluoro-2-(4-pyridylmethylthio)benzamide

Compound No. 1-96

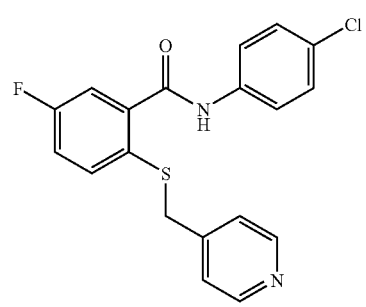

$^1$H-NMR (400 MHz, DMSO-$d_6$)

δ 4.22 (s, 2H), 7.28 (m, 1H), 7.29 (dd, J=4.4, 1.7 Hz, 2H), 7.42 (dd, J=8.8, 2.0 Hz, 2H), 7.43-7.50 (m, 2H), 7.74 (d, J=8.8 Hz, 2H), 8.44 (dd, J=4.4, 1.7 Hz, 2H), 10.50 (s, 1H)

N-(4-Chlorophenyl)-4-(4-pyridylmethylthio)pyridine-3-carboxamide

Compound No. 1-97

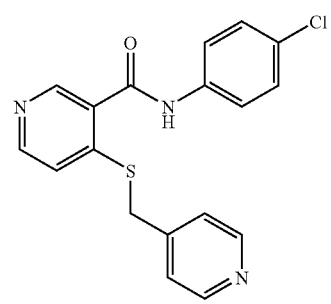

$^1$H-NMR (400 MHz, DMSO-$d_6$)

δ 4.39 (s, 2H), 7.42 (d, J=8.8 Hz, 2H), 7.46 (dd, J=4.6, 1.5 Hz, 2H), 7.51 (d, J=5.4 Hz, 1H), 7.74 (d, J=8.8 Hz, 2H), 8.50 (d, J=5.4 Hz, 1H), 8.51 (dd, J=4.6, 1.5 Hz, 2H), 8.67 (s, 1H), 10.70 (s, 1H)

N-(4-Chlorophenyl)-3-(4-pyridylmethylthio)pyridine-2-carboxamide

Compound No. 1-98

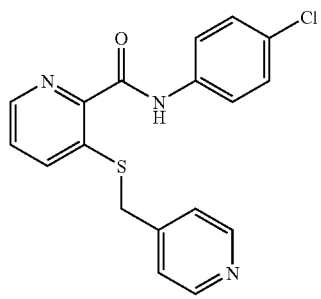

¹H-NMR (400 MHz, DMSO-d₆)

δ 4.31 (s, 2H), 7.41 (dd, J=8.8, 2.0 Hz, 2H), 7.46 (dd, J=4.4, 1.5 Hz, 2H), 7.56 (dd, J=8.2, 4.5 Hz, 1H), 7.88 (d, J=8.8 Hz, 2H), 7.98 (dd, J=8.2, 1.3 Hz, 1H), 8.46 (dd, J=4.5, 1.3 Hz, 1H), 8.51 (dd, J=4.4, 1.5 Hz, 2H), 10.75 (s, 1H)

N-(4-Chloro-3-methylphenyl)-2-(4-pyridylmethylthio)benzamide

Compound No. 1-99

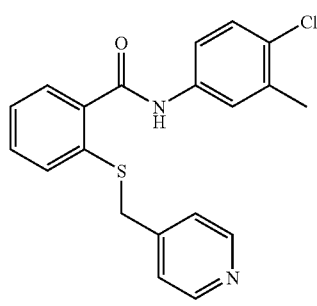

¹H-NMR (400 MHz, DMSO-d₆)

δ 2.32 (s, 3H), 4.26 (s, 2H), 7.27-7.58 (m, 8H), 7.76 (s, 1H), 8.46 (dd, J=4.4, 1.7 Hz, 2H), 10.40 (s, 1H)

N-(3-Chloro-4-methylphenyl)-2-(4-pyridylmethylthio)benzamide

Compound No. 1-100

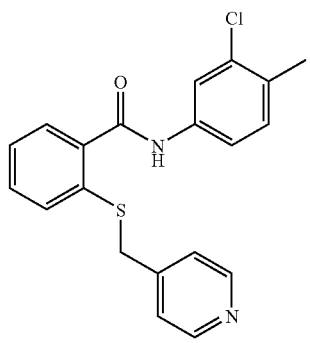

¹H-NMR (50 MHz, DMSO-d₆)

δ 2.30 (s, 3H), 4.25 (s, 2H), 7.28-7.53 (m, 8H), 7.91 (d, J=1.5 Hz, 1H), 8.45 (dd, J=5.7, 1.7 Hz, 2H), 10.40 (s, 1H)

N-(2,3-Dimethylphenyl)-2-(4-pyridylmethylthio)benzamide

Compound No. 1-101

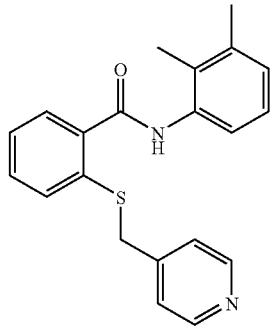

¹H-NMR (400 MHz, DMSO-d₆)

123

δ 2.16 (s, 3H), 2.27 (s, 3H), 4.27 (s, 2H), 7.06-7.47 (m, 8H), 7.57 (m, 1H), 8.47 (dd, J=4.5, 1.6 Hz, 2H), 9.86 (s, 1H)

N-(5-Chloro-2,4-dimethoxyphenyl)-2-(4-pyridylmethylthio)benzamide

Compound No. 1-102

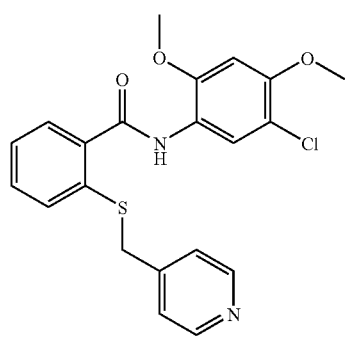

$^1$H-NMR (500 MHz, DMSO-$d_6$)

δ 3.87 (s, 3H), 3.90 (s, 3H), 4.25 (s, 2H), 6.88 (s, 1H), 7.28 (t, J=7.2 Hz, 1H), 7.36 (dd, J=4.3, 1.5 Hz, 2H), 7.37-7.43 (m, 2H), 7.56 (d, J=7.2 Hz, 1H), 7.84 (s, 1H), 8.46 (dd, J=4.3, 1.5 Hz, 2H), 9.48 (s, 1H)

N-(3-Bromophenyl)-2-(4-pyridylmethylthio)benzamide

Compound No. 1-103

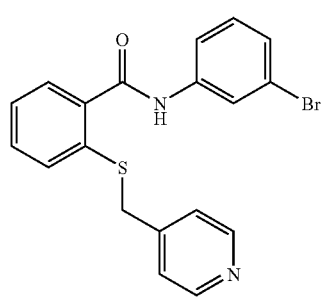

$^1$H-NMR (500 MHz, DMSO-$d_6$)

124

δ 4.26 (s, 2H), 7.28-7.48 (m, 7H), 7.53 (dd, J=7.6, 1.2 Hz, 1H), 7.64 (d, J=7.3 Hz, 1H), 8.07 (s, 1H), 8.45-8.46 (m, 2H), 10.53 (s, 1H)

N-(3,5-Dimethylphenyl)-2-(4-pyridylmethylthio)benzamide

Compound No. 1-104

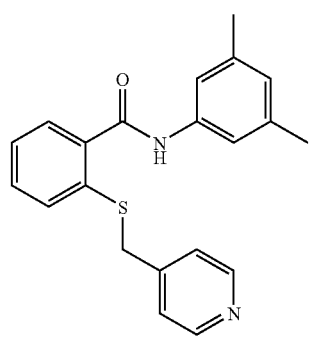

$^1$H-NMR (500 MHz, DMSO-$d_6$)

δ 2.25 (s, 6H), 4.25 (s, 2H), 6.74 (s, 1H), 7.28 (dt, J=7.3, 1.2 Hz, 1H), 7.35-7.49 (m, 7H), 8.45-8.46 (m, 2H), 10.19 (s, 1H)

N-(3-Dimethylaminophenyl)-2-(4-pyridylmethylthio)benzamide

Compound No. 1-105

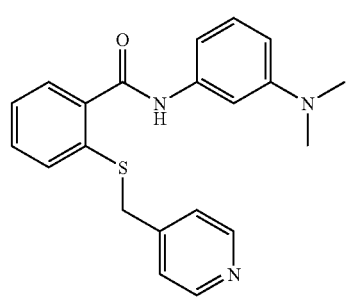

$^1$H-NMR (500 MHz, DMSO-$d_6$)

δ 2.88 (s, 6H), 4.25 (s, 2H), 6.48 (dd, J=8.1, 1.7 Hz, 1H), 7.06-7.13 (m, 2H), 7.17 (s, 1H), 7.26-7.50 (m, 6H), 8.45-8.46 (m, 2H), 10.13 (s, 1H)

N-(3,5-Dimethylphenyl)-2-(4-pyridylmethylthio)pyridine-3-carboxamide

Compound No. 1-106

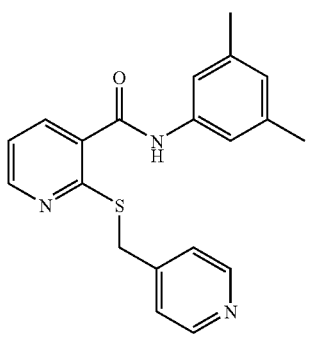

¹H-NMR (500 MHz, DMSO-d₆)

δ 2.50 (s, 6H), 4.41 (s, 2H), 6.76 (s, 1H), 7.28 (dd, J=7.6, 4.9 Hz, 1H), 7.32 (s, 2H), 7.39-7.40 (m, 2H), 7.92 (dd, J=7.6, 1.8 Hz, 1H), 8.45-8.46 (m, 2H), 8.57-8.58 (m, 1H), 10.30 (s, 1H)

N-(3-Dimethylaminophenyl)-2-(4-pyridylmethylthio)pyridine-3-carboxamide

Compound No. 1-107

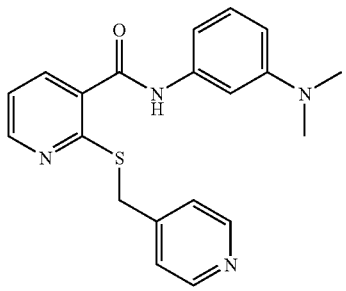

¹H-NMR (500 MHz, DMSO-d₆)

δ 2.88 (s, 6H), 4.41 (s, 2H), 6.49 (m, 1H), 7.03 (d, J=7.9 Hz, 1H), 7.11-7.14 (m, 2H), 7.28 (dd, J=7.6, 4.9 Hz, 1H), 7.39-7.41 (m, 2H), 7.93 (dd, J=7.6, 1.5 Hz, 1H), 8.44-8.46 (m, 2H), 8.57 (dd, J=4.9, 1.8 Hz, 1H), 10.25 (s, 1H)

N-(4-Bromo-3-trifluoromethylphenyl)-2-(4-pyridylmethylthio)pyridine-3-carboxamide Compound No. 1-108

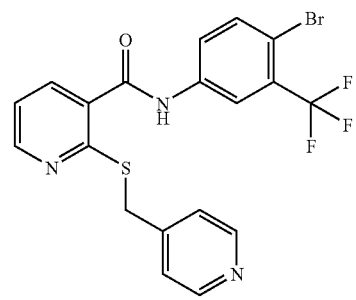

¹H-NMR (400 MHz, DMSO-d₆)

δ 4.43 (s, 2H), 7.32 (dd, J=7.6, 4.6 Hz, 1H), 7.40 (dd, J=7.4, 1.5 Hz, 2H), 7.85-7.93 (m, 2H), 8.04 (dd, J=7.6, 1.7 Hz, 1H), 8.27 (d, J=1.7 Hz, 1H), 8.46 (dd, J=4.4, 1.5 Hz, 2H), 8.62 (dd, J=4.6, 1.7 Hz, 1H), 10.88 (s, 1H)

N-(4-Fluoro-3-methylphenyl)-2-(4-pyridylmethylthio)pyridine-3-carboxamide

Compound No. 1-109

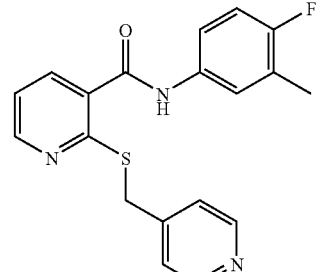

¹H-NMR (400 MHz, DMSO-d₆)

δ 2.23 (s, 3H), 4.42 (s, 2H), 7.12 (t, J=9.3 Hz, 1H), 7.29 (dd, J=7.6, 4.9 Hz, 1H), 7.40 (dd, J=4.4, 1.7 Hz, 2H), 7.46-7.53

(m, 1H), 7.63 (dd, J=6.8, 2.2 Hz, 1H), 7.95 (dd, J=7.6, 1.7 Hz, 1H), 8.45 (dd, J=4.4, 1.7 Hz, 2H), 8.59 (dd, J=4.9, 1.7 Hz, 1H), 10.44 (s, 1H)

N-(3-Fluoro-4-methylphenyl)-2-(4-pyridylmethylthio)pyridine-3-carboxamide

Compound No. 1-110

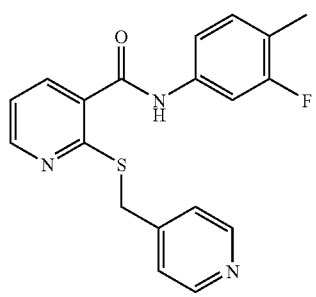

$^1$H-NMR (400 MHz, DMSO-$d_6$)

δ 2.23 (d, J=1.7 Hz, 3H), 4.42 (s, 2H), 7.12 (t, J=9.1 Hz, 1H), 7.29 (dd, J=7.6, 4.8 Hz, 1H), 7.40 (dd, J=4.4, 1.7 Hz, 2H), 7.49 (m, 1H), 7.63 (dd, J=6.8, 2.2 Hz, 1H), 7.95 (dd, J=7.6, 1.7 Hz, 1H), 8.46 (dd, J=4.4, 1.7 Hz, 2H), 8.59 (dd, J=4.8, 1.7 Hz, 1H), 10.45 (s, 1H)

N-(4-Bromo-3-methylphenyl)-2-(4-pyridylmethylthio)benzamide

Compound No. 1-111

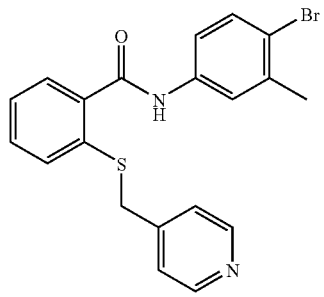

$^1$H-NMR (500 MHz, DMSO-$d_6$)

δ 2.34 (s, 3H), 4.25 (s, 2H), 7.29 (ddd, J=7.6, 7.3, 0.9 Hz, 1H), 7.35 (dd, J=4.6, 1.5 Hz, 2H), 7.41 (ddd, J=8.2, 7.6, 1.5 Hz, 1H), 7.44-7.56 (m, 4H), 7.75 (s, 1H), 8.45 (dd, J=4.6, 1.5 Hz, 2H), 10.42 (s, 1H)

N-(4-n-Propylphenyl)-2-(4-pyridylmethylthio)benzamide

Compound No. 1-112

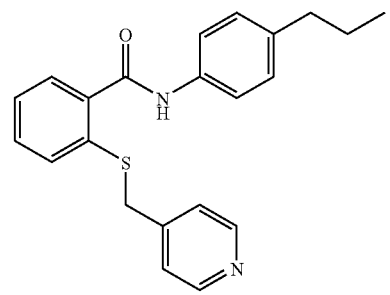

$^1$H-NMR (500 MHz, DMSO-$d_6$)

δ 0.89 (t, J=7.3 Hz, 3H), 1.57 (dt, J=7.6, 7.3 Hz, 2H), 2.52 (t, J=7.6 Hz, 2H), 4.25 (s, 2H), 7.15 (d, J=8.2 Hz, 2H), 7.28 (ddd, J=7.6, 7.3, 0.9 Hz, 1H), 7.36 (dd, J=4.6, 1.5 Hz, 2H), 7.40 (ddd, J=7.9, 7.6, 0.9 Hz, 1H), 7.45 (dd, J=7.9, 0.9 Hz, 1H), 7.50 (d, J=6.7 Hz, 1H), 7.62 (d, J=8.2 Hz, 2H), 8.45 (dd, J=4.6, 1.5 Hz, 2H), 10.27 (s, 1H)

N-(4-Methyl-3-nitrophenyl)-2-(4-pyridylmethylthio)pyridine-3-carboxamide

Compound No. 1-113

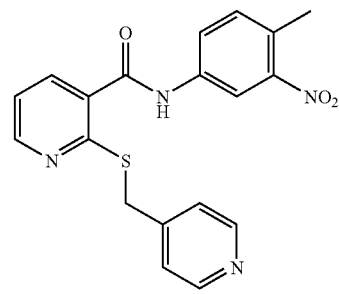

$^1$H-NMR (400 MHz, DMSO-$d_6$)

δ 2.50 (s, 3H), 4.42 (s, 2H), 7.32 (dd, J=7.6, 4.9 Hz, 1H), 7.40 (dd, J=4.4, 1.7 Hz, 2H), 7.50 (d, J=8.3 Hz, 1H), 7.85 (dd,

J=8.3, 2.2 Hz, 1H), 8.03 (dd, J=7.6, 1.7 Hz, 1H), 8.45 (dd, J=4.4, 1.5 Hz, 2H), 8.48 (d, J=2.2 Hz, 1H), 8.61 (dd, J=4.9, 1.7 Hz, 1H), 10.83 (s, 1H)

2-(4-Pyridylmethylthio)-N-(3-trifluoromethylphenyl)pyridine-3-carboxamide

Compound No. 1-114

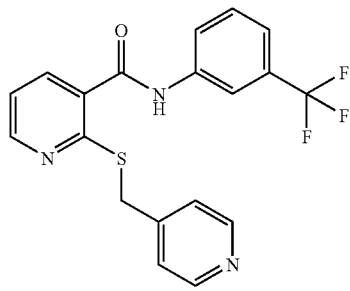

¹H-NMR (400 MHz, DMSO-d₆)

δ 4.43 (s, 2H), 7.32 (dd, J=7.6, 4.9 Hz, 1H), 7.41 (dd, J=4.4, 1.5 Hz, 2H), 7.48 (d, J=7.6 Hz, 1H), 7.61 (t, J=8.1 Hz, 1H), 7.91 (d, J=8.1 Hz, 1H), 8.03 (dd, J=7.6, 1.7 Hz, 1H), 8.19 (s, 1H), 8.46 (dd, J=4.4, 1.5 Hz, 2H), 8.62 (dd, J=4.9, 1.7 Hz, 1H), 10.81 (s, 1H)

N-[3-(1-Ethynyl)phenyl]-2-(4-pyridylmethylthio)pyridine-3-carboxamide

Compound No. 1-115

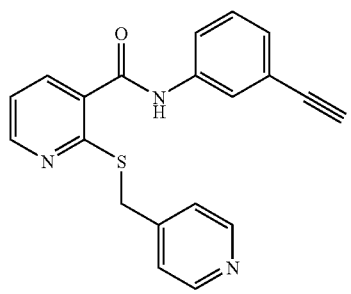

¹H-NMR (400 MHz, DMSO-d₆)

δ 4.21 (s, 1H), 4.23 (s, 2H), 7.23 (dt, J=7.6, 1.2 Hz, 1H), 7.30 (dd, J=7.8, 4.9 Hz, 1H), 7.36 (t, J=8.1 Hz, 1H), 7.40 (dd, J=4.4, 1.7 Hz, 2H), 7.69 (d, J=8.1 Hz, 1H), 7.87 (s, 1H), 7.98 (dd, J=7.6, 1.7 Hz, 1H), 8.45 (dd, J=4.4, 1.7 Hz, 2H), 8.60 (dd, J=4.9, 1.7 Hz, 1H), 10.57 (s, 1H)

N-[4-(N'-n-Propylureido)phenyl]-2-(4-pyridylmethylthio)pyridine-3-carboxamide

Compound No. 1-116

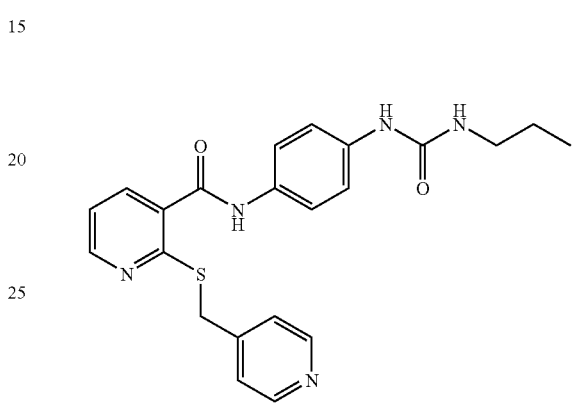

¹H-NMR (400 MHz, DMSO-d₆)

δ 0.87 (t, J=7.3 Hz, 3H), 1.43 (q, J=7.3 Hz, 2H), 3.00-3.06 (m, 2H), 4.40 (s, 2H), 6.13 (m, 1H), 7.26 (d, J=4.9 Hz, 2H), 7.25-7.40 (m, 3H), 7.40 (d, J=4.6 Hz, 2H), 7.53 (d, J=8.8 Hz, 2H), 7.93 (dd, J=7.6, 1.5 Hz, 1H), 8.45 (d, J=5.9 Hz, 2H), 10.30 (s, 1H)

4-Chloro-N-(4-chlorophenyl)-2-(4-pyridylmethylthio)benzamide

Compound No. 1-117

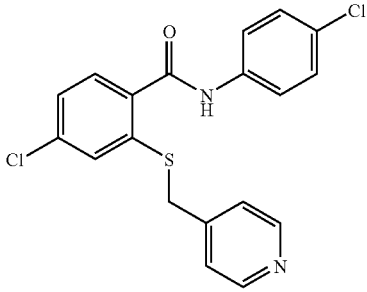

¹H-NMR (500 MHz, DMSO-d₆)

δ 4.81 (s, 2H), 7.28-7.33 (m, 4H), 7.39 (dd, J=5.2, 2.4 Hz, 1H), 7.52 (dd, J=8.6, 2.4 Hz, 1H), 7.58 (dd, J=6.8, 1.8 Hz, 2H), 8.27 (d, J=8.6 Hz, 1H), 8.60 (dd, J=4.6, 1.5 Hz, 2H), 10.07 (s, 1H)

N-(2,2-Dimethylpropyl)-2-(4-pyridylmethylthio)benzamide

Compound No. 1-118

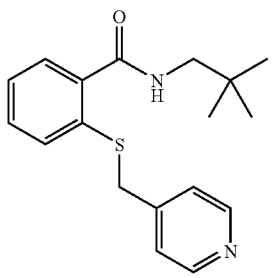

¹H-NMR (400 MHz, DMSO-d₆)

δ 0.91 (s, 9H), 3.04 (d, J=6.4 Hz, 2H), 4.22 (s, 2H), 7.21 (td, J=7.3, 1.7 Hz, 1H), 7.34 (m, 5H), 8.29 (t, J=6.4 Hz, 1H), 8.46 (dd, J=4.4, 1.8 Hz, 2H).

N-(3-tert-Butylphenyl)-2-(4-pyridylmethylthio)pyridine-3-carboxamide

Compound No. 1-119

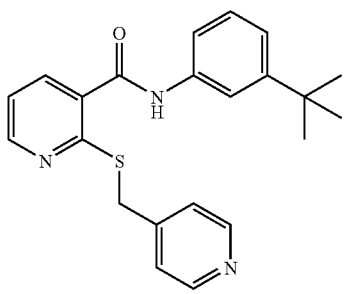

¹H-NMR (500 MHz, DMSO-d₆)

δ 1.28 (s, 9H), 4.42 (s, 2H), 7.15 (ddd, J=7.6, 1.8, 0.9 Hz, 1H), 7.25-7.30 (m, 2H), 7.40 (dd, J=4.5, 1.6 Hz, 2H), 7.57 (d, J=7.9 Hz, 1H), 7.71 (s, 1H), 7.96 (dd, J=7.6, 1.8 Hz, 1H), 8.45 (dd, J=4.5, 1.6 Hz, 2H), 8.58 (dd, J=4.8, 1.8 Hz, 1H), 10.39 (s, 1H)

2-(4-Pyridylmethylthio)-N-(3-trifluoromethoxyphenyl)benzamide

Compound No. 1-120

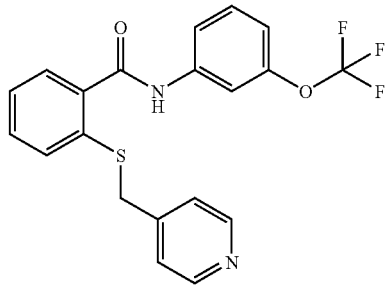

¹H-NMR (500 MHz, CDCl₃)

δ 4.03 (s, 2H), 7.03 (ddd, J=7.0, 2.0, 0.9 Hz, 1H), 7.08 (dd, J=4.6, 1.8 Hz, 2H), 7.32-7.40 (m, 4H), 7.47 (d, J=7.6 Hz, 1H), 7.68 (s, 1H), 7.74 (dd, J=7.0, 0.9 Hz, 1H), 8.42 (dd, J=4.6, 1.8 Hz, 2H), 8.48 (s, 1H)

2-(4-Pyridylmethylthio)-N-(4-trifluoromethoxyphenyl)benzamide

Compound No. 1-121

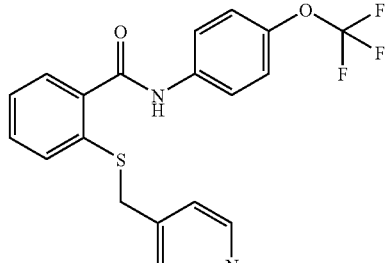

¹H-NMR (400 MHz, DMSO-d₆)

δ 4.26 (s, 2H), 7.30 (td, J=7.3, 1.2 Hz, 1H), 7.33-7.38 (m, 4H), 7.43 (td, J=7.1, 1.5 Hz, 1H), 7.48 (dd, J=8.0, 1.1 Hz, 1H), 7.53 (dd, J=7.6, 1.5 Hz, 1H), 7.83 (d, J=9.0 Hz, 2H), 8.45 (dd, J=4.4, 1.7 Hz, 2H), 10.56 (s, 1H)

N-(3,5-Di-tert-butylphenyl)-2-(4-pyridylmethylthio)pyridine-3-carboxamide

Compound No. 1-122

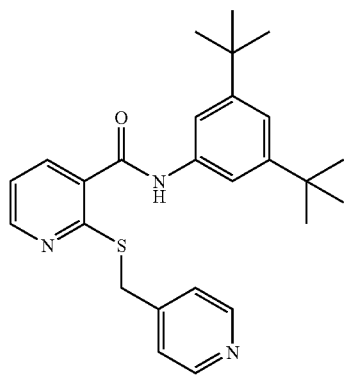

¹H-NMR (400 MHz, DMSO-d₆)
δ 1.28 (s, 18H), 4.41 (s, 2H), 7.16 (t, J=1.7 Hz, 1H), 7.28 (dd, J=7.6, 4.9 Hz, 1H), 7.39-7.41 (m, 2H), 7.59 (d, J=1.2 Hz, 2H), 7.96 (dd, J=7.6, 1.5 Hz, 1H), 8.45 (dd, J=4.4, 1.7 Hz, 2H), 8.58 (dd, J=4.9, 1.7 Hz, 1H), 10.33 (s, 1H)

N-(3,5-Dimethoxycarbonylphenyl)-2-(4-pyridylmethylthio)pyridine-3-carboxamide

Compound No. 1-123

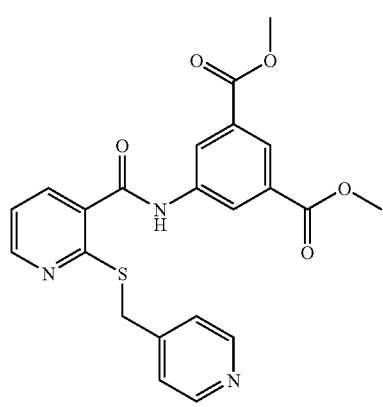

¹H-NMR (500 MHz, DMSO-d₆)

δ 3.91 (s, 6H), 4.43 (s, 2H), 7.32 (dd, J=7.6, 4.9 Hz, 1H), 7.41 (dd, J=4.4, 1.7 Hz, 2H), 8.08 (dd, J=7.7, 1.8 Hz, 1H), 8.23 (t, J=1.5 Hz, 1H), 8.46 (dd, J=4.4, 1.7 Hz, 2H), 8.61-8.62 (m, 3H), 10.89 (s, 1H)

N-(3,5-Dichlorophenyl)-2-(4-pyridylmethylthio)benzamide

Compound No. 1-124

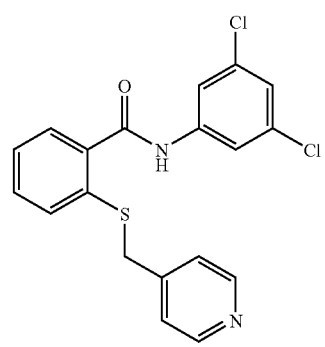

¹H-NMR (400 MHz, DMSO-d₆)
δ 4.26 (s, 2H), 7.29-7.78 (m, 7H), 7.80 (d, J=1.7 Hz, 2H), 8.46 (dd, J=5.4, 1.7 Hz, 2H), 10.70 (s, 1H)

N-(3-Chloro-4-fluorophenyl)-2-(4-pyridylmethylthio)benzamide

Compound No. 1-125

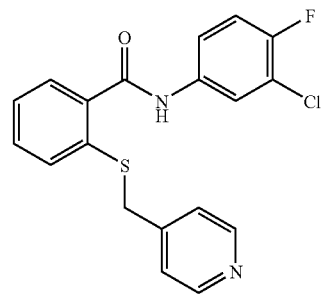

¹H-NMR (400 MHz, DMSO-d₆)

δ 4.26 (s, 2H), 7.28-7.64 (m, 8H), 8.04 (dd, J=6.8, 2.4 Hz, 1H), 8.46 (dd, J=4.4, 1.5 Hz, 2H), 10.58 (s, 1H)

N-(3-Methoxy-5-trifluoromethylphenyl)-2-(4-pyridylmethylthio)pyridine-3-carboxamide Compound No. 1-126

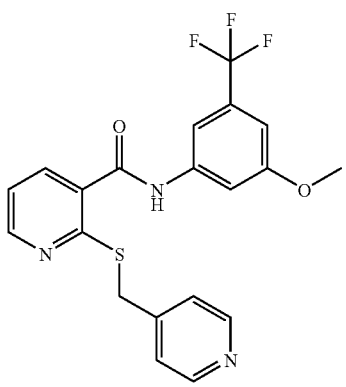

¹H-NMR (500 MHz, DMSO-d₆)
δ 3.83 (s, 3H), 4.43 (s, 2H), 7.01 (d, J=1.5 Hz, 1H), 7.32 (dd, J=7.6, 4.9 Hz, 1H), 7.40 (dd, J=4.3, 1.5 Hz, 2H), 7.57 (s, 1H), 7.74 (s, 1H), 8.02 (dd, J=7.6, 1.8 Hz, 1H), 8.45 (dd, J=4.3, 1.5 Hz, 2H), 8.62 (dd, J=4.9, 1.8 Hz, 1H), 10.74 (s, 1H)

N-[3,5-Bis(trifluoromethyl)phenyl]-2-(4-pyridylmethylthio)pyridine-3-carboxamide Compound No. 1-127

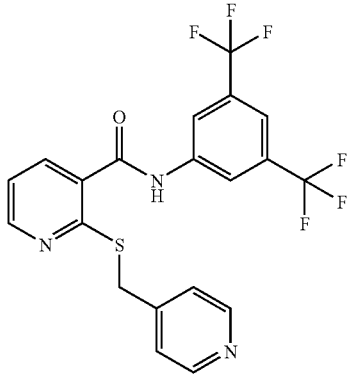

¹H-NMR (500 MHz, DMSO-d₆)
δ 4.43 (s, 2H), 7.35 (dd, J=7.8, 4.8 Hz, 1H), 7.41 (dd, J=4.6, 1.5 Hz, 2H), 7.86 (s, 1H), 8.10 (dd, J=7.8, 1.8 Hz, 1H), 8.39 (s, 2H), 8.46 (dd, J=4.6, 1.5 Hz, 2H), 8.64 (dd, J=4.8, 1.8 Hz, 1H), 11.08 (s, 1H)

N-(4-Nitrophenyl)-2-(4-pyridylmethylthio)pyridine-3-carboxamide

Compound No. 1-128

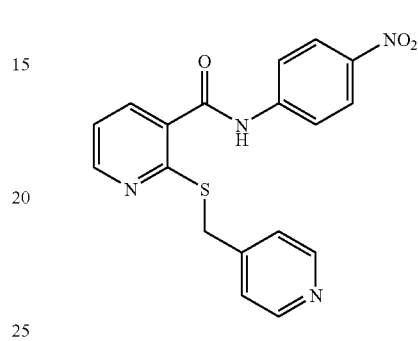

¹H-NMR (400 MHz, DMSO-d₆)
δ 4.43 (s, 2H), 7.32 (dd, J=7.8, 4.9 Hz, 1H), 7.40 (dd, J=4.4, 1.7 Hz, 2H), 7.96 (d, J=9.1 Hz, 2H), 8.05 (dd, J=7.6, 1.7 Hz, 1H), 8.28 (d, J=9.1 Hz, 2H), 8.45 (dd, J=4.4, 1.7 Hz, 2H), 8.63 (dd, J=4.9, 1.7 Hz, 1H), 11.05 (s, 1H)

N-(3,5-Dibenzyloxycarbonylphenyl)-2-(4-pyridylmethylthio)pyridine-3-carboxamide

Compound No. 1-129

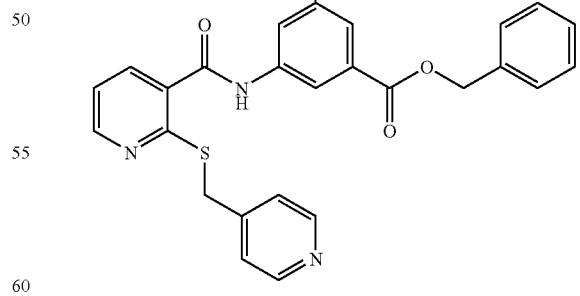

¹H-NMR (400 MHz, DMSO-d₆)
δ 4.42 (s, 2H), 5.40 (s, 4H), 7.31 (dd, J=7.6, 4.9 Hz, 1H), 7.35-7.49 (m, 12H), 8.05 (dd, J=7.6, 1.8 Hz, 1H), 8.28 (t,

J=1.6 Hz, 1H), 8.45 (dd, J=4.4, 1.5 Hz, 2H), 8.61 (dd, J=4.9, 1.7 Hz, 1H), 8.65 (d, J=1.5 Hz, 2H), 10.91 (s, 1H)

N-(3-Ethylphenyl)-2-(4-pyridylmethylthio)pyridine-3-carboxamide

Compound No. 1-130

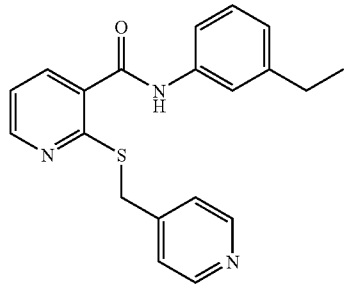

¹H-NMR (400 MHz, DMSO-d₆)

δ 1.18 (t, J=7.6 Hz, 3H), 2.59 (q, J=7.6 Hz, 2H), 4.42 (s, 2H), 6.97 (m, 1H), 7.25 (t, J=7.6 Hz, 1H), 7.28 (dd, J=7.6, 4.9 Hz, 1H), 7.41 (dd, J=4.9, 1.5 Hz, 2H), 7.49 (d, J=7.9 Hz, 1H), 7.58 (s, 1H), 7.95 (dd, J=7.6, 1.5 Hz, 1H), 8.46 (dd, J=4.6, 1.2 Hz, 2H), 8.58 (dd, J=4.9, 1.5 Hz, 1H), 10.40 (s, 1H)

3-Chloro-N-(4-chlorophenyl)-2-(4-pyridylmethylthio)benzamide

Compound No. 1-131

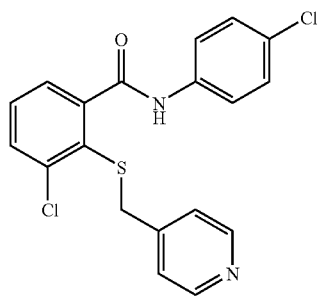

¹H-NMR (400 MHz, DMSO-d₆)

δ 4.60 (s, 2H), 7.27 (dd, J=4.4, 1.7 Hz, 2H), 7.39 (dd, J=6.8, 1.9 Hz, 2H), 7.49-7.53 (m, 2H), 7.64 (dd, J=6.8, 1.9 Hz, 2H), 7.74 (dd, J=6.6, 2.9 Hz, 1H), 8.43 (dd, J=4.4, 1.7 Hz, 2H), 10.44 (s, 1H)

2-(4-Pyridylmethylthio)-N-(2-quinolyl)pyridine-3-carboxamide

Compound No. 1-132

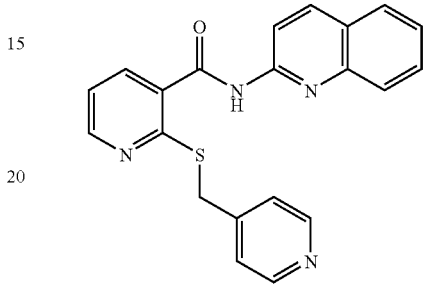

¹H-NMR (500 MHz, DMSO-d₆)

δ 4.43 (s, 2H), 7.28 (dd, J=7.6, 4.9 Hz, 1H), 7.41 (dd, J=4.6, 1.5 Hz, 2H), 7.53 (td, J=7.0, 1.1 Hz, 1H), 7.73 (td, J=7.0, 1.1 Hz, 1H), 7.83 (d, J=8.6 Hz, 1H), 7.96 (d, J=8.6 Hz, 1H), 8.08 (dd, J=7.6, 1.5 Hz, 1H), 8.29 (d, J=9.0 Hz, 1H), 8.42 (d, J=9.0 Hz, 1H), 8.45 (dd, J=4.6, 1.5 Hz, 2H), 8.60 (dd, J=4.9, 1.5 Hz, 1H), 11.37 (s, 1H)

2-(4-Pyridylmethylthio)-N-(5-quinolyl)pyridine-3-carboxamide

Compound No. 1-133

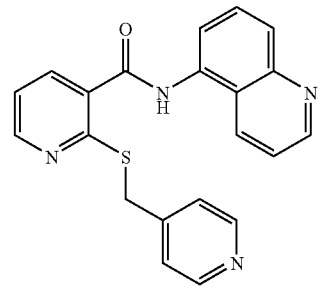

¹H-NMR (500 MHz, DMSO-d₆)

δ 4.46 (s, 2H), 7.35 (t, J=6.5 Hz, 1H), 7.43 (d, J=5.4 Hz, 2H), 7.57 (dd, J=8.6, 4.3 Hz, 1H), 7.79 (m, 2H), 7.95 (d, J=8.3

Hz, 1H), 8.18 (d, J=6.5 Hz, 1H), 8.47 (d, J=5.4 Hz, 2H), 8.51 (d, J=8.3 Hz, 1H), 8.63 (d, J=4.0 Hz, 1H), 8.94 (d, J=2.7 Hz, 1H), 10.69 (s, 1H)

N-(2-Methylquinoline-6-yl)-2-(4-pyridylmethylthio)pyridine-3-carboxamide

Compound No. 1-134

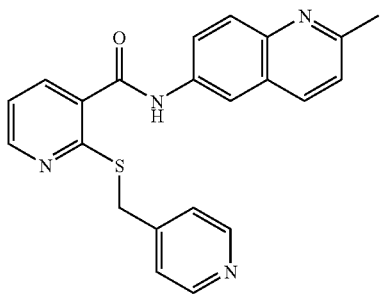

¹H-NMR (500 MHz, DMSO-d₆)

δ 2.64 (s, 3H), 4.44 (s, 2H), 7.32 (dd, J=7.3, 4.9 Hz, 1H), 7.40 (m, 3H), 7.84 (m, 1H), 7.90 (d, J=9.1 Hz, 1H), 8.03 (dd, J=7.6, 1.5 Hz, 1H), 8.22 (d, J=8.6 Hz, 1H), 8.45 (m, 3H), 8.62 (dd, J=4.9, 1.5 Hz, 1H), 10.75 (s, 1H)

2-(4-Pyridylmethylthio)-N-(8-quinolyl)pyridine-3-carboxamide

Compound No. 1-135

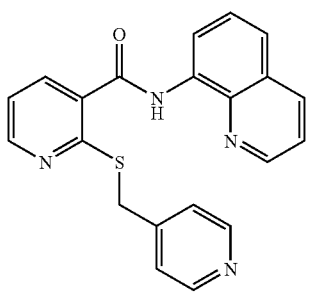

¹H-NMR (500 MHz, DMSO-d₆)

δ 4.46 (s, 2H), 7.36 (dd, J=7.7, 4.9 Hz, 1H), 7.43 (dd, J=4.6, 1.5 Hz, 2H), 7.67-7.68 (m, 2H), 7.78 (dd, J=8.2, 1.2 Hz, 1H), 8.17 (dd, J=7.6, 1.8 Hz, 1H), 8.46-8.47 (m, 2H), 8.66-8.67 (m, 2H), 8.93 (dd, J=4.6, 1.5 Hz, 2H), 10.56 (s, 1H)

N-(5-Indanyl)-2-(4-pyridylmethylthio)pyridine-3-carboxamide

Compound No. 1-136

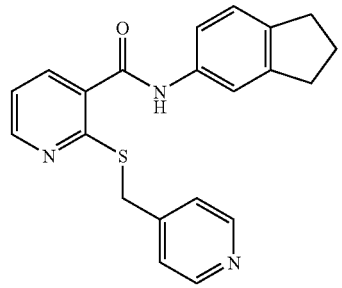

¹H-NMR (500 MHz, DMSO-d₆)

δ 2.01 (t, J=7.6 Hz, 2H), 2.81-2.83 (m, 4H), 4.41 (s, 2H), 7.17 (d, J=8.0 Hz, 1H), 7.28 (dd, J=7.6, 4.8 Hz, 1H), 7.40-7.41 (m, 3H), 7.61 (s, 1H), 7.93 (dd, J=7.6, 1.5 Hz, 1H), 8.45 (dd, J=4.6, 1.5 Hz, 2H), 8.58 (dd, J=4.8, 1.8 Hz, 1H), 10.34 (s, 1H)

N-(3-Chloro-4-trifluoromethoxyphenyl)-2-(4-pyridylmethylthio)pyridine-3-carboxamide Compound No. 1-137

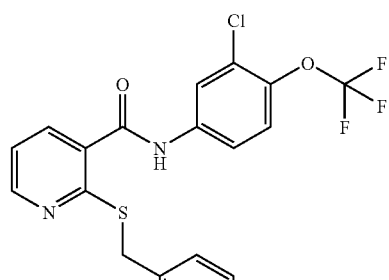

¹H-NMR (400 MHz, DMSO-d₆)

δ 4.43 (s, 2H), 7.32 (dd, J=7.6, 4.8 Hz, 1H), 7.40 (d, J=4.9 Hz, 2H), 7.58 (d, J=9.0 Hz, 1H), 7.71 (dd, J=9.0, 2.4 Hz, 1H), 8.01 (dd, J=7.6, 1.7 Hz, 1H), 8.08 (d, J=2.4 Hz, 1H), 8.45 (dd, J=4.9, 1.5 Hz, 2H), 8.61 (dd, J=4.8, 1.7 Hz, 1H), 10.82 (s, 1H)

N-(2-Methylbenzothiazol-5-yl)-2-(4-pyridylmethylthio)pyridine-3-carboxamide

Compound No. 1-138

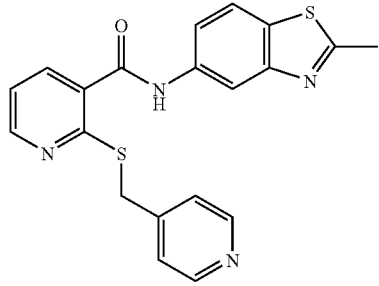

¹H-NMR (400 MHz, DMSO-d₆)

δ 2.80 (s, 3H), 4.43 (s, 2H), 7.31 (dd, J=7.6, 4.9 Hz, 1H), 7.41 (dd, J=4.4, 1.5 Hz, 2H), 7.67 (d, J=7.8 Hz, 1H), 7.98 (d, J=7.8 Hz, 1H), 8.02 (dd, J=7.6, 1.5 Hz, 1H), 8.35 (s, 1H), 8.45 (dd, J=4.4, 1.5 Hz, 2H), 8.60 (dd, J=4.9, 1.5 Hz, 1H), 10.61 (s, 1H)

N-(2-Methylindol-5-yl)-2-(4-pyridylmethylthio)pyridine-3-carboxamide

Compound No. 1-139

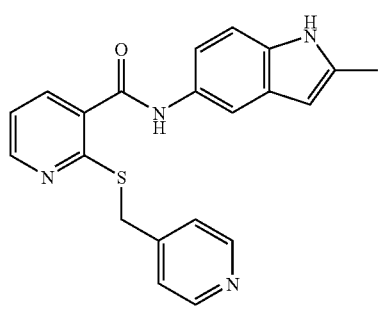

¹H-NMR (400 MHz, DMSO-d₆)

δ 2.37 (s, 3H), 4.41 (s, 2H), 6.09 (s, 1H), 7.21 (s, 1H), 7.28 (dd, J=7.6, 4.9 Hz, 1H), 7.40 (d, J=4.4, 1.5 Hz, 2H), 7.81 (s, 1H), 7.94 (dd, J=7.6, 1.6 Hz, 1H), 8.45 (dd, J=4.4, 1.5 Hz, 2H), 8.57 (dd, J=4.9, 1.6 Hz, 1H), 10.21 (s, 1H), 10.86 (s, 1H)

N-(3-Methylphenyl)-2-(4-pyridylmethylthio)benzamide

Compound No. 1-140

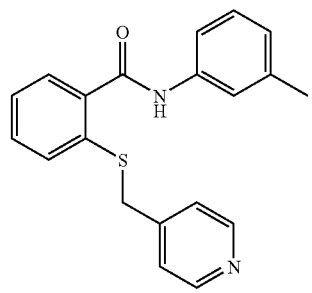

¹H-NMR (400 MHz, DMSO-d₆)

δ 2.30 (s, 3H), 4.25 (s, 2H), 6.91 (d, J=7.6 Hz, 1H), 7.21 (t, J=7.8 Hz, 1H), 7.28 (t, J=7.3 Hz, 1H), 7.36 (d, J=4.8 Hz, 2H), 7.40 (t, J=7.3 Hz, 1H), 7.48-7.49 (m, 3H), 7.59 (s, 1H), 8.46 (d, J=4.8 Hz, 2H), 10.27 (s, 1H)

N-(3-Ethylphenyl)-2-(4-pyridylmethylthio)benzamide

Compound No. 1-141

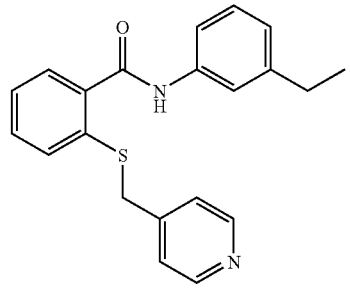

¹H-NMR (400 MHz, DMSO-d₆)

δ 1.18 (t, J=7.6 Hz, 3H), 2.58 (q, J=7.6 Hz, 2H), 4.26 (s, 2H), 6.94 (d, J=7.6 Hz, 1H), 7.24 (t, J=7.6 Hz, 1H), 7.28 (td, J=7.3, 1.2 Hz, 1H), 7.36 (dd, J=4.6, 1.5 Hz, 2H), 7.41 (dd,

J=7.3, 1.5 Hz, 1H), 7.46 (m, 1H), 7.51 (m, 2H), 7.62 (s, 1H), 8.46 (dd, J=4.6, 1.5 Hz, 2H), 10.29 (s, 1H)

N-(3-Fluoro-4-methylphenyl)-2-(4-pyridylmethylthio)benzamide

Compound No. 1-142

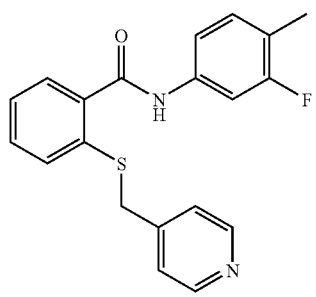

¹H-NMR (400 MHz, DMSO-d₆)

δ 2.20 (s, 3H), 4.26 (s, 2H), 7.23 (t, J=8.6 Hz, 1H), 7.29 (t, J=7.3 Hz, 1H), 7.35 (dd, J=4.3, 1.5 Hz, 2H), 7.37 (m, 1H), 7.41 (m, 1H), 7.46 (m, 1H), 7.51 (d, J=7.6 Hz, 1H), 7.63 (d, J=11.9 Hz, 1H), 8.46 (dd, J=4.3, 1.5 Hz, 2H), 10.46 (s, 1H)

N-(4-Fluoro-3-methylphenyl)-2-(4-pyridylmethylthio)benzamide

Compound No. 1-143

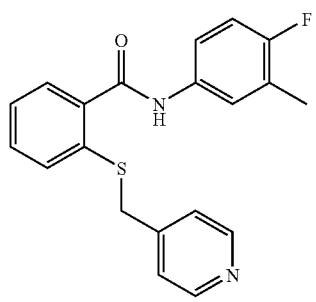

¹H-NMR (400 MHz, DMSO-d₆)

δ 2.23 (d, J=1.4 Hz, 3H), 4.25 (s, 2H), 7.11 (t, J=9.3 Hz, 1H), 7.28 (td, J=7.5, 1.2 Hz, 1H), 7.36 (dd, J=4.4, 1.5 Hz, 2H), 7.41 (td, J=8.7, 1.5 Hz, 1H), 7.46 (dd, J=8.1, 1.0 Hz, 1H), 7.50-7.51 (m, 2H), 7.66 (m, 1H), 8.46 (dd, J=4.4, 1.5 Hz, 2H), 10.34 (s, 1H)

N-(5-Benzotriazolyl)-2-(4-pyridylmethylthio)pyridine-3-carboxamide

Compound No. 1-144

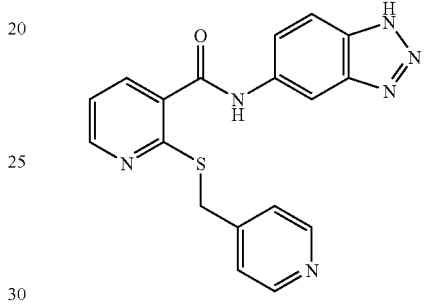

¹H-NMR (400 MHz, DMSO-d₆)

δ 4.43 (s, 2H), 7.31 (dd, J=7.7, 4.9 Hz, 1H), 7.40 (dd, J=4.5, 1.7 Hz, 2H), 7.52 (d, J=8.9 Hz, 1H), 7.93 (d, J=8.5 Hz, 1H), 8.01 (dd, J=7.7, 1.5 Hz, 1H), 8.41 (s, 1H), 8.44 (dd, J=4.5, 1.7 Hz, 2H), 8.60 (dd, J=4.9, 1.5 Hz, 1H), 10.73 (s, 1H), 15.58 (s, 1H)

N-(5-Indolyl)-2-(4-pyridylmethylthio)pyridine-3-carboxamide

Compound No. 1-145

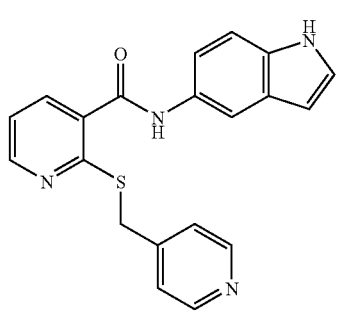

¹H-NMR (400 MHz, DMSO-d₆)

δ 4.42 (s, 2H), 6.41 (s, 1H), 7.29 (m, 1H), 7.32-7.35 (m, 3H), 7.41 (d, J=6.1 Hz, 2H), 7.95-7.97 (m, 2H), 8.45 (dd, J=4.5, 1.5 Hz, 2H), 8.57 (dd, J=4.9, 1.6 Hz, 1H), 10.27 (s, 1H), 11.04 (s, 1H)

N-(3,5-Dimethoxyphenyl)-2-(4-pyridylmethylthio)pyridine-3-carboxamide

Compound No. 1-146

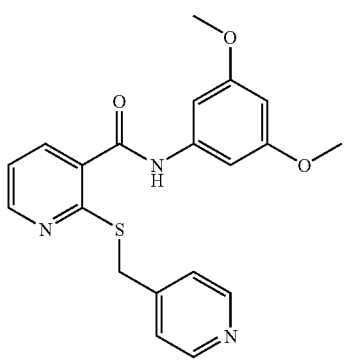

¹H-NMR (500 MHz, DMSO-d₆)

δ 3.72 (s, 6H), 4.42 (s, 2H), 6.28 (t, J=2.3 Hz, 1H), 6.96 (s, 2H), 7.29 (dd, J=7.6, 4.9 Hz, 1H), 7.40 (dd, J=4.6, 1.6 Hz, 2H), 7.93 (d, J=7.6, 1.5 Hz, 1H), 8.45 (dd, J=4.6, 1.6 Hz, 2H), 8.58 (dd, J=4.9, 1.5 Hz, 1H), 10.39 (s, 1H)

2-(4-Pyridylmethylthio)-N-(4-vinylphenyl)pyridine-3-carboxamide

Compound No. 1-147

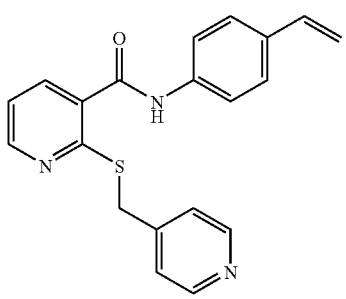

¹H-NMR (400 MHz, DMSO-d₆)

δ 4.42 (s, 2H), 5.20 (dd, J=10.9, 1.0 Hz, 1H), 5.77 (dd, J=17.7, 1.0 Hz, 1H), 6.69 (dd, J=17.7, 10.9 Hz, 1H), 7.29 (dd, J=7.6, 4.9 Hz, 1H), 7.40 (dd, J=4.4, 1.5 Hz, 2H), 7.46 (d, J=8.8 Hz, 2H), 7.68 (d, J=8.8 Hz, 2H), 7.97 (dd, J=7.6, 1.6 Hz, 1H), 8.45 (dd, J=4.4, 1.5 Hz, 2H), 8.59 (dd, J=4.9, 1.6 Hz, 1H), 10.53 (s, 1H)

N-(3-Methanesulfonylaminophenyl)-2-(4-pyridylmethylthio)pyridine-3-carboxamide

Compound No. 1-148

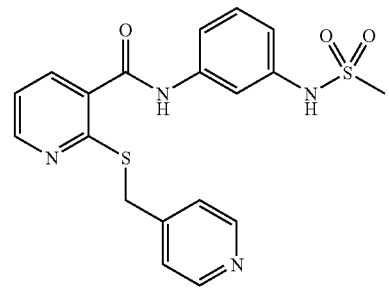

¹H-NMR (400 MHz, DMSO-d₆)

δ 3.00 (s, 3H), 4.42 (s, 2H), 6.95 (ddd, J=8.1, 2.0, 0.8 Hz, 1H), 7.27-7.31 (m, 2H), 7.40 (dd, J=4.4, 1.6 Hz, 2H), 7.44 (d, J=8.1 Hz, 1H), 7.66 (d, J=2.0 Hz, 1H), 7.96 (dd, J=7.6, 1.7 Hz, 1H), 8.45 (dd, J=4.4, 1.6 Hz, 2H), 8.58 (dd, J=4.7, 1.7 Hz, 1H), 9.80 (s, 1H), 10.54 (s, 1H)

N-(1-Acetyl-2,3-dihydroindol-5-yl)-2-(4-pyridylmethylthio)pyridine-3-carboxamide Compound No. 1-149

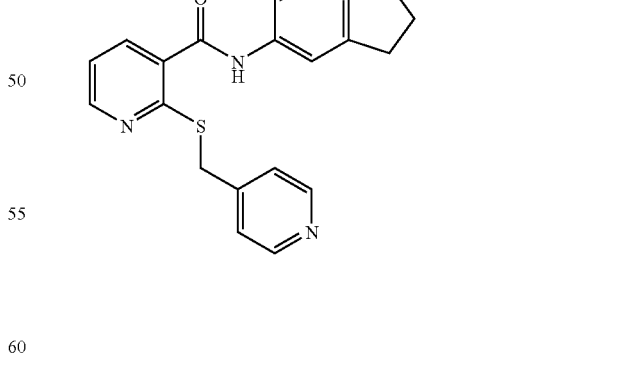

¹H-NMR (400 MHz, DMSO-d₆)

δ 2.14 (s, 3H), 3.15 (t, J=8.3 Hz, 2H), 4.09 (t, J=8.3 Hz, 2H), 4.41 (s, 2H), 7.28 (dd, J=7.6, 4.9 Hz, 1H), 7.37 (m, 1H), 7.40 (dd, J=4.4, 1.7 Hz, 2H), 7.65 (s, 1H), 7.94 (d, J=7.6 Hz,

1H), 7.98 (d, J=8.6 Hz, 1H), 8.45 (dd, J=4.4, 1.7 Hz, 2H), 8.58 (dd, J=4.9, 1.8 Hz, 1H), 10.39 (s, 1H)

N-(6-Indolyl)-2-(4-pyridylmethylthio)pyridine-3-carboxamide

Compound No. 1-150

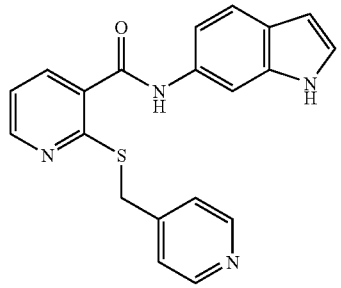

¹H-NMR (400 MHz, DMSO-d₆)

δ 4.21 (s, 2H), 6.38 (s, 1H), 7.16 (d, J=8.5 Hz, 1H), 7.27-7.30 (m, 2H), 7.41 (d, J=5.7 Hz, 2H), 7.47 (d, J=8.3 Hz, 1H), 7.96 (d, J=6.4 Hz, 1H), 8.05 (s, 1H), 8.45 (d, J=5.7 Hz, 2H), 8.58 (d, J=3.2 Hz, 1H), 10.37 (s, 1H), 11.06 (s, 1H)

N-(4-Cyanomethylphenyl)-2-(4-pyridylmethylthio)pyridine-3-carboxamide

Compound No. 1-151

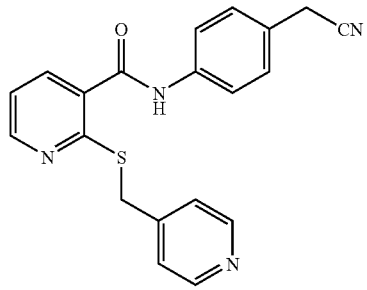

¹H-NMR (400 MHz, DMSO-d₆)

δ 4.00 (s, 2H), 4.41 (s, 2H), 7.29 (dd, J=7.6, 4.9 Hz, 1H), 7.32 (d, J=8.6 Hz, 2H), 7.40 (dd, J=4.5, 1.6 Hz, 2H), 7.70 (dd, J=8.6 Hz, 2H), 7.98 (dd, J=7.6, 1.5 Hz, 1H), 8.45 (dd, J=4.5, 1.6 Hz, 2H), 8.58 (dd, J=4.9, 1.5 Hz, 1H), 10.55 (s, 1H)

N-(5-Methyl-3-trifluoromethylphenyl)-2-(4-pyridylmethylthio)pyridine-3-carboxamide Compound No. 1-152

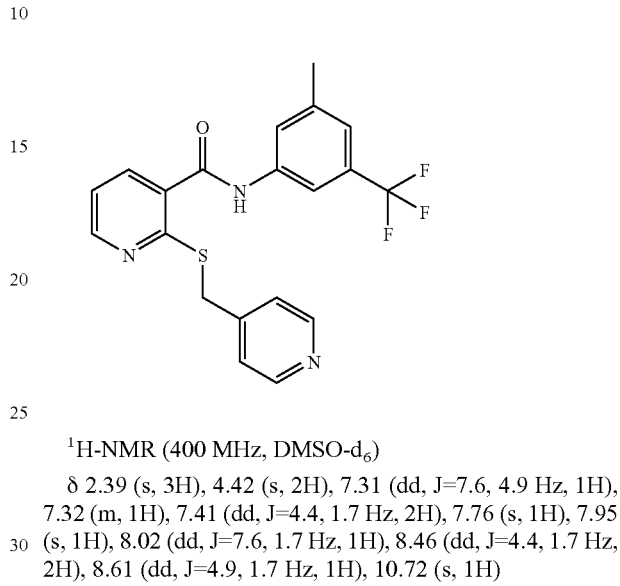

¹H-NMR (400 MHz, DMSO-d₆)

δ 2.39 (s, 3H), 4.42 (s, 2H), 7.31 (dd, J=7.6, 4.9 Hz, 1H), 7.32 (m, 1H), 7.41 (dd, J=4.4, 1.7 Hz, 2H), 7.76 (s, 1H), 7.95 (s, 1H), 8.02 (dd, J=7.6, 1.7 Hz, 1H), 8.46 (dd, J=4.4, 1.7 Hz, 2H), 8.61 (dd, J=4.9, 1.7 Hz, 1H), 10.72 (s, 1H)

N-(4-Nitro-3-trifluoromethylphenyl)-2-(4-pyridylmethylthio)pyridine-3-carboxamide Compound No. 1-153

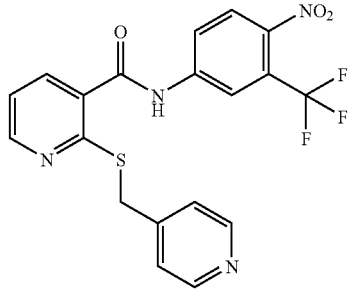

¹H-NMR (400 MHz, DMSO-d₆)

δ 4.44 (s, 2H), 7.35 (dd, J=7.6, 4.9 Hz, 1H), 7.41 (dd, J=4.4, 1.5 Hz, 2H), 8.10 (dd, J=7.6, 1.8 Hz, 1H), 8.19 (dd, J=9.0, 2.2

Hz, 1H), 8.27 (d, J=9.0 Hz, 1H), 8.37 (d, J=2.2 Hz, 1H), 8.45 (dd, J=4.4, 1.5 Hz, 2H), 8.65 (dd, J=4.9, 1.8 Hz, 1H), 11.23 (s, 1H)

N-(3-Chloro-4-cyanophenyl)-2-(4-pyridylmethylthio)pyridine-3-carboxamide

Compound No. 1-154

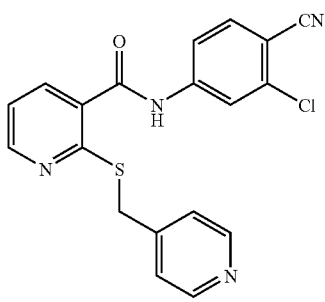

¹H-NMR (400 MHz, DMSO-d₆)

δ 4.43 (s, 2H), 7.34 (dd, J=7.6, 4.9 Hz, 1H), 7.40 (dd, J=4.4, 1.7 Hz, 2H), 7.76 (dd, J=8.7, 2.0 Hz, 1H), 7.96 (d, J=8.7 Hz, 1H), 8.04 (dd, J=7.6, 1.6 Hz, 1H), 8.13 (d, J=2.0 Hz, 1H), 8.46 (dd, J=4.4, 1.7 Hz, 2H), 8.63 (dd, J=4.9, 1.6 Hz, 1H), 11.05 (s, 1H)

N-(5-Indazolyl)-2-(4-pyridylmethylthio)benzamide

Compound No. 1-155

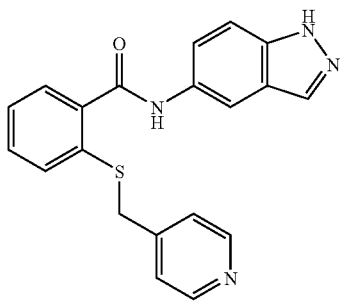

¹H-NMR (400 MHz, DMSO-d₆)

δ 4.26 (s, 2H), 7.27-7.56 (m, 8H), 8.06 (s, 1H), 8.26 (s, 1H), 8.46 (dd, J=4.4, 1.5 Hz, 2H), 10.36 (s, 1H), 13.01 (s, 1H)

N-(6-Indazolyl)-2-(4-pyridylmethylthio)benzamide

Compound No. 1-156

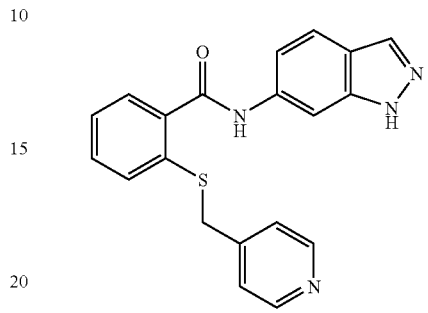

¹H-NMR (500 MHz, DMSO-d₆)

δ 4.27 (s, 2H), 7.26 (d, J=8.6 Hz, 1H), 7.31 (t, J=7.6 Hz, 1H), 7.36 (d, J=5.8 Hz, 2H), 7.42 (t, J=8.6 Hz, 1H), 7.48 (d, J=7.6 Hz, 1H), 7.54 (d, J=6.7 Hz, 1H), 7.68 (d, J=8.6 Hz, 1H), 7.99 (s, 1H), 8.25 (s, 1H), 8.45 (d, J=5.8 Hz, 2H), 10.50 (s, 1H), 12.93 (s, 1H)

N-(4-Cyano-3-trifluoromethylphenyl)-2-(4-pyridylmethylthio)pyridine-3-carboxamide Compound No. 1-157

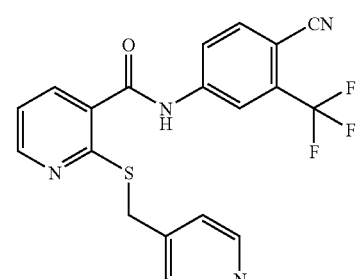

¹H-NMR (500 MHz, DMSO-d₆)

δ 4.43 (s, 2H), 7.35 (dd, J=7.6, 4.9 Hz, 1H), 7.40 (dd, J=4.6, 1.8 Hz, 2H), 8.08 (dd, J=7.6, 1.5 Hz, 1H), 8.11-8.17 (m, 2H), 8.36 (d, J=1.8 Hz, 1H), 8.46 (dd, J=4.6, 1.8 Hz, 2H), 8.64 (dd, J=4.9, 1.5 Hz, 1H), 11.19 (s, 1H)

2-(4-Pyridylmethylthio)-N-(4-trifluoromethylthiophenyl)pyridine-3-carboxamide

Compound No. 1-158

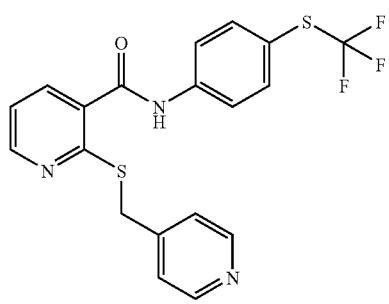

¹H-NMR (500 MHz, DMSO-d₆)

δ 4.43 (s, 2H), 7.31 (dd, J=7.6, 4.8 Hz, 1H), 7.40 (dd, J=4.6, 1.8 Hz, 2H), 7.71 (d, J=6.8 Hz, 2H), 7.86 (dd, J=6.8, 2.2 Hz, 2H), 8.00 (dd, J=7.6, 1.8 Hz, 1H), 8.45 (dd, J=4.6, 1.8 Hz, 2H), 8.61 (dd, J=4.8, 1.8 Hz, 1H), 10.79 (s, 1H)

N-(3-Chloro-4-trifluoromethylthiophenyl)-2-(4-pyridylmethylthio)pyridine-3-carboxamide Compound No. 1-159

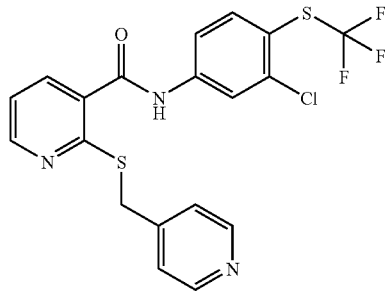

¹H-NMR (400 MHz, DMSO-d₆)

δ 4.43 (s, 2H), 7.33 (dd, J=7.8, 4.9 Hz, 1H), 7.40 (dd, J=4.4, 1.5 Hz, 2H), 7.76 (dd, J=8.6, 2.2 Hz, 1H), 7.89 (d, J=8.6 Hz, 1H), 8.03 (dd, J=7.8, 1.7 Hz, 1H), 8.15 (d, J=2.2 Hz, 1H), 8.45 (dd, J=4.4, 1.5 Hz, 2H), 8.62 (dd, J=4.9, 1.7 Hz, 1H), 10.93 (s, 1H)

N-(5-Indanyl)-2-(4-pyridylmethylthio)benzamide

Compound No. 1-160

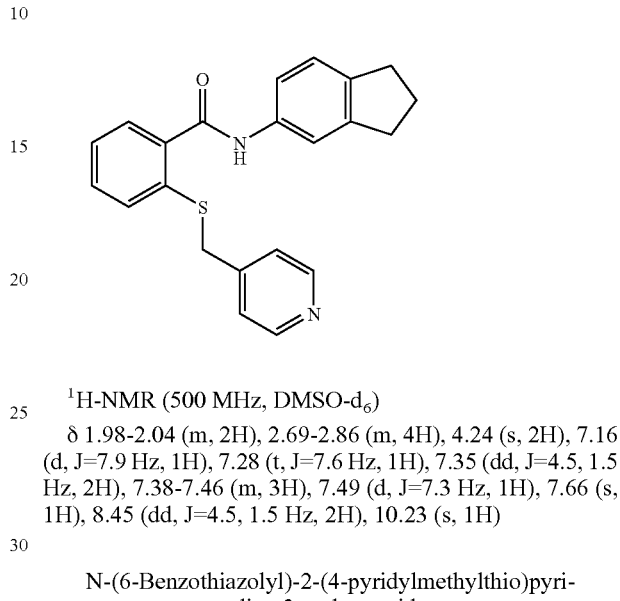

¹H-NMR (500 MHz, DMSO-d₆)

δ 1.98-2.04 (m, 2H), 2.69-2.86 (m, 4H), 4.24 (s, 2H), 7.16 (d, J=7.9 Hz, 1H), 7.28 (t, J=7.6 Hz, 1H), 7.35 (dd, J=4.5, 1.5 Hz, 2H), 7.38-7.46 (m, 3H), 7.49 (d, J=7.3 Hz, 1H), 7.66 (s, 1H), 8.45 (dd, J=4.5, 1.5 Hz, 2H), 10.23 (s, 1H)

N-(6-Benzothiazolyl)-2-(4-pyridylmethylthio)pyridine-3-carboxamide

Compound No. 1-161

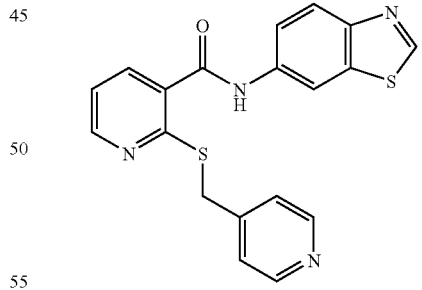

¹H-NMR (500 MHz, DMSO-d₆)

δ 4.43 (s, 2H), 7.32 (dd, J=7.6, 4.9 Hz, 1H), 7.41 (dd, J=4.4, 1.6 Hz, 2H), 7.71 (dd, J=8.5, 1.5 Hz, 1H), 8.02 (dd, J=7.6, 1.8

Hz, 1H), 8.06 (d, J=8.5 Hz, 1H), 8.45 (dd, J=4.4, 1.6 Hz, 2H), 8.61 (dd, J=4.9, 1.8 Hz, 1H), 8.64 (d, J=1.5 Hz, 1H), 9.31 (s, 1H), 10.74 (s, 1H)

N-(2-Methylthiobenzothiazol-6-yl)-2-(4-pyridylmethylthio)pyridine-3-carboxamide

Compound No. 1-162

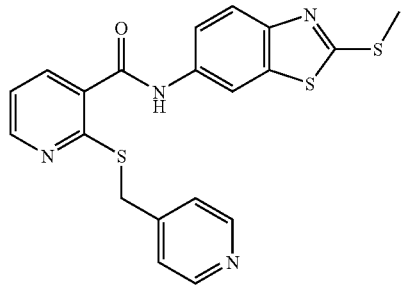

¹H-NMR (500 MHz, DMSO-d₆)

δ 2.79 (s, 3H), 4.43 (s, 2H), 7.31 (dd, J=7.6, 4.9 Hz, 1H), 7.40 (dd, J=4.5, 1.5 Hz, 2H), 7.62 (dd, J=8.8, 1.5 Hz, 1H), 7.82 (d, J=8.8 Hz, 1H), 8.00 (dd, J=7.6, 1.8 Hz, 1H), 8.45 (dd, J=4.5, 1.5 Hz, 2H), 8.49 (d, J=1.5 Hz, 1H), 8.60 (dd, J=4.9, 1.8 Hz, 1H), 10.69 (s, 1H)

N-(Coumarin-6-yl)-2-(4-pyridylmethylthio)pyridine-3-carboxamide

Compound No. 1-163

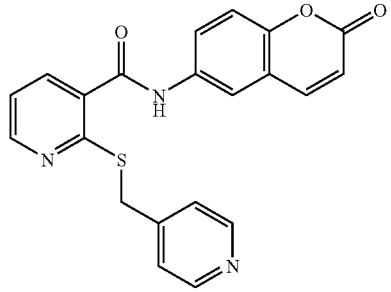

¹H-NMR (500 MHz, DMSO-d₆)

δ 4.43 (s, 2H), 6.51 (d, J=9.8 Hz, 1H), 7.31 (dd, J=7.6, 4.9 Hz, 1H), 7.40 (dd, J=4.4, 1.5 Hz, 2H), 7.42 (d, J=9.8 Hz, 1H), 7.75 (dd, J=9.0, 2.2 Hz, 1H), 8.01 (dd, J=7.6, 1.8 Hz, 1H), 8.13 (d, J=9.0 Hz, 1H), 8.19 (d, J=2.2 Hz, 1H), 8.46 (dd, J=4.4, 1.6 Hz, 2H), 8.61 (dd, J=4.9, 1.8 Hz, 1H), 10.70 (s, 1H)

N-(6-Phthalidyl)-2-(4-pyridylmethylthio)pyridine-3-carboxamide

Compound No. 1-164

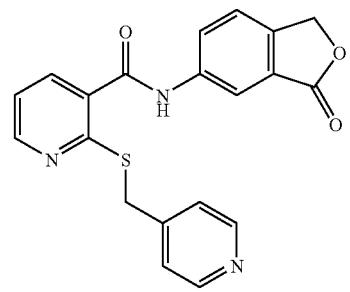

¹H-NMR (500 MHz, DMSO-d₆)

δ 4.40 (s, 2H), 5.38 (s, 2H), 7.29 (dd, J=7.6, 4.7 Hz, 1H), 7.40 (dd, J=4.3, 1.5 Hz, 2H), 7.62 (d, J=7.9 Hz, 1H), 7.92 (dd, J=7.9, 1.2 Hz, 1H), 8.05 (dd, J=7.6, 1.8 Hz, 1H), 8.27 (d, J=1.6 Hz, 1H), 8.45 (dd, J=4.3, 1.5 Hz, 2H), 8.58 (dd, J=4.7, 1.8 Hz, 1H), 10.82 (s, 1H)

2-(4-Pyridylmethylthio)-N-(6-quinolyl)benzamide

Compound No. 1-165

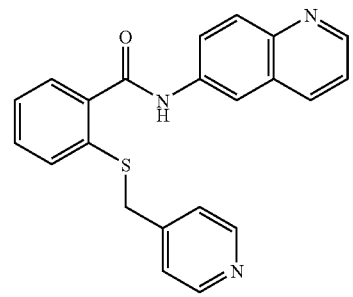

¹H-NMR (400 MHz, DMSO-d₆)

δ4.28 (s, 2H), 7.32 (m, 1H), 7.36-7.37 (m, 2H), 7.45 (m, 1H), 7.49-7.52 (m, 2H), 7.59-7.61 (m, 1H), 7.91 (d, J=9.0 Hz,

1H), 8.00 (d, J=9.0 Hz, 1H), 8.34 (d, J=9.0 Hz, 1H), 8.46 (dd, J=4.4, 1.7 Hz, 2H), 8.56 (s, 1H), 8.81 (dd, J=4.2, 1.7 Hz, 1H), 10.72 (s, 1H)

N-(2,2-Difluoro-1,3-benzodioxol-5-yl)-2-(4-pyridylmethylthio)pyridine-3-carboxamide Compound No. 1-166

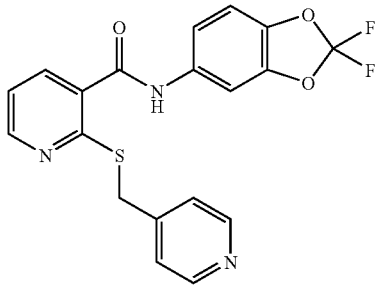

¹H-NMR (500 MHz, DMSO-d₆)

δ 4.42 (s, 2H), 7.31 (dd, J=7.6, 4.9 Hz, 1H), 7.39-7.40 (m, 4H), 7.83 (s, 1H), 7.98 (dd, J=7.6, 1.8 Hz, 1H), 8.46 (dd, J=4.5, 1.8 Hz, 2H), 8.60 (dd, J=4.9, 1.8 Hz, 1H), 10.68 (s, 1H)

2-(4-Pyridylmethylthio)-N-(2,2,3,3-tetrafluoro-1,4-benzodioxane-6-yl)-pyridine-3-carboxamide Compound No. 1-167

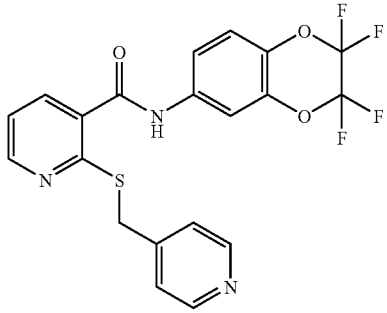

¹H-NMR (500 MHz, DMSO-d₆)

δ 4.43 (s, 2H), 7.31 (dd, J=7.6, 4.9 Hz, 1H), 7.40 (dd, J=4.3, 1.5 Hz, 2H), 7.49 (d, J=8.9 Hz, 1H), 7.54 (dd, J=8.9, 2.1 Hz, 1H), 7.87 (d, J=2.1 Hz, 1H), 7.99 (dd, J=7.6, 1.8 Hz, 1H), 8.46 (dd, J=4.3, 1.5 Hz, 2H), 8.61 (dd, J=4.9, 1.8 Hz, 1H), 10.78 (s, 1H)

N-(1,3-Benzodioxol-5-yl)-2-(4-pyridylmethylthio)pyridine-3-carboxamide

Compound No. 1-168

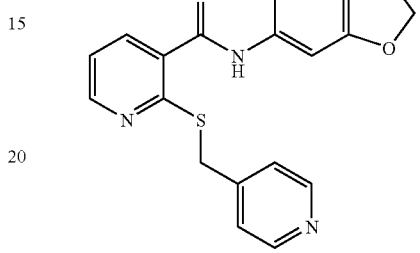

¹H-NMR (500 MHz, DMSO-d₆)

δ 4.41 (s, 2H), 6.00 (s, 2H), 6.89 (d, J=8.6 Hz, 1H), 7.10 (dd, J=8.6, 1.3 Hz, 1H), 7.28 (dd, J=7.6, 4.9 Hz, 1H), 7.36 (s, 1H), 7.40 (dd, J=4.3, 1.5 Hz, 2H), 7.93 (dd, J=7.6, 1.5 Hz, 1H), 8.46 (dd, J=4.3, 1.5 Hz, 2H), 8.58 (dd, J=4.9, 1.8 Hz, 1H), 10.36 (s, 1H)

N-(1-Acetyl-2,3-dihydroindol-6-yl)-2-(4-pyridylmethylthio)pyridine-3-carboxamide Compound No. 1-169

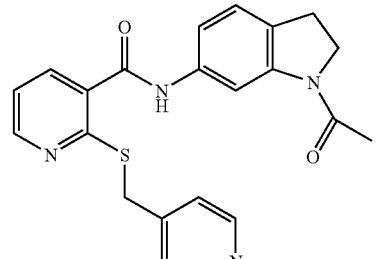

¹H-NMR (400 MHz, DMSO-d₆)

δ 2.16 (s, 3H), 3.10 (t, J=8.3 Hz, 2H), 4.10 (t, J=8.3 Hz, 2H), 4.41 (s, 2H), 7.17 (d, J=6.1 Hz, 1H), 7.26 (dd, J=7.6, 4.9 Hz, 1H), 7.40 (d, J=6.1 Hz, 2H), 7.47 (m, 1H), 7.95 (dd, J=7.6, 1.5 Hz, 1H), 8.33 (s, 1H), 8.45 (d, J=6.1 Hz, 2H), 8.56 (dd, J=4.9, 1.6 Hz, 1H), 10.43 (s, 1H)

N-(1-Oxoindane-5-yl)-2-(4-pyridylmethylthio)pyridine-3-carboxamide

Compound No. 1-170

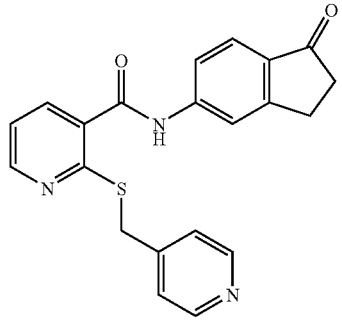

¹H-NMR (500 MHz, DMSO-d₆)

δ 2.58-2.63 (m, 2H), 3.10 (t, J=5.3 Hz, 2H), 4.43 (s, 2H), 7.31 (dd, J=7.5, 4.9 Hz, 1H), 7.40 (dd, J=4.4, 1.7 Hz, 2H), 7.63 (s, 2H), 8.00 (dd, J=7.5, 1.7 Hz, 1H), 8.03 (s, 1H), 8.45 (dd, J=4.4, 1.7 Hz, 2H), 8.61 (dd, J=4.9, 1.7 Hz, 1H), 10.83 (s, 1H)

N-(4-n-Propoxyphenyl)-2-(4-pyridylmethylthio)pyridine-3-carboxamide

Compound No. 1-171

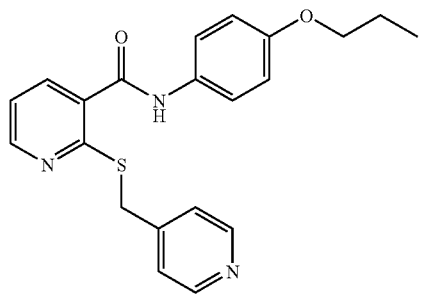

¹H-NMR (500 MHz, DMSO-d₆)

δ 0.97 (t, J=7.5 Hz, 3H), 1.70-1.74 (m, 2H), 3.90 (t, J=7.5 Hz, 2H), 4.41 (s, 2H), 6.91 (d, J=9.2 Hz, 2H), 7.27 (dd, J=7.5, 4.6 Hz, 1H), 7.40 (dd, J=4.5, 1.5 Hz, 2H), 7.59 (d, J=9.2 Hz, 2H), 7.94 (dd, J=7.5, 1.8 Hz, 1H), 8.45 (dd, J=4.5, 1.5 Hz, 2H), 8.57 (dd, J=4.6, 1.8 Hz, 1H), 10.31 (s, 1H)

N-(4-Isopropylphenyl)-2-(4-pyridylmethylthio)pyridine-3-carboxamide

Compound No. 1-172

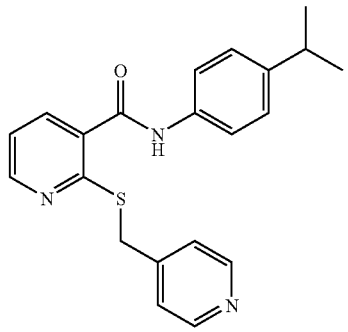

¹H-NMR (500 MHz, DMSO-d₆)

δ 1.19 (d, J=6.7 Hz, 6H), 2.86 (m, 1H), 4.42 (s, 2H), 7.21 (d, J=8.6 Hz, 2H), 7.28 (dd, J=7.6, 4.9 Hz, 1H), 7.40 (dd, J=4.6, 1.6 Hz, 2H), 7.60 (d, J=8.6 Hz, 2H), 7.94 (dd, J=7.6, 1.8 Hz, 1H), 8.45 (dd, J=4.6, 1.6 Hz, 2H), 8.59 (dd, J=4.9, 1.8 Hz, 1H), 10.39 (s, 1H)

N-(4-Ethylphenyl)-2-(4-pyridylmethylthio)pyridine-3-carboxamide

Compound No. 1-173

¹H-NMR (500 MHz, DMSO-d₆)

δ 1.17 (t, J=7.5 Hz, 3H), 2.57 (q, J=7.5 Hz, 2H), 4.41 (s, 2H), 7.18 (d, J=8.5 Hz, 2H), 7.28 (dd, J=7.6, 4.9 Hz, 1H), 7.40 (dd, J=4.3, 1.5 Hz, 2H), 7.59 (d, J=8.5 Hz, 2H), 7.94 (dd,

J=7.6, 1.6 Hz, 1H), 8.45 (dd, J=4.3, 1.5 Hz, 2H), 8.58 (dd, J=4.9, 1.6 Hz, 1H), 10.38 (s, 1H)

N-(4-Methylthiophenyl)-2-(4-pyridylmethylthio)pyridine-3-carboxamide

Compound No. 1-174

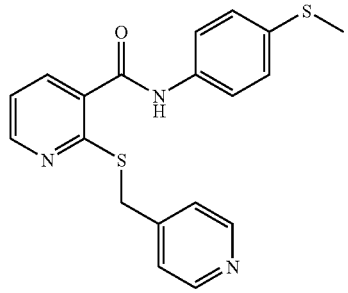

¹H-NMR (500 MHz, DMSO-d₆)

δ 2.46 (s, 3H), 4.42 (s, 2H), 7.25-7.30 (m, 3H), 7.40 (dd, J=4.4, 1.5 Hz, 2H), 7.65 (d, J=8.5 Hz, 2H), 7.95 (dd, J=7.6, 1.5 Hz, 1H), 8.45 (dd, J=4.4, 1.5 Hz, 2H), 8.58 (dd, J=4.9, 1.5 Hz, 1H), 10.47 (s, 1H)

N-(3-Methyl-4-trifluoromethoxyphenyl)-2-(4-pyridylmethylthio)pyridine-3-carboxamide Compound No. 1-175

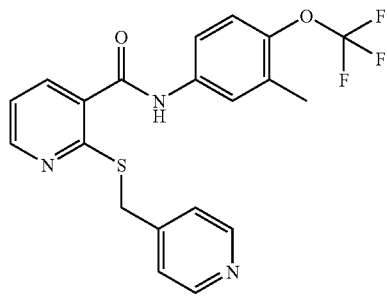

¹H-NMR (500 MHz, DMSO-d₆)

δ 2.27 (s, 3H), 4.42 (s, 2H), 7.28-7.32 (m, 2H), 7.40 (dd, J=4.4, 1.7 Hz, 2H), 7.59 (dd, J=8.7, 2.2 Hz, 1H), 7.72 (d, J=2.2 Hz, 1H), 7.96 (dd, J=7.6, 1.7 Hz, 1H), 8.45 (dd, J=4.4, 1.7 Hz, 2H), 8.60 (dd, J=4.9, 1.7 Hz, 1H), 10.58 (s, 1H)

N-(4-n-Butyrylphenyl)-2-(4-pyridylmethylthio)pyridine-3-carboxamide

Compound No. 1-176

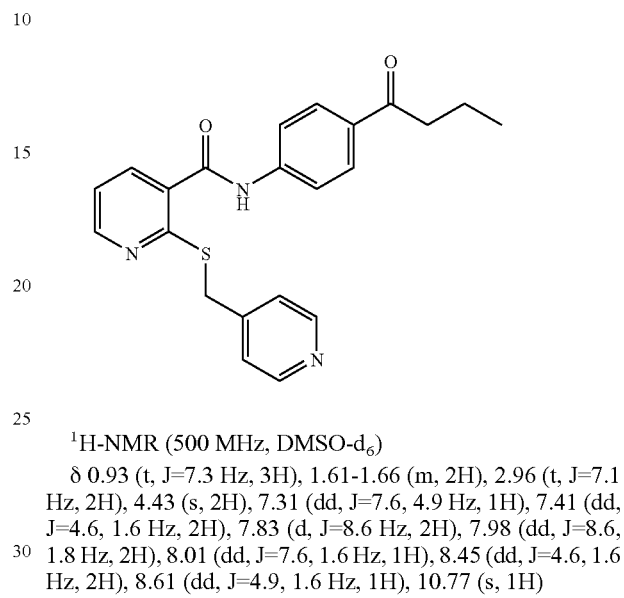

¹H-NMR (500 MHz, DMSO-d₆)

δ 0.93 (t, J=7.3 Hz, 3H), 1.61-1.66 (m, 2H), 2.96 (t, J=7.1 Hz, 2H), 4.43 (s, 2H), 7.31 (dd, J=7.6, 4.9 Hz, 1H), 7.41 (dd, J=4.6, 1.6 Hz, 2H), 7.83 (d, J=8.6 Hz, 2H), 7.98 (dd, J=8.6, 1.8 Hz, 2H), 8.01 (dd, J=7.6, 1.6 Hz, 1H), 8.45 (dd, J=4.6, 1.6 Hz, 2H), 8.61 (dd, J=4.9, 1.6 Hz, 1H), 10.77 (s, 1H)

N-(1-Oxo-1,2,3,4-tetrahydronaphthalene-6-yl)-2-(4-pyridylmethylthio)-pyridine-3-carboxamide Compound No. 1-177

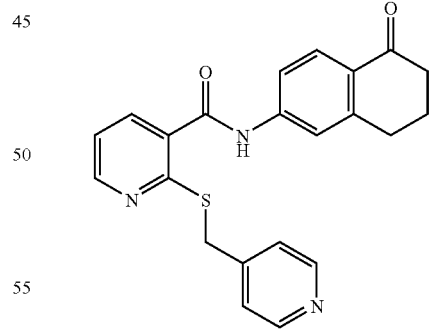

¹H-NMR (500 MHz, CDCl₃)

δ 2.13-2.17 (m, 2H), 2.65 (t, J=6.7 Hz, 2H), 2.98 (t, J=6.1 Hz, 2H), 4.48 (s, 2H), 7.17 (dd, J=7.6, 4.9 Hz, 1H), 7.39 (dd, J=8.6, 1.8 Hz, 1H), 7.35 (dd, J=4.5, 1.5 Hz, 2H), 7.81 (d,

J=1.8 Hz, 1H), 7.92 (dd, J=7.6, 1.6 Hz, 1H), 8.01 (s, 1H), 8.04 (d, J=8.6 Hz, 1H), 8.50 (dd, J=4.5, 1.5 Hz, 2H), 8.57 (dd, J=4.9, 1.6 Hz, 1H)

N-(4-Cyclohexylphenyl)-2-(4-pyridylmethylthio)pyridine-3-carboxamide

Compound No. 1-178

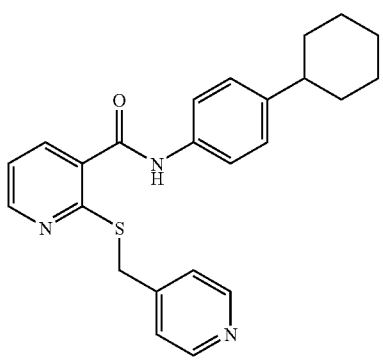

¹H-NMR (500 MHz, DMSO-d₆)
δ 1.16-1.27 (m, 1H), 1.31-1.43 (m, 4H), 1.69 (d, J=6.5 Hz, 1H), 1.73-1.81 (m, 4H), 2.45 (m, 1H), 4.41 (s, 2H), 7.19 (d, J=8.6 Hz, 2H), 7.28 (dd, J=7.6, 4.9 Hz, 1H), 7.40 (dd, J=4.6, 1.5 Hz, 2H), 7.58 (d, J=8.6 Hz, 2H), 7.93 (dd, J=7.6, 1.5 Hz, 1H), 8.45 (dd, J=4.6, 1.5 Hz, 2H), 8.58 (dd, J=4.9, 1.5 Hz, 1H), 10.37 (s, 1H)

2-(4-Pyridylmethylthio)-N-(3-trifluoromethylthiophenyl)pyridine-3-carboxamide Compound No. 1-179

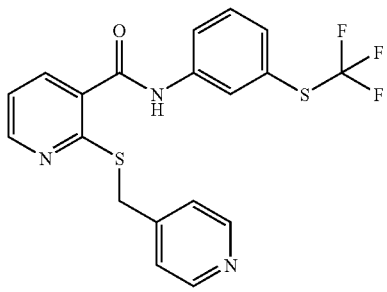

¹H-NMR (400 MHz, DMSO-d₆)
δ 4.43 (s, 2H), 7.31 (dd, J=7.6, 4.8 Hz, 1H), 7.40 (dd, J=4.4, 1.7 Hz, 2H), 7.46 (d, J=8.1 Hz, 1H), 7.54 (t, J=8.1 Hz, 1H), 7.86 (d, J=8.1 Hz, 1H), 8.02 (dd, J=7.6, 1.7 Hz, 1H), 8.16 (s, 1H), 8.45 (dd, J=4.4, 1.7 Hz, 2H), 8.60 (dd, J=4.8, 1.7 Hz, 1H), 10.74 (s, 1H)

N-(3,5-Dimethyl-4-trifluoromethoxyphenyl)-2-(4-pyridylmethylthio)pyridine-3-carboxamide Compound No. 1-180

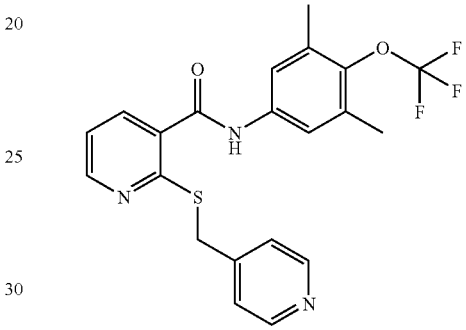

¹H-NMR (500 MHz, DMSO-d₆)
δ 2.26 (s, 6H), 4.42 (s, 2H), 7.29 (dd, J=7.6, 4.9 Hz, 1H), 7.40 (dd, J=4.5, 1.8 Hz, 2H), 7.52 (s, 2H), 7.95 (dd, J=7.6, 1.5 Hz, 1H), 8.45 (dd, J=4.5, 1.8 Hz, 2H), 8.59 (dd, J=4.9, 1.5 Hz, 1H), 10.51 (s, 1H)

N-(3-Nitrophenyl)-2-(4-pyridylmethylthio)pyridine-3-carboxamide

Compound No. 1-181

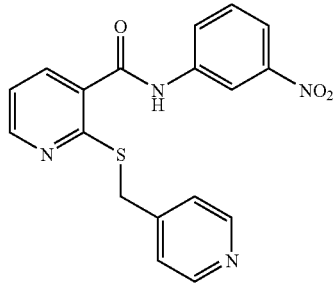

¹H-NMR (400 MHz, DMSO-d₆)

δ 4.43 (s, 2H), 7.33 (dd, J=7.8, 4.7 Hz, 1H), 7.41 (dd, J=4.4, 1.5 Hz, 2H), 7.67 (m, 1H), 7.98-8.05 (m, 3H), 8.46 (dd, J=4.4, 1.5 Hz, 2H), 8.63 (dd, J=4.7, 1.8 Hz, 1H), 8.74 (m, 1H), 10.90 (s, 1H)

N-(3-Cyano-4-methylphenyl)-2-(4-pyridylmethylthio)pyridine-3-carboxamide

Compound No. 1-182

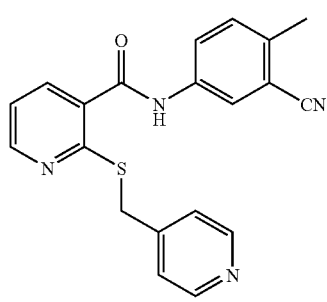

$^1$H-NMR (400 MHz, DMSO-$d_6$)

δ 2.45 (s, 3H), 4.42 (s, 2H), 7.31 (dd, J=7.5, 4.7 Hz, 1H), 7.40 (dd, J=4.4, 1.5 Hz, 2H), 7.46 (d, J=8.5 Hz, 1H), 7.82 (dd, J=8.5, 2.2 Hz, 1H), 8.00 (dd, J=7.5, 1.7 Hz, 1H), 8.10 (d, J=2.2 Hz, 1H), 8.46 (dd, J=4.4, 1.5 Hz, 2H), 8.61 (dd, J=4.7, 1.7 Hz, 1H), 10.70 (s, 1H)

N-(3-Cyanophenyl)-2-(4-pyridylmethylthio)pyridine-3-carboxamide

Compound No. 1-183

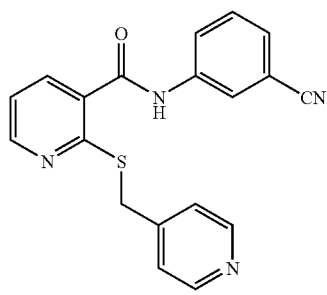

$^1$H-NMR (400 MHz, DMSO-$d_6$)

δ 4.43 (s, 2H), 7.32 (dd, J=7.6, 4.8 Hz, 1H), 7.40 (dd, J=4.4, 1.7 Hz, 2H), 7.56-7.61 (m, 2H), 7.94 (m, 1H), 8.02 (dd, J=7.6, 1.7 Hz, 1H), 8.17 (d, J=1.0 Hz, 1H), 8.46 (dd, J=4.4, 1.7 Hz, 2H), 8.62 (dd, J=4.8, 1.7 Hz, 1H), 10.80 (s, 1H)

N-(3-Chloro-4-methoxyphenyl)-2-(4-pyridylmethylthio)pyridine-3-carboxamide

Compound No. 1-184

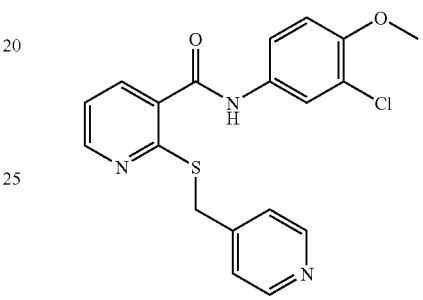

$^1$H-NMR (400 MHz, DMSO-$d_6$)

δ 3.84 (s, 3H), 4.42 (s, 2H), 7.15 (d, J=8.8 Hz, 1H), 7.29 (d, J=7.6, 4.9 Hz, 1H), 7.40 (d, J=6.1 Hz, 2H), 7.56 (dd, J=8.8, 2.4 Hz, 1H), 7.86 (d, J=2.4 Hz, 1H), 7.97 (dd, J=7.6, 1.7 Hz, 1H), 8.45 (d, J=6.1 Hz, 2H), 8.59 (dd, J=4.9, 1.7 Hz, 1H), 10.47 (s, 1H)

N-(4-Fluoro-3-nitrophenyl)-2-(4-pyridylmethylthio)pyridine-3-carboxamide

Compound No. 1-185

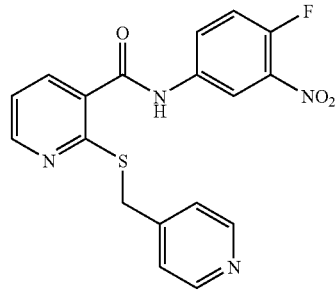

$^1$H-NMR (400 MHz, DMSO-$d_6$)

δ 4.43 (s, 2H), 7.33 (dd, J=7.6, 4.7 Hz, 1H), 7.41 (d, J=5.8 Hz, 2H), 7.62 (m, 1H), 8.00 (m, 1H), 8.04 (dd, J=7.6, 1.5 Hz, 1H), 8.46 (d, J=5.8 Hz, 2H), 8.62-8.64 (m, 2H), 10.92 (s, 1H)

N-(3-Aminophenyl)-2-(4-pyridylmethylthio)pyridine-3-carboxamide

Compound No. 1-186

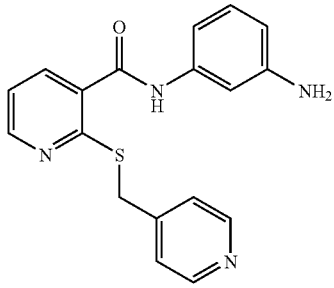

¹H-NMR (400 MHz, DMSO-d₆)
δ 4.41 (s, 2H), 5.11 (s, 2H), 6.31 (ddd, J=8.0, 2.2, 1.0 Hz, 1H), 6.76 (d, J=8.0 Hz, 1H), 6.95 (m, 1H), 7.05 (s, 1H), 7.28 (m, 1H), 7.40 (dd, J=4.4, 1.7 Hz, 2H), 7.89 (dd, J=7.6, 1.7 Hz, 1H), 8.45 (dd, J=4.4, 1.7 Hz, 2H), 8.56 (dd, J=4.9, 1.7 Hz, 1H), 10.20 (s, 1H)

N-(3-Bromo-4-trifluoromethoxyphenyl)-2-(4-pyridylmethylthio)pyridine-3-carboxamide Compound No. 1-187

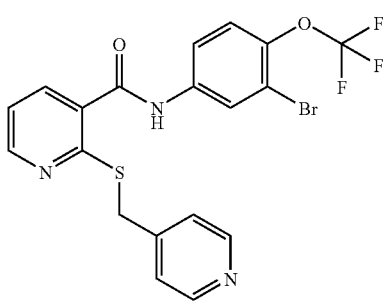

¹H-NMR (400 MHz, DMSO-d₆)
δ 4.43 (s, 2H), 7.32 (m, 1H), 7.40 (dd, J=4.4, 1.7 Hz, 2H), 7.56 (dd, J=9.1, 1.2 Hz, 1H), 7.75 (dd, J=9.1, 1.2 Hz, 1H), 8.01 (dd, J=7.6, 1.8 Hz, 1H), 8.22 (d, J=2.4 Hz, 1H), 8.45 (dd, J=4.4, 1.7 Hz, 2H), 8.62 (dd, J=4.9, 1.8 Hz, 1H), 10.79 (s, 1H)

N-(3-Fluoro-4-methoxyphenyl)-2-(4-pyridylmethylthio)pyridine-3-carboxamide

Compound No. 1-188

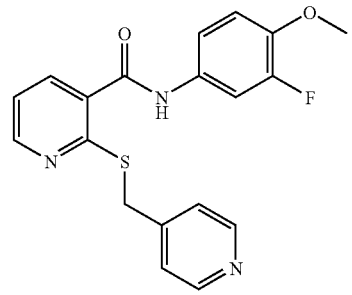

¹H-NMR (400 MHz, DMSO-d₆)
δ 3.82 (s, 3H), 4.42 (s, 2H), 7.16 (m, 1H), 7.29 (dd, J=7.6, 4.9 Hz, 1H), 7.38-7.41 (m, 3H), 7.65 (dd, J=13.6, 2.4 Hz, 1H), 7.96 (dd, J=7.6, 1.7 Hz, 1H), 8.45 (dd, J=4.4, 1.5 Hz, 2H), 8.59 (dd, J=4.9, 1.7 Hz, 1H), 10.49 (s, 1H)

N-(4-Difluoromethoxyphenyl)-2-(4-pyridylmethylthio)pyridine-3-carboxamide

Compound No. 1-189

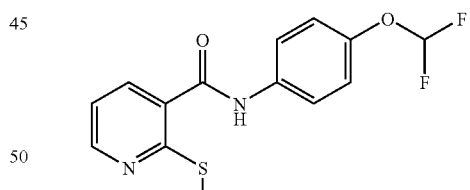

¹H-NMR (400 MHz, DMSO-d₆)
δ 4.42 (s, 2H), 7.18-7.20 (m, 3H), 7.30 (dd, J=7.6, 4.9 Hz, 1H), 7.40 (dd, J=4.6, 1.7 Hz, 2H), 7.73 (d, J=9.0 Hz, 2H), 7.97

(dd, J=7.6, 1.7 Hz, 1H), 8.46 (dd, J=4.6, 1.7 Hz, 2H), 8.59 (dd, J=4.9, 1.7 Hz, 1H), 10.56 (s, 1H)

N-(3-Ethoxyphenyl)-2-(4-pyridylmethylthio)pyridine-3-carboxamide

Compound No. 1-190

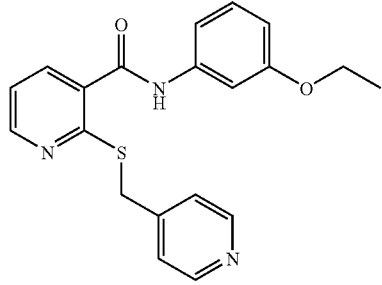

¹H-NMR (500 MHz, DMSO-d₆)

δ 1.33 (t, J=7.0 Hz, 3H), 4.00 (q, J=7.0 Hz, 2H), 4.42 (s, 2H), 6.68 (m, 1H), 7.22-7.24 (m, 2H), 7.29 (dd, J=7.6, 4.9 Hz, 1H), 7.37 (s, 1H), 7.40 (dd, J=4.6, 1.8 Hz, 2H), 7.95 (dd, J=7.6, 1.5 Hz, 1H), 8.45 (dd, J=4.6, 1.8 Hz, 2H), 8.59 (dd, J=4.9, 1.5 Hz, 1H), 10.42 (s, 1H)

N-(4-sec-Butylphenyl)-2-(4-pyridylmethylthio)pyridine-3-carboxamide

Compound No. 1-191

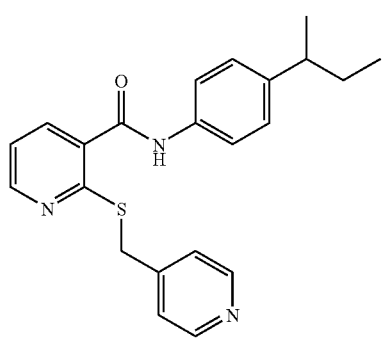

¹H-NMR (500 MHz, DMSO-d₆)

δ 0.76 (t, J=7.3 Hz, 3H), 1.17 (d, J=7.0 Hz, 3H), 1.50-1.57 (m, 2H), 2.56 (m, 1H), 4.41 (s, 2H), 7.17 (d, J=8.4 Hz, 2H), 7.28 (dd, J=7.6, 4.7 Hz, 1H), 7.40 (dd, J=4.4, 1.6 Hz, 2H), 7.60 (d, J=8.4 Hz, 2H), 7.94 (dd, J=7.6, 1.8 Hz, 1H), 8.45 (dd, J=4.4, 1.6 Hz, 2H), 8.58 (dd, J=4.7, 1.8 Hz, 1H), 10.38 (s, 1H)

N-(3,5-Difluorophenyl)-2-(4-pyridylmethylthio)pyridine-3-carboxamide

Compound No. 1-192

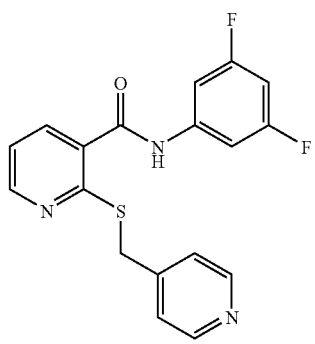

¹H-NMR (500 MHz, DMSO-d₆)

δ 4.43 (s, 2H), 7.00 (m, 1H), 7.32 (dd, J=7.6, 4.9 Hz, 1H), 7.40 (dd, J=4.6, 1.5 Hz, 2H), 7.43 (dd, J=9.5, 1.8 Hz, 2H), 8.00 (dd, J=7.6, 1.7 Hz, 1H), 8.45 (dd, J=4.6, 1.5 Hz, 2H), 8.61 (dd, J=4.9, 1.7 Hz, 1H), 10.82 (s, 1H)

2-(4-Pyridylmethylthio)-N-(3,4,5-trichlorophenyl)pyridine-3-carboxamide

Compound No. 1-193

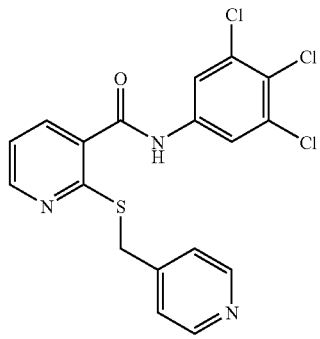

¹H-NMR (500 MHz, DMSO-d₆)

δ 4.43 (s, 2H), 7.33 (dd, J=7.6, 4.9 Hz, 1H), 7.40 (dd, J=4.4, 1.6 Hz, 2H), 7.98 (s, 2H), 8.03 (dd, J=7.6, 1.8 Hz, 1H), 8.46 (dd, J=4.4, 1.6 Hz, 2H), 8.62 (dd, J=4.9, 1.8 Hz, 1H), 10.84 (s, 1H)

N-(3-Methylthiophenyl)-2-(4-pyridylmethylthio)pyridine-3-carboxamide

Compound No. 1-194

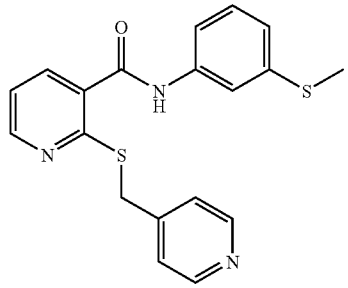

¹H-NMR (500 MHz, DMSO-d₆)
δ 2.47 (s, 3H), 4.42 (s, 2H), 7.01 (d, J=7.9 Hz, 1H), 7.27-7.31 (m, 2H), 7.40 (dd, J=4.5, 1.6 Hz, 2H), 7.46 (d, J=7.9 Hz, 1H), 7.67 (s, 1H), 7.97 (dd, J=7.6, 1.5 Hz, 1H), 8.45 (dd, J=4.5, 1.6 Hz, 2H), 8.59 (dd, J=4.9, 1.5 Hz, 1H), 10.48 (s, 1H)

N-(4-Chloro-3-nitrophenyl)-2-(4-pyridylmethylthio)pyridine-3-carboxamide

Compound No. 1-195

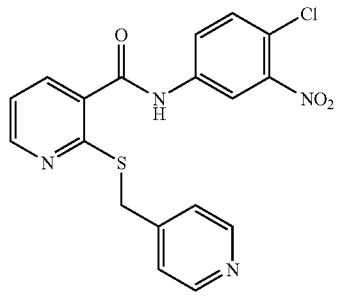

¹H-NMR (500 MHz, DMSO-d₆)
δ 4.43 (s, 2H), 7.33 (dd, J=7.6, 4.9 Hz, 1H), 7.40 (dd, J=4.4, 1.7 Hz, 2H), 7.78 (d, J=8.9 Hz, 1H), 7.92 (d, J=8.9 Hz, 1H), 8.05 (dd, J=7.6, 1.8 Hz, 1H), 8.45 (dd, J=4.4, 1.7 Hz, 2H), 8.52 (d, J=2.7 Hz, 1H), 8.63 (dd, J=4.9, 1.8 Hz, 1H), 11.00 (s, 1H)

N-(3,4-Dicyanophenyl)-2-(4-pyridylmethylthio)pyridine-3-carboxamide

Compound No. 1-196

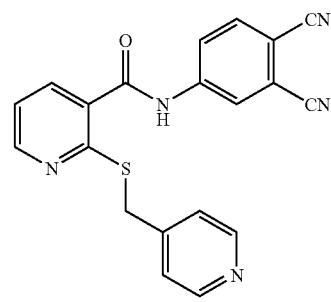

¹H-NMR (500 MHz, DMSO-d₆)
δ 4.43 (s, 2H), 7.34 (dd, J=7.6, 4.9 Hz, 1H), 7.40 (dd, J=4.3, 1.5 Hz, 2H), 8.05-8.13 (m, 3H), 8.36 (d, J=1.5 Hz, 1H), 8.45 (dd, J=4.3, 1.5 Hz, 2H), 8.64 (dd, J=4.9, 1.5 Hz, 1H), 11.19 (s, 1H)

N-(4-Diethylaminophenyl)-2-(4-pyridylmethylthio)pyridine-3-carboxamide

Compound No. 1-197

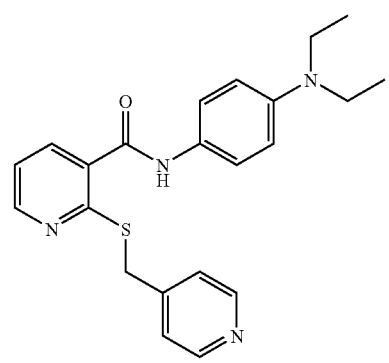

¹H-NMR (500 MHz, DMSO-d₆)
δ 1.07 (t, J=7.0 Hz, 6H), 3.29-3.33 (m, 4H), 4.40 (s, 2H), 6.64 (d, J=9.2 Hz, 2H), 7.26 (dd, J=7.6, 4.9 Hz, 1H), 7.40 (dd,

J=4.3, 1.5 Hz, 2H), 7.46 (d, J=9.2 Hz, 2H), 7.90 (dd, J=7.6, 1.8 Hz, 1H), 8.45 (dd, J=4.3, 1.5 Hz, 2H), 8.55 (dd, J=4.9, 1.8 Hz, 1H), 10.11 (s, 1H)

N-(3-Benzyloxyphenyl)-2-(4-pyridylmethylthio)pyridine-3-carboxamide

Compound No. 1-198

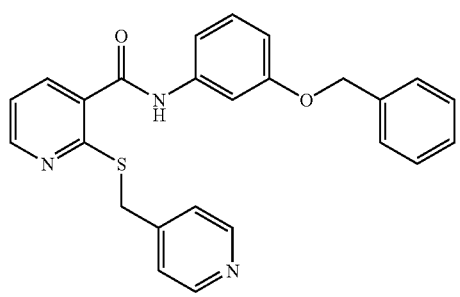

¹H-NMR (500 MHz, DMSO-d₆)
δ 4.42 (s, 2H), 5.09 (s, 2H), 6.78 (m, 1H), 7.25 (d, J=5.2 Hz, 2H), 7.29 (dd, J=7.6, 4.9 Hz, 1H), 7.32 (m, 1H), 7.35-7.41 (m, 4H), 7.43-7.48 (m, 3H), 7.94 (dd, J=7.6, 1.8 Hz, 1H), 8.45 (dd, J=4.3, 1.5 Hz, 2H), 8.58 (dd, J=4.9, 1.8 Hz, 1H), 10.45 (s, 1H)

N-(3-Phenoxyphenyl)-2-(4-pyridylmethylthio)pyridine-3-carboxamide

Compound No. 1-199

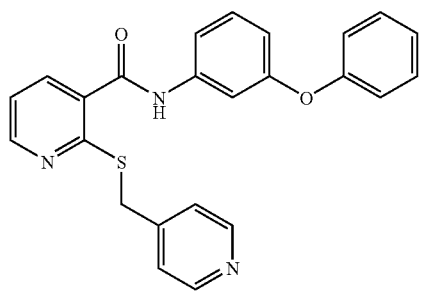

¹H-NMR (500 MHz, DMSO-d₆)
δ 4.41 (s, 2H), 6.77 (m, 1H), 7.03-7.06 (m, 2H), 7.16 (m, 1H), 7.27 (dd, J=7.6, 4.9 Hz, 1H), 7.33-7.48 (m, 7H), 7.94 (dd, J=7.6, 1.8 Hz, 1H), 8.45 (dd, J=4.3, 1.5 Hz, 2H), 8.58 (dd, J=4.9, 1.8 Hz, 1H), 10.45 (s, 1H)

N-(3,4-Dichlorophenyl)-2-(4-pyridylmethylthio)benzamide

Compound No. 1-200

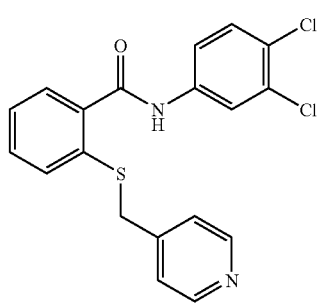

¹H-NMR (500 MHz, DMSO-d₆)
δ 4.26 (s, 2H), 7.31 (m, 1H), 7.35 (d, J=5.8 Hz, 2H), 7.44 (m, 1H), 7.48 (dd, J=7.9, 1.2 Hz, 1H), 7.54 (dd, J=7.3, 1.2 Hz, 1H), 7.62 (s, 1H), 7.65 (dd, J=8.9, 2.1 Hz, 1H), 8.10 (d, J=2.1 Hz, 1H), 8.46 (d, J=5.8 Hz, 2H), 10.65 (s, 1H)

N-(4-Methylphenyl)-2-(4-pyridylmethylthio)benzamide

Compound No. 1-201

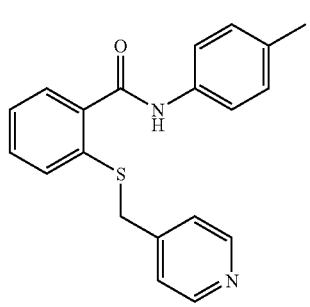

¹H-NMR (500 MHz, DMSO-d₆)

δ 2.27 (s, 3H) 4.25 (s, 2H), 7.14 (d, J=8.2 Hz, 2H), 7.28 (m, 1H), 7.35 (d, J=5.8 Hz, 2H), 7.40 (dd, J=7.6 Hz, 1H), 7.45 (m, 1H), 7.50 (d, J=6.7 Hz, 1H), 7.61 (d, J=8.2 Hz, 2H), 8.45 (d, J=5.8 Hz, 2H), 10.25 (s, 1H)

N-(3,4-Difluorophenyl)-2-(4-pyridylmethylthio)benzamide

Compound No. 1-202

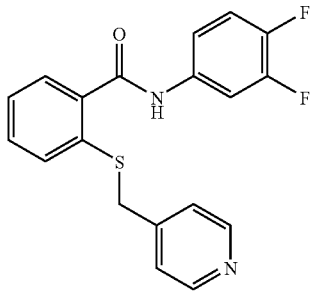

¹H-NMR (500 MHz, DMSO-d₆)
δ 4.26 (s, 2H), 7.30 (m, 1H), 7.35 (d, J=5.8 Hz, 2H), 7.39-7.50 (m, 3H), 7.53 (m, 1H), 7.88 (m, 1H), 7.62 (s, 1H), 8.46 (d, J=5.8 Hz, 2H), 10.58 (s, 1H)

N-(4-Chloro-3-trifluoromethylphenyl)-2-(4-pyridylmethylthio)benzamide

Compound No. 1-203

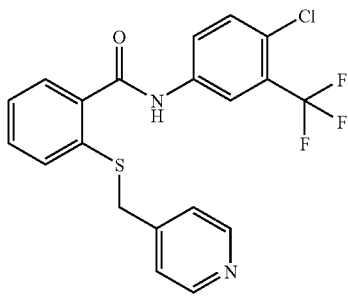

¹H-NMR (400 MHz, DMSO-d₆)
δ 4.27 (s, 2H), 7.32 (t, J=7.6 Hz, 1H), 7.36 (d, J=6.1 Hz, 2H), 7.45 (t, J=7.6 Hz, 1H), 7.50 (d, J=7.6 Hz, 1H), 7.58 (d, J=7.6 Hz, 1H), 7.72 (d, J=8.8 Hz, 1H), 7.99 (d, J=8.8 Hz, 1H), 8.33 (s, 1H), 8.45 (d, J=6.1 Hz, 2H), 10.80 (s, 1H)

N-(4-Methyl-3-trifluoromethylphenyl)-2-(4-pyridylmethylthio)pyridine-3-carboxamide Compound No. 1-204

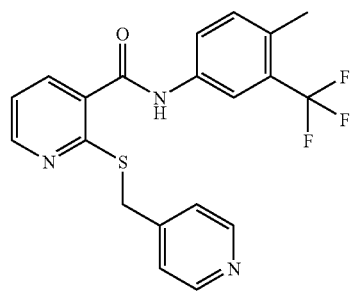

¹H-NMR (400 MHz, DMSO-d₆)
δ 2.50 (s, 3H), 4.42 (s, 2H), 7.31 (dd, J=7.6, 4.9 Hz, 1H), 7.40 (d, J=5.6 Hz, 2H), 7.43 (d, J=8.3 Hz, 1H), 7.82 (d, J=8.3 Hz, 1H), 8.01 (dd, J=7.6, 1.2 Hz, 1H), 8.11 (s, 1H), 8.45 (d, J=5.6 Hz, 2H), 8.60 (dd, J=4.9, 1.2 Hz, 1H), 10.68 (s, 1H)

N-(4-Methoxy-3-trifluoromethylphenyl)-2-(4-pyridylmethylthio)pyridine-3-carboxamide Compound No. 1-205

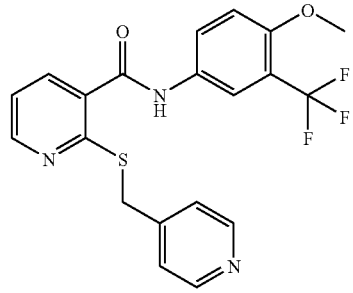

¹H-NMR (400 MHz, DMSO-d₆)
δ 3.88 (s, 3H), 4.42 (s, 2H), 7.29 (d, J=9.0 Hz, 1H), 7.30 (dd, J=7.6, 4.9 Hz, 1H), 7.40 (dd, J=4.4, 1.5 Hz, 2H), 7.88 (dd,

J=9.0, 2.2 Hz, 1H), 8.01 (dd, J=7.6, 1.7 Hz, 1H), 8.05 (d, J=2.2 Hz, 1H), 8.46 (dd, J=4.4, 1.5 Hz, 2H), 8.60 (dd, J=4.9, 1.7 Hz, 1H), 10.58 (s, 1H)

2-(4-Pyridylmethylthio)-N-(3-trifluoromethylphenyl)benzamide

Compound No. 1-206

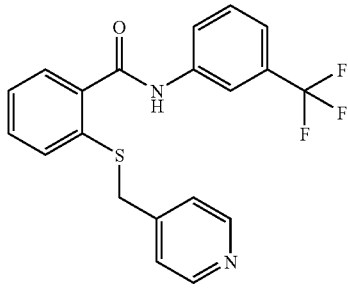

¹H-NMR (500 MHz, DMSO-d₆)

δ 4.27 (s, 2H), 7.31 (m, 1H), 7.36 (d, J=5.9 Hz, 2H), 7.40-7.50 (m, 3H), 7.57 (dd, J=7.3, 1.2 Hz, 1H), 7.60 (d, J=7.8 Hz, 1H), 7.92 (d, J=7.8 Hz, 1H), 8.23 (s, 1H), 8.45 (d, J=5.9 Hz, 2H), 10.70 (s, 1H)

N-(4-Isopropoxyphenyl)-2-(4-pyridylmethylthio)benzamide

Compound No. 1-207

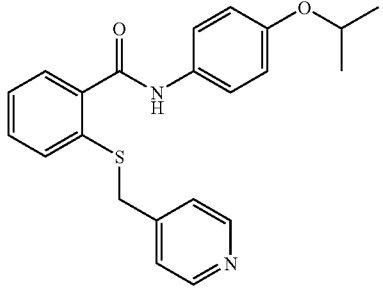

¹H-NMR (400 MHz, DMSO-d₆)

δ 1.25 (d, J=6.1 Hz, 6H), 4.25 (s, 2H), 4.56 (m, 1H), 6.89 (d, J=9.0 Hz, 2H), 7.28 (dd, J=8.1, 6.3 Hz, 1H), 7.36 (d, J=5.9 Hz, 2H), 7.39 (d, J=8.1 Hz, 1H), 7.44 (dd, J=8.1, 7.1 Hz, 1H), 7.48 (d, J=6.3 Hz, 1H), 7.60 (d, J=9.0 Hz, 2H), 8.45 (d, J=5.9 Hz, 2H), 10.19 (s, 1H)

N-(3,4-Dimethylphenyl)-2-(4-pyridylmethylthio)benzamide

Compound No. 1-208

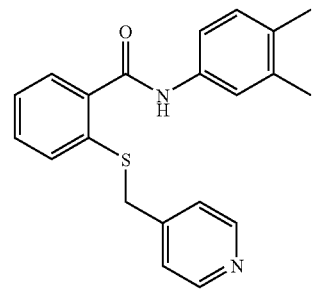

¹H-NMR (400 MHz, DMSO-d₆)

δ 2.19 (s, 3H), 2.21 (s, 3H), 4.25 (s, 2H), 7.08 (d, J=8.1 Hz, 1H), 7.27 (m, 1H), 7.36 (dd, J=4.4, 1.5 Hz, 2H), 7.37-7.53 (m, 5H), 8.45 (dd, J=4.4, 1.5 Hz, 2H), 10.18 (s, 1H)

N-(3-Isoquinolyl)-2-(4-pyridylmethylthio)benzamide

Compound No. 1-209

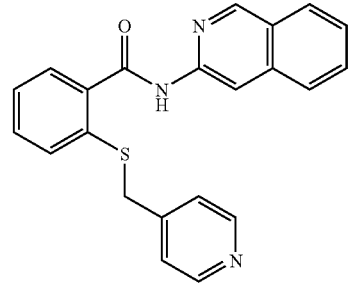

¹H-NMR (500 MHz, DMSO-d₆)

δ 4.26 (s, 2H), 7.29 (m, 1H), 7.37 (d, J=5.8 Hz, 2H), 7.40-7.44 (m, 2H), 7.57 (m, 1H), 7.61 (m, 1H), 7.75 (m, 1H), 7.98 (d, J=8.2 Hz, 1H), 8.08 (d, J=8.2 Hz, 1H), 8.46 (d, J=5.8 Hz, 2H), 8.60 (s, 1H), 9.18 (s, 1H), 10.98 (s, 1H)

2-(4-Pyridylmethylthio)-N-(4-trifluoromethylphenyl)benzamide

Compound No. 1-210

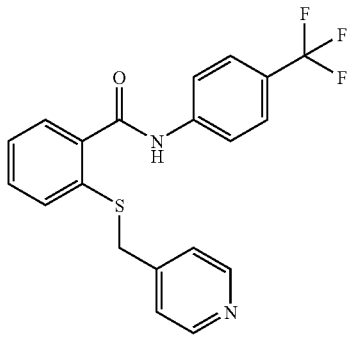

¹H-NMR (500 MHz, DMSO-d₆)

δ 4.26 (s, 2H), 7.31 (m, 1H), 7.35 (d, J=5.8 Hz, 2H), 7.44 (m, 1H), 7.49 (d, J=7.3 Hz, 1H), 7.56 (dd, J=7.3, 1.2 Hz, 1H), 7.72 (d, J=8.6 Hz, 2H), 7.94 (d, J=8.6 Hz, 2H), 8.45 (d, J=5.8 Hz, 2H), 10.73 (s, 1H)

N-(3-Methyl-5-trifluoromethylphenyl)-2-(4-pyridylmethylthio)benzamide

Compound No. 1-211

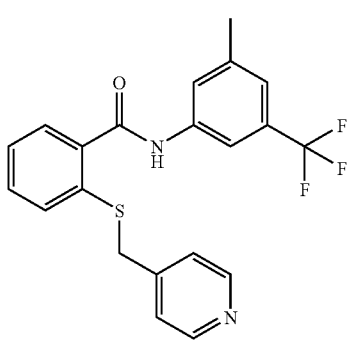

¹H-NMR (500 MHz, DMSO-d₆)

δ 2.39 (s, 3H), 4.26 (s, 2H), 7.28-7.33 (m, 2H), 7.35 (d, J=6.1 Hz, 2H), 7.40-7.50 (m, 2H), 7.55 (dd, J=7.6, 1.2 Hz, 1H), 7.78 (s, 1H), 7.98 (s, 1H), 8.45 (d, J=6.1 Hz, 2H), 10.60 (s, 1H)

N-(4-Isopropyl-3-methylphenyl)-2-(4-pyridylmethylthio)pyridine-3-carboxamide

Compound No. 1-212

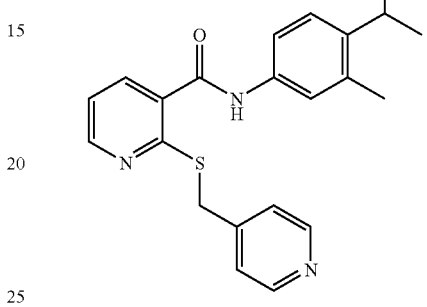

¹H-NMR (500 MHz, DMSO-d₆)

δ 1.16 (d, J=6.7 Hz, 6H), 2.28 (s, 3H), 3.07 (m, 1H), 4.41 (s, 2H), 7.19 (d, J=8.0 Hz, 1H), 7.28 (dd, J=7.6, 4.9 Hz, 1H), 7.40 (dd, J=4.6, 1.8 Hz, 2H), 7.45 (d, J=8.0 Hz, 1H), 7.46 (s, 1H), 7.92 (dd, J=7.6, 1.8 Hz, 1H), 8.45 (dd, J=4.6, 1.8 Hz, 2H), 8.57 (dd, J=4.9, 1.8 Hz, 1H), 10.30 (s, 1H)

N-(3,5-Dimethylphenyl)-2-(2-fluoropyridin-4-ylmethylthio)pyridine-3-carboxamide

Compound No. 1-213

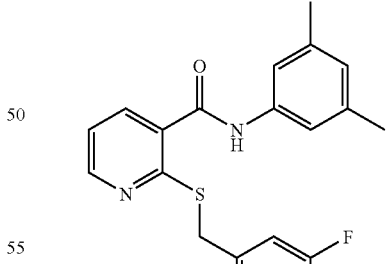

¹H-NMR (500 MHz, DMSO-d₆)

δ 2.26 (s, 6H), 4.46 (s, 2H), 6.76 (s, 1H), 7.18 (s, 1H), 7.29 (dd, J=7.3, 4.6 Hz, 1H), 7.32 (s, 2H), 7.38 (d, J=5.2 Hz, 1H), 7.94 (dd, J=7.3, 1.5 Hz, 1H), 8.13 (d, J=5.2 Hz, 1H), 8.58 (dd, J=4.6, 1.5 Hz, 1H), 10.32 (s, 1H)

2-(2-Fluoropyridin-4-ylmethylthio)-N-(4-trifluoromethoxyphenyl)pyridine-3-carboxamide Compound No. 1-214

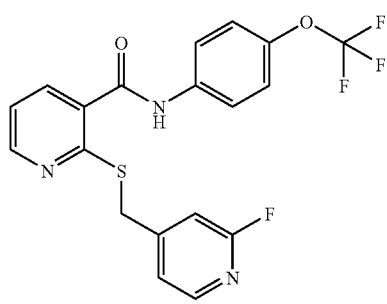

¹H-NMR (500 MHz, DMSO-d₆)
δ 4.47 (s, 2H), 7.18 (s, 1H), 7.32 (dd, J=7.6, 4.9 Hz, 1H), 7.35-7.40 (m, 3H), 7.81 (d, J=8.2 Hz, 2H), 8.00 (dd, J=7.6, 1.8 Hz, 1H), 8.13 (d, J=5.2 Hz, 1H), 8.61 (dd, J=4.9, 1.8 Hz, 1H), 10.67 (s, 1H)

2-(2-Fluoropyridin-4-ylmethylthio)-N-(5-indanyl)pyridine-3-carboxamide

Compound No. 1-215

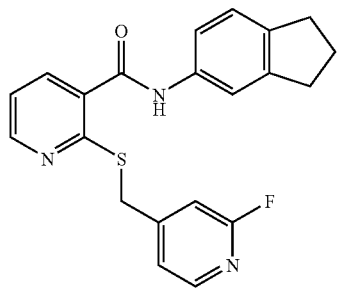

¹H-NMR (500 MHz, DMSO-d₆)
δ 1.98-2.06 (m, 2H), 2.79-2.90 (m, 4H), 4.46 (s, 2H), 7.16-7.20 (m, 2H), 7.29 (dd, J=7.3, 4.9 Hz, 1H), 7.38 (dd, J=4.6, 1.5 Hz, 2H), 7.61 (s, 1H), 7.95 (dd, J=7.3, 1.5 Hz, 1H), 8.13 (d, J=5.2 Hz, 1H), 8.58 (dd, J=4.9, 1.5 Hz, 1H), 10.35 (s, 1H)

2-(2-Chloropyridin-4-ylmethylthio)-N-(5-indanyl)pyridine-3-carboxamide

Compound No. 1-216

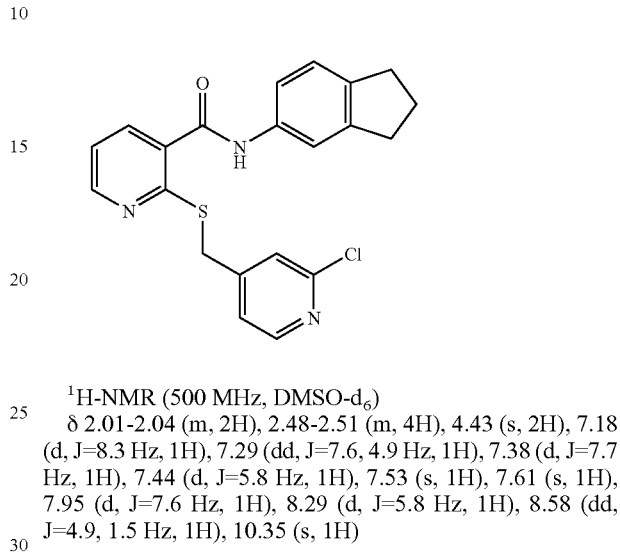

¹H-NMR (500 MHz, DMSO-d₆)
δ 2.01-2.04 (m, 2H), 2.48-2.51 (m, 4H), 4.43 (s, 2H), 7.18 (d, J=8.3 Hz, 1H), 7.29 (dd, J=7.6, 4.9 Hz, 1H), 7.38 (d, J=7.7 Hz, 1H), 7.44 (d, J=5.8 Hz, 1H), 7.53 (s, 1H), 7.61 (s, 1H), 7.95 (d, J=7.6 Hz, 1H), 8.29 (d, J=5.8 Hz, 1H), 8.58 (dd, J=4.9, 1.5 Hz, 1H), 10.35 (s, 1H)

2-(2-Chloropyridin-4-ylmethylthio)-N-(3-methylphenyl)pyridine-3-carboxamide

Compound No. 1-217

¹H-NMR (500 MHz, DMSO-d₆)
δ 2.30 (s, 3H), 4.43 (s, 2H), 6.94 (d, J=7.3 Hz, 1H), 7.23 (t, J=8.0 Hz, 1H), 7.30 (dd, J=7.6, 4.9 Hz, 1H), 7.45 (m, 2H), 7.53-7.55 (m, 2H), 7.96 (dd, J=7.6, 1.5 Hz, 1H), 8.29 (d, J=5.2 Hz, 1H), 8.58 (dd, J=4.9, 1.5 Hz, 1H), 10.39 (s, 1H)

2-(2-Chloropyridin-4-ylmethylthio)-N-(3,4-dimethylphenyl)pyridine-3-carboxamide

Compound No. 1-218

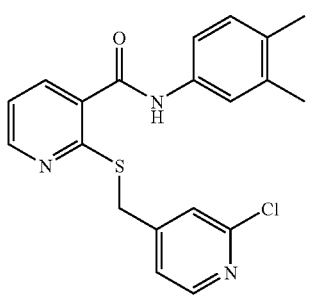

¹H-NMR (500 MHz, DMSO-d₆)
δ 2.19 (s, 3H), 2.21 (s, 3H), 4.42 (s, 2H), 7.09 (d, J=8.3 Hz, 1H), 7.29 (dd, J=7.6, 4.9 Hz, 1H), 7.39 (d, J=8.3 Hz, 1H), 7.44 (dd, J=5.2, 1.6 Hz, 1H), 7.48 (s, 1H), 7.53 (d, J 0.6 Hz, 1H), 7.95 (dd, J=7.6, 1.5 Hz, 1H), 8.29 (d, J=5.2 Hz, 1H), 8.58 (dd, J=4.9, 1.5 Hz, 1H), 10.31 (s, 1H)

2-(2-Chloropyridin-4-ylmethylthio)-N-(3-isopropylphenyl)pyridine-3-carboxamide

Compound No. 1-219

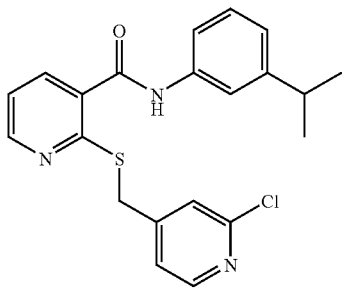

¹H-NMR (500 MHz, DMSO-d₆)
δ 1.20 (d, J=6.7 Hz, 6H), 2.87 (m, 1H), 4.43 (s, 2H), 7.00 (d, J=7.6 Hz, 1H), 7.26 (t, J=8.0 Hz, 1H), 7.30 (dd, J=7.6, 4.9 Hz, 1H), 7.44 (dd, J=4.9, 1.4 Hz, 1H), 7.51 (m, 1H), 7.53 (m, 1H), 7.59 (s, 1H), 7.98 (dd, J=7.6, 1.5 Hz, 1H), 8.29 (d, J=4.9 Hz, 1H), 8.58 (dd, J=4.9, 1.5 Hz, 1H), 10.40 (s, 1H)

N-(4-Bromo-3-methylphenyl)-2-(2-chloropyridin-4-ylmethylthio)pyridine-3-carboxamide Compound No. 1-220

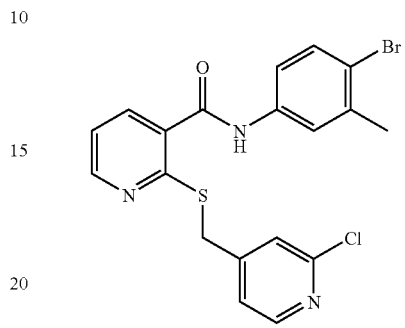

¹H-NMR (500 MHz, DMSO-d₆)
δ 2.34 (s, 3H), 4.43 (s, 2H), 7.31 (dd, J=7.3, 4.9 Hz, 1H), 7.42-7.46 (m, 2H), 7.51-7.54 (m, 2H), 7.72 (d, J=2.1 Hz, 1H), 7.79 (dd, J=7.3, 1.8 Hz, 1H), 8.29 (d, J=4.9 Hz, 1H), 8.59 (dd, J=4.9, 1.8 Hz, 1H), 10.53 (s, 1H)

2-(2 Chloropyridin-4-ylmethylthio)-N-(4-n-propylphenyl)pyridine-3-carboxamide

Compound No. 1-221

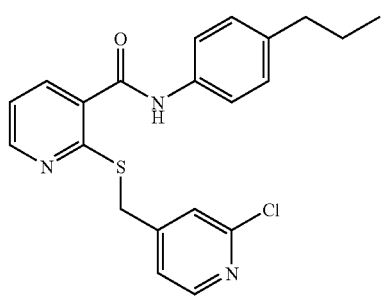

¹H-NMR (500 MHz, DMSO-d₆)
δ 0.88 (t, J=7.3 Hz, 3H), 1.54-1.59 (m, 2H), 2.50-2.54 (m, 2H), 4.43 (s, 2H), 7.16 (d, J=8.6 Hz, 2H), 7.30 (dd, J=7.6, 4.9 Hz, 1H), 7.44 (dd, J=4.9, 1.4 Hz, 1H), 7.53 (d, J=0.6 Hz, 1H), 7.57-7.60 (m, 2H), 7.96 (dd, J=7.6, 1.5 Hz, 1H), 8.29 (m, 1H), 8.58 (dd, J=4.9, 1.5 Hz, 1H), 10.39 (s, 1H)

2-(2-Chloropyridin-4-ylmethylthio)-N-(4-fluoro-3-methylphenyl)pyridine-3-carboxamide Compound No. 1-222

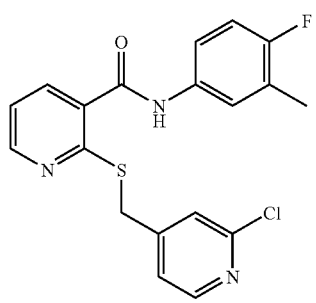

¹H-NMR (500 MHz, DMSO-d₆)
δ 2.23 (s, 3H), 4.43 (s, 2H), 7.12 (t, J=9.2 Hz, 1H), 7.30 (dd, J=7.6, 4.9 Hz, 1H), 7.44 (dd, J=5.2, 1.2 Hz, 1H), 7.48 (m, 1H), 7.53 (d, J=0.6 Hz, 1H), 7.63 (d, J=4.9 Hz, 1H), 7.97 (dd, J=7.6, 1.5 Hz, 1H), 8.30 (d, J=5.2 Hz, 1H), 8.59 (dd, J=4.9, 1.5 Hz, 1H), 10.45 (s, 1H)

N-(4-tert-Butylphenyl)-2-(2-chloropyridin-4-ylmethylthio)pyridine-3-carboxamide

Compound No. 1-223

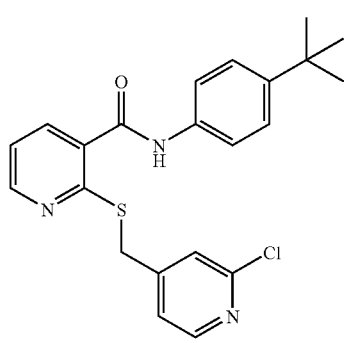

¹H-NMR (500 MHz, DMSO-d₆)
δ 1.27 (s, 9H), 4.43 (s, 2H), 7.30 (dd, J=7.6, 4.9 Hz, 1H), 7.36 (d, J=8.9 Hz, 2H), 7.44 (dd, J=5.2, 1.5 Hz, 1H), 7.53 (d, J=0.9 Hz, 1H), 7.58-7.61 (m, 2H), 7.96 (dd, J=7.6, 1.8 Hz, 1H), 8.30 (d, J=5.2 Hz, 1H), 8.58 (dd, J=4.9, 1.8 Hz, 1H), 10.40 (s, 1H)

N-(4-Chlorophenyl)-2-(2-chloropyridin-4-ylmethylthio)pyridine-3-carboxamide

Compound No. 1-224

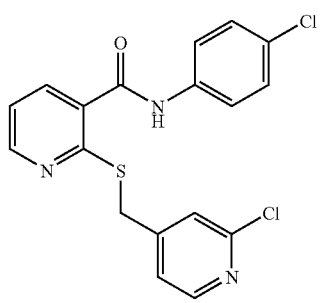

¹H-NMR (500 MHz, DMSO-d₆)
δ 4.43 (s, 2H), 7.31 (dd, J=7.6, 4.8 Hz, 1H), 7.41-7.45 (m, 3H), 7.53 (s, 1H), 7.73 (d, J=8.9 Hz, 2H), 8.00 (dd J=7.6, 1.8 Hz, 1H), 8.30 (d, J=5.1 Hz, 1H), 8.60 (dd, J=4.8, 1.8 Hz, 1H), 10.61 (s, 1H)

N-(3-Chlorophenyl)-2-(2-chloropyridin-4-ylmethylthio)pyridine-3-carboxamide

Compound No. 1-225

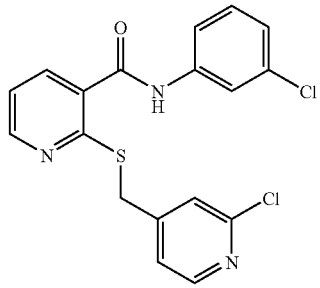

¹H-NMR (400 MHz, DMSO-d₆)

δ 4.44 (s, 2H), 7.19 (m, 1H), 7.31-7.45 (m, 3H), 7.54 (s, 1H), 7.59 (m, 1H), 7.90 (m, 1H), 8.01 (m, 1H), 8.29 (d, J=5.1 Hz, 1H), 8.61 (dd, J=4.9, 1.7 Hz, 1H), 10.66 (s, 1H)

2-(2-Chloropyridin-4-ylmethylthio)-N-(3,5-dimethylphenyl)pyridine-3-carboxamide

Compound No. 1-226

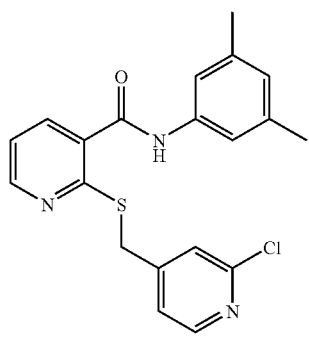

¹H-NMR (400 MHz, DMSO-d₆)

δ 2.26 (s, 6H), 4.43 (s, 2H), 6.77 (d, J=0.7 Hz, 1H), 7.28-7.32 (m, 3H), 7.44 (dd, J=5.1, 1.5 Hz, 1H), 7.53 (dd, J=1.5, 0.7 Hz, 1H), 7.95 (dd, J=7.6, 1.7 Hz, 1H), 8.30 (dd, J=5.1, 0.7 Hz, 1H), 8.58 (dd, J=4.8, 1.7 Hz, 1H), 10.33 (s, 1H)

2-(2-Chloropyridin-4-ylmethylthio)-N-(4-trifluoromethoxyphenyl)pyridine-3-carboxamide Compound No. 1-227

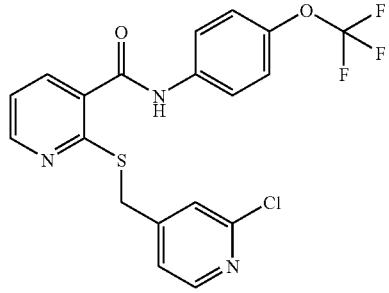

¹H-NMR (400 MHz, DMSO-d₆)

δ 4.44 (s, 2H), 7.31-7.45 (m, 4H), 7.54 (d, J=0.7 Hz, 1H), 7.81 (dd, J=7.1, 2.0 Hz, 2H), 8.01 (dd, J=7.6, 1.8 Hz, 1H), 8.30 (d, J=5.1 Hz, 1H), 8.61 (dd, J=4.8, 1.8 Hz, 1H), 10.68 (s, 1H)

2-(3-Chloropyridin-4-ylmethylthio)-N-(3,5-dimethylphenyl)pyridine-3-carboxamide

Compound No. 1-228

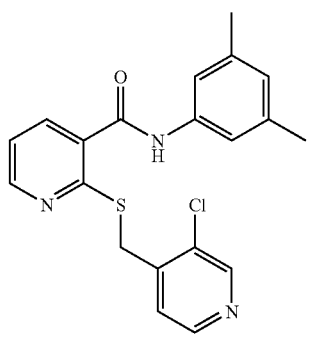

¹H-NMR (500 MHz, DMSO-d₆)

δ 2.25 (s, 6H), 4.50 (s, 2H), 6.76 (s, 1H), 7.30 (dd, J=7.6, 4.9 Hz, 1H), 7.32 (s, 2H), 7.59 (d, J=4.9 Hz, 1H), 7.97 (dd, J=7.6, 1.5 Hz, 1H), 8.42 (d, J=4.9 Hz, 1H), 8.58-8.60 (m, 2H), 10.32 (s, 1H)

2-(2,6-Dichloropyridin-4-ylmethylthio)-N-(3,5-dimethylphenyl)pyridine-3-carboxamide Compound No. 1-229

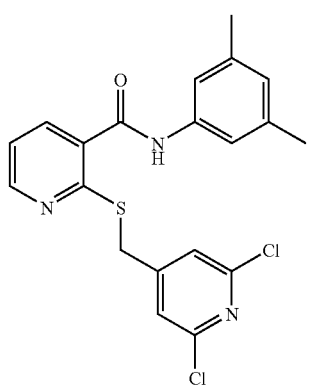

¹H-NMR (500 MHz, DMSO-d₆)

δ 2.26 (s, 6H), 4.43 (s, 2H), 6.77 (s, 1H), 7.30-7.33 (m, 3H), 7.59 (s, 2H), 7.97 (dd, J=7.4, 1.8 Hz, 1H), 8.59 (dd, J=4.8, 1.5 Hz, 1H), 10.32 (s, 1H)

2-(2-Bromopyridin-4-ylmethylthio)-N-(3,5-dimethylphenyl)pyridine-3-carboxamide

Compound No. 1-230

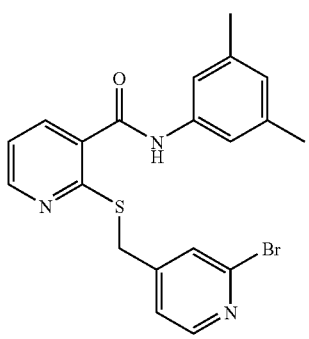

¹H-NMR (400 MHz, DMSO-d₆)
δ 2.26 (s, 6H), 4.41 (s, 2H), 6.76 (d, J=0.7 Hz, 1H), 7.29 (dd, J=7.6, 4.8 Hz, 1H), 7.32 (s, 2H), 7.47 (dd, J=5.1, 1.4 Hz, 1H), 7.67 (s, 1H), 7.93 (dd, J=7.6, 1.7 Hz, 1H), 8.27 (dd, J=5.1, 1.7 Hz, 1H), 8.58 (dd, J=4.8, 1.7 Hz, 1H), 10.32 (s, 1H)

N-(3,5-Dimethylphenyl)-2-(2-methylthiopyridin-4-ylmethylthio)pyridine-3-carboxamide Compound No. 1-231

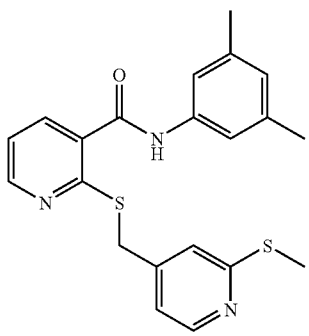

¹H-NMR (500 MHz, CDCl₃)
δ 2.32 (s, 6H), 2.53 (s, 3H), 4.38 (s, 2H) 6.81 (s, 1H), 7.02 (dd, J=5.0, 1.3 Hz, 1H), 7.12 (dd, J=7.6, 4.9 Hz, 1H), 7.24- 7.26 (m, 3H), 7.75 (s, 1H), 7.86 (dd, J=7.6, 1.5 Hz, 1H), 8.32 (d, J=5.0 Hz, 1H), 8.52 (dd, J=4.9, 1.5 Hz, 1H)

N-(4-Chlorophenyl)-2-(2-methylthiopyridin-4-ylmethylthio)pyridine-3-carboxamide

Compound No. 1-232

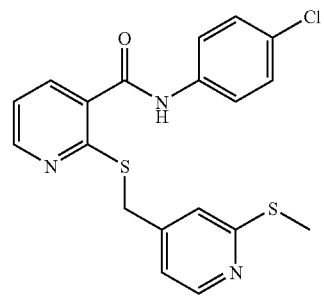

¹H-NMR (500 MHz, DMSO-d₆)
δ 2.46 (s, 3H), 4.37 (s, 2H), 7.12 (dd, J=4.9, 1.5 Hz, 1H), 7.29-7.31 (m, 2H), 7.39-7.41 (m, 2H), 7.71 (d, J=4.5 Hz, 2H), 7.98 (dd, J=7.6, 1.8 Hz, 1H), 8.31 (d, J=4.5 Hz, 1H), 8.60 (dd, J=4.9, 1.8 Hz, 1H), 10.60 (s, 1H)

N-(3-Chlorophenyl)-2-(2-cyanopyridin-4-ylmethylthio)pyridine-3-carboxamide

Compound No. 1-233

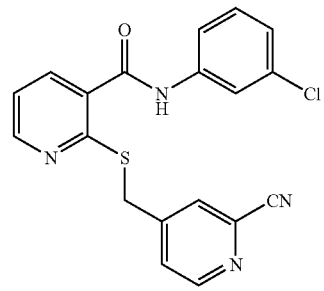

¹H-NMR (400 MHz, DMSO-d₆)
δ 4.48 (s, 2H), 7.19 (ddd, J=7.8, 1.9, 0.9 Hz, 1H), 7.31 (dd, J=7.6, 4.9 Hz, 1H), 7.39 (d, J=8.1 Hz, 1H), 7.58 (d, J=8.1 Hz, 1H), 7.77 (dd, J=4.9, 1.7 Hz, 1H), 7.89 (t, J=1.9 Hz, 1H), 8.02 (dd, J=7.6, 1.7 Hz, 1H), 8.06 (d, J=0.9 Hz, 1H), 8.59-8.64 (m, 2H), 10.65 (s, 1H)

2-(2-Cyanopyridin-4-ylmethylthio)-N-(3-methylphenyl)pyridine-3-carboxamide

Compound No. 1-234

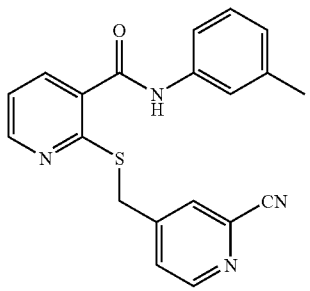

¹H-NMR (400 MHz, DMSO-d₆)
δ 2.30 (s, 3H), 4.47 (s, 2H), 6.94 (d, J=7.7 Hz, 1H), 7.23 (d, J=7.7 Hz, 1H), 7.30 (dd, J=7.6, 4.9 Hz, 1H), 7.46 (d, J=8.0 Hz, 1H), 7.55 (s, 1H), 7.77 (dd, J=5.1, 1.7 Hz, 1H), 7.98 (dd, J=7.6, 1.7 Hz, 1H), 8.06 (d, J=1.0 Hz, 1H), 8.58 (dd, J=4.9, 1.7 Hz, 1H), 8.64 (dd, J=5.1, 1.7 Hz, 1H), 10.40 (s, 1H)

N-(4-Chlorophenyl)-1-(2-cyanopyridin-4-ylmethylthio)pyridine-3-carboxamide

Compound No. 1-235

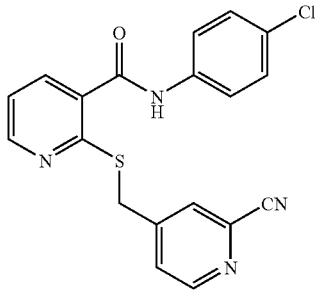

¹H-NMR (500 MHz, DMSO-d₆)
δ 4.47 (s, 2H), 7.31 (dd, J=7.6, 4.9 Hz, 1H), 7.41-7.44 (m, 2H), 7.72-7.78 (m, 3H), 8.01 (dd, J=7.6, 1.5 Hz, 1H), 8.06 (s, 1H), 8.59-8.64 (m, 2H), 10.60 (s, 1H)

2-(2-Cyanopyridin-4-ylmethylthio)-N-(3,5-dimethylphenyl)pyridine-3-carboxamide

Compound No. 1-236

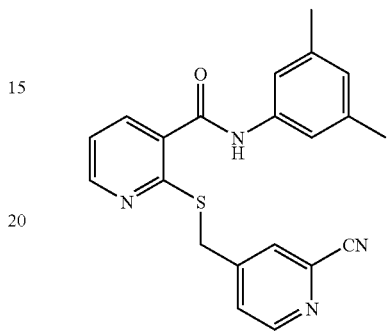

¹H-NMR (500 MHz, DMSO-d₆)
δ 2.26 (s, 6H), 4.47 (s, 2H), 6.77 (s, 1H), 7.28-7.32 (m, 3H), 7.77 (dd, J=4.9, 1.5 Hz, 1H), 7.96 (dd, J=7.6, 1.5 Hz, 1H), 8.06 (s, 1H), 8.57 (dd, J=4.9, 1.5 Hz, 1H), 8.64 (d, J=5.2 Hz, 1H), 10.31 (s, 1H)

2-(2-Cyanopyridin-4-ylmethylthio)-N-(4-trifluoromethoxyphenyl)pyridine-3-carboxamide Compound No. 1-237

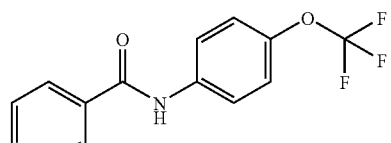

¹H-NMR (500 MHz, DMSO-d₆)
δ 4.48 (s, 2H), 7.32 (m, 1H), 7.38 (d, J=8.9 Hz, 2H), 7.77 (dd, J=5.2, 1.5 Hz, 1H), 7.81 (d, J=8.9 Hz, 2H), 8.02 (dd,

J=7.6, 1.5 Hz, 1H), 8.06 (s, 1H), 8.60 (dd, J=4.9, 1.5 Hz, 1H), 8.64 (d, J=5.2 Hz, 1H), 10.66 (s, 1H)

2-(2-Cyanopyridin-4-ylmethylthio)-N-(4-fluoro-3-methylphenyl)pyridine-3-carboxamide Compound No. 1-238

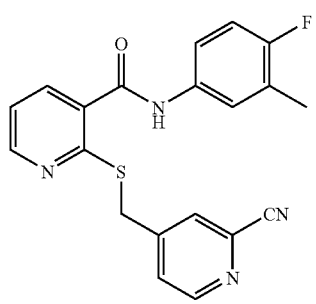

¹H-NMR (500 MHz, DMSO-d₆)
δ 2.23 (s, 3H), 4.47 (s, 2H), 7.13 (d, J=9.2 Hz, 1H), 7.30 (dd, J=7.6, 4.9 Hz, 1H), 7.49 (m, 1H), 7.63 (m, 1H), 7.77 (dd, J=4.9, 1.8 Hz, 1H), 7.98 (dd, J=7.6, 1.8 Hz, 1H), 8.06 (s, 1H), 8.58 (dd, J=4.9, 1.8 Hz, 1H), 8.63 (dd, J=4.9, 0.7 Hz, 1H), 10.44 (s, 1H)

2-(2-Cyanopyridin-4-ylmethylthio)-N-(5-indanyl)pyridine-3-carboxamide

Compound No. 1-239

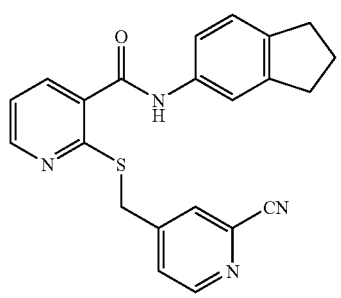

¹H-NMR (500 MHz, DMSO-d₆)
δ 2.01 (q, J=7.4 Hz, 2H), 2.81-2.87 (m, 4H), 4.46 (s, 2H), 7.18 (d, J=8.1 Hz, 1H), 7.29 (dd, J=7.6, 4.7 Hz, 1H), 7.39 (d, J=8.1 Hz, 1H), 7.61 (s, 1H), 7.77 (dd, J=5.0, 1.7 Hz, 1H), 7.96 (dd, J=7.6, 1.5 Hz, 1H), 8.06 (d, J=0.9 Hz, 1H), 8.57 (dd, J=4.7, 1.5 Hz, 1H), 8.63 (dd, J=5.0, 0.9 Hz, 1H), 10.34 (s, 1H)

N-(4-tert-Butylphenyl)-2-(2-cyanopyridin-4-ylmethylthio)pyridine-3-carboxamide

Compound No. 1-240

¹H-NMR (400 MHz, DMSO-d₆)
δ 1.28 (s, 9H), 4.47 (s, 2H), 7.30 (dd, J=7.6, 4.9 Hz, 1H), 7.37 (dd, J=6.6, 2.0 Hz, 2H), 7.61 (d, J=8.6 Hz, 2H), 7.77 (dd, J=4.9, 1.7 Hz, 1H), 7.97 (dd, J=7.7, 1.6 Hz, 1H), 8.06 (d, J=1.0 Hz, 1H), 8.58 (dd, J=4.9, 1.7 Hz, 1H), 8.63 (dd, J=5.0, 0.6 Hz, 1H), 10.40 (s, 1H)

2-(2-Ethoxycarbonylpyridine-4-ylmethylthio)-N-(3,5-dimethylphenyl)-pyridine-3-carboxamide Compound No. 1-241

¹H-NMR (400 MHz, DMSO-d₆)
δ 1.31 (t, J=7.1 Hz, 3H), 2.25 (s, 6H), 4.32 (q, J=7.1 Hz, 2H), 4.49 (s, 2H), 6.76 (s, 1H), 7.29 (m, 1H), 7.32 (s, 2H), 7.66

(dd, J=4.9, 1.7 Hz, 1H), 7.94 (dd, J=7.6, 1.7 Hz, 1H), 8.10 (d, J=1.0 Hz, 1H), 8.56-8.59 (m, 2H), 10.31 (s, 1H)

N-(4-Chlorophenyl)-3-(4-pyridylmethylthio)pyrazine-2-carboxamide

Compound No. 1-242

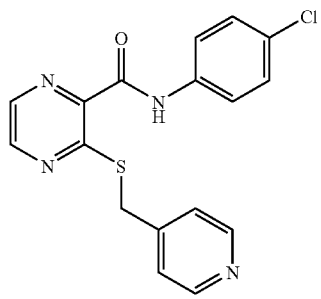

¹H-NMR (500 MHz, DMSO-d₆)

δ 4.39 (s, 2H), 7.41 (dd, J=6.7, 2.1 Hz, 2H), 7.43 (dd, J=4.6, 1.5 Hz, 2H), 7.86 (dd, J=6.7, 2.1 Hz, 2H), 8.47 (dd, J=4.6, 1.5 Hz, 2H), 8.50 (d, J=2.5 Hz, 1H), 8.74 (d, J=2.5 Hz, 1H), 10.84 (br s, 1H)

N-(3,5-Dimethylphenyl)-3-(4-pyridylmethylthio)pyrazine-2-carboxamide

Compound No. 1-243

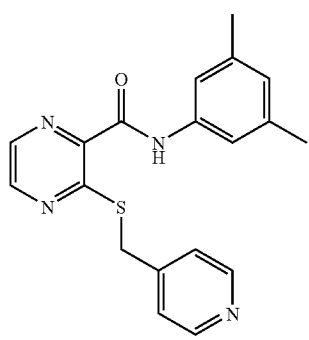

¹H-NMR (500 MHz, DMSO-d₆)

δ 2.26 (s, 6H), 4.39 (s, 2H), 6.78 (s, 1H), 7.44 (dd, J=4.4, 1.7 Hz, 2H), 7.45 (s, 2H), 8.48 (dd, J=4.4, 1.7 Hz, 2H), 8.49 (d, J=2.5 Hz, 1H), 8.74 (d, J=2.5 Hz, 1H), 10.46 (br s, 1H)

N-(4-Methoxyphenyl)-3-(4-pyridylmethylthio)thiophene-2-carboxamide

Compound No. 1-244

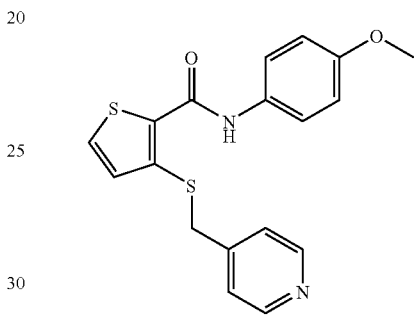

¹H-NMR (400 MHz, DMSO-d₆)

δ 3.74 (s, 3H), 4.28 (s, 2H), 6.91 (dd, J=6.8, 2.2 Hz, 2H), 7.23 (d, J=6.4 Hz, 1H), 7.34 (dd, J=4.4, 1.5 Hz, 2H), 7.53 (dd, J=6.8, 2.2 Hz, 2H), 7.81 (d, J=6.4 Hz, 1H), 8.46 (dd, J=4.4, 1.5 Hz, 2H), 9.87 (s, 1H)

N-(4-Fluorophenyl)-3-(4-pyridylmethylthio)thiophene-2-carboxamide

Compound No. 1-245

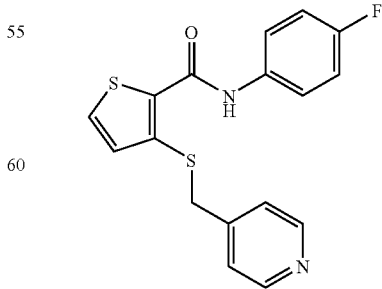

¹H-NMR (400 MHz, DMSO-d₆)

δ 4.28 (s, 2H), 7.18 (d, J=9.0 Hz, 2H), 7.24 (d, J=5.4 Hz, 1H), 7.34 (d, J=4.7 Hz, 2H), 7.65 (d, J=9.0 Hz, 2H), 7.84 (d, J=5.4 Hz, 1H), 8.45 (dd, J=4.7, 1.5 Hz, 2H), 10.04 (s, 1H)

N-(4-Isopropoxyphenyl)-3-(4-pyridylmethylthio)thiophene-2-carboxamide

Compound No. 1-246

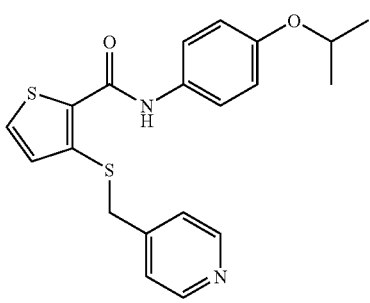

¹H-NMR (500 MHz, DMSO-d$_6$)
δ 1.25 (d, J=6.1 Hz, 6H), 4.27 (s, 2H), 4.56 (m, 1H), 6.88 (dd, J=7.0, 2.1 Hz, 2H), 7.22 (d, J=5.4 Hz, 1H), 7.33 (dd, J=4.5, 1.7 Hz, 2H), 7.50 (dd, J=7.0, 2.1 Hz, 2H), 7.80 (d, J=5.4 Hz, 1H), 8.46 (dd, J=4.5, 1.7 Hz, 2H), 9.85 (s, 1H)

N-(4-Dimethylaminophenyl)-3-(4-pyridylmethylthio)thiophene-2-carboxamide

Compound No. 1-247

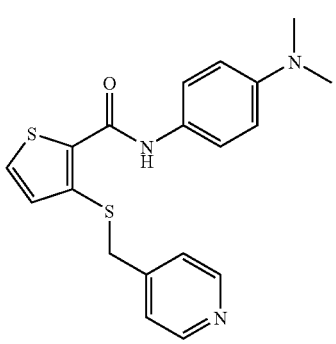

¹H-NMR (500 MHz, CDCl$_3$)

δ 2.95 (s, 6H), 3.99 (s, 2H), 6.73 (dd, J=6.8, 2.2 Hz, 2H), 6.93 (d, J=5.2 Hz, 1H), 7.02 (dd, J=4.3, 1.7 Hz, 2H), 7.42 (dd, J=6.8, 2.2 Hz, 2H), 7.44 (d, J=5.2 Hz, 1H), 8.47 (dd, J=4.3, 1.7 Hz, 2H), 9.69 (s, 1H)

N-(3-Fluoro-4-methylphenyl)-3-(4-pyridylmethylthio)thiophene-2-carboxamide

Compound No. 1-248

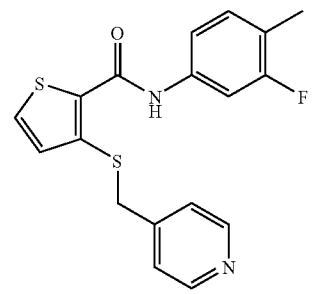

¹H-NMR (500 MHz, DMSO-d$_6$)
δ 2.19 (d, J=1.6 Hz, 3H), 4.28 (s, 2H), 7.22 (m, 1H), 7.25 (d, J=5.2 Hz, 1H), 7.32 (m, 1H), 7.34 (dd, J=4.3, 1.5 Hz, 2H), 7.54 (dd, J=12.2, 2.1 Hz, 1H), 7.84 (d, J=5.2 Hz, 1H), 8.46 (dd, J=4.3, 1.5 Hz, 2H), 10.08 (s, 1H)

N-(3-Chlorophenyl)-3-(4-pyridylmethylthio)thiophene-2-carboxamide

Compound No. 1-249

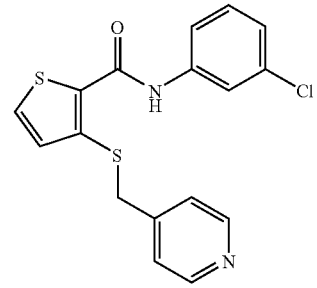

¹H-NMR (500 MHz, DMSO-d$_6$)
δ 4.00 (s, 2H), 6.98 (d, J=5.2 Hz, 1H), 7.01 (dd, J=4.5, 1.6 Hz, 2H), 7.12 (ddd, J=8.1, 2.0, 0.9 Hz, 1H), 7.28 (m, 1H), 7.42

(ddd, J=8.1, 2.0, 0.9 Hz, 1H), 7.52 (d, J=5.2 Hz, 1H), 7.64 (t, J=2.0 Hz, 1H), 8.47 (d, J=4.5 Hz, 2H), 9.90 (s, 1H)

N-(4-Chlorophenyl)-3-(4-pyridylmethylthio)thiophene-2-carboxamide

Compound No. 1-250

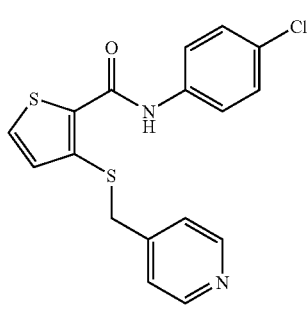

¹H-NMR (500 MHz, DMSO-d₆)
δ 3.99 (s, 2H), 6.98-7.00 (m, 3H), 7.31 (dd, J=6.9, 2.0 Hz, 2H), 7.48-7.50 (m, 3H), 8.46 (dd, J=4.4, 1.8 Hz, 2H), 9.87 (s, 1H)

3-(2-Chloropyridin-4-ylmethylthio)-N-(3,5-dimethylphenyl)thiophene-2-carboxamide Compound No. 1-251

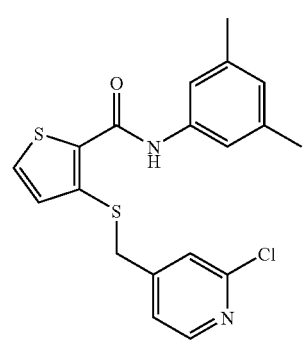

¹H-NMR (500 MHz, DMSO-d₆)

δ 2.25 (s, 6H), 4.28 (s, 2H), 6.75 (d, J=0.6 Hz, 1H), 7.23-7.25 (m, 3H), 7.32 (d, J=5.2 Hz, 1H), 7.45 (d, J=0.9 Hz, 1H), 7.84 (d, J=5.2 Hz, 1H), 8.28 (m, 1H), 9.86 (s, 1H)

N-(4-Fluoro-3-methylphenyl)-3-(4-pyridylmethylthio)thiophene-2-carboxamide

Compound No. 1-252

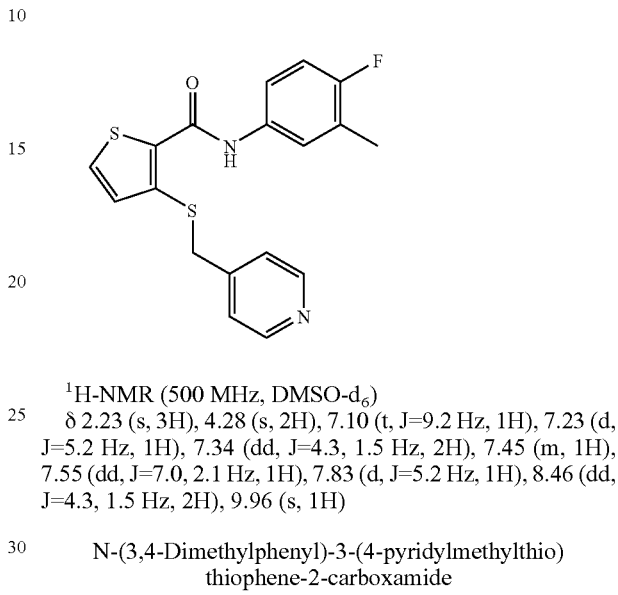

¹H-NMR (500 MHz, DMSO-d₆)
δ 2.23 (s, 3H), 4.28 (s, 2H), 7.10 (t, J=9.2 Hz, 1H), 7.23 (d, J=5.2 Hz, 1H), 7.34 (dd, J=4.3, 1.5 Hz, 2H), 7.45 (m, 1H), 7.55 (dd, J=7.0, 2.1 Hz, 1H), 7.83 (d, J=5.2 Hz, 1H), 8.46 (dd, J=4.3, 1.5 Hz, 2H), 9.96 (s, 1H)

N-(3,4-Dimethylphenyl)-3-(4-pyridylmethylthio)thiophene-2-carboxamide

Compound No. 1-253

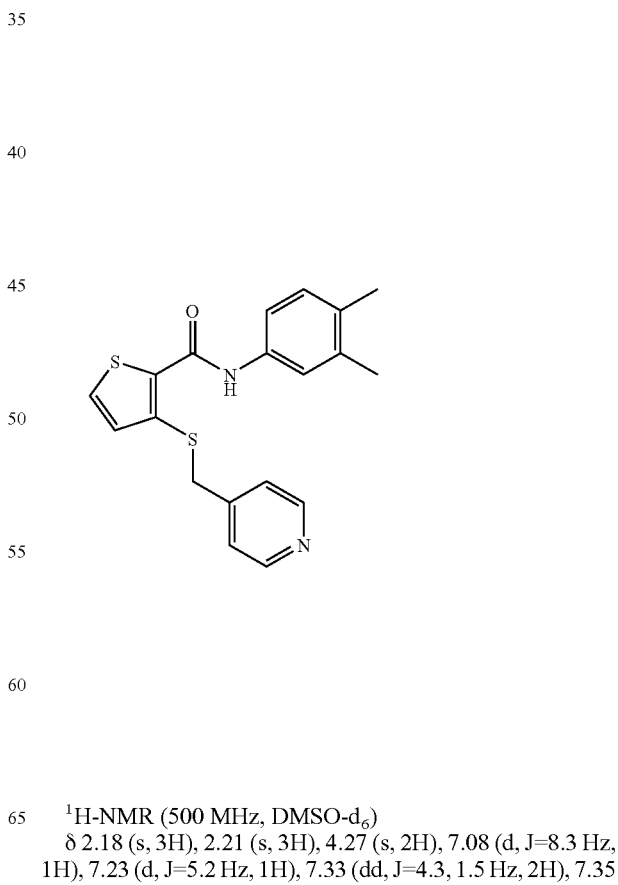

¹H-NMR (500 MHz, DMSO-d₆)
δ 2.18 (s, 3H), 2.21 (s, 3H), 4.27 (s, 2H), 7.08 (d, J=8.3 Hz, 1H), 7.23 (d, J=5.2 Hz, 1H), 7.33 (dd, J=4.3, 1.5 Hz, 2H), 7.35

(dd, J=8.3, 2.1 Hz, 1H), 7.40 (d, J=2.1 Hz, 1H), 7.81 (d, J=5.2 Hz, 1H), 8.45 (dd, J=4.3, 1.5 Hz, 2H), 9.84 (s, 1H)

3-(4-Pyridylmethylthio)-N-(3-trifluoromethoxyphenyl)thiophene-2-carboxamide

Compound No. 1-254

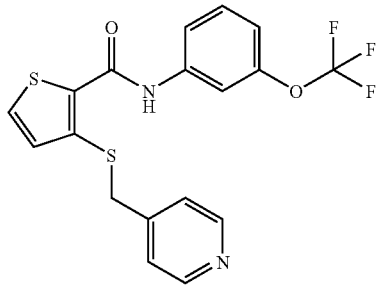

¹H-NMR (500 MHz, DMSO-d₆)

δ 4.30 (s, 2H), 7.08 (dt, J=8.2, 1.2 Hz, 1H), 7.26 (d, J=5.2 Hz, 1H), 7.35 (dd, J=4.6, 1.5 Hz, 2H), 7.46 (t, J=8.2 Hz, 1H), 7.63 (dt, J=8.2, 1.2 Hz, 1H), 7.79 (br s, 1H), 7.87 (d, J=5.2 Hz, 1H), 8.46 (dd, J=4.6, 1.5 Hz, 2H), 10.25 (s, 1H)

3-(4-Pyridylmethylthio)-N-(4-trifluoromethylphenyl)thiophene-2-carboxamide

Compound No. 1-255

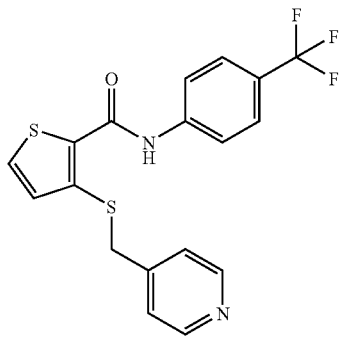

¹H-NMR (500 MHz, DMSO-d₆)

δ 4.01 (s, 2H), 7.00 (dd, J=4.3, 1.5 Hz, 2H), 7.01 (d, J=5.2 Hz, 1H), 7.54 (d, J=5.2 Hz, 1H), 7.61 (d, J=8.6 Hz, 2H), 7.67 (d, J=8.6 Hz, 2H), 8.45 (dd, J=4.3, 1.5 Hz, 2H), 10.03 (s, 1H)

N-(4-tert-Butylphenyl)-3-(4-pyridylmethylthio)thiophene-2-carboxamide

Compound No. 1-256

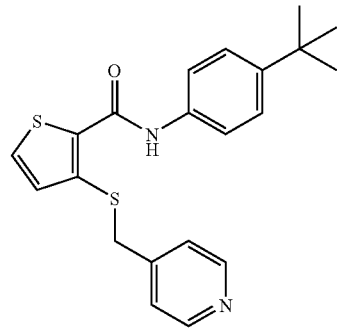

¹H-NMR (500 MHz, DMSO-d₆)

δ 1.27 (s, 9H), 4.28 (s, 2H), 7.23 (d, J=5.2 Hz, 1H), 7.34 (dd, J=4.3, 1.5 Hz, 2H), 7.35 (d, J=8.6 Hz, 2H), 7.54 (d, J=8.6 Hz, 2H), 7.82 (d, J=5.2 Hz, 1H), 8.46 (dd, J=4.3, 1.5 Hz, 2H), 9.93 (s, 1H)

N-(3,4-Dichlorophenyl)-3-(4-pyridylmethylthio)thiophene-2-carboxamide

Compound No. 1-257

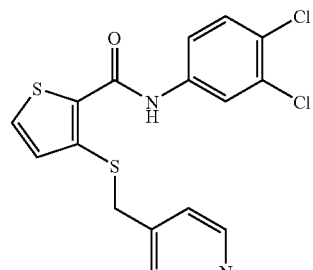

¹H-NMR (500 MHz, DMSO-d₆)

δ 4.30 (s, 2H), 7.26 (d, J=5.2 Hz, 1H), 7.35 (dd, J=4.6, 1.5 Hz, 2H), 7.59 (d, J=8.9 Hz, 1H), 7.62 (dd, J=8.9, 2.1 Hz, 1H), 7.87 (d, J=5.2 Hz, 1H), 8.01 (d, J=2.1 Hz, 1H), 8.46 (dd, J=4.6, 1.5 Hz, 2H), 10.24 (s, 1H)

N-(4-Methylphenyl)-3-(4-pyridylmethylthio)thiophene-2-carboxamide

Compound No. 1-258

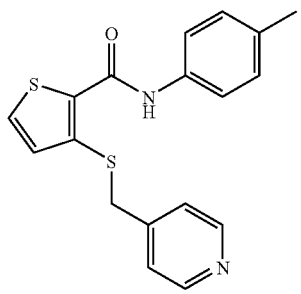

¹H-NMR (500 MHz, DMSO-d₆)

δ 2.27 (s, 3H), 4.28 (s, 2H), 7.14 (d, J=8.3 Hz, 2H), 7.23 (d, J=5.2 Hz, 1H), 7.33 (dd, J=4.3, 1.5 Hz, 2H), 7.51 (d, J=8.3 Hz, 2H), 7.82 (d, J=5.2 Hz, 1H), 8.45 (dd, J=4.3, 1.5 Hz, 2H), 9.91 (s, 1H)

N-(3-Methoxyphenyl)-3-(4-pyridylmethylthio)thiophene-2-carboxamide

Compound No. 1-259

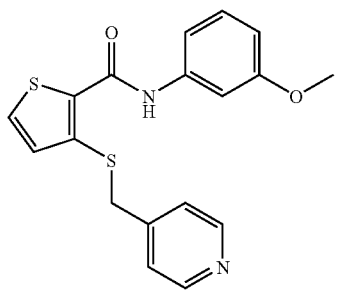

¹H-NMR (500 MHz, DMSO-d₆)

δ 3.75 (s, 3H), 4.28 (s, 2H), 6.68 (ddd, J=7.6, 2.4, 1.5 Hz, 1H), 7.19-7.23 (m, 2H), 7.25 (d, J=5.2 Hz, 1H), 7.32 (dd, J=2.4, 1.5 Hz, 1H), 7.34 (dd, J=4.6, 1.5 Hz, 2H), 7.83 (d, J=5.2 Hz, 1H), 8.46 (dd, J=4.6, 1.5 Hz, 2H), 9.97 (s, 1H)

N-[2-(4-Chlorophenyl)ethyl]-3-(4-pyridylmethylthio)thiophene-2-carboxamide

Compound No. 1-260

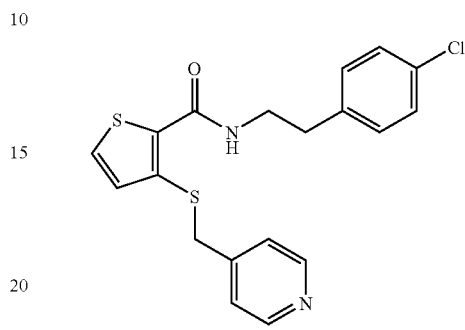

¹H-NMR (500 MHz, DMSO-d₆)

δ 2.79 (t, J=7.0 Hz, 2H), 3.41 (td, J=7.0, 5.5 Hz, 2H), 4.21 (s, 2H), 7.14 (d, J=5.2 Hz, 1H), 7.26 (dd, J=6.4, 2.1 Hz, 2H), 7.28 (dd, J=4.3, 1.5 Hz, 2H), 7.34 (dd, J=6.4, 2.4 Hz, 2H), 7.71 (d, J=5.2 Hz, 1H), 8.07 (t, J=5.5 Hz, 1H), 8.47 (dd, J=4.3, 1.5 Hz, 2H)

N-(4-Morpholinophenyl)-3-(4-pyridylmethylthio)thiophene-2-carboxamide

Compound No. 1-261

¹H-NMR (400 MHz, DMSO-d₆)

δ 3.07 (t, J=4.9 Hz, 4H), 3.74 (t, J=4.9 Hz, 4H), 4.27 (s, 2H), 6.92 (d, J=9.3 Hz, 2H), 7.22 (d, J=5.1 Hz, 1H), 7.33 (dd,

J=4.4, 1.5 Hz, 2H), 7.48 (d, J=9.3 Hz, 2H), 7.80 (d, J=5.1 Hz, 1H), 8.45 (dd, J=4.4, 1.5 Hz, 2H), 9.81 (s, 1H)

N-(4-Chlorophenyl)-N-methyl-3-(4-pyridylmethylthio)thiophene-2-carboxamide

Compound No. 1-262

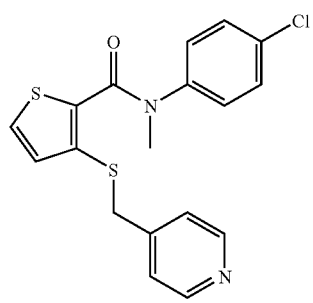

$^1$H-NMR (500 MHz, DMSO-d$_6$)

δ 3.42 (s, 3H), 4.03 (s, 2H), 6.67 (d, J=5.1 Hz, 1H), 7.05 (dd, J=8.5 Hz, 2H), 7.16 (d, J=5.1 Hz, 1H), 7.23-7.30 (m, 4H), 8.52 (d, J=5.9 Hz, 2H)

N-(3-Methylphenyl)-3-(4-pyridylmethylthio)thiophene-2-carboxamide

Compound No. 1-263

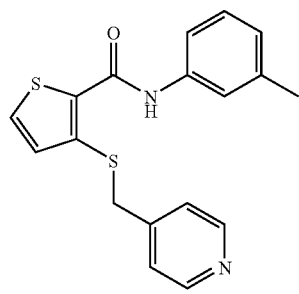

$^1$H-NMR (400 MHz, DMSO-d$_6$)

δ 2.30 (s, 3H), 4.28 (s, 2H), 6.92 (d, J=7.2 Hz, 1H), 7.19-7.25 (m, 2H), 7.33 (dd, J=4.4, 1.7 Hz, 2H), 7.41 (d, J=8.0 Hz, 1H), 7.47 (s, 1H), 7.83 (d, J=5.1 Hz, 1H), 8.46 (dd, J=4.4, 1.7 Hz, 2H), 9.92 (s, 1H)

N-(3-tert-Butylphenyl)-3-(4-pyridylmethylthio)thiophene-2-carboxamide

Compound No. 1-264

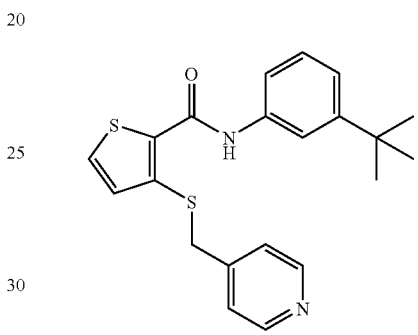

$^1$H-NMR (500 MHz, DMSO-d$_6$)

δ 1.28 (s, 9H), 4.28 (s, 2H), 7.13 (ddd, J=8.0, 1.9, 1.0 Hz, 1H), 7.24-7.27 (m, 2H), 7.34 (dd, J=4.3, 1.5 Hz, 2H), 7.49 (ddd, J=8.0, 1.9, 1.0 Hz, 1H), 7.63 (m, 1H), 7.83 (d, J=5.2 Hz, 1H), 8.46 (dd, J=4.3, 1.5 Hz, 2H), 9.93 (s, 1H)

N-Phenyl-3-(4-pyridylmethylthio)thiophene-2-carboxamide

Compound No. 1-265

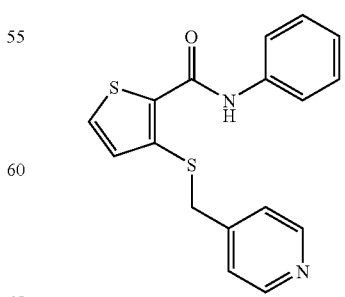

$^1$H-NMR (500 MHz, DMSO-d$_6$)

δ 4.28 (s, 2H), 7.11 (m, 1H), 7.24 (d, J=5.5 Hz, 1H), 7.32-7.36 (m, 4H), 7.61-7.64 (m, 2H), 7.83 (m, 1H), 8.46 (dd, J=4.4, 1.6 Hz, 2H), 10.00 (s, 1H)

N-[2-(4-Methoxyphenyl)ethyl]-3-(4-pyridylmethylthio)thiophene-2-carboxamide

Compound No. 1-266

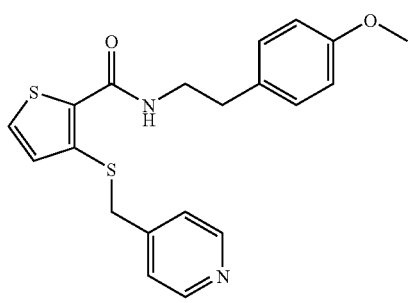

$^1$H-NMR (400 MHz, DMSO-$d_6$)
δ 2.72 (t, J=7.3 Hz, 2H), 3.35-3.40 (m, 2H), 3.71 (s, 3H), 4.20 (s, 2H), 6.86 (dd, J=6.6, 1.9 Hz, 2H), 7.14-7.16 (m, 3H), 7.27 (dd, J=4.4, 1.7 Hz, 2H), 7.71 (d, J=-5.1 Hz, 1H), 8.06 (t, J=5.6 Hz, 1H), 8.46 (dd, J=4.4, 1.7 Hz, 2H)

N-(3-Chloro-4-fluorophenyl)-3-(4-pyridylmethylthio)thiophene-2-carboxamide

Compound No. 1-267

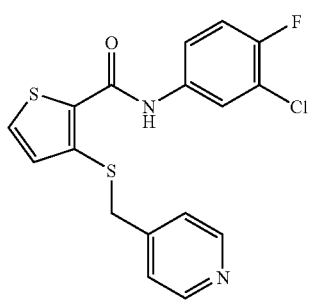

$^1$H-NMR (500 MHz, DMSO-$d_6$)

δ 4.29 (s, 2H), 7.25 (d, J=2.0 Hz, 1H), 7.36 (dd, J=4.4, 1.7 Hz, 2H), 7.40 (m, 1H), 7.60 (m, 1H), 7.86 (d, J=5.2 Hz, 1H), 7.94 (dd, J=7.0, 2.6 Hz, 1H), 8.47 (dd, J=4.4, 1.7 Hz, 2H), 10.17 (s, 1H)

N-(4-Chloro-3-methylphenyl)-3-(4-pyridylmethylthio)thiophene-2-carboxamide

Compound No. 1-268

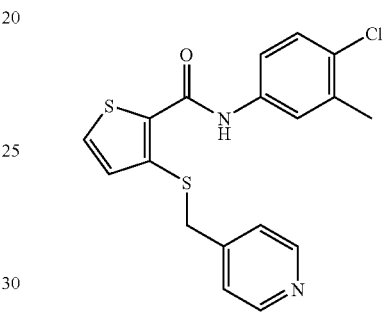

$^1$H-NMR (400 MHz, DMSO-$d_6$)
δ 2.32 (s, 3H), 4.28 (s, 2H), 7.24 (d, J=5.4 Hz, 1H), 7.33-7.37 (m, 3H), 7.50 (dd, J=8.5, 2.4 Hz, 1H), 7.64 (d, J=2.4 Hz, 1H), 7.84 (d, J=5.4 Hz, 1H), 8.46 (dd, J=4.4, 1.7 Hz, 2H), 10.04 (s, 1H)

N-(3,4-Difluorophenyl)-3-(4-pyridylmethylthio)thiophene-2-carboxamide

Compound No. 1-269

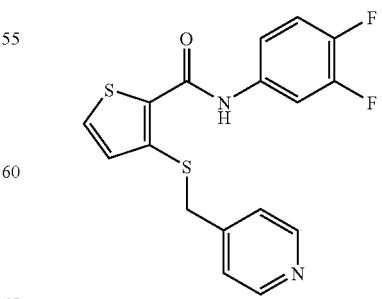

$^1$H-NMR (400 MHz, DMSO-$d_6$)

207

δ 4.29 (s, 2H), 7.25 (d, J=5.2 Hz, 1H), 7.35 (dd, J=4.3, 1.5 Hz, 2H), 7.40-7.43 (m, 2H), 7.78 (m, 1H), 7.86 (d, J=5.2 Hz, 1H), 8.46 (dd, J=4.3, 1.5 Hz, 2H), 10.18 (s, 1H)

N-(4-n-Propylphenyl)-3-(4-pyridylmethylthio)thiophene-2-carboxamide

Compound No. 1-270

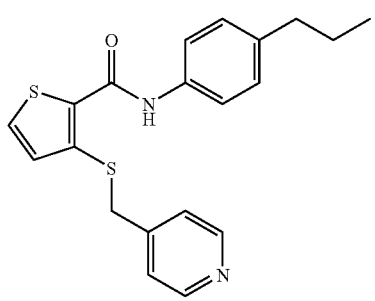

¹H-NMR (400 MHz, DMSO-d₆)
δ 0.89 (t, J=7.3 Hz, 3H), 1.55-1.60 (m, 2H), 2.49-2.51 (m, 2H), 4.28 (s, 2H), 7.14 (d, J=8.5 Hz, 2H), 7.23 (d, J=5.4 Hz, 1H), 7.33 (dd, J=4.4, 1.7 Hz, 2H), 7.51-7.53 (m, 2H), 7.82 (d, J=5.4 Hz, 1H), 8.45 (dd, J=4.4, 1.7 Hz, 2H), 9.93 (s, 1H)

N-(4-Bromophenyl)-3-(4-pyridylmethylthio)thiophene-2-carboxamide

Compound No. 1-272

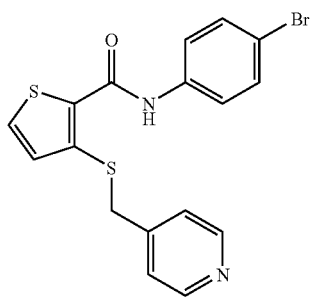

¹H-NMR (400 MHz, DMSO-d₆)

208

δ 4.29 (s, 2H), 7.25 (d, J=5.2 Hz, 1H), 7.34 (dd, J=4.4, 1.7 Hz, 2H), 7.52 (dd, J=6.8, 2.0 Hz, 2H), 7.62 (dd, J=6.8, 2.0 Hz, 2H), 7.85 (d, J=5.2 Hz, 1H), 8.46 (dd, J=4.4, 1.7 Hz, 2H), 10.12 (s, 1H)

3-(4-Pyridylmethylthio)-N-(4-trifluoromethoxyphenyl)thiophene-2-carboxamide

Compound No. 1-273

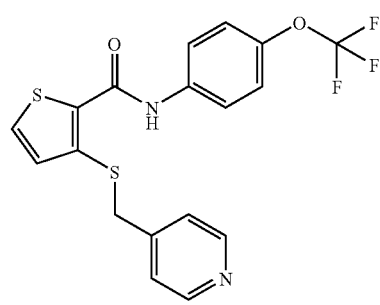

¹H-NMR (400 MHz, DMSO-d₆)
δ 4.29 (s, 2H), 7.25 (d, J=5.2 Hz, 1H), 7.34-7.36 (m, 4H), 7.73-7.77 (m, 2H), 7.85 (d, J=5.2 Hz, 1H), 8.46 (dd, J=4.4, 1.5 Hz, 2H), 10.18 (s, 1H)

N-(3-Isoquinolyl)-3-(4-pyridylmethylthio)thiophene-2-carboxamide

Compound No. 1-274

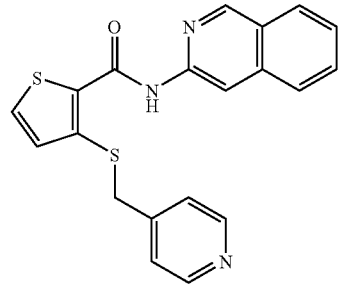

¹H-NMR (500 MHz, DMSO-d₆) 4.34 (s, 2H), 7.28-7.31 (m, 3H), 7.58 (m, 1H), 7.75 (m, 1H), 7.92-7.96 (m, 2H), 8.10 (d, J=7.9 Hz, 1H), 8.39 (dd, J=4.2, 1.5 Hz, 2H), 8.47 (s, 1H), 9.20 (s, 1H), 10.58 (s, 1H)

N-(3,5-Dimethylphenyl)-3-(4-pyridylmethylthio)thiophene-2-carboxamide

Compound No. 1-275

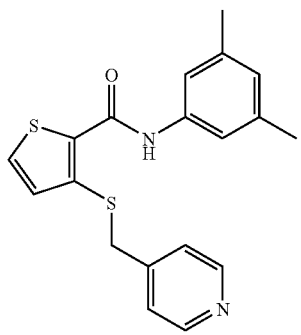

¹H-NMR (400 MHz, DMSO-d₆)
δ 2.25 (s, 6H), 4.28 (s, 2H), 6.74 (d, J=0.7 Hz, 1H), 7.23 (d, J=5.1 Hz, 1H), 7.25 (d, J=0.7 Hz, 2H), 7.33 (dd, J=4.4, 1.5 Hz, 2H), 7.82 (d, J=5.1 Hz, 1H), 8.45 (dd, J=4.4, 1.5 Hz, 2H), 9.85 (s, 1H)

3-(4-Pyridylmethylthio)-N-(3-trifluoromethylphenyl)thiophene-2-carboxamide

Compound No. 1-276

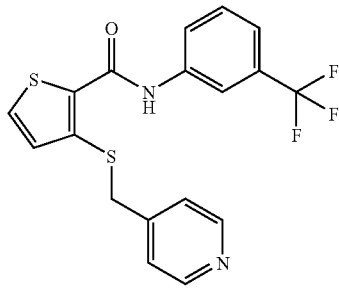

¹H-NMR (400 MHz, CDCl₃)

δ 4.02 (s, 2H), 7.00 (d, J=5.1 Hz, 1H), 7.01 (d, J=5.1 Hz, 2H), 7.40 (d, J=7.8 Hz, 1H), 7.48 (m, 1H), 7.54 (d, J=5.1 Hz, 1H), 7.76 (s, 1H), 7.79 (d, J=5.1 Hz, 1H), 8.47 (d, J=5.1 Hz, 2H), 10.00 (br s, 1H)

N-(3,5-Dichlorophenyl)-3-(4-pyridylmethylthio)thiophene-2-carboxamide

Compound No. 1-277

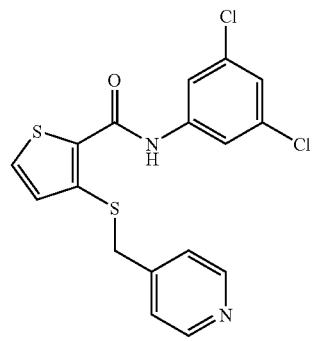

¹H-NMR (400 MHz, CDCl₃)
δ 4.01 (s, 2H), 6.99-7.01 (m, 3H), 7.25-7.26 (m, 2H), 7.48 (m, 1H), 7.54 (d, J=5.1 Hz, 1H), 8.48-8.49 (m, 2H), 9.93 (br s, 1H)

N-(3-Chloro-4-methylphenyl)-3-(4-pyridylmethylthio)thiophene-2-carboxamide

Compound No. 1-278

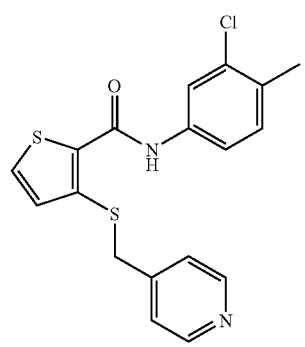

¹H-NMR (400 MHz, DMSO-d₆)
δ 2.29 (s, 3H), 4.29 (s, 2H), 7.25 (d, J=5.1 Hz, 1H), 7.30 (d, J=8.3 Hz, 1H), 7.35 (dd, J=4.4, 1.5 Hz, 2H), 7.47 (dd, J=8.3, 2.0 Hz, 1H), 7.80 (d, J=2.0 Hz, 1H), 7.85 (d, J=5.1 Hz, 1H), 8.46 (dd, J=4.4, 1.5 Hz, 2H), 10.07 (s, 1H)

N-(2,2-Dimethylpropyl)-3-(4-pyridylmethylthio)thiophene-2-carboxamide

Compound No. 1-279

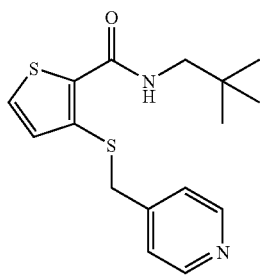

¹H-NMR (500 MHz, CDCl₃)

δ 0.95 (s, 9H), 3.18 (d, J=6.1 Hz, 2H), 3.97 (s, 2H), 6.89 (d, J=5.2 Hz, 1H), 7.02 (dd, J=4.3, 1.5 Hz, 2H), 7.41 (d, J=5.2 Hz, 1H), 7.91 (br s, 1H), 8.51 (dd, J=4.3, 1.5 Hz, 2H)

2-(Piperidine-1-yl)carbonyl-3-(4-pyridylmethylthio)thiophene

Compound No. 1-280

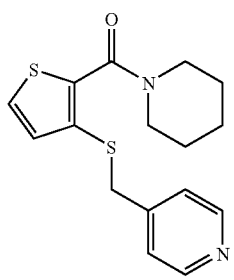

¹H-NMR (500 MHz, CDCl₃)

δ 1.66-1.69 (m, 6H), 3.47-3.50 (m, 4H), 3.98 (s, 2H), 6.71 (d, J=5.0 Hz, 1H), 7.17 (dd, J=4.6, 1.5 Hz, 2H), 7.23 (d, J=5.0 Hz, 1H), 8.49 (dd, J=4.6, 1.5 Hz, 2H)

N-Cyclohexyl-3-(4-pyridylmethylthio)thiophene-2-carboxamide

Compound No. 1-281

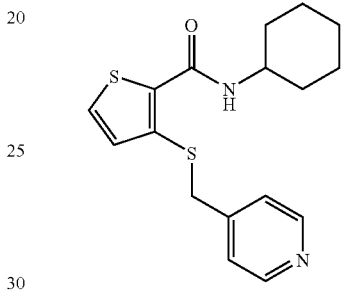

¹H-NMR (500 MHz, CDCl₃)

δ1.19-1.29 (m, 4H), 1.37-1.46 (m, 2H), 1.59-1.63 (m, 2H), 1.67-1.72 (m, 2H), 3.93 (m, 1H), 3.96 (s, 2H), 6.89 (d, J=5.2 Hz, 1H), 7.02 (dd, J=4.3, 1.5 Hz, 2H), 7.39 (d, J=5.2 Hz, 1H), 7.80 (d, J=6.7 Hz, 1H), 8.51 (dd, J=4.3, 1.5 Hz, 2H)

N-(4-Bromo-3-methylphenyl)-3-(4-pyridylmethylthio)thiophene-2-carboxamide

Compound No. 1-282

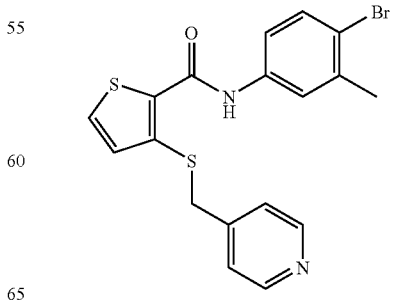

¹H-NMR (500 MHz, CDCl₃)

δ 2.40 (s, 3H), 4.00 (s, 2H), 6.98 (d, J=5.1 Hz, 1H), 7.01 (dd, J=4.4, 1.7 Hz, 2H), 7.25 (dd, J=8.6, 2.4 Hz, 1H), 7.47-7.51 (m, 3H), 8.47 (dd, J=4.4, 1.7 Hz, 2H), 9.82 (br s, 1H)

N-(5-Indanyl)-3-(4-pyridylmethylthio)thiophene-2-carboxamide

Compound No. 1-283

δ 4.25 (s, 2H), 7.34 (dd, J=4.4, 1.6 Hz, 2H), 7.40 (dd, J=6.9, 2.2 Hz, 2H), 7.56 (s, 2H), 7.74 (dd, J=6.9, 2.2 Hz, 2H), 8.48 (dd, J=4.4, 1.6 Hz, 2H), 10.10 (s, 1H)

N-(3-Methylphenyl)-2-(4-pyridylmethylthio)thiophene-3-carboxamide

Compound No. 1-285

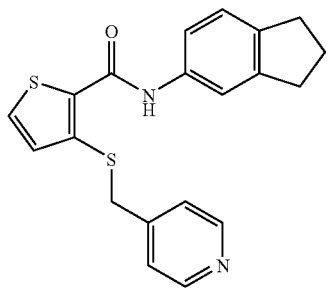

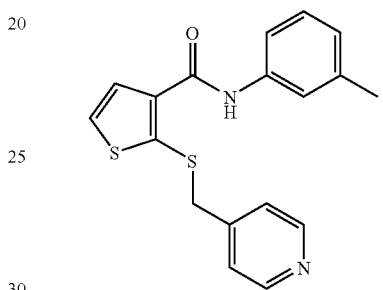

$^1$H-NMR (400 MHz, DMSO-d$_6$)
δ 1.98-2.05 (m, 2H), 2.82-2.85 (m, 4H), 4.27 (s, 2H), 7.16 (d, J=8.1 Hz, 1H), 7.23 (d, J=5.1 Hz, 1H), 7.32-7.34 (m, 3H), 7.52 (s, 1H), 7.81 (d, J=5.1 Hz, 1H), 8.45-8.46 (m, 2H), 9.89 (s, 1H).

N-(4-Chlorophenyl)-2-(4-pyridylmethylthio)thiophene-3-carboxamide

Compound No. 1-284

$^1$H-NMR (400 MHz, DMSO-d$_6$)
δ 2.30 (s, 3H), 4.25 (s, 2H), 6.91 (d, J=7.8 Hz, 1H), 7.21 (t, J=7.8 Hz, 1H), 7.35 (dd, J=4.4, 1.7 Hz, 2H), 7.48 (d, J=7.8 Hz, 1H), 7.54-7.56 (m, 3H), 8.48 (dd, J=4.4, 1.7 Hz, 2H), 9.91 (s, 1H)

N-(4-Chlorophenyl)-1-methyl-5-(4-pyridylmethylthio)pyrazole-4-carboxamide

Compound No. 1-286

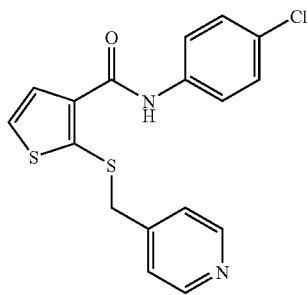

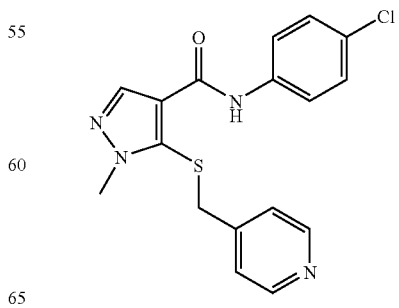

$^1$H-NMR (400 MHz, DMSO-d$_6$)

$^1$H-NMR (400 MHz, CDCl$_3$)

δ 3.65 (s, 3H), 3.95 (s, 2H), 6.92 (dd, J=4.4, 1.5 Hz, 2H), 7.32 (dd, J=7.1, 1.7 Hz, 2H), 7.52 (dd, J=7.1, 1.7 Hz, 2H), 8.12 (s, 1H), 8.47 (dd, J=4.4, 1.5 Hz, 2H), 8.86 (s, 1H)

N-(5-Indanyl)-2-(4-pyridylmethylthio)thiophene-3-carboxamide

Compound No. 1-287

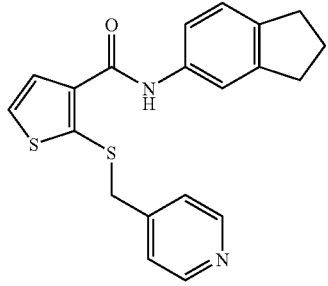

¹H-NMR (500 MHz, DMSO-d₆)
δ 1.99-2.05 (m, 2H), 2.81-2.87 (m, 4H), 4.24 (s, 2H), 7.17 (d, J=7.9 Hz, 1H), 7.33-7.34 (m, 2H), 7.40 (d, J=7.9 Hz, 1H), 7.54 (s, 2H), 7.61 (s, 1H), 8.47-8.48 (m, 2H), 9.87 (br s, 1H)

2-(4-Pyridylmethylthio)-N-(4-trifluoromethoxyphenyl)thiophene-3-carboxamide

Compound No. 1-288

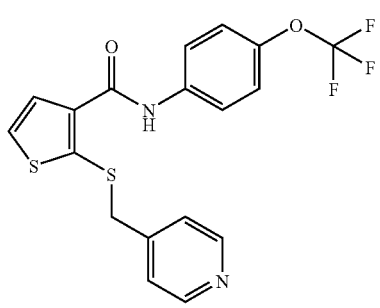

¹H-NMR (500 MHz, DMSO-d₆)

δ 4.25 (s, 2H), 7.34-7.36 (m, 4H), 7.56 (s, 2H), 7.81 (dt, J=9.8, 2.7 Hz, 2H), 8.48 (dd, J=4.6, 1.8 Hz, 2H), 10.16 (s, 1H)

N-(4-Bromo-3-methylphenyl)-2-(4-pyridylmethylthio)thiophene-3-carboxamide

Compound No. 1-289

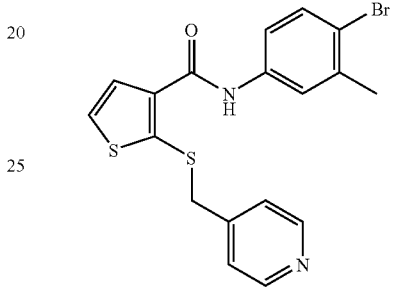

¹H-NMR (500 MHz, DMSO-d₆)
δ 2.34 (s, 3H), 4.25 (s, 2H), 7.34 (dd, J=4.4, 1.7 Hz, 2H), 7.49 (dd, J=8.8, 2.4 Hz, 1H), 7.53 (d, J=8.8 Hz, 1H), 7.55 (d, J=5.5 Hz, 1H), 7.56 (d, J=5.5 Hz, 1H), 7.72 (d, J=2.4 Hz, 1H), 8.48 (dd, J=4.4, 1.7 Hz, 2H), 10.02 (s, 1H)

2-(4-Pyridylmethylthio)-N-(4-trifluoromethylphenyl)thiophene-3-carboxamide

Compound No. 1-290

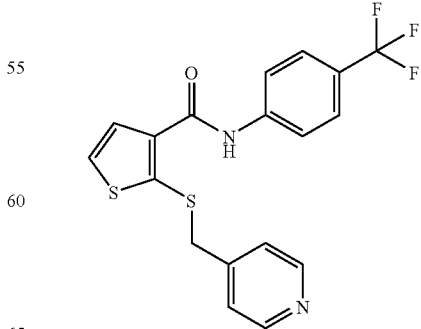

¹H-NMR (500 MHz, CDCl₃)

δ 4.01 (s, 2H), 6.98 (dd, J=4.6, 1.5 Hz, 2H), 7.38 (d, J=5.5 Hz, 1H), 7.61 (d, J=8.6 Hz, 2H), 7.65 (d, J=5.5 Hz, 1H), 7.68 (d, J=8.6 Hz, 2H), 8.44 (dd, J=4.6, 1.5 Hz, 2H), 9.43 (s, 1H)

N-(3,5-Dimethylphenyl)-2-(4-pyridylmethylthio)thiophene-3-carboxamide

Compound No. 1-291

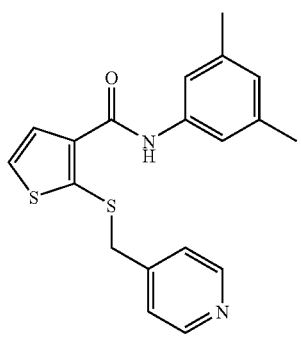

$^1$H-NMR (500 MHz, DMSO-$d_6$)
δ 2.26 (s, 6H), 4.24 (s, 2H), 6.74 (s, 1H), 7.32-7.35 (m, 4H), 7.53 (d, J=5.4 Hz, 1H), 7.56 (d, J=5.4 Hz, 1H), 8.48-8.49 (m, 2H), 9.82 (s, 1H)

N-(3-Methylphenyl)-4-(4-pyridylmethylthio)thiophene-3-carboxamide

Compound No. 1-292

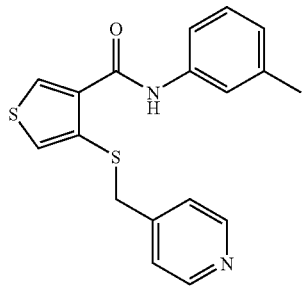

$^1$H-NMR (400 MHz, DMSO-$d_6$)
δ 2.30 (s, 3H), 4.19 (s, 2H), 6.91 (d, J=7.3 Hz, 1H), 7.21 (t, J=7.8 Hz, 1H), 7.29 (d, J=Hz, 1H), 7.39 (dd, J=4.5, 1.5 Hz, 2H), 7.47 (d, J=8.5 Hz, 1H), 7.56 (s, 1H), 8.29 (d, J=3.2 Hz, 1H), 8.48 (dd, J=4.5, 1.5 Hz, 2H), 10.10 (s, 1H)

N-(4-Chlorophenyl)-4-(4-pyridylmethylthio)thiophene-3-carboxamide

Compound No. 1-293

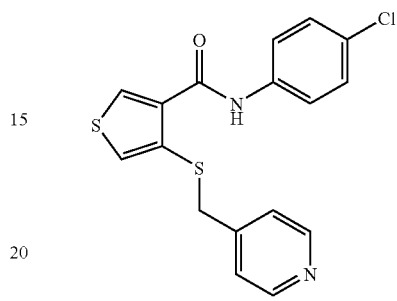

$^1$H-NMR (400 MHz, DMSO-$d_6$)
δ 4.25 (s, 2H), 6.91 (d, J=7.6 Hz, 1H), 7.21 (t, J=7.8 Hz, 1H), 7.34 (dd, J=4.7, 1.7 Hz, 2H), 7.48 (m, 1H), 7.54-7.56 (m, 3H), 8.48 (dd, J=4.4, 1.7 Hz, 2H), 9.90 (s, 1H)

N-(4-Chlorophenyl)-3-(4-pyridylmethylthio)benzamide

Compound No. 1-294

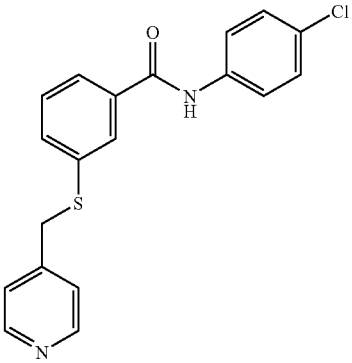

$^1$H-NMR (500 MHz, DMSO-$d_6$)
δ 4.36 (s, 2H), 7.37 (dd, J=4.3, 1.8 Hz, 2H), 7.42 (dd, J=6.7, 2.2 Hz, 2H), 7.46 (d, J=7.6 Hz, 1H), 7.55 (ddd, J=8.0, 1.8, 1.2

Hz, 1H), 7.75 (ddd, J=8.0, 1.8, 1.2 Hz, 1H), 7.80 (dd, J=6.7, 2.2 Hz, 2H), 7.88 (m, 1H), 8.48 (dd, J=4.3, 1.8 Hz, 2H), 10.37 (s, 1H)

N-(4-Chlorophenyl)-4-(4-pyridylmethylthio)benzamide

Compound No. 1-295

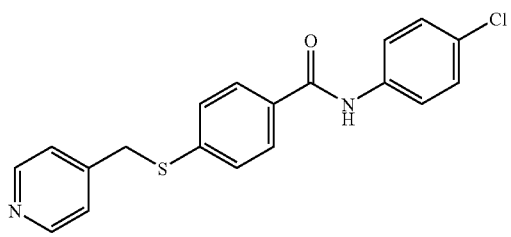

¹H-NMR (400 MHz, DMSO-d₆)
δ 4.40 (s, 2H), 7.37-7.48 (m, 6H), 7.79 (d, J=8.8 Hz, 2H), 7.86 (d, J=8.8 Hz, 2H), 8.49 (dd, J=4.4, 1.7 Hz, 2H), 10.29 (s, 1H)

N-(Indazol-6-yl)-2-(4-pyridylmethylthio)pyridine-3-carboxamide

Compound No. 1-296

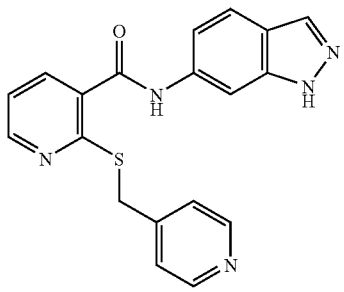

¹H-NMR (400 MHz, DMSO-d₆)
δ 4.43 (s, 2H), 7.24 (d, J=8.8 Hz, 1H), 7.30 (dd, J=7.6, 4.9 Hz, 1H), 7.41 (dd, J=4.4, 1.5 Hz, 2H), 7.70 (d, J=8.8 Hz, 1H), 7.95-8.00 (m, 2H), 8.21 (s, 1H), 8.45 (dd, J=4.4, 1.5 Hz, 2H), 8.60 (dd, J=4.9, 1.7 Hz, 1H), 10.60 (s, 1H), 12.95 (s, 1H)

2-(2-Bromopyridin-4-ylmethylthio)-N-(5-indanyl)pyridine-3-carboxamide

Compound No. 1-297

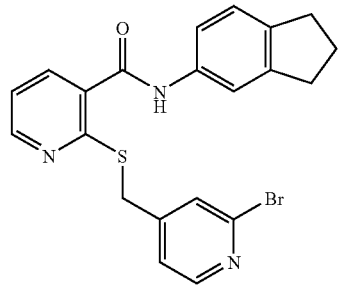

¹H-NMR (500 MHz, DMSO-d₆)
δ 2.00-2.09 (m, 2H), 2.80-2.87 (m, 4H), 4.41 (s, 2H), 7.18 (d, J=7.6 Hz, 1H), 7.29 (d, J=7.6, 4.9 Hz, 1H), 7.38 (d, J=7.6 Hz, 1H), 7.47 (dd, J=4.9, 1.8 Hz, 1H), 7.61 (s, 1H), 7.67 (s, 1H), 7.95 (d, J=7.6 Hz, 1H), 8.27 (d, J=5.2 Hz, 1H), 8.58 (dd, J=4.9, 1.8 Hz, 1H), 10.36 (s, 1H)

2-(2-Bromopyridin-4-ylmethylthio)-N-(4-trifluoromethoxyphenyl)pyridine-3-carboxamide Compound No. 1-298

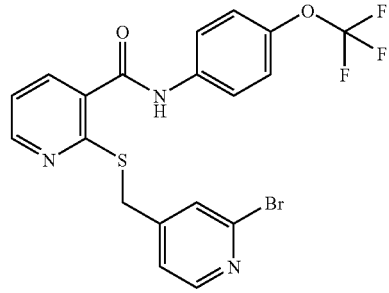

¹H-NMR (500 MHz, DMSO-d₆)
δ 4.42 (s, 2H), 7.32 (dd, J=7.6, 4.9 Hz, 1H), 7.38 (d, J=8.7 Hz, 2H), 7.47 (dd, J=4.9, 1.7 Hz, 1H), 7.67 (s, 1H), 7.80 (d,

J=8.7 Hz, 2H), 8.00 (dd, J=7.6, 1.7 Hz, 1H), 8.27 (d, J=4.9 Hz, 1H), 8.60 (dd, J=4.9, 1.7 Hz, 1H), 10.68 (s, 1H)

2-(2-Benzyloxypyridin-4-ylmethylthio)-N-(3,5-dimethylphenyl)pyridine-3-carboxamide Compound No. 1-299

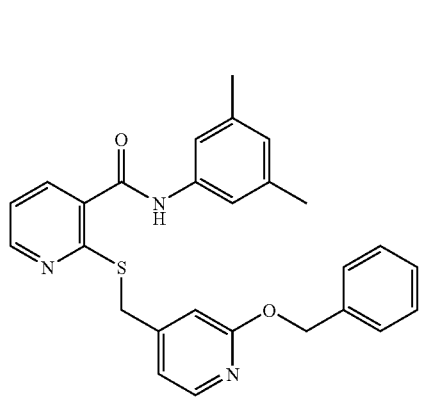

¹H-NMR (500 MHz, CDCl₃)
δ 2.31 (s, 6H), 4.42 (s, 2H), 5.34 (s, 2H), 6.81 (s, 1H), 6.87 (s, 1H), 6.94 (dd, J=5.2, 1.5 Hz, 1H), 7.11 (dd, J=7.6, 4.9 Hz, 1H), 7.26-7.28 (m, 2H), 7.30 (d, J=8.6 Hz, 1H), 7.36 (dd, J=8.6, 7.0 Hz, 2H), 7.43 (d, J=7.0 Hz, 2H), 7.79 (s, 1H), 7.87 (dd, J=7.6, 1.5 Hz, 1H), 8.07 (d, J=5.2 Hz, 1H), 8.52 (dd, J=4.9, 1.5 Hz, 1H)

N-(3,5-Dimethylphenyl)-2-(2-methoxypyridin-4-ylmethylthio)pyridine-3-carboxamide Compound No. 1-300

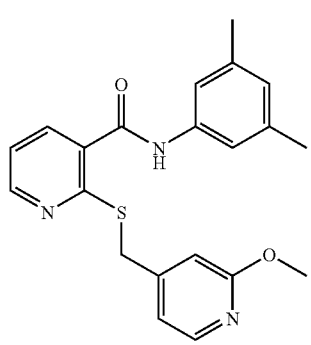

¹H-NMR (500 MHz, DMSO-d₆)
δ 2.25 (s, 6H), 3.80 (s, 3H), 4.37 (s, 2H), 6.76 (s, 1H), 6.81 (d, J=0.5 Hz, 1H), 6.99 (dd, J=5.2, 1.5 Hz, 1H), 7.28 (dd,

J=7.6, 4.9 Hz, 1H), 7.32 (s, 2H), 7.92 (dd, J=7.6, 1.8 Hz, 1H), 8.04 (d, J=5.2 Hz, 1H), 8.58 (dd, J=4.9, 1.8 Hz, 1H), 10.31 (s, 1H)

N-(5-Indanyl)-2-(2-methoxypyridin-4-ylmethylthio)pyridine-3-carboxamide

Compound No. 1-301

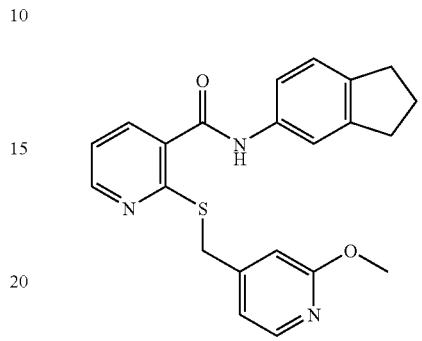

¹H-NMR (500 MHz, DMSO-d₆)
δ 1.99-2.03 (m, 2H), 2.81-2.85 (m, 4H), 3.80 (s, 3H), 4.37 (s, 2H), 6.81 (d, J=0.6 Hz, 1H), 6.99 (dd, J=5.2, 1.5 Hz, 1H), 7.18 (d, J=7.9 Hz, 1H), 7.28 (dd, J=7.7, 4.8 Hz, 1H), 7.38 (d, J=7.9 Hz, 1H), 7.61 (s, 1H), 7.92 (dd, J=7.7, 1.5 Hz, 1H), 8.04 (dd, J=5.2, 0.5 Hz, 1H), 8.58 (dd, J=4.8, 1.5 Hz, 1H), 10.34 (s, 1H)

N-(3,5-Dimethylphenyl)-2-(2-ethoxypyridin-4-ylmethylthio)pyridine-3-carboxamide

Compound No. 1-302

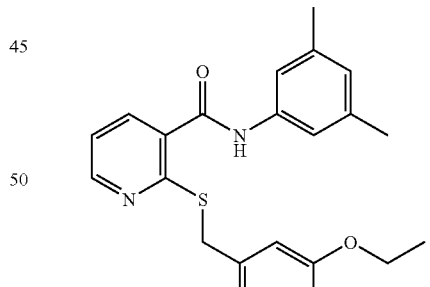

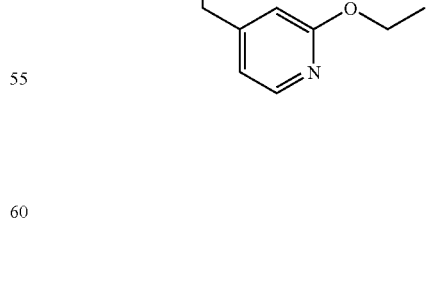

¹H-NMR (500 MHz, DMSO-d₆)
δ 1.27 (d, J=7.0 Hz, 3H), 2.25 (s, 6H), 4.22-4.27 (m, 2H), 4.37 (s, 2H), 6.76 (s, 1H), 6.77 (s, 1H), 6.97 (dd, J=5.2, 1.2 Hz,

1H), 7.28 (dd, J=7.6, 4.8 Hz, 1H), 7.32 (s, 2H), 7.92 (dd, J=7.6, 1.7 Hz, 1H), 8.02 (d, J=5.2 Hz, 1H), 8.58 (dd, J=4.8, 1.7 Hz, 1H), 10.31 (s, 1H)

2-(2-Ethoxypyridin-4-ylmethylthio)-N-(5-indanyl) pyridine-3-carboxamide

Compound No. 1-303

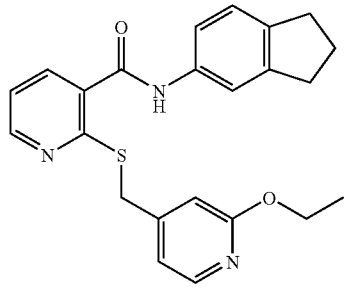

¹H-NMR (500 MHz, DMSO-d₆)
δ 1.27 (t, J=7.0 Hz, 3H), 1.98-2.04 (m, 2H), 2.80-2.86 (m, 4H), 4.25 (q, J=7.0 Hz, 2H), 4.37 (s, 2H), 6.77 (s, 1H), 6.97 (dd, J=5.2, 1.4 Hz, 1H), 7.18 (d, J=7.9 Hz, 1H), 7.28 (dd, J=7.6, 4.9 Hz, 1H), 7.38 (d, J=7.9 Hz, 1H), 7.61 (s, 1H), 7.92 (dd, J=7.6, 1.7 Hz, 1H), 8.02 (d, J=5.2 Hz, 1H), 8.58 (dd, J=4.9, 1.7 Hz, 1H), 10.34 (s, 1H)

N-(3,5-Dimethylphenyl)-2-(2-isopropoxypyridine-4-ylmethylthio)pyridine-3-carboxamide Compound No. 1-304

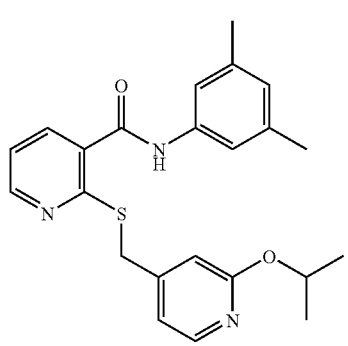

¹H-NMR (500 MHz, DMSO-d₆)
δ 1.25 (d, J=6.1 Hz, 6H), 2.25 (s, 6H), 4.36 (s, 2H), 5.20 (m, 1H), 6.72 (s, 1H), 6.76 (s, 1H), 6.94 (dd, J=5.2, 1.2 Hz, 1H), 7.28 (dd, J=7.6, 4.9 Hz, 1H), 7.32 (s, 2H), 7.92 (dd, J=7.6, 1.7 Hz, 1H), 8.02 (d, J=5.2 Hz, 1H), 8.58 (dd, J=4.9, 1.7 Hz, 1H), 10.31 (s, 1H)

N-(5-Indanyl)-2-(2-isopropoxypyridine-4-ylmethylthio)pyridine-3-carboxamide

Compound No. 1-305

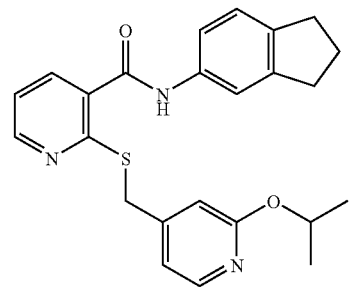

¹H-NMR (500 MHz, DMSO-d₆)
δ 1.24 (d, J=6.1 Hz, 6H), 1.98-2.04 (m, 2H), 2.80-2.86 (m, 4H), 4.36 (s, 2H), 5.19 (m, 1H), 6.71 (s, 1H), 6.94 (dd, J=5.2, 1.4 Hz, 1H), 7.18 (d, J=7.6 Hz, 1H), 7.28 (dd, J=7.6, 4.9 Hz, 1H), 7.38 (d, J=7.6 Hz, 1H), 7.61 (s, 1H), 7.93 (dd, J=7.6, 1.7 Hz, 1H), 8.01 (d, J=5.2 Hz, 1H), 8.58 (dd, J=4.9, 1.7 Hz, 1H), 10.34 (s, 1H)

N-(3,5-Dimethylphenyl)-2-(2-methoxycarbonylpyridin-4-ylmethylthio) pyridine-3-carboxamide Compound No. 1-306

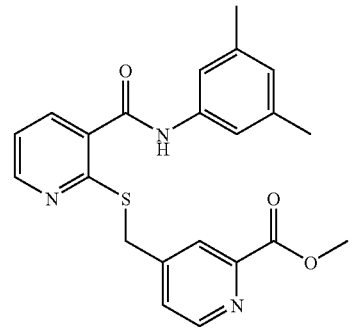

¹H-NMR (400 MHz, DMSO-d₆)
δ 2.25 (s, 6H), 3.86 (s, 3H), 4.50 (s, 2H), 6.76 (s, 1H), 7.28 (dd, J=7.6, 4.9 Hz, 1H), 7.32 (s, 2H), 7.66 (dd, J=4.9, 1.7 Hz,

1H), 7.93 (dd, J=7.6, 1.7 Hz, 1H), 8.11 (d, J=0.9 Hz, 1H), 8.55-8.60 (m, 2H), 10.30 (s, 1H)

N-(3,5-Dimethylphenyl)-2-(2-methylpyridin-4-ylmethylthio)pyridine-3-carboxamide Compound No. 1-307

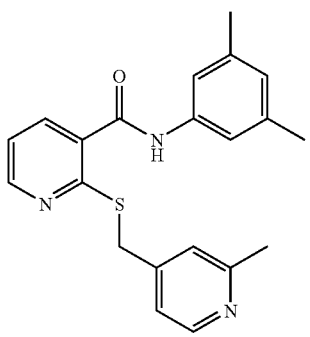

$^1$H-NMR (500 MHz, DMSO-$d_6$)

δ 2.25 (s, 6H), 2.41 (s, 3H), 4.37 (s, 2H), 6.76 (s, 1H), 7.19 (dd, J=5.2, 1.2 Hz, 1H), 7.26 (s, 1H), 7.28 (dd, J=7.6, 4.9 Hz, 1H), 7.32 (s, 2H), 7.92 (dd, J=7.6, 1.5 Hz, 1H), 8.31 (d, J=4.9 Hz, 1H), 8.58 (dd, J=4.9, 1.5 Hz, 1H), 10.31 (s, 1H)

2-(2-Methylpyridin-4-ylmethylthio)-N-(4-trifluoromethoxyphenyl)pyridine-3-carboxamide Compound No. 1-308

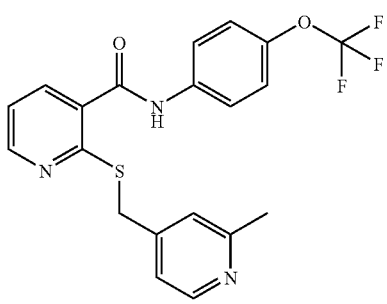

$^1$H-NMR (500 MHz, DMSO-$d_6$)

δ 2.41 (s, 3H), 4.38 (s, 2H), 7.19 (m, 1H), 7.26 (s, 1H), 7.31 (dd, J=7.6, 4.9 Hz, 1H), 7.37 (d, J=8.9 Hz, 2H), 7.81 (d, J=8.9 Hz, 2H), 7.98 (dd, J=7.6, 1.8 Hz, 1H), 8.31 (d, J=5.2 Hz, 1H), 8.61 (dd, J=4.9, 1.8 Hz, 1H), 10.66 (s, 1H)

Example 2

N-(4-Chlorophenyl)-2-[2-(4-pyridyl)ethylthio]pyridine-3-carboxamide

Compound No. 2-1

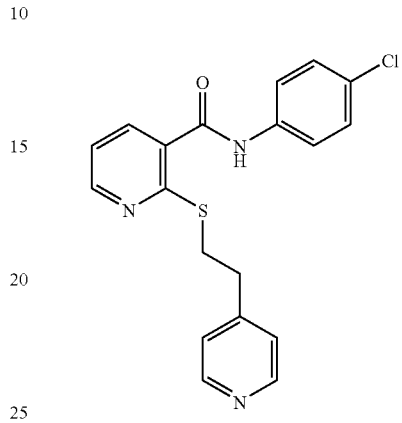

To a suspension of 60% sodium hydride (35 mg, 0.88 mmol) in N,N-dimethylformamide (1 mL), a solution of 4-pyridineethanethiol (104 mg, 0.75 mmol) in N,N-dimethylformamide (1.5 mL) and a solution of 2-chloro-N-(4-chlorophenyl)pyridine-3-carboxamide (200 mg, 0.75 mmol, Reference compound No. 2-1) in N,N-dimethylformamide (1.5 mL) were added under ice-cooling successively. The reaction mixture was stirred at room temperature for 2 hours, and then ethyl acetate (40 mL) was added thereto. The ethyl acetate layer was washed with water (40 mL) and brine (40 mL) and dried over anhydrous magnesium sulfate, then the solvent was evaporated under reduced pressure. The precipitated solid was filtered off and washed with diethyl ether:ethyl acetate (3:1). The solid was dried under reduced pressure to give 240 mg of the target compound as a white solid. (Yield 88%)

$^1$H-NMR (400 MHz, DMSO-$d_6$)

δ 2.95 (t, J=7.8 Hz, 2H), 3.43 (t, J=7.8 Hz, 2H), 7.25-7.31 (m, 3H), 7.42 (d, J=8.8 Hz, 2H), 7.73 (d, J=8.8 Hz, 2H), 7.94 (dd, J=7.6, 1.5 Hz, 1H), 8.46 (d, J=5.6 Hz, 2H), 8.61 (dd, J=7.6, 1.5 Hz, 1H), 10.59 (s, 1H)

2-(4-Pyridylmethylthio)-N-(4-trifluoromethylsulfonylphenyl)pyridine-3-carboxamide Compound No. 2-2

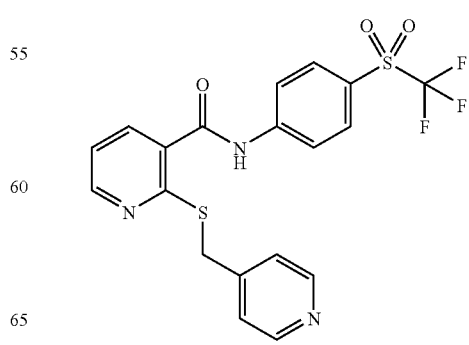

4-Pyridinemethanethiol hydrochloride (0.32 g, 2.0 mmol) and potassium carbonate (0.63 g, 4.5 mmol) were added to a solution of 2-chloro-N-(4-trifluoromethylsulfonylphenyl)pyridine-3-carboxamide (0.65 g, 1.8 mmol, Reference compound No. 2-2) in ethanol (10 mL) under a nitrogen atmosphere, then the mixture was stirred at 65° C. for 8 hours. The reaction mixture was diluted with ethyl acetate (100 mL), then the ethyl acetate layer was washed with a saturated aqueous sodium hydrogencarbonate solution (100 mL) and brine (100 mL), and then dried over anhydrous magnesium sulfate. The solvent was evaporated under reduced pressure, then the resulting residue was purified by silica gel column chromatography to give 0.29 g of the target compound as a white solid. (Yield 37%)

$^1$H-NMR (500 MHz, DMSO-$d_6$)

δ 4.44 (s, 2H), 7.34 (dd, J=7.6, 4.8 Hz, 1H), 7.40 (dd, J=4.6, 1.6 Hz, 2H), 8.07 (dd, J=7.6, 1.5 Hz, 1H), 8.13 (s, 4H), 8.45 (dd, J=4.6, 1.6 Hz, 2H), 8.64 (dd, J=4.8, 1.5 Hz, 1H), 11.19 (s, 1H)

Example 3

N-(4-Chlorophenyl)-2-(4-pyridylmethylsulfinyl)pyridine-3-carboxamide

Compound No. 3-1

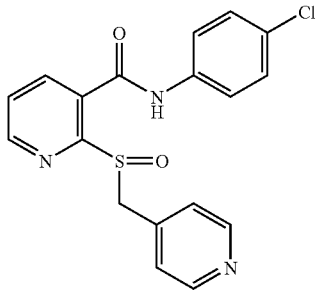

A solution of m-chloroperoxybenzoic acid (65%, 160 mg, 0.60 mmol) in chloroform (2 mL) was added to a solution of N-(4-chlorophenyl)-2-(4-pyridylmethylthio)pyridine-3-carboxamide (300 mg, 0.84 mmol, Compound No. 1-1) in chloroform (18 mL) under ice-cooling, then the mixture was stirred at room temperature for 2 hours. The precipitated solid in the reaction mixture was filtered off, and dried under reduced pressure to give 220 mg of the target compound as a pale yellow solid. (Yield 69%)

$^1$H-NMR (400 MHz, DMSO-$d_6$)

δ 4.25 (d, J=12.5 Hz, 1H), 4.50 (d, J=12.5 Hz, 1H), 7.23 (dd, J=4.6, 1.5 Hz, 2H), 7.46 (d, J=8.8 Hz, 2H), 7.75 (m, 1H), 7.75 (d, J=8.8 Hz, 2H), 8.32 (dd, J=7.8, 1.5 Hz, 1H), 8.51 (dd, J=4.6, 1.5 Hz, 2H), 8.87 (m, 1H), 10.80 (s, 1H)

Example 4

N-(4-Chlorophenyl)-2-(1-oxopyridin-4-ylmethylthio)pyridine-3-carboxamide

Compound No. 4-1

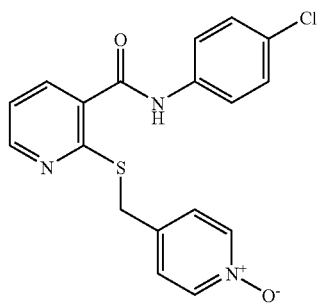

N,N-Diisopropylethylamine (0.16 mL, 0.92 mmol) and O-(7-azabenzotriazol-1-yl)-N,N,N',N'-tetramethyluronium hexafluorophosphate (212 mg, 0.56 mmol) were added to a solution of 2-(1-oxopyridin-4-ylmethylthio) pyridine-3-carboxylic acid (124 mg, 0.47 mmol, Reference compound No. 4-1) and 4-chloroaniline (72 mg, 0.56 mmol) in N,N-dimethylformamide (1.5 mL), then the mixture was stirred at room temperature for 15 hours. Ethyl acetate (30 mL) was added to the reaction mixture, then the ethyl acetate layer was washed with a saturated aqueous sodium hydrogencarbonate solution (50 mL) twice and brine (50 mL) twice, and then dried over anhydrous magnesium sulfate. The solvent was evaporated under reduced pressure, the precipitated solid was filtered off and washed with diethyl ether:ethyl acetate (5:1). This solid was dried at 50° C. under reduced pressure to give 113 mg of the target compound as a brown solid. (Yield 65%)

$^1$H-NMR (500 MHz, DMSO-$d_6$)

δ 4.38 (s, 2H), 7.30 (dd, J=7.6, 4.9 Hz, 1H), 7.41-7.44 (m, 4H), 7.72 (d, J=8.8 Hz, 2H), 7.98 (dd, J=7.6, 1.5 Hz, 1H), 8.09 (dd, J=5.2, 1.8. Hz, 2H), 8.60 (dd, J=4.9, 1.8 Hz, 1H), 10.6 (s, 1H)

Below compounds (No. 4-2~11) were obtained by a method similar to Example 4.

N-(6-Indazolyl)-2-(1-oxopyridin-4-ylmethylthio)pyridine-3-carboxamide

Compound No. 4-2

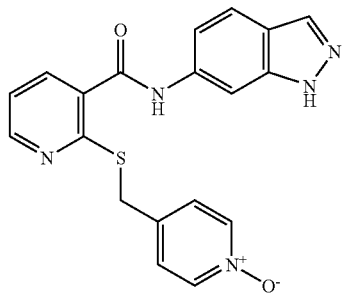

$^1$H-NMR (400 MHz, DMSO-$d_6$)

δ 4.39 (s, 2H), 7.24 (d, J=8.8 Hz, 1H), 7.33 (m, 1H), 7.42 (d, J=7.1 Hz, 2H), 7.70 (d, J=8.8 Hz, 1H), 7.97-8.01 (m, 2H), 8.01 (d, J=7.1 Hz, 2H), 8.21 (s, 1H), 8.60 (dd, J=4.9, 1.6 Hz, 1H), 10.60 (s, 1H), 12.97 (s, 1H)

N-(3-Methylphenyl)-2-(1-oxopyridin-4-ylmethylthio)pyridine-3-carboxamide

Compound No. 4-3

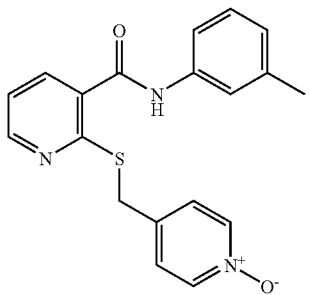

$^1$H-NMR (400 MHz, DMSO-$d_6$)

δ 2.30 (s, 3H), 4.38 (s, 2H), 6.93 (d, J=7.6 Hz, 1H), 7.20-7.31 (m, 2H), 7.41 (d, J=7.1 Hz, 2H), 7.44 (m, 1H), 7.55 (s, 1H), 7.95 (dd, J=7.6, 1.7 Hz, 1H), 8.09 (d, J=7.1 Hz, 2H), 8.59 (dd, J=4.9, 1.7 Hz, 1H), 10.38 (s, 1H)

N-(3,5-Dimethylphenyl)-2-(1-oxopyridin-4-ylmethylthio)pyridine-3-carboxamide

Compound No. 4-4

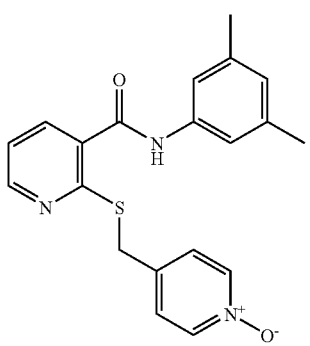

$^1$H-NMR (400 MHz, DMSO-$d_6$)

δ 2.25 (s, 6H), 4.38 (s, 2H), 6.76 (s, 1H), 7.27-7.34 (m, 3H), 7.40-7.42 (m, 2H), 7.93 (dd, J=Hz, 1H), 8.09 (dd, J=5.1, 2.0 Hz, 2H), 8.58 (dd, J=4.7, 1.7 Hz, 1H), 10.30 (s, 1H)

N-(3,4-Dimethylphenyl)-2-(1-oxopyridin-4-ylmethylthio)pyridine-3-carboxamide

Compound No. 4-5

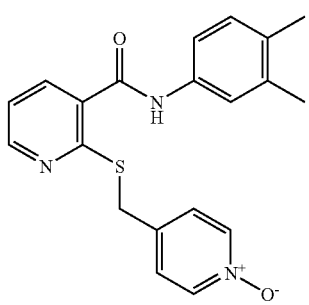

$^1$H-NMR (500 MHz, DMSO-$d_6$)

δ 2.19 (s, 3H), 2.21 (s, 3H), 4.37 (s, 2H), 7.09 (d, J=8.2 Hz, 1H), 7.28 (dd, J=7.6, 4.9 Hz, 1H), 7.38 (s, 1H), 7.41 (dd, J=7.3, 2.0 Hz, 2H), 7.48 (s, 1H), 7.94 (dd, J=7.6, 1.5 Hz, 1H), 8.09 (dd, J=4.9, 2.0 Hz, 2H), 8.58 (dd, J=4.9, 1.5 Hz, 1H), 10.29 (s, 1H)

N-(3-Isopropylphenyl)-2-(1-oxopyridin-4-ylmethylthio)pyridine-3-carboxamide

Compound No. 4-6

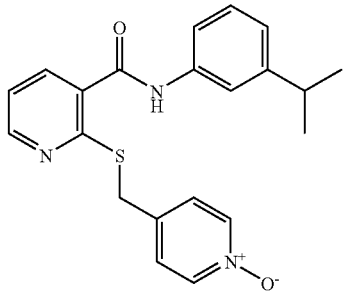

$^1$H-NMR (500 MHz, DMSO-$d_6$)

δ 1.20 (d, J=6.7 Hz, 6H), 2.87 (m, 1H), 4.38 (s, 2H), 7.00 (d, J=7.6 Hz, 1H), 7.24-7.31 (m, 2H), 7.41 (d, J=7.0 Hz, 2H), 7.51 (d, J=7.6 Hz, 1H), 7.59 (s, 1H), 7.96 (dd, J=7.7, 1.5 Hz, 1H), 8.09 (d, J=7.0 Hz, 2H), 8.59 (dd, J=4.8, 1.5 Hz, 1H), 10.39 (s, 1H)

N-(4-Fluoro-3-methylphenyl)-2-(1-oxopyridin-4-ylmethylthio)pyridine-3-carboxamide Compound No. 4-7

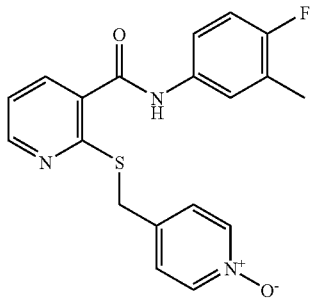

¹H-NMR (500 MHz, DMSO-d₆)

δ 2.23 (s, 3H), 4.38 (s, 2H), 7.12 (d, J=9.2 Hz, 1H), 7.30 (dd, J=7.7, 4.9 Hz, 1H), 7.41 (dd, J=5.2, 1.8 Hz, 2H), 7.48 (m, 1H), 7.63 (m, 1H), 7.95 (dd, J=7.7, 1.5 Hz, 1H), 8.09 (dd, J=5.2, 2.7 Hz, 2H), 8.59 (dd, J=4.9, 1.5 Hz, 1H), 10.43 (s, 1H)

N-(5-Indanyl)-2-(1-oxopyridin-4-ylmethylthio)pyridine-3-carboxamide

Compound No. 4-8

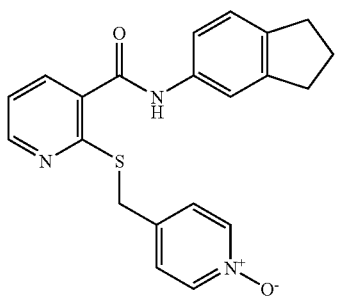

¹H-NMR (500 MHz, DMSO-d₆)

δ 1.98-2.03 (m, 2H), 2.80-2.89 (m, 4H), 4.37 (s, 2H), 7.18 (d, J=7.9 Hz, 1H), 7.29 (dd, J=7.6, 4.9 Hz, 1H), 7.39 (m, 1H), 7.41 (d, J=7.3 Hz, 2H), 7.61 (s, 1H), 7.93 (dd, J=7.6, 1.5 Hz, 1H), 8.09 (dd, J=5.2, 2.1 Hz, 2H), 8.58 (dd, J=4.9, 1.5 Hz, 1H), 10.30 (s, 1H)

2-(1-Oxopyridin-4-ylmethylthio)-N-(4-trifluoromethoxyphenyl)pyridine-3-carboxamide Compound No. 4-9

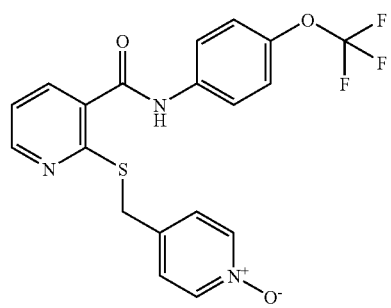

¹H-NMR (500 MHz, DMSO-d₆)

δ 4.39 (s, 2H), 7.31 (dd, J=7.6, 4.9 Hz, 1H), 7.36-7.38 (m, 2H), 7.41 (d, J=7.0 Hz, 2H), 7.79-7.81 (m, 2H), 7.99 (dd, J=7.6, 1.8 Hz, 1H), 8.09 (d, J=7.0 Hz, 2H), 8.60 (dd, J=4.9, 1.8 Hz, 1H), 10.66 (s, 1H)

N-(4-tert-Butylphenyl)-2-(1-oxopyridin-4-ylmethylthio)pyridine-3-carboxamide

Compound No. 4-10

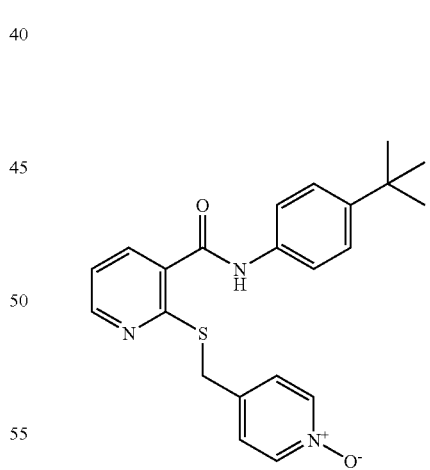

¹H-NMR (500 MHz, DMSO-d₆)

δ 1.27 (s, 9H), 4.38 (s, 2H), 7.29 (dd, J=7.6, 4.9 Hz, 1H), 7.36 (dd, J=6.8, 2.0 Hz, 2H), 7.41 (dd, J=5.2, 2.1 Hz, 2H), 7.60 (d, J=8.8 Hz, 2H), 7.94 (dd, J=7.6, 1.5 Hz, 1H), 8.09 (dd, J=5.2, 2.1 Hz, 2H), 8.58 (dd, J=4.9, 1.5 Hz, 1H), 10.38 (s, 1H)

N-(3-Chloro-4-trifluoromethoxyphenyl)-2-(1-oxopyridin-4-ylmethylthio)-pyridine-3-carboxamide Compound No. 4-11

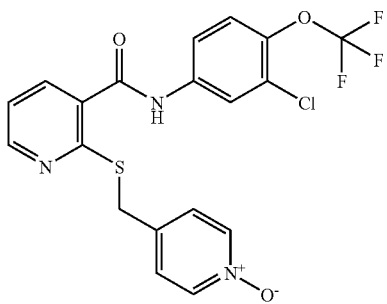

¹H-NMR (500 MHz, CDCl₃)

δ 4.40 (s, 2H), 7.15 (dd, J=7.6, 4.8 Hz, 1H), 7.31 (d, J=7.0 Hz, 2H), 7.56 (dd, J=8.1, 2.6 Hz, 1H), 7.91 (dd, J=7.6, 1.8 Hz, 1H), 7.92-7.98 (m, 4H), 8.52 (dd, J=4.8, 1.8 Hz, 1H), 8.63 (s, 1H)

Example 5

N-(4-Chlorophenyl)-2-[1-(4-pyridyl)ethylthio]pyridine-3-carboxamide

Compound No. 5-1

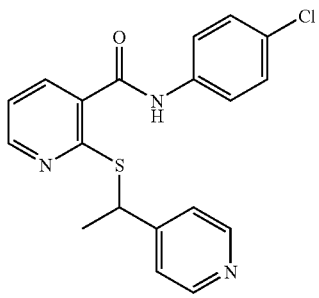

N,N-Diisopropylethylamine (0.29 mL, 1.7 mmol) and O-(7-azabenzotriazol-1-yl)-N,N,N',N'-tetramethyluronium hexafluorophosphate (330 mg, 0.87 mmol) were added to a solution of 2-[1-(4-pyridyl)ethylthio]pyridine-3-carboxylic acid (200 mg, 0.77 mmol, Reference compound No. 5-1) and 4-chloroaniline (110 mg, 0.85 mmol) in N,N-dimethylformamide (2.0 mL), then the mixture was stirred at room temperature for 13 hours. Ethyl acetate (30 mL) was added to the reaction mixture, the ethyl acetate layer was washed with a saturated aqueous sodium hydrogencarbonate solution (30 mL) twice and brine (30 mL) twice, then dried over anhydrous magnesium sulfate. The resulting residue by evaporated under reduced pressure was purified by silica gel column chromatography to give 41 mg of the target compound as a colorless solid. (Yield 14%)

¹H-NMR (500 MHz, DMSO-d₆)

δ 1.63 (d, J=7.1 Hz, 3H), 5.16 (q, J=7.1 Hz, 1H), 7.27 (dd, J=7.6, 4.6 Hz, 1H), 7.40-7.43 (m, 2H), 7.46 (dd, J=4.4, 1.5 Hz, 2H), 7.72 (d, J=8.5 Hz, 2H), 7.93 (dd, J=7.6, 1.8 MHz, 1H), 8.47 (dd, J=4.4, 1.5 Hz, 2H), 8.57 (dd, J=4.6, 1.8 Hz, 1H), 10.60 (s, 1H)

Below compound (No. 5-2) was obtained by a method similar to Example 5.

N-(3-Chlorophenyl)-2-[1-(4-pyridyl)ethylthio]pyridine-3-carboxamide

Compound No. 5-2

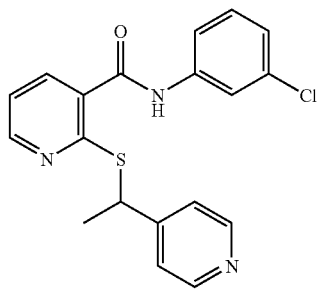

¹H-NMR (400 MHz, DMSO-d₆)

δ 1.63 (d, J=7.3 Hz, 3H), 5.16 (q, J=7.3 Hz, 1H), 7.18 (ddd, J=8.1, 2.1, 0.9 Hz, 1H), 7.28 (dd, J=7.8, 4.9 Hz, 1H), 7.39 (m, 1H), 7.46 (dd, J=4.4, 1.5 Hz, 2H), 7.57 (d, J=8.0 Hz, 1H), 7.89 (m, 1H), 7.94 (dd, J=7.8, 1.7 Hz, 1H), 8.47 (dd, J=4.4, 1.5 Hz, 2H), 8.58 (dd, J=4.9, 1.7 Hz, 1H), 10.60 (s, 1H)

Example 6

2-(2-Carboxypyridin-4-ylmethylthio)-N-(3,5-dimethylphenyl)pyridine-3-carboxamide Compound No. 6-1

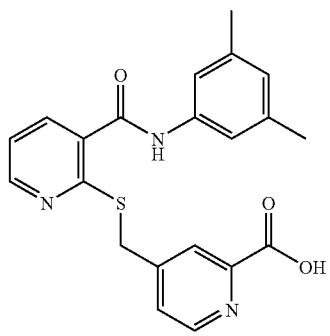

A 1N aqueous sodium hydroxide solution (0.5 mL) was added to a solution of N-(3,5-dimethylphenyl)-2-(2-ethoxycarbonylpyridin-4-ylmethylthio)pyridine-3-carboxamide (95 mg, 0.22 mmol, Compound No. 1-241) in methanol (2 mL), then the mixture was stirred at room temperature for 1.5 hours. 1N hydrochloric acid (1 mL) was added to the reaction mixture, and this mixture was diluted with ethyl acetate (35 mL). The mixture was washed with brine (20 mL), and then the organic layer was dried over anhydrous magnesium sulfate. The solvent was evaporated under reduced pressure, then the resulting residue was filtered off. The solid was washed with diethyl ether, and then dried at 50° C. under reduced pressure to give 74 mg of the target compound as an orange solid. (Yield 84%)

¹H-NMR (500 MHz, DMSO-d₆)

δ 2.25 (s, 6H), 4.50 (s, 2H), 6.76 (s, 1H), 7.28 (dd, J=7.8, 5.0 Hz, 1H), 7.32 (s, 2H), 7.64 (dd, J=4.9, 1.5 Hz, 1H), 7.94 (dd, J=7.8, 1.8 Hz, 1H), 8.09 (d, J=0.9 Hz, 1H), 8.56-8.59 (m, 2H), 10.31 (s, 1H), 12.50-13.50 (br s, 1H)

Example 7

N-(3,5-Dimethylphenyl)-2-(2-n-propylaminocarbonylpyridin-4-yl-methylthio)pyridine-3-carboxamide Compound No. 7-1

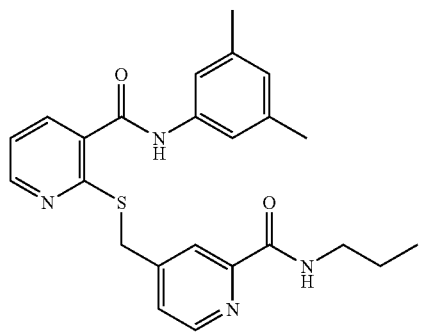

N,N-Diisopropylethylamine (40 μL, 0.23 mmol) and O-(7-azabenzotriazol-1-yl)-N,N,N',N'-tetramethyluronium hexafluorophosphate (51 mg, 0.14 mmol) were added to a solution of 2-(2-carboxypyridine-4-ylmethylthio)-N-(3,5-dimethylphenyl)pyridine-3-carboxamide (42 mg, 0.11 mmol, Compound No. 6-1) and n-propylamine (34 μL, 0.41 mmol) in N,N-dimethylformamide (1 mL) at room temperature, this mixture was stirred at 40° C. for 3 hours. The reaction mixture was diluted with ethyl acetate (20 mL), then the ethyl acetate layer was washed with a saturated aqueous sodium hydrogencarbonate solution (40 mL) and brine (30 mL) and dried over anhydrous magnesium sulfate. The solvent was evaporated under reduced pressure, and the resulting residue was washed with diethyl ether. This solid was dried at 50° C. under reduced pressure to give 21 mg of the target compound as a white solid. (Yield 46%)

¹H-NMR (500 MHz, DMSO-d₆)

δ 0.85 (t, J=7.3 Hz, 3H), 1.48-1.56 (m, 2H), 2.25 (s, 6H), 3.20-3.25 (m, 2H), 4.50 (s, 2H), 6.76 (s, 1H), 7.28 (dd, J=7.3, 4.9 Hz, 1H), 7.32 (s, 2H), 7.60 (dd, J=4.9, 1.8 Hz, 1H), 7.93 (dd, J=7.3, 1.7 Hz, 1H), 8.06 (d, J=0.9 Hz, 1H), 8.51 (d, J=4.9 Hz, 1H), 8.56 (dd, J=4.9, 1.7 Hz, 1H), 8.71 (t, J=5.1 Hz, 1H), 10.31 (s, 1H)

Below compounds (No. 7-2~4) were obtained by a method similar to Example 7.

2-[2-(4-Chlorophenylaminocarbonyl)pyridin-4-ylmethylthio]-N-(3,5-dimethylphenyl)pyridine-3-carboxamide Compound No. 7-2

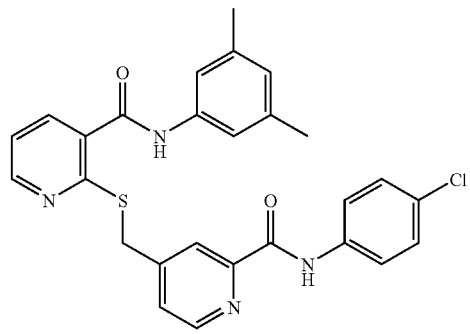

¹H-NMR (500 MHz, DMSO-d₆)

δ 2.25 (s, 6H), 4.55 (s, 2H), 6.76 (s, 1H), 7.29 (dd, J=7.6, 4.9 Hz, 1H), 7.32 (s, 2H), 7.39-7.43 (m, 2H), 7.70 (dd, J=4.9, 1.8 Hz, 1H), 7.92-7.96 (m, 3H), 8.20 (d, J=1.2 Hz, 1H), 8.58 (dd, J=4.9, 1.8 Hz, 1H), 8.62 (d, J=5.2 Hz, 1H), 10.32 (s, 1H), 10.75 (s, 1H)

N-(3,5-Dimethylphenyl)-2-(2-methylaminocarbonylpyridin-4-ylmethylthio)pyridine-3-carboxamide Compound No. 7-3

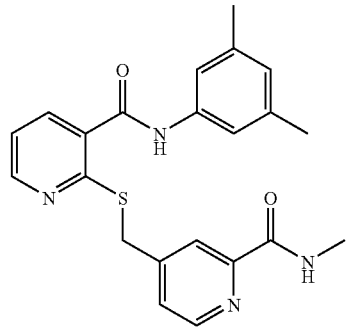

¹H-NMR (400 MHz, DMSO-d₆)

δ 2.25 (s, 6H), 2.79 (d, J=4.9 Hz, 3H), 4.50 (s, 2H), 6.76 (s, 1H), 7.28 (dd, J=7.5, 4.9 Hz, 1H), 7.32 (s, 2H), 7.59 (m, 1H), 7.94 (m, 1H), 8.06 (s, 1H), 8.50 (d, J=5.1 Hz, 1H), 8.56 (dd, J=4.9, 1.7 Hz, 1H), 8.71 (d, J=4.9 Hz, 1H), 10.32 (s, 1H)

N-(3,5-Dimethylphenyl)-2-[2-(2-methoxyethylaminocarbonyl)pyridin-4-ylmethylthio]pyridine-3-carboxamide Compound No. 7-4

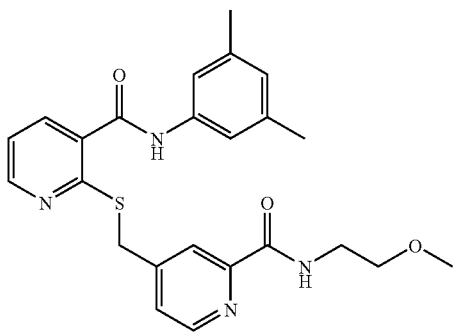

$^1$H-NMR (400 MHz, DMSO-$d_6$)
δ 2.25 (s, 6H), 3.25 (s, 3H), 3.44-3.45 (m, 4H), 4.51 (s, 2H), 6.76 (s, 1H), 7.28 (dd, J=7.6, 4.9 Hz, 1H), 7.32 (s, 2H), 7.61 (d, J=4.9 Hz, 1H), 7.93 (d, J=7.6 Hz, 1H), 8.07 (s, 1H), 8.51 (d, J=5.1 Hz, 1H), 8.56 (dd, J=4.9, 1.7 Hz, 1H), 8.64 (s, 1H), 10.32 (s, 1H)

Example 8

2-(2-Carbamoylpyridin-4-ylmethylthio)-N-(3,5-dimethylphenyl)pyridine-3-carboxamide Compound No. 8-1

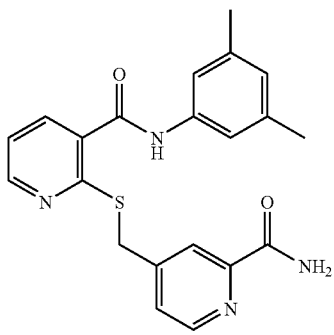

Triphenylphosphine (200 mg, 0.76 mmol) and carbon tetrabromide (273 mg, 0.82 mmol) were added to a solution of 2-carbamoyl-4-(hydroxymethyl)pyridine (101 mg, 0.66 mmol, Reference compound No. 13-1) in methylene chloride (3 mL), then the mixture was stirred at room temperature for 3 hours. The solvent of the reaction solution was evaporated under reduced pressure, and then the resulting residue was purified by silica gel column chromatography to give 4-bromomethyl-2-carbamoylpyridine. Triethylamine (134 μL, 0.96 mmol) was added dropwise to a solution of this bromo-intermediate and N-(3,5-dimethylphenyl)-2-thiopyridone-3-carboxamide (103 mg, 0.40 mmol, Reference compound No. 18-1) in N,N-dimethylformamide (1 mL) at room temperature, then the mixture was stirred for 15 hours. The reaction mixture was diluted with ethyl acetate (50 mL), then the ethyl acetate layer was washed with a saturated aqueous sodium hydrogencarbonate solution (100 mL) and brine (50 mL), and then dried over anhydrous magnesium sulfate. The solvent was evaporated under reduced pressure, and then the resulting residue was purified by silica gel column chromatography to give 40 mg of the target compound as a white solid. (Yield 16%)

$^1$H-NMR (500 MHz, DMSO-$d_6$)
δ 2.25 (s, 6H), 4.50 (s, 2H), 6.76 (s, 1H), 7.28 (dd, J=7.6, 4.9 Hz, 1H), 7.32 (s, 2H), 7.59-7.61 (m, 2H), 7.93 (dd, J=7.6, 1.8 Hz, 1H), 8.05 (s, 1H), 8.07 (d, J=0.9 Hz, 1H), 8.51 (d, J=5.2 Hz, 1H), 8.56 (dd, J=4.9, 1.8 Hz, 1H), 10.32 (s, 1H)

Example 9

N-(3,5-Dimethylphenyl)-1-methyl-5-(4-pyridylmethylthio)pyrazole-4-carboxamide

Compound No. 9-1

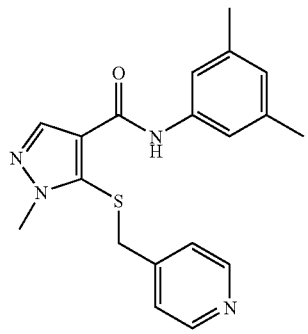

4-(4-Formyl-3-methoxyphenoxy)butyrylaminomethylpolystyrene (100 mg, 0.055 mmol) was swollen with a solution of ethyl orthoformate (3.0 mL) in anhydrous N,N-dimethylformamide (3.0 mL). 3,5-Dimethylaniline (130 mg, 1.1 mmol) and acetic acid (0.033 mL) were added thereto, then the whole was shaken at room temperature for 14 hours. Sodium triacetoxyborohydride (63 mg, 0.29 mmol) was added to the reaction mixture, then this reaction mixture was shaken at room temperature for 14 hours. The reaction mixture was filtered, and then this polystyrene resin was washed with methanol (6.0 mL) and then with chloroform (6.0 mL) three times alternately. The resin was washed with diethyl ether (6.0 mL), and dried under reduced pressure to give amine-derivative polystyrene (I).

On the other hand, 5-iodo-1-methylpyrazole-4-carboxylic acid (150 mg, 0.58 mmol), given by hydrolysis of 5-iodo-1-methylpyrazole-4-carboxylic acid ethyl ester (Reference compound No. 15-2), and oxalyl chloride (0.053 mL, 0.61 mmol) were stirred at 50° C. for 1 hour. N,N-Diisopropylethylamine (0.51 mL, 2.9 mmol) and amine-derivative polystyrene(I) were added to a solution of 5-iodo-1-methylpyrazole-4-carbonyl chloride prepared by an above method in anhydrous methylene chloride (3.3 mL), and then the whole was shaken at room temperature for 19 hours. The reaction mixture, was filtered, the polystyrene resin was washed with methanol (6.0 mL) and chloroform (6.0 mL) four times alternately, and then the resin was washed with diethyl ether (6.0 mL), and dried under reduced pressure to give amide-derivative polystyrene (II). This resin(II), tris(dibenzylideneacetone)dipalladium(0) (160 mg, 0.17 mmol), 1,1-bis(diphenylphosphino)ferrocene (400 mg, 0.73 mmol), and N,N-diisopropylethylamine (0.60 mL, 3.3 mmol) were suspended in N,N-dimethylacetamide (5.0 mL). This suspension was frozen, allowed to stand under reduced pressure, and melted. This procedure was repeated twice and dissolved oxygen in the solvent was removed, 4-pyridinemethanethiol hydrochloride (0.40 g, 2.70 mmol) was added thereto, and then the reaction mixture was stirred at 60° C. under an argon atmosphere for 24 hours. The reaction mixture was filtered, the resulting resin was washed with N,N-dimethylformamide (6.0 mL) twice, with methanol (6.0 mL) and chloroform (6.0 mL) three times alternately, and with diethyl ether (6.0 mL), then dried under reduced pressure. A solution of 20% trifluoroacetic acid in methylene chloride (5.0 mL) was added to this resin, the whole was shaken at room temperature for 30 minutes, and then polystyrene resin was filtered out. The filtrate was diluted with methylene chloride (4.0 mL), and then a saturated aqueous sodium hydrogencarbonate solution was added to adjust to pH 7. The methylene chloride layer was evaporated under reduced pressure, and then the resulting residue was purified by silica gel column chromatography to give 7.0 mg of the title compound as a yellow solid. (Yield 36%)

$^1$H-NMR (500 MHz, CDCl$_3$)

δ 2.33 (s, 6H), 3.59 (s, 3H), 3.97 (s, 2H), 6.80 (s, 1H), 6.94 (dd, J=4.4, 1.6 Hz, 2H), 7.22 (s, 2H), 8.11 (s, 1H), 8.48 (dd, J=4.4, 1.6 Hz, 2H), 8.81 (s, 1H)

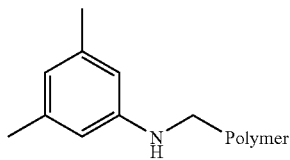

[I]

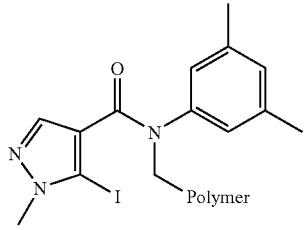

[II]

Below compounds (No. 9-2~47) were obtained by a method similar to Example 9.

N-(5-Indanyl)-1-methyl-5-(4-pyridylmethylthio)pyrazole-4-carboxamide

Compound No. 9-2

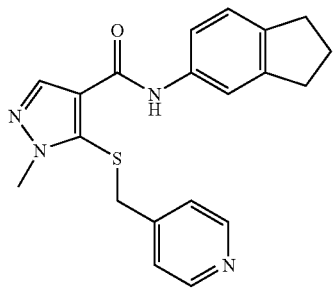

$^1$H-NMR (500 MHz, CDCl$_3$)

δ 2.08-2.11 (m, 2H), 2.88-2.95 (m, 4H), 3.60 (s, 3H), 3.97 (s, 2H), 6.94 (d, J=5.7 Hz, 2H), 7.19 (d, J=7.9 Hz, 1H), 7.26 (m, 1H), 7.54 (s, 1H), 8.11 (s, 1H), 8.48 (d, J=5.7 Hz, 2H), 8.83 (s, 1H)

N-(4-Chloro-3-methylphenyl)-1-methyl-5-(4-pyridylmethylthio)pyrazole-4-carboxamide Compound No. 9-3

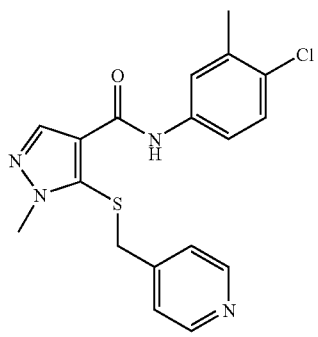

$^1$H-NMR (500 MHz, CDCl$_3$)

δ 2.39 (s, 3H), 3.63 (s, 3H), 3.96 (s, 2H), 6.93 (dd, J=4.6, 1.5 Hz, 2H), 7.30 (d, J=8.6 Hz, 1H), 7.34 (dd, J=8.6, 2.5 Hz, 1H), 7.48 (d, J=2.5 Hz, 1H), 8.11 (s, 1H), 8.47 (dd, J=4.6, 1.5 Hz, 2H), 8.82 (s, 1H)

1-Methyl-5-(4-pyridylmethylthio)-N-(4-trifluoromethoxyphenyl)pyrazole-4-carboxamide Compound No. 9-4

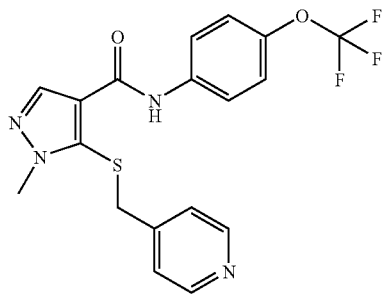

$^1$H-NMR (400 MHz, CDCl$_3$)

δ 3.67 (s, 3H), 3.96 (s, 2H), 6.92 (dd, J=4.4, 1.6 Hz, 2H), 7.61 (d, J=8.2 Hz, 2H), 7.70 (d, J=8.2 Hz, 2H), 8.15 (s, 1H), 8.46 (dd, J=4.4, 1.6 Hz, 2H), 9.04 (s, 1H)

1-Methyl-5-(4-pyridylmethylthio)-N-(4-trifluoromethylphenyl)pyrazole-4-carboxamide Compound No. 9-5

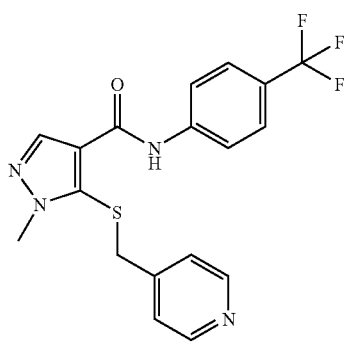

¹H-NMR (500 MHz, CDCl₃)
δ 3.64 (s, 3H), 3.96 (s, 2H), 6.91-6.92 (m, 2H), 7.21 (d, J=8.9 Hz, 2H), 7.60 (d, J=8.9 Hz, 2H), 8.13 (s, 1H), 8.45-8.47 (m, 2H), 8.96 (s, 1H)

N-(4-Isopropoxyphenyl)-1-methyl-5-(4-pyridylmethylthio)pyrazole-4-carboxamide

Compound No. 9-6

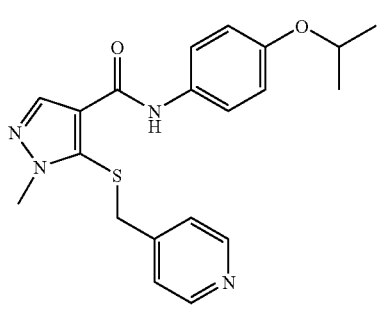

¹H-NMR (500 MHz, CDCl₃)

δ 1.34 (d, J=6.1 Hz, 6H), 3.61 (s, 3H), 3.96 (s, 2H), 4.54 (m, 1H), 6.89 (dt, J=9.8, 2.8 Hz, 2H), 6.93 (dd, J=4.4, 1.5 Hz, 2H), 7.46 (dt, J=9.8, 2.8 Hz, 2H), 8.11 (s, 1H), 8.47 (dd, J=4.4, 1.5 Hz, 2H), 8.74 (s, 1H)

N-(5-Indanyl)-2-(4-pyridylmethylthio)-4,5,6,7-tetrahydrobenzothiophene-3-carboxamide Compound No. 9-7

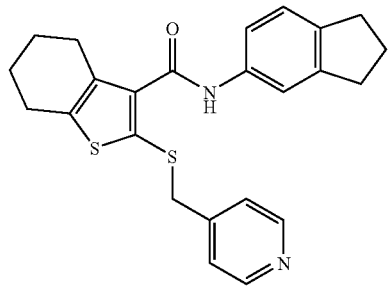

¹H-NMR (500 MHz, CDCl₃)
δ 1.74-1.84 (m, 4H), 2.06-2.12 (m, 2H), 2.68 (t, J=6.1 Hz, 2H), 2.78 (t, J=6.0 Hz, 2H), 2.88-2.94 (m, 4H), 3.92 (s, 2H), 7.07 (dd, J=4.3, 1.5 Hz, 2H), 7.20 (s, 2H), 7.55 (s, 1H), 8.17 (s, 1H), 8.46 (dd, J=4.3, 1.5 Hz, 2H)

N-(3,5-Dimethylphenyl)-2-(4-pyridylmethylthio)-4,5,6,7-tetrahydrobenzothiophene-3-carboxamide Compound No. 9-8

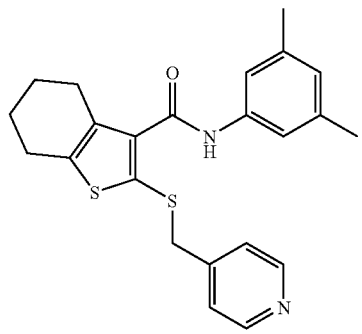

¹H-NMR (500 MHz, CDCl₃)

δ 1.77-1.82 (m, 4H), 2.33 (s, 6H), 2.68 (t, J=6.1 Hz, 2H), 2.79 (t, J=6.1 Hz, 2H), 3.92 (s, 2H), 6.80 (s, 1H), 7.07 (dd, J=4.5, 1.6 Hz, 2H), 7.19 (s, 2H), 8.16 (s, 1H), 8.47 (dd, J=4.5, 1.6 Hz, 2H)

N-(4-Chloro-3-methylphenyl)-2-(4-pyridylmethylthio)-4,5,6,7-tetrahydrobenzothiophene-3-carboxamide Compound No. 9-9

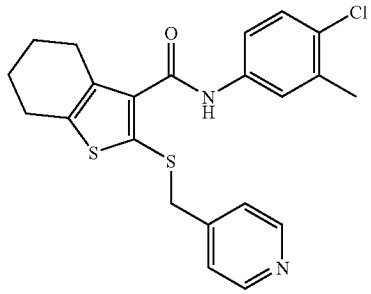

¹H-NMR (500 MHz, CDCl₃)

δ 1.76-1.84 (m, 4H), 2.39 (s, 3H), 2.70 (t, J=6.1 Hz, 2H), 2.78 (t, J=6.1 Hz, 2H), 3.92 (s, 2H), 7.05 (dd, J=4.3, 1.5 Hz, 2H), 7.27-7.29 (m, 2H), 7.48 (s, 1H), 8.22 (s, 1H), 8.47 (dd, J=4.3, 1.5 Hz, 2H)

2-(4-Pyridylmethylthio)-N-(4-trifluoromethoxyphenyl)-4,5,6,7-tetrahydrobenzothiophene-3-carboxamide Compound No. 9-10

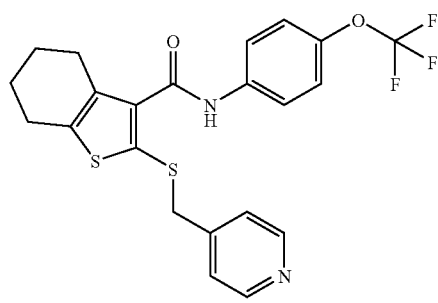

¹H-NMR (500 MHz, CDCl₃)

δ 1.77-1.86 (m, 4H), 2.71 (t, J=6.2 Hz, 2H), 2.79 (t, J=6.2 Hz, 2H), 3.92 (s, 2H), 7.03 (dd, J=4.3, 1.5 Hz, 2H), 7.61 (d, J=8.8 Hz, 2H), 7.66 (d, J=8.8 Hz, 2H), 8.46 (dd, J=4.3, 1.5 Hz, 2H), 8.49 (s, 1H)

2-(4-Pyridylmethylthio)-N-(4-trifluoromethylphenyl)-4,5,6,7-tetrahydrobenzothiophene-3-carboxamide Compound No. 9-11

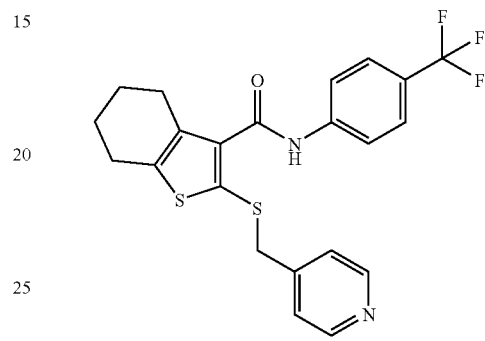

¹H-NMR (500 MHz, CDCl₃)

δ 1.75-1.84 (m, 4H), 2.70 (t, J=6.3 Hz, 2H), 2.78 (t, J=6.1 Hz, 2H), 3.92 (s, 2H), 7.04 (dd, J=4.6, 1.5 Hz, 2H), 7.21 (d, J=8.6 Hz, 2H), 7.57 (d, J=8.6 Hz, 2H), 8.30 (br s, 1H), 8.46 (dd, J=4.6, 1.5 Hz, 2H)

N-(4-Isopropoxyphenyl)-2-(4-pyridylmethylthio)-4,5,6,7-tetrahydrobenzothiophene-3-carboxamide Compound No. 9-12

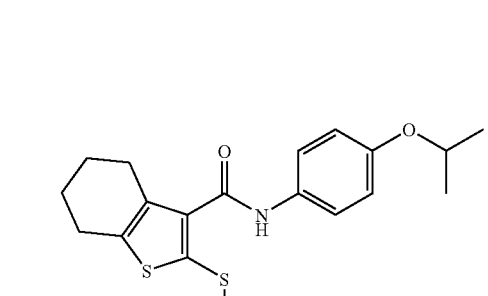

¹H-NMR (500 MHz, CDCl₃)

δ 1.34 (d, J=6.1 Hz, 6H), 1.78-1.82 (m, 4H), 2.69 (t, J=6.0 Hz, 2H), 2.78 (t, J=6.0 Hz, 2H), 3.92 (s, 2H), 4.53 (m, 1H), 6.89 (d, J=8.9 Hz, 2H), 7.07 (dd, J=4.4, 1.7 Hz, 2H), 7.44 (d, J=8.9 Hz, 2H), 8.05 (s, 1H), 8.47 (dd, J=4.4, 1.7 Hz, 2H)

N-(3-Methylphenyl)-5-(4-pyridylmethylthio)furan-2-carboxamide

Compound No. 9-13

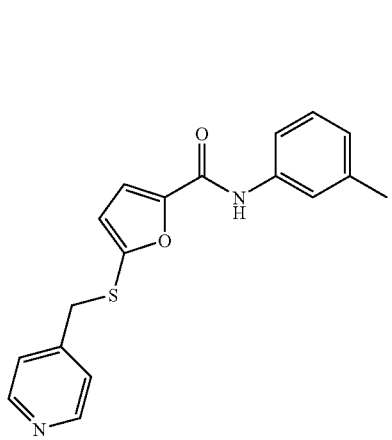

¹H-NMR (500 MHz, CDCl₃)
δ
2.38 (s, 3H), 3.98 (s, 2H), 6.98 (m, 1H), 7.12-7.13 (m, 3H), 7.25-7.26 (m, 2H), 7.41 (dd, J=8.2, 2.4 Hz, 1H), 7.48 (s, 1H), 7.79 (s, 1H), 8.57 (dd, J=4.3, 1.5 Hz, 2H)

N-(5-Indanyl)-5-(4-pyridylmethylthio)furan-2-carboxamide

Compound No. 9-14

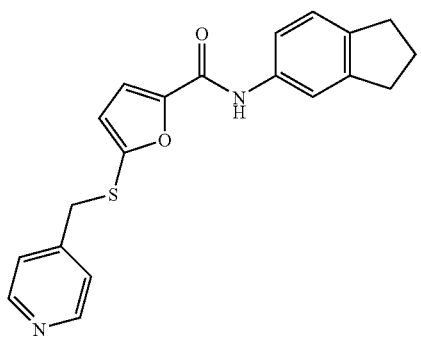

¹H-NMR (500 MHz, CDCl₃)

δ 2.06-2.13 (m, 2H), 2.88-2.95 (m, 4H), 3.98 (s, 2H), 6.48 (d, J=3.4 Hz, 1H), 7.12-7.14 (m, 3H), 7.21 (d, J=8.1 Hz, 1H), 7.29 (dd, J=8.1, 2.0 Hz, 1H), 7.58 (s, 1H), 7.78 (s, 1H), 8.57 (dd, J=4.6, 1.8 Hz, 2H)

N-(3-Fluoro-4-methylphenyl)-5-(4-pyridylmethylthio)furan-2-carboxamide

Compound No. 9-15

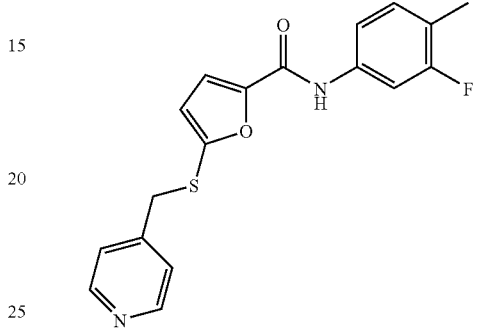

¹H-NMR (500 MHz, CDCl₃)
δ 2.26 (d, J=1.8 Hz, 3H), 3.98 (s, 2H), 6.49 (d, J=3.7 Hz, 1H), 7.13-7.16 (m, 5H), 7.54 (dd, J=12.2, 1.8 Hz, 1H), 7.77 (s, 1H), 8.57 (dd, J=4.3, 1.5 Hz, 2H)

N-(3-Isopropylphenyl)-5-(4-pyridylmethylthio)furan-2-carboxamide

Compound No. 9-16

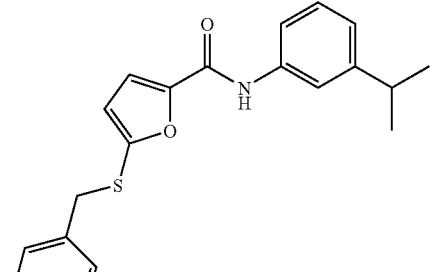

¹H-NMR (500 MHz, CDCl₃)
δ 1.28 (d, J=6.7 Hz, 6H), 2.94 (m, 1H), 3.99 (s, 2H), 6.48 (d, J=3.4 Hz, 1H), 7.04 (d, J=7.6 Hz, 1H), 7.13-7.14 (m, 3H), 7.30 (t, J=7.8 Hz, 1H), 7.46 (m, 1H), 7.50 (m, 1H), 7.79 (s, 1H), 8.57 (dd, J=4.6, 1.5 Hz, 2H)

N-(4-Fluoro-3-methylphenyl)-5-(4-pyridylmethylthio)furan-2-carboxamide

Compound No. 9-17

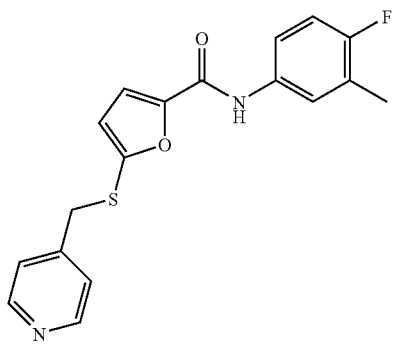

$^1$H-NMR (500 MHz, CDCl$_3$)

δ 2.30 (d, J=1.8 Hz, 3H), 3.98 (s, 2H), 6.49 (d, J=3.4 Hz, 1H), 7.00 (t, J=8.9 Hz, 1H), 7.13-7.14 (m, 3H), 7.37 (m, 1H), 7.49 (dd, J=6.7, 2.4 Hz, 1H), 7.71 (s, 1H), 8.57 (dd, J=4.6, 1.8 Hz, 2H)

N-(3-Isoquinolyl)-5-(4-pyridylmethylthio)furan-2-carboxamide

Compound No. 9-18

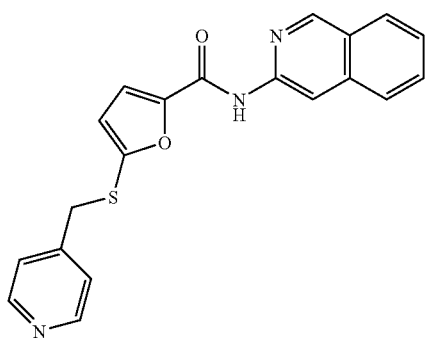

$^1$H-NMR (500 MHz, CDCl$_3$)

δ 4.04 (s, 2H), 6.46 (d, J=3.4 Hz, 1H), 7.14 (dd, J=4.4, 1.6 Hz, 2H), 7.20 (d, J=3.4 Hz, 1H), 7.52 (m, 1H), 7.69 (m, 1H), 7.87 (dd, J=8.2, 0.9 Hz, 1H), 7.93 (dd, J=8.2, 0.9 Hz, 1H), 8.56 (dd, J=4.4, 1.6 Hz, 2H), 8.67 (s, 1H), 8.79 (s, 1H), 9.05 (s, 1H)

N-(3-Chlorophenyl)-5-(4-pyridylmethylthio)furan-2-carboxamide

Compound No. 9-19

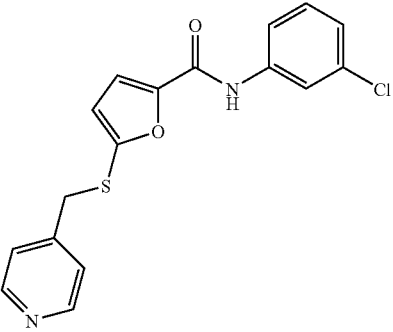

$^1$H-NMR (500 MHz, CDCl$_3$)

δ 3.99 (s, 2H), 6.50 (d, J=3.4 Hz, 1H), 7.13-7.16 (m, 4H), 7.30 (t, J=8.1 Hz, 1H), 7.45 (ddd, J=8.2, 2.1, 0.9 Hz, 1H), 7.78 (br s, 1H), 7.78 (t, J=2.1 Hz, 1H), 8.58 (dd, J=4.3, 1.5 Hz, 2H)

N-(3-Chloro-4-trifluoromethoxyphenyl)-5-(4-pyridylmethylthio)furan-2-carboxamide Compound No. 9-20

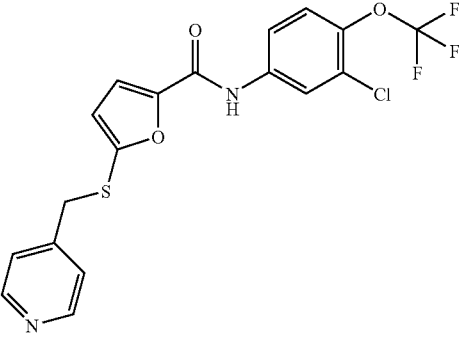

$^1$H-NMR (500 MHz, CDCl$_3$)

δ 3.99 (s, 2H), 6.52 (d, J=3.6 Hz, 1H), 7.15 (dd, J=4.3, 1.5 Hz, 2H), 7.17 (d, J=3.6 Hz, 1H), 7.32 (m, 1H), 7.50 (dd, J=8.9, 2.4 Hz, 1H), 7.75 (br s, 1H), 7.92 (d, J=2.7 Hz, 1H), 8.58 (dd, J=4.3, 1.5 Hz, 2H)

N-(3-Chloro-4-methylphenyl)-5-(4-pyridylmethylthio)furan-2-carboxamide

Compound No. 9-21

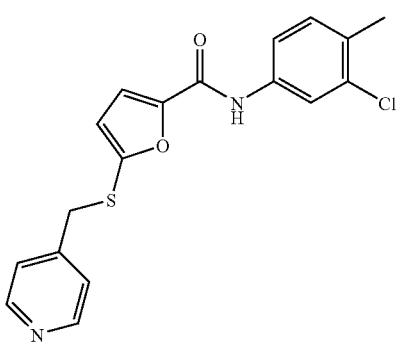

¹H-NMR (500 MHz, CDCl₃)
δ 2.36 (s, 3H), 3.98 (s, 2H), 6.49 (d, J=3.4 Hz, 1H), 7.13-7.14 (m, 3H), 7.21 (d, J=Hz, 1H), 7.38 (dd, J=8.1, 2.1 Hz, 1H), 7.73 (br s, 1H), 7.74 (d, J=2.1 Hz, 1H), 8.57 (dd, J=4.3, 1.5 Hz, 2H)

N-(4-tert-Butylphenyl)-5-(4-pyridylmethylthio)furan-2-carboxamide

Compound No. 9-22

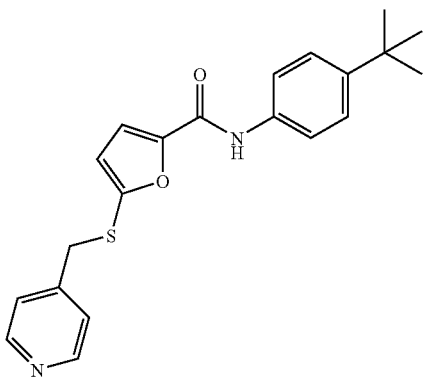

¹H-NMR (500 MHz, CDCl₃)
δ 1.33 (s, 9H), 3.98 (s, 2H), 6.49 (d, J=3.4 Hz, 1H), 7.13-7.14 (m, 3H), 7.39 (d, J=8.9 Hz, 2H), 7.54 (d, J=8.9 Hz, 2H), 7.74 (br s, 1H), 8.57 (dd, J=4.3, 1.5 Hz, 2H)

5-(4-Pyridylmethylthio)-N-(6-quinolyl)furan-2-carboxamide

Compound No. 9-23

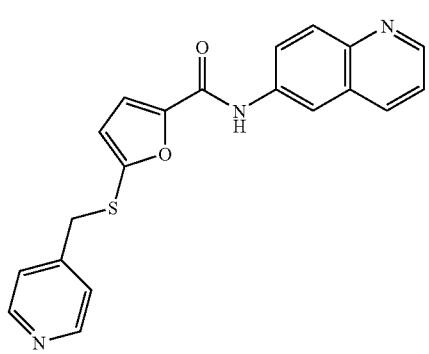

¹H-NMR (500 MHz, CDCl₃)
δ 4.01 (s, 2H), 6.53 (d, J=3.4 Hz, 1H), 7.16 (dd, J=4.4, 1.7 Hz, 2H), 7.20 (d, J=3.4 Hz, 1H), 7.42 (dd, J=8.8, 4.3 Hz, 1H), 7.71 (dd, J=8.8, 2.4 Hz, 1H), 8.00 (brs, 1H), 8.12 (d, J=9.2 Hz, 1H), 8.17 (m, 1H), 8.44 (d, J=2.4 Hz, 1H), 8.59 (dd, J=4.4, 1.7 Hz, 2H), 8.87 (dd, J=4.0, 1.5 Hz, 1H)

N-(4-Bromo-3-methylphenyl)-5-(4-pyridylmethylthio)furan-2-carboxamide

Compound No. 9-24

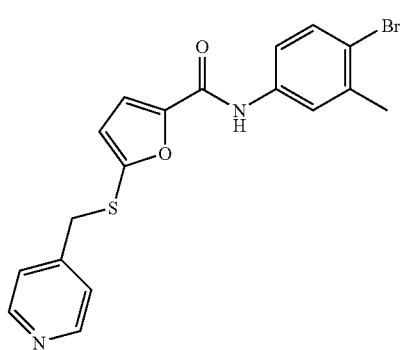

¹H-NMR (500 MHz, CDCl₃)

δ 2.42 (s, 3H), 3.98 (s, 2H), 6.49 (d, J=3.4 Hz, 1H), 7.13-7.14 (m, 3H), 7.33 (dd, J=8.6, 2.4 Hz, 1H), 7.51 (d, J=8.6 Hz, 1H), 7.56 (d, J=2.4 Hz, 1H), 7.73 (br s, 1H), 8.57 (dd, J=4.6, 1.8 Hz, 2H)

5-(4-Pyridylmethylthio)-N-(4-trifluoromethoxyphenyl)furan-2-carboxamide

Compound No. 9-25

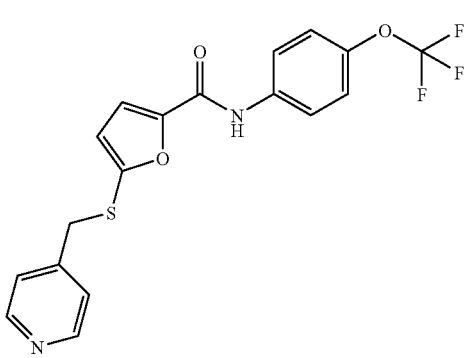

¹H-NMR (500 MHz, CDCl₃)

δ 3.98 (s, 2H), 6.51 (d, J=3.5 Hz, 1H), 7.15 (dd, J=4.4, 1.5 Hz, 2H), 7.16 (d, J=3.5 Hz, 1H), 7.23 (d, J=8.2 Hz, 2H), 7.66 (d, J=0.9 Hz, 2H), 7.78 (br s, 1H), 8.58 (dd, J=4.4, 1.5 Hz, 2H)

N-(4-Dimethylaminophenyl)-5-(4-pyridylmethylthio)furan-2-carboxamide

Compound No. 9-26

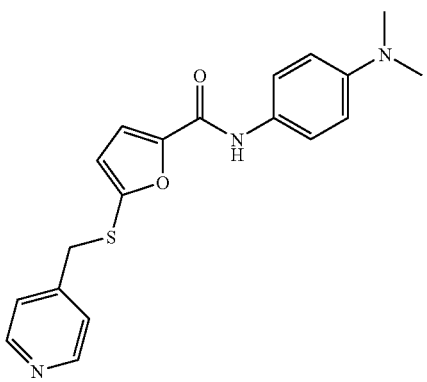

¹H-NMR (500 MHz, CDCl₃)

δ 2.95 (s, 6H), 3.97 (s, 2H), 6.47 (d, J=3.5 Hz, 1H), 6.74 (d, J=9.0 Hz, 2H), 7.09 (d, J=Hz, 1H), 7.13 (dd, J=4.6, 1.7 Hz, 2H), 7.47 (d, J=9.0 Hz, 2H), 7.67 (br s, 1H), 8.56 (dd, J=4.6, 1.7 Hz, 2H)

N-(1-Acetyl-2,3-dihydroindol-5-yl)-5-(4-pyridylmethylthio)furan-2-carboxamide

Compound No. 9-27

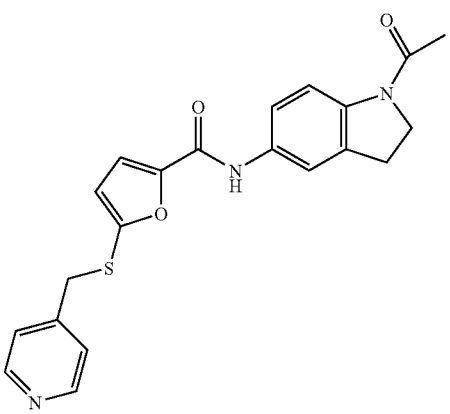

¹H-NMR (500 MHz, CDCl₃)

δ 2.23 (s, 3H), 3.23 (t, J=8.5 Hz, 2H), 3.98 (s, 2H), 4.09 (t, J=8.5 Hz, 2H), 6.47 (d, J=3.4 Hz, 1H), 7.12-7.17 (m, 4H), 7.78 (d, J=2.0 Hz, 1H), 7.83 (br s, 1H), 8.19 (d, J=8.5 Hz, 1H), 8.56 (dd, J=4.4, 1.5 Hz, 2H)

N-(4-Isopropoxyphenyl)-5-(4-pyridylmethylthio)furan-2-carboxamide

Compound No. 9-28

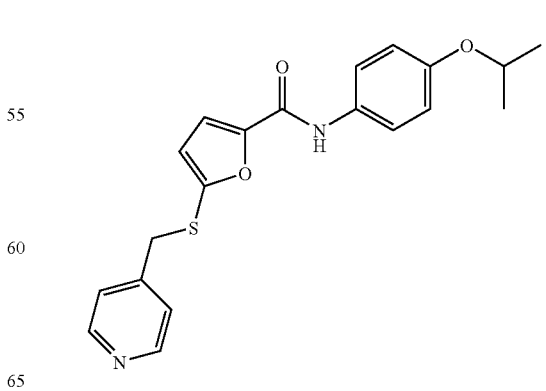

¹H-NMR (400 MHz, CDCl₃)

δ 1.34 (d, J=6.1 Hz, 6H), 3.97 (s, 2H), 4.52 (m, 1H), 6.48 (d, J=3.4 Hz, 1H), 6.89 (dd, J=6.6, 2.2 Hz, 2H), 7.10 (m, 3H), 7.51 (dd, J=6.6, 2.2 Hz, 2H), 7.73 (s, 1H), 8.56 (dd, J=4.4, 1.7 Hz, 2H)

5-(4-Pyridylmethylthio)-N-(4-trifluoromethylthiophenyl)furan-2-carboxamide

Compound No. 9-29

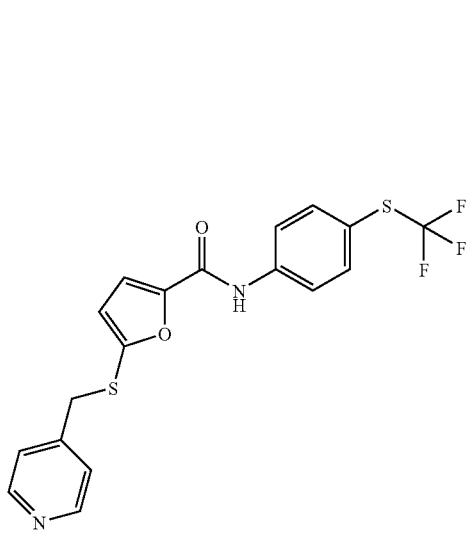

¹H-NMR (400 MHz, CDCl₃)

δ 3.99 (s, 2H), 6.52 (d, J=3.4 Hz, 1H), 7.15 (dd, J=4.4, 1.7 Hz, 2H), 7.18 (d, J=3.4 Hz, 1H), 7.66 (d, J=8.8 Hz, 2H), 7.71 (d, J=8.8 Hz, 2H), 7.84 (s, 1H), 8.58 (dd, J=4.4, 1.7 Hz, 2H)

N-(4-Bromophenyl)-5-(4-pyridylmethylthio)furan-2-carboxamide

Compound No. 9-30

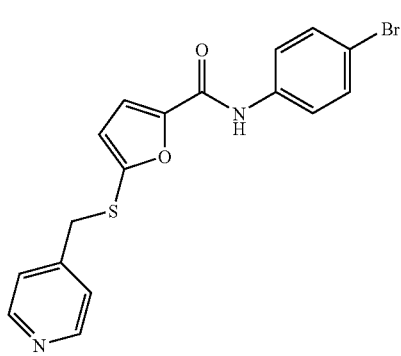

¹H-NMR (400 MHz, CDCl₃)

δ 3.98 (s, 2H), 6.50 (d, J=3.4 Hz, 1H), 7.14 (dd, J=4.4, 1.7 Hz, 2H), 7.15 (d, J=3.4 Hz, 1H), 7.49 (d, J=9.2 Hz, 2H), 7.54 (d, J=9.2 Hz, 2H), 7.77 (br s, 1H), 8.57 (dd, J=4.4, 1.5 Hz, 2H)

N-(3-Methylphenyl)-5-(4-pyridylmethylthio)thiophene-2-carboxamide

Compound No. 9-31

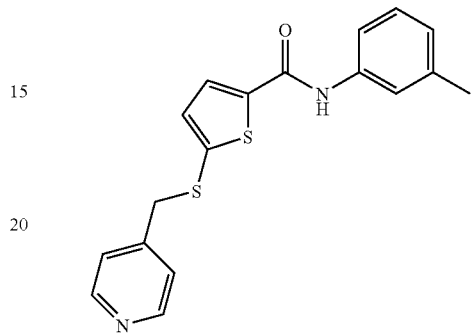

¹H-NMR (500 MHz, CDCl₃)

δ 2.35 (s, 3H), 3.98 (s, 2H), 6.87 (d, J=3.9 Hz, 1H), 6.97 (d, J=7.6 Hz, 1H), 7.13 (dd, J=Hz, 2H), 7.23 (t, J=7.9 Hz, 1H), 7.35 (m, 1H), 7.39 (d, J=3.9 Hz, 1H), 7.43 (m, 1H), 7.60 (s, 1H), 8.53 (dd, J=4.3, 1.5 Hz, 2H)

N-(5-Indanyl)-5-(4-pyridylmethylthio)thiophene-2-carboxamide

Compound No. 9-32

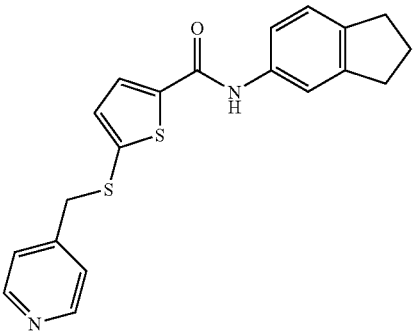

¹H-NMR (500 MHz, CDCl₃)

δ 2.07-2.10 (m, 2H), 2.86-2.92 (m, 4H), 3.98 (s, 2H), 6.87 (d, J=3.9 Hz, 1H), 7.13 (dd, J=4.4, 1.5 Hz, 2H), 7.18 (d, J=8.2

Hz, 1H), 7.23 (dd, J=7.9, 2.1 Hz, 1H), 7.38 (d, J=3.9 Hz, 1H), 7.51 (s, 1H), 7.57 (br s, 1H), 8.53 (dd, J=4.4, 1.5 Hz, 2H)

N-(3-Fluoro-4-methylphenyl)-5-(4-pyridylmethylthio)thiophene-2-carboxamide

Compound No. 9-33

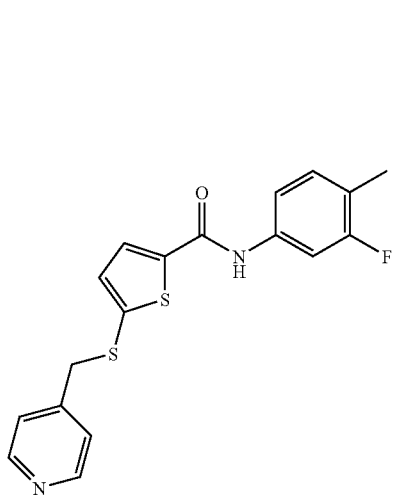

$^1$H-NMR (500 MHz, CDCl$_3$)

δ 2.24 (d, J=1.8 Hz, 3H), 3.99 (s, 2H), 6.86 (d, J=3.9 Hz, 1H), 7.13 (m, 4H), 7.40 (d, J=3.9 Hz, 1H), 7.47 (m, 1H), 7.71 (s, 1H), 8.52 (dd, J=4.6, 1.5 Hz, 2H)

N-(3-Isopropylphenyl)-5-(4-pyridylmethylthio)thiophene-2-carboxamide

Compound No. 9-34

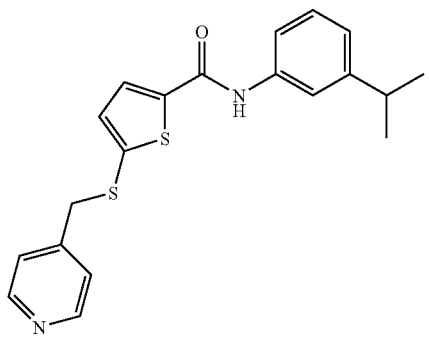

$^1$H-NMR (500 MHz, CDCl$_3$)

δ 1.25 (d, J=7.0 Hz, 6H), 2.91 (m, 1H), 3.99 (s, 2H), 6.87 (d, J=4.0 Hz, 1H), 7.03 (d, J=7.8 Hz, 1H), 7.13 (dd, J=4.6, 1.5 Hz, 2H), 7.27 (t, J=0.8 Hz, 1H), 7.38 (dd, J=Hz, 1H), 7.40 (d, J=4.0 Hz, 1H), 7.46 (t, J=2.1 Hz, 1H), 7.62 (s, 1H), 8.53 (dd, J=4.6, 1.5 Hz, 2H)

N-(4-Fluoro-3-methylphenyl)-5-(4-pyridylmethylthio)thiophene-2-carboxamide

Compound No. 9-35

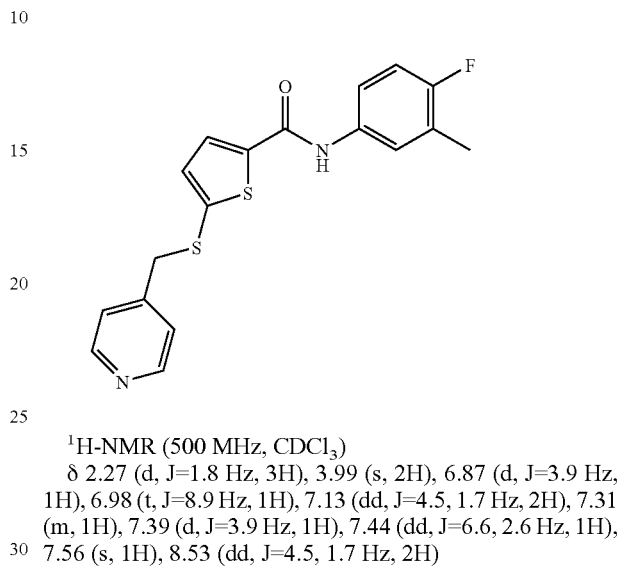

$^1$H-NMR (500 MHz, CDCl$_3$)

δ 2.27 (d, J=1.8 Hz, 3H), 3.99 (s, 2H), 6.87 (d, J=3.9 Hz, 1H), 6.98 (t, J=8.9 Hz, 1H), 7.13 (dd, J=4.5, 1.7 Hz, 2H), 7.31 (m, 1H), 7.39 (d, J=3.9 Hz, 1H), 7.44 (dd, J=6.6, 2.6 Hz, 1H), 7.56 (s, 1H), 8.53 (dd, J=4.5, 1.7 Hz, 2H)

N-(3-Isoquinolyl)-5-(4-pyridylmethylthio)thiophene-2-carboxamide

Compound No. 9-36

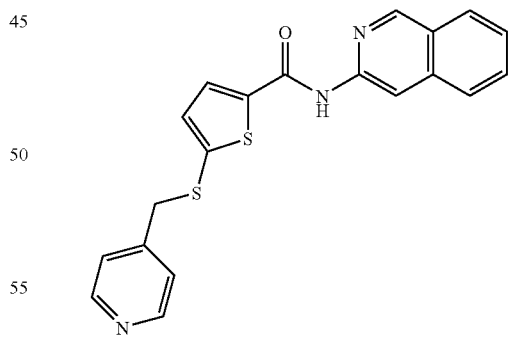

$^1$H-NMR (500 MHz, CDCl$_3$)

δ 4.02 (s, 2H), 6.92 (d, J=4.0 Hz, 1H), 7.16 (dd, J=4.5, 1.5 Hz, 2H), 7.49-7.53 (m, 2H), 7.68 (m, 1H), 7.85 (d, J=8.2 Hz,

1H), 7.92 (d, J=7.6 Hz, 1H), 8.45 (s, 1H), 8.54 (dd, J=4.5, 1.5 Hz, 2H), 8.64 (s, 1H), 9.00 (s, 1H)

N-(3-Chlorophenyl)-5-(4-pyridylmethylthio)thiophene-2-carboxamide

Compound No. 9-37

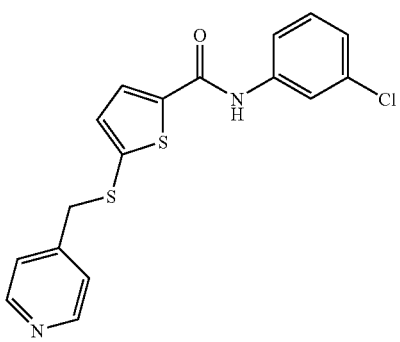

¹H-NMR (500 MHz, CDCl₃)

δ 4.00 (s, 2H), 6.89 (d, J=3.9 Hz, 1H), 7.13 (m, 1H), 7.14 (dd, J=4.6, 1.5 Hz, 2H), 7.28 (t, J=8.1 Hz, 1H), 7.40 (d, J=3.9 Hz, 1H), 7.43 (ddd, J=8.1, 2.1, 0.9 Hz, 1H), 7.57 (s, 1H), 7.70 (t, J=2.1 Hz, 1H), 8.53 (dd, J=4.6, 1.5 Hz, 2H)

N-(3-Chloro-4-trifluoromethoxyphenyl)-5-(4-pyridylmethylthio)thiophene-2-carboxamide Compound No. 9-38

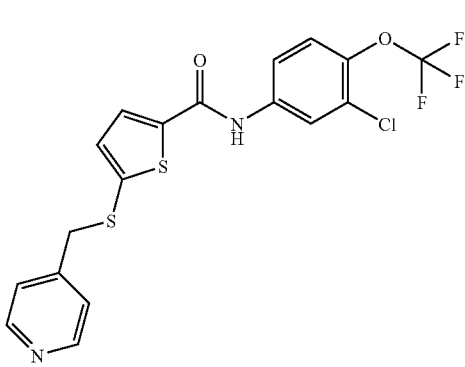

¹H-NMR (500 MHz, CDCl₃)

δ 4.01 (s, 2H), 6.89 (d, J=3.9 Hz, 1H), 7.15 (dd, J=4.3, 1.5 Hz, 2H), 7.30 (m, 1H), 7.43 (d, J=3.9 Hz, 1H), 7.49 (dd, J=8.9, 2.4 Hz, 1H), 7.68 (s, 1H), 7.85 (d, J=2.7 Hz, 1H), 8.53 (dd, J=4.3, 1.5 Hz, 2H)

N-(3-Chloro-4-methylphenyl)-5-(4-pyridylmethylthio)thiophene-2-carboxamide

Compound No. 9-39

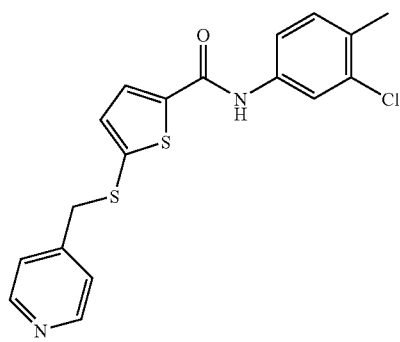

¹H-NMR (500 MHz, CDCl₃)

δ 2.34 (s, 3H), 3.99 (s, 2H), 6.87 (d, J=3.9 Hz, 1H), 7.13 (dd, J=4.6, 1.5 Hz, 2H), 7.18 (d, J=8.2 Hz, 1H), 7.35 (dd, J=8.2, 2.1 Hz, 1H), 7.40 (d, J=3.9 Hz, 1H), 7.66 (d, J=2.1 Hz, 1H), 7.70 (br s, 1H), 8.52 (dd, J=4.6, 1.5 Hz, 2H)

N-(4-tert-Butylphenyl)-5-(4-pyridylmethylthio)thiophene-2-carboxamide

Compound No. 9-40

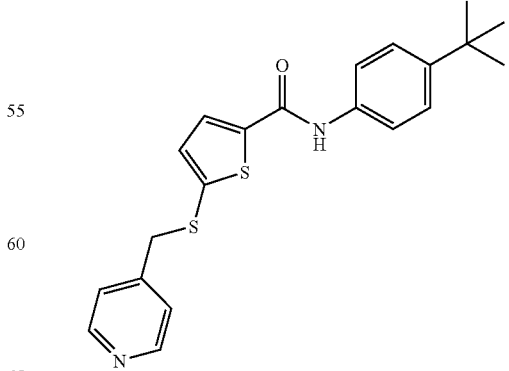

¹H-NMR (500 MHz, CDCl₃)

δ 1.31 (s, 9H), 3.98 (s, 2H), 6.86 (d, J=3.7 Hz, 1H), 7.13 (dd, J=4.4, 1.6 Hz, 2H), 7.37 (d, J=8.8 Hz, 2H), 7.39 (d, J=3.7 Hz, 1H), 7.49 (d, J=8.8 Hz, 2H), 7.64 (s, 1H), 8.52 (dd, J=4.4, 1.6 Hz, 2H)

5-(4-Pyridylmethylthio)-N-(6-quinolyl)thiophene-2-carboxamide

Compound No. 9-41

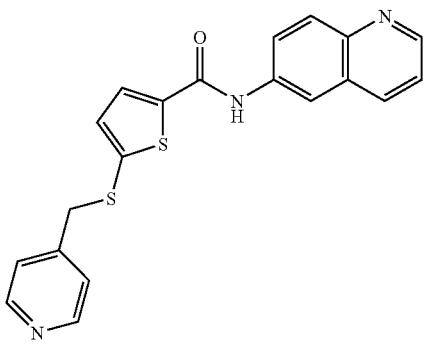

¹H-NMR (500 MHz, CDCl₃)

δ 4.01 (s, 2H), 6.91 (d, J=3.9 Hz, 1H), 7.15 (dd, J=4.6, 1.5 Hz, 2H), 7.41 (dd, J=8.2, 4.3 Hz, 1H), 7.49 (d, J=4.0 Hz, 1H), 7.65 (dd, J=8.9, 2.4 Hz, 1H), 7.97 (s, 1H), 8.08 (d, J=9.2 Hz, 1H), 8.14 (dd, J=8.2, 1.5 Hz, 1H), 8.42 (d, J=2.4 Hz, 1H), 8.54 (dd, J=4.6, 1.5 Hz, 2H), 8.86 (dd, J=4.3, 1.5 Hz, 1H)

N-(4-Bromo-3-methylphenyl)-5-(4-pyridylmethylthio)thiophene-2-carboxamide

Compound No. 9-42

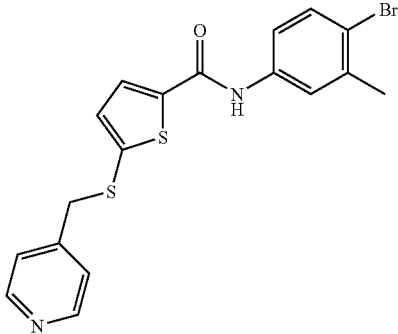

¹H-NMR (500 MHz, CDCl₃)

δ 2.39 (s, 3H), 3.99 (s, 2H), 6.88 (d, J=4.0 Hz, 1H), 7.13 (dd, J=4.6, 1.5 Hz, 2H), 7.28 (dd, J=8.6, 2.5 Hz, 1H), 7.39 (d, J=4.0 Hz, 1H), 7.48 (d, J=8.6 Hz, 1H), 7.52 (d, J=2.5 Hz, 1H), 7.58 (br s, 1H), 8.53 (dd, J=4.6, 1.5 Hz, 2H)

5-(4-Pyridylmethylthio)-N-(4-trifluoromethoxyphenyl)thiophene-2-carboxamide

Compound No. 9-43

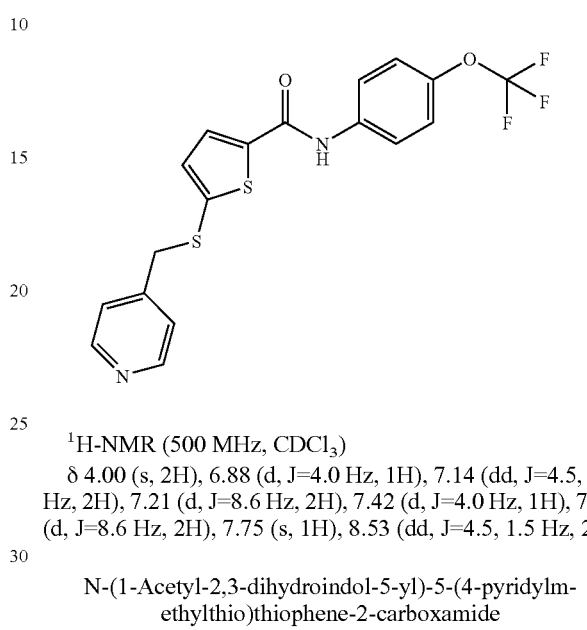

¹H-NMR (500 MHz, CDCl₃)

δ 4.00 (s, 2H), 6.88 (d, J=4.0 Hz, 1H), 7.14 (dd, J=4.5, 1.5 Hz, 2H), 7.21 (d, J=8.6 Hz, 2H), 7.42 (d, J=4.0 Hz, 1H), 7.62 (d, J=8.6 Hz, 2H), 7.75 (s, 1H), 8.53 (dd, J=4.5, 1.5 Hz, 2H)

N-(1-Acetyl-2,3-dihydroindol-5-yl)-5-(4-pyridylmethylthio)thiophene-2-carboxamide Compound No. 9-44

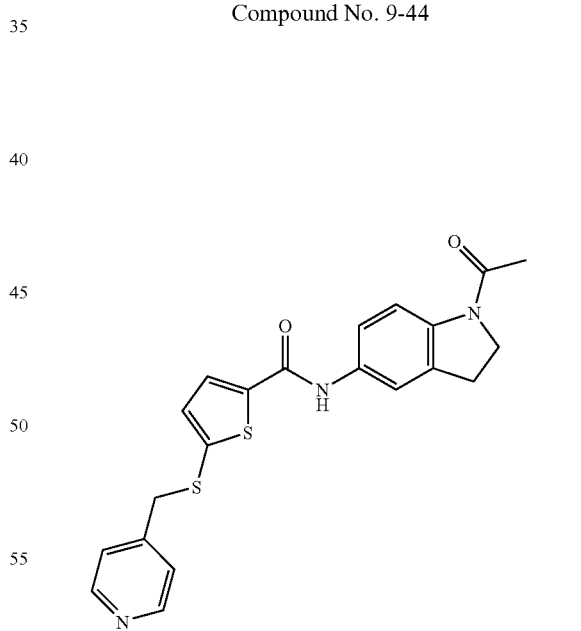

¹H-NMR (500 MHz, CDCl₃)

δ 2.23 (s, 3H), 3.22 (t, J=8.6 Hz, 2H), 3.99 (s, 2H), 4.08 (t, J=8.6 Hz, 2H), 6.88 (d, J=Hz, 1H), 7.06 (dd, J=8.6, 2.1 Hz,

1H), 7.13 (dd, J=4.6, 1.5 Hz, 2H), 7.39 (d, J=Hz, 1H), 7.56 (s, 1H), 7.76 (s, 1H), 8.16 (d, J=8.6 Hz, 1H), 8.53 (dd, J=4.6, 1.5 Hz, 2H)

N-(4-Isopropoxyphenyl)-5-(4-pyridylmethylthio)thiophene-2-carboxamide

Compound No. 9-45

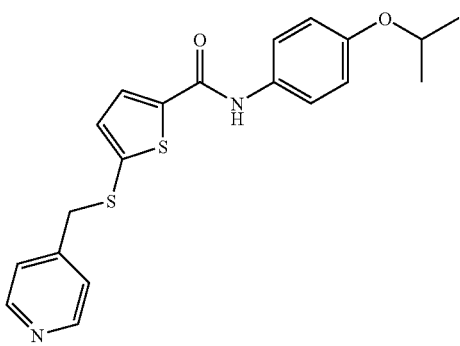

¹H-NMR (500 MHz, CDCl₃)

δ 1.33 (d, J=5.8 Hz, 6H), 3.98 (s, 2H), 4.52 (m, 1H), 6.87 (d, J=4.0 Hz, 1H), 6.87 (d, J=8.9 Hz, 2H), 7.13 (dd, J=4.3, 1.5 Hz, 2H), 7.38 (d, J=4.0 Hz, 1H), 7.45 (d, J=8.9 Hz, 2H), 7.54 (br s, 1H), 8.52 (dd, J=4.3, 1.5 Hz, 2H)

5-(4-Pyridylmethylthio)-N-(4-trifluoromethylthiophenyl)thiophene-2-carboxamide

Compound No. 9-46

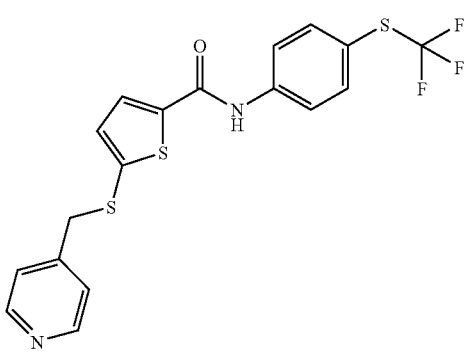

¹H-NMR (500 MHz, CDCl₃)

δ 4.01 (s, 2H), 6.90 (d, J=4.0 Hz, 1H), 7.14 (dd, J=4.5, 1.5 Hz, 2H), 7.43 (d, J=4.0 Hz, 1H), 7.63-7.68 (m, 4H), 7.10 (s, 1H), 8.53 (dd, J=4.5, 1.5 Hz, 2H)

N-(4-Bromophenyl)-5-(4-pyridylmethylthio)thiophene-2-carboxamide

Compound No. 9-47

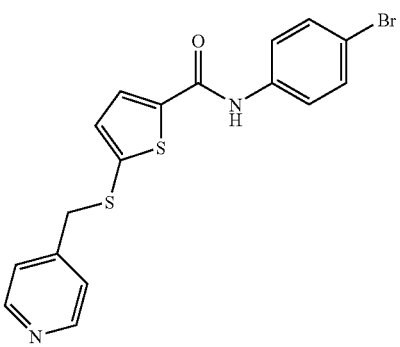

¹H-NMR (500 MHz, CDCl₃)

δ 3.99 (s, 2H), 6.87 (d, J=3.9 Hz, 1H), 7.13 (dd, J=4.6, 1.5 Hz, 2H), 7.41 (d, J=3.9 Hz, 1H), 7.45-7.50 (m, 4H), 7.77 (s, 1H), 8.52 (dd, J=4.6, 1.5 Hz, 2H)

Example 10

N-(3,5-Dimethylphenyl)-2-[4-(1-methylpyridinio)methylthio]pyridine-3-carboxamide iodide Compound No. 10-1

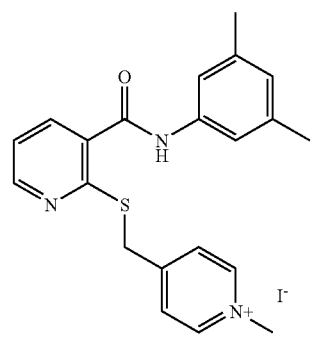

Methyl iodide (36 μL, 0.57 mmol) was added to a solution of N-(3,5-dimethylphenyl)-2-(4-pyridylmethylthio)pyridine-3-carboxamide (100 mg, 0.29 mmol, Compound No. 1-106) in acetone (3 mL) at room temperature, the whole was stirred under shaded condition for 28 hours. The solvent was evaporated under reduced pressure, and then the resulting residue was purified by silica gel column chromatography to give 80 mg of the target compound as a yellow oil. (Yield 57%)

¹H-NMR (500 MHz, CDCl₃)

δ 2.28 (s, 6H), 4.37 (s, 3H), 4.56 (s, 2H), 6.75 (s, 1H), 7.15 (dd, J=7.7, 4.9 Hz, 1H), 7.40 (s, 2H), 7.82 (dd, J=7.7, 1.5 Hz,

1H), 7.96 (d, J=6.1 Hz, 2H), 8.48 (dd, J=4.9, 1.5 Hz, 1H), 8.60 (d, J=6.1 Hz, 2H), 8.63 (s, 1H)

Example 11

N-(3-Fluoro-5-trifluoromethylphenyl)-2-(4-pyridyl-methylthio)benzamide

Compound No. 11-1

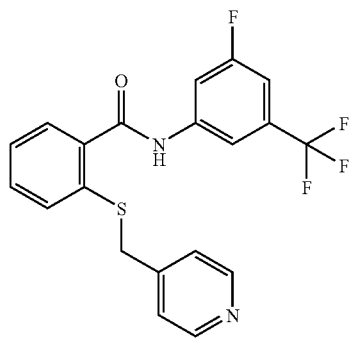

N,N-Diisopropylethylamine (1.5 mL, 8.8 mmol) was added to a suspension of N-(3-fluoro-5-trifluoromethylphenyl)-2-iodobenzamide (1.00 g, 2.4 mmol, Reference compound No. 2-3), bis(dibenzylideneacetone)dipalladium (0.12 g, 0.20 mmol), and 1,1'-bis(diphenylphosphino)ferrocene (0.28 g, 0.49 mmol) in N,N-dimethylacetamide (20 mL) at room temperature, then the reaction bottle was sealed. The mixture was coagulated with liquid nitrogen, sealed under reduced pressure, allowed to stand to room temperature, and then the dissolved oxygen was removed (the operation of degasification). The operation of degasification was conducted further, and then the reaction mixture was stirred at 60° C. under an argon atmosphere for 19 hours. The reaction mixture was allowed to stand, diluted with ethyl acetate (70 mL), then filtrated through celite. The filtrate was washed with brine (70 mL) twice, dried over anhydrous magnesium sulfate, then evaporated under reduced pressure. the resulting residue was purified by silica gel column chromatography to give 0.29 g of the target compound as a colorless solid. (Yield 29%)

$^1$H-NMR (500 MHz, DMSO-d$_6$)

δ 4.27 (s, 2H), 7.32 (m, 1H), 7.35 (d, J=6.1 Hz, 2H), 7.41 (d, J=8.2 Hz, 1H), 7.46 (m, 1H), 7.50 (d, J=8.2 Hz, 1H), 7.58 (d, J=7.3 Hz, 1H), 7.88 (d, J=11.0 Hz, 1H), 7.98 (s, 1H), 8.45 (d, J=6.1 Hz, 2H), 10.87 (s, 1H)

Below compounds (No. 11-2~5) were obtained by a method similar to Example 11.

N-(4-Chlorophenyl)-5-(4-pyridylmethylthio)furan-2-carboxamide

Compound No. 11-2

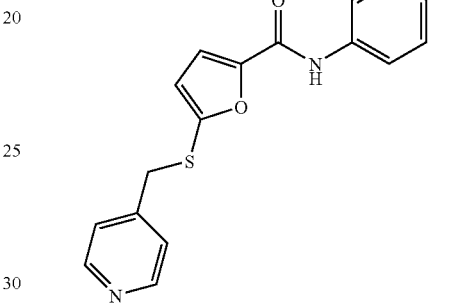

$^1$H-NMR (400 MHz, DMSO-d$_6$)

δ 4.25 (s, 2H), 6.63 (d, J=3.7 Hz, 1H), 7.24 (dd, J=4.4, 1.7 Hz, 2H), 7.28 (d, J=3.7 Hz, 1H), 7.41 (d, J=9.0 Hz, 2H), 7.77 (d, J=9.0 Hz, 2H), 8.48 (dd, J=4.4, 1.7 Hz, 2H), 10.26 (s, 1H)

N-(4-Chlorophenyl)-5-(4-pyridylmethylthio)thiophene-2-carboxamide

Compound No. 11-3

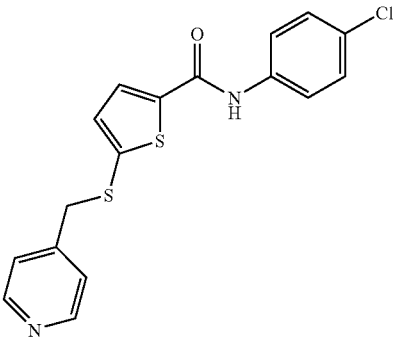

$^1$H-NMR (400 MHz, DMSO-d$_6$)

δ 4.23 (s, 2H), 7.13 (d, J=3.9 Hz, 1H), 7.28 (dd, J=4.4, 1.7 Hz, 2H), 7.40 (d, J=9.0 Hz, 2H), 7.72 (d, J=9.0 Hz, 2H), 7.85 (d, J=3.9 Hz, 1H), 8.49 (dd, J=4.4, 1.7 Hz, 2H), 10.31 (s, 1H)

N-(3,5-Dimethylphenyl)-1-(4-pyridylmethylthio)furan-2-carboxamide

Compound No. 11-4

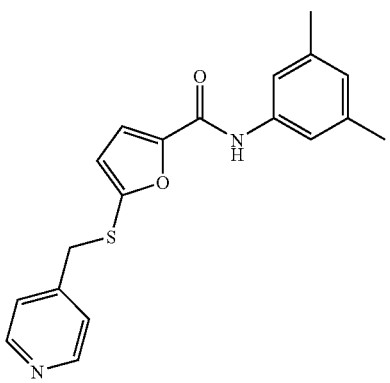

$^1$H-NMR (500 MHz, DMSO-d$_6$)
δ 2.26 (s, 6H), 4.25 (s, 2H), 6.61 (d, J=3.4 Hz, 1H), 6.76 (s, 1H), 7.23 (dd, J=4.3, 1.5 Hz, 2H), 7.24 (d, J=3.4 Hz, 1H), 7.36 (s, 2H), 8.48 (dd, J=4.3, 1.5 Hz, 2H), 9.94 (s, 1H)

N-(3,5-Dimethylphenyl)-5-(4-pyridylmethylthio)thiophene-2-carboxamide

Compound No. 11-5

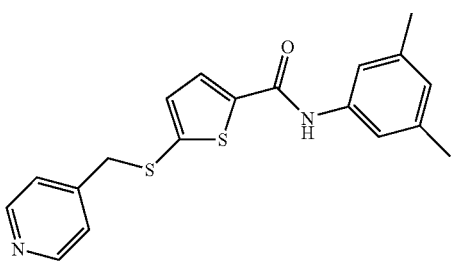

$^1$H-NMR (500 MHz, CDCl$_3$)
δ 2.31 (s, 6H), 3.98 (s, 2H), 6.79 (s, 1H), 6.86 (d, J=4.0 Hz, 1H), 7.13 (dd, J=4.6, 1.8 Hz, 2H), 7.21 (s, 2H), 7.38 (d, J=4.0 Hz, 1H), 7.55 (br s, 1H), 8.52 (dd, J=4.6, 1.8 Hz, 2H)

Formulation Examples

Typical formulation examples of the present compound are shown below.

| 1) Tablet in 100 mg | |
|---|---|
| Present compound | 1 mg |
| Lactose | 66.4 mg |
| Cornstarch | 20 mg |
| Calcium carboxymethylcellulose | 6 mg |

-continued

| 1) Tablet in 100 mg | |
|---|---|
| Hydroxypropylcellulose | 4 mg |
| Magnesium stearate | 0.6 mg |

Tablets according to the above-mentioned formulation are coated with 2 mg/tablet of a coating agent, which is a conventional coating agent such as hydroxypropylmethylcellulose, macrogol or silicone resin, to obtain desired coated tablets. Desired tablets can be obtained by changing appropriately the kinds and the amounts of the present compound and the additives.

| 2) Capsule in 150 mg | |
|---|---|
| Present compound | 5 mg |
| Lactose | 145 mg |

Desired capsules can be obtained by changing appropriately the mixing ratio of the present compound to lactose.

| 3) Ophthalmic solution in 100 ml | |
|---|---|
| Present compound | 100 mg |
| Sodium chloride | 900 mg |
| Polysorbate 80 | 200 mg |
| Sodium hydroxide | quantum sufficient |
| Hydrochloric acid | quantum sufficient |
| Sterile purified water | quantum sufficient |

Desired ophthalmic solutions can be obtained by changing appropriately the kinds and the amounts of the present compound and the additives.

Pharmacological Tests
1. Evaluation Tests of Angiogenesis Inhibitory Effects

As one of widely-used methods of evaluating angiogenesis inhibitory effects of drugs, a cell growth inhibitory action test using a VEGF-induced HUVEC growth reaction evaluation system was reported in Cancer Res., 59, 99-106 (1999). According to the method described in the above-mentioned literature, cell growth inhibitory action tests of the present compounds were carried out, their cell growth inhibition rates were calculated, and angiogenesis inhibitory effects of the present compounds were evaluated using the obtained rates as indexes.

Preparation of Test Compound Solutions

Each test compound was dissolved in dimethyl sulfoxide (hereinafter abbreviated as "DMSO"), and the obtained solution was diluted with commercially available phosphoric acid buffer solution (hereinafter abbreviated as "PBS") to prepare a 20 μg/ml test compound solution.

Preparation of HUVEC Suspension

HUVEC was suspended in a 0.5% fetal bovine serum (hereinafter abbreviated as "FBS")-containing F12K medium to prepare a $2 \times 10^4$ cells/ml HUVEC suspension.

Preparation of VEGF Solution

VEGF was dissolved in 0.1% bovine serum albumin-containing PBS, and the obtained solution was diluted with the 0.5% FBS-containing F12K medium to prepare a 400 ng/ml VEGF solution.

Method of Test and Method of Measurement
1) The HUVEC suspension was inoculated in each amount of 100 μl into each well of a 96-well plate coated with I type collagen ($2 \times 10^3$ cells per well).

2) One day after inoculation, the test compound solution was added in an amount of 5 μl per well.
3) One hour after adding the test compound solution, the VEGF solution was added in an amount of 5 μl per well.
4) Three days after adding the VEGF solution, cell counting kit-8 (Dojin Chemical Co., Ltd.) was added in an amount of 10 μl per well.
5) After three hours, the above-mentioned plate was attached to an absorptiometer (multi label counter ARVO), and absorbance at 450 nm of each well suspension (hereinafter referred to as "test compound suspension") was measured.
6) A test was carried out in the same manner as in 1) to 5) except that 1.0% DMSO was used instead of the test compound solution. Its result was used as a control.

Incubation was carried out under conditions of 37° C., 5% carbon dioxide and 95% air in an incubator throughout the above-mentioned test steps.

Calculation of Cell Growth Inhibition Rates

Cell growth inhibition rates, which are indexes of angiogenesis inhibitory effects, were calculated by the following calculation equation.

Calculation Equation

Cell growth inhibition rate (%)=100−{(Absorbance of test compound suspension−$A$)/(absorbance of control−$A$)}×100

A: Absorbance of Only Cell Suspension (Cell+Medium)

Test Results and Discussion

As examples of test results, Table 1 shows cell growth inhibition rates (%) of test compounds (Compound Nos. 1-1, 1-20, 1-21, 1-22, 1-23, 1-30, 1-35, 1-38, 1-42, 1-47, 1-48, 1-49, 1-50, 1-51, 1-54, 1-55, 1-61, 1-64, 1-65, 1-69, 1-70, 1-72, 1-74, 1-75, 1-77, 1-78, 1-79, 1-80, 1-83, 1-84, 1-85, 1-87, 1-90, 1-91, 1-92, 1-93, 1-95, 1-96, 1-99, 1-102, 1-104, 1-106, 1-111, 1-136, 1-137, 1-158, 1-175, 1-209, 1-213, 1-214, 1-215, 1-216, 1-226, 1-227, 1-228, 1-230, 1-231, 1-232, 1-236, 1-241, 1-246, 1-248, 1-249, 1-250, 1-251, 1-252, 1-253, 1-255, 1-256, 1-263, 1-269, 1-270, 1-273, 1-274, 1-275, 1-276, 1-283, 1-284, 1-285, 1-287, 1-289, 1-290, 1-291, 1-292, 1-296, 1-300, 1-307, 1-308, 4-1, 4-3, 4-4, 4-5, 4-6, 4-7, 4-8, 4-9, 4-10, 4-11, 5-2, 6-1, 7-1, 7-2, 7-3, 7-4 and 8-1).

TABLE 1

| Compound | Cell growth inhibition rate (%) |
|---|---|
| 1-1 | 100 |
| 1-20 | 100 |
| 1-21 | 99 |
| 1-22 | 100 |
| 1-23 | 100 |
| 1-30 | 100 |
| 1-35 | 100 |
| 1-38 | 100 |
| 1-42 | 94 |
| 1-47 | 100 |
| 1-48 | 100 |
| 1-49 | 100 |
| 1-50 | 94 |
| 1-51 | 98 |
| 1-54 | 100 |
| 1-55 | 100 |
| 1-61 | 65 |
| 1-64 | 100 |
| 1-65 | 100 |
| 1-69 | 95 |
| 1-70 | 58 |
| 1-72 | 100 |
| 1-74 | 100 |
| 1-75 | 100 |

TABLE 1-continued

| Compound | Cell growth inhibition rate (%) |
|---|---|
| 1-77 | 100 |
| 1-78 | 100 |
| 1-79 | 100 |
| 1-80 | 100 |
| 1-83 | 100 |
| 1-84 | 100 |
| 1-85 | 95 |
| 1-87 | 100 |
| 1-90 | 100 |
| 1-91 | 100 |
| 1-92 | 100 |
| 1-93 | 72 |
| 1-95 | 100 |
| 1-96 | 70 |
| 1-99 | 100 |
| 1-102 | 55 |
| 1-104 | 100 |
| 1-106 | 100 |
| 1-111 | 100 |
| 1-136 | 100 |
| 1-137 | 100 |
| 1-158 | 100 |
| 1-175 | 100 |
| 1-209 | 99 |
| 1-213 | 100 |
| 1-214 | 92 |
| 1-215 | 100 |
| 1-216 | 100 |
| 1-226 | 100 |
| 1-227 | 60 |
| 1-228 | 100 |
| 1-230 | 100 |
| 1-231 | 100 |
| 1-232 | 75 |
| 1-236 | 100 |
| 1-241 | 96 |
| 1-246 | 76 |
| 1-248 | 75 |
| 1-249 | 100 |
| 1-250 | 86 |
| 1-251 | 77 |
| 1-252 | 100 |
| 1-253 | 100 |
| 1-255 | 85 |
| 1-256 | 100 |
| 1-263 | 100 |
| 1-269 | 53 |
| 1-270 | 99 |
| 1-273 | 100 |
| 1-274 | 95 |
| 1-275 | 100 |
| 1-276 | 100 |
| 1-283 | 100 |
| 1-284 | 100 |
| 1-285 | 100 |
| 1-287 | 95 |
| 1-289 | 100 |
| 1-290 | 100 |
| 1-291 | 100 |
| 1-292 | 100 |
| 1-296 | 100 |
| 1-300 | 100 |
| 1-307 | 100 |
| 1-308 | 92 |
| 4-1 | 93 |
| 4-3 | 100 |
| 4-4 | 100 |
| 4-5 | 100 |
| 4-6 | 100 |
| 4-7 | 100 |
| 4-8 | 98 |
| 4-9 | 100 |
| 4-10 | 100 |
| 4-11 | 100 |
| 5-2 | 96 |
| 6-1 | 72 |
| 7-1 | 100 |

TABLE 1-continued

| Compound | Cell growth inhibition rate (%) |
|---|---|
| 7-2 | 100 |
| 7-3 | 100 |
| 7-4 | 100 |
| 8-1 | 100 |

As shown in Table 1, the present compounds demonstrated excellent cell growth inhibitory actions. Accordingly, the present compounds have excellent angiogenesis inhibitory effects.

2. Evaluation Tests of Anticancer Effects

As one of widely-used methods of evaluating anticancer effects of drugs, a tumor growth inhibitory action test using mouse cancer models was reported in Cancer Res., 59, 5209-5218 (1999). According to the method described in the above-mentioned literature, tumor growth inhibitory action tests of the present compounds were carried out, their tumor tissue weight inhibition rates were calculated, and anticancer effects of the present compounds were evaluated using the obtained rates as indexes.

Preparation of Test Compound Suspension

A 1% aqueous methyl cellulose solution was added to each test compound to suspend it with a sonicator thereby to prepare a 10 mg/ml test compound suspension.

Preparation of B16 Cell Suspension

Physiological saline was added to B16 cells to prepare a $3.3 \times 10^7$ cells/ml B16 cell suspension.

Method of Test and Method of Measurement

1) The back of each mouse (female, six weeks old, C57BL/6 mouse) was depilated using a depilatory under Nembutal anesthesia.

2) Several days after depilation, the B16 cell suspension (300 µl) was injected intradermally into the back of the mouse under Nembutal anesthesia.

3) From the B16 cell injection day (i.e. zero day) to tenth day, the test compound suspension (100 mg/kg/day) was administered orally once a day every day.

4) Ten days after injection of the cells, the mouse was euthanized with a $CO_2$ gas.

5) A tumor tissue was extirpated from the mouse, and weight of the tumor tissue was measured with an electronic balance.

6) A test was carried out in the same manner as in 1) to 5) except that the 1% aqueous methyl cellulose solution was used instead of the test compound suspension, and its result was used as a control.

Calculation of Tumor Tissue Weight Inhibition Rate

Tumor tissue weight inhibition rates (the average of nine mice per group), which are indexes of anticancer effects were calculated, from the following calculation equation.

Calculation Equation

Tumor tissue weight inhibition rate (%)=100−($Mx/Mo$)×100

Mo: Tumor tissue weight of control group
Mx: Tumor tissue weight of test compound solution administration group Test results and discussion As examples of test results, Table 2 shows tumor tissue weight inhibition rates of test compound (Compound Nos. 1-21, 1-22, 1-23, 1-38, 1-48, 1-51, 1-54, 1-80, 1-99, 1-104, 1-106, 1-136, 1-137, 1-158, 1-230, 1-296, 4-4, 4-8, 4-9 and 4-11).

TABLE 2

| Compound | Tumor tissue weight inhibition rate (%) |
|---|---|
| 1-21 | 65 |
| 1-22 | 45 |
| 1-23 | 57 |
| 1-38 | 43 |
| 1-48 | 73 |
| 1-51 | 59 |
| 1-54 | 69 |
| 1-80 | 66 |
| 1-99 | 64 |
| 1-104 | 49 |
| 1-106 | 71 |
| 1-136 | 53 |
| 1-137 | 66 |
| 1-158 | 76 |
| 1-230 | 66 |
| 1-296 | 71 |
| 4-4 | 77 |
| 4-8 | 80 |
| 4-9 | 77 |
| 4-11 | 62 |

As shown in Table 2, the present compounds demonstrated excellent tumor growth inhibitory actions. Accordingly, the present compounds have excellent anticancer effects.

3. Evaluation Tests of Antiarthritic Effects

As one of widely-used methods of evaluating antiarthritic effects of drugs, a paw edema inhibitory action test using rat adjuvant arthritis models is known. Paw edema inhibitory action tests of the present compounds were carried out, their paw edema inhibition rates were calculated, and antiarthritic effects of the present compounds were evaluated using the obtained rates as indexes.

Preparation of Test Compound Suspension

A 1% aqueous methyl cellulose solution was added to each test compound to suspend it thereby to prepare a 2 mg/ml test compound suspension.

Preparation of Adjuvant

Liquid paraffin was added to Mycobacterium-butyricum to suspend it to prepare 6 mg/ml adjuvant.

Experimental Method

1) The adjuvant (0.1 ml) was injected subcutaneously into a left hind paw sole of each rat (male, nine weeks old, Lewis rat) to induce arthritis.

2) From the adjuvant injection day (i.e. zero day) to 20th day, the test compound suspension (10 mg/kg/day) was administered orally once a day every day consecutively.

3) On the adjuvant injection day, after one day, four days, seven days, 11 days, 14 days, 18 days and 21 days, each paw volume of both hind paws was measured with a plethysmometer.

4) A test was carried out in the same manner as in 1) to 3) except that the 1% aqueous methyl cellulose solution was used instead of the test compound suspension, and its result was used as a control.

Method of Evaluation

Each paw edema inhibition rate of paw edema in an adjuvant-untreated paw (secondary inflammation paw) in each test compound administration group was calculated to paw edema in a secondary inflammation paw in a control group, and antiarthritic effects of the present compounds were evaluated using the obtained rates as indexes.

Calculation of Paw Edema Inhibition Rates

Paw edema rates were calculated from the following calculation equation 1, and then paw edema inhibition rates (the average of eight rats per group), which are indexes of the antiarthritic effects, were calculated from the calculation equation 2.

Paw edema rate (%)=(Paw volume after adjuvant treatment/paw volume before adjuvant treatment)×100    Calculation equation 1

Paw edema inhibition rate (%)=100−{($Sx$−100)/($So$−100)}×100    Calculation equation 2

$So$: Paw edema rate of control group
$Sx$: Paw edema rate of test compound suspension administration group
Test Results and Discussion As examples of test results, Table 3 shows paw edema inhibition rates (%) of test compounds (Compound Nos. 1-22, 1-38, 1-54, 1-104, 1-106, 1-137, 1-158 and 4-4) obtained-21 days after.

TABLE 3

| Compound | Paw edema inhibition rate (%) |
|---|---|
| 1-22 | 27 |
| 1-38 | 25 |
| 1-54 | 60 |
| 1-104 | 32 |
| 1-106 | 46 |
| 1-137 | 39 |
| 1-158 | 22 |
| 4-4 | 21 |

As shown in Table 3, the present compounds demonstrated paw edema inhibitory actions. Accordingly, the present compounds have excellent antiarthritic effects.

4. Evaluation Tests of Choroidal Neovascularization Inhibitory Effects

As one of widely-used methods of evaluating choroidal neovascularization inhibitory effects of drugs, a neovascularization incidence test using rat choroidal neovascularization models was reported in Graefe's Arch. Cli. Exp. Opthalmol., 235, 313-319 (1997). According to the method described in the above-mentioned literature, neovascularization incidence tests of the present compounds were carried out, ratios of neovascularization incidence rates of present compounds administration groups were calculated to a neovascularization incidence rate of vehicle administration group (control group), and choroidal neovascularization inhibitory effects of the present compounds were evaluated using the obtained ratios as indexes.

Preparation of Test Compound Solutions

A 1% aqueous methyl cellulose solution was added to each test compound to suspend it thereby to prepare a 6 mg/10 ml test compound suspension.

Preparation of Laser-Induced Rat Choroidal Neovascularization Models

1) A 7:1 mixed solution (1 ml/kg) of a 5% ketamine hydrochloride injection and a 2% xylazine hydrochloride injection was administered intramuscularly to rats (Brown Norway, male, eight weeks old, weight: 200 to 250 g) to anesthetize them systemically.

2) A tropicamide-phenylephrine hydrochloride ophthalmic solution (trade name: Mydrin-P) was instilled into eyes to cause mydriasis, and then photocoagulation was performed in a Bruch's membrane of each rat using a krypton laser photocoagulation apparatus. The laser irradiation was carried out at eight spots per eye sparsely avoiding thick retinal vessels in a posterior section of ocular fundus and focusing on the retinal deep site. Photocoagulation conditions were adjusted to 100 μm of spot size, 100 mM of output and 0.1 sec. of coagulation time.

3) After the photocoagulation, the ocular fundus was photographed to confirm photocoagulation (laser irradiation) sites.

Method of Test and Method of Measurement

1) From the laser irradiation day (i.e. zero day) to sixth day, the test compound suspension (30 mg/kg/day) was administered orally once a day for seven days every day.

2) As the vehicle administration group (control group), a test was carried out in the same manner as in 1) except that the 1% aqueous methyl cellulose solution was used instead of the test compound suspension, and its result was used as a control.

Method of Evaluation

1) Seven days after the photocoagulation, 0.1 ml of a 10% aqueous fluorescein solution was injected into a tail vein of the rat, and fluorescein fundus photography was performed.

2) Next, in the fluorescein fundus photography, a spot where fluorescence leak was not observed was judged as negative, and a spot where fluorescence leak was observed was judged as positive. Photocoagulation sites where a little fluorescence leak was observed were judged as positive when two sites are present.

3) Neovascularization incidence rates were calculated according to the calculation equation 1. Ratios of the neovascularization incidence rates of the test compound administration groups to that of the vehicle administration group were calculated according to the calculation equation 2 from neovascularization incidence rates of respective administration groups.

Neovascularization incidence rate (%)=(Positive photocoagulation site number/total photocoagulation site number)×100    Calculation equation 1

Ratio of neovascularization incidence rate of test compound administration group to that of vehicle administration group(control group)(% of control)=$Ax$/$Ao$×100    Calculation equation 2

$Ao$: Neovascularization incidence rate of vehicle administration group (control group)(% of control)
$Ax$: Neovascularization incidence rate of test compound administration group
Test Results and Discussion As examples of test results, Table 4 shows ratios (% of control) of the neovascularization incidence rates of the test compound (Compound Nos. 1-21, 1-23, 1-54, 1-80, 1-106, 1-136, 1-137, 1-296 and 4-4) administration groups to that of the vehicle administration group (control group)

TABLE 4

| Compound | Ratio of neovascularization incidence rate (% of Control) |
|---|---|
| 1-21 | 15 |
| 1-23 | 26 |
| 1-54 | 51 |
| 1-80 | 18 |
| 1-106 | 22 |
| 1-136 | 38 |
| 1-137 | 65 |
| 1-296 | 24 |
| 4-4 | 26 |

The values are the average of three to four individuals and six to eight eyes.

As shown in Table 4, the present compounds demonstrate lower neovascularization incidence rates than that of the vehicle and have choroidal neovascularization inhibitory effects.

INDUSTRIAL APPLICABILITY

The present invention provides therapeutic agents for diseases in which angiogenesis or augmentation of vascular permeability is involved, particularly as therapeutic agents for cancer, rheumatoid arthritis, age-related macular degeneration, diabetic retinopathy, retinopathy of prematurity, retinal vein occlusion, polyploid choroidal angiopathy, diabetic macular edema, psoriasis vulgaris, pultaceous arteriosclerosis and the like.

What is claimed is:

1. A compound represented by the following formula [I] or a pharmaceutically acceptable salt thereof:

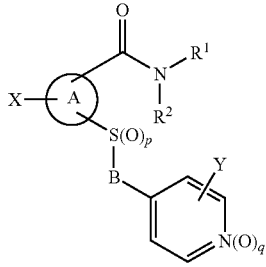

[I]

wherein the ring A is a benzene ring;
and a partial structure [C]

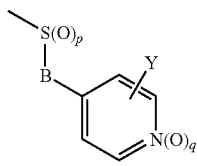

[C]

and a partial structure [D]

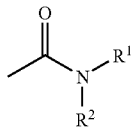

[D]

are bonded to adjacent carbon atoms on the benzene ring;
B is an alkylene;
$R^1$ and $R^2$ are the same or different, and are hydrogen, hydroxy, substituted or unsubstituted alkoxy, substituted or unsubstituted aryloxy, unsubstituted alkyl, substituted or unsubstituted cycloalkyl, substituted or unsubstituted aryl, substituted or unsubstituted heterocycle, amino, substituted or unsubstituted alkylamino, substituted or unsubstituted arylamino, substituted or unsubstituted acyl or an alkyl substituted by one or more groups selected from the group consisting of halogen, hydroxy, alkoxy, aryloxy, cycloalkyl, alkenyl, unsubstituted aryl, aryl substituted by halogen, aryl substituted by alkoxy, a heterocycle, amino, alkylamino, arylamino, mercapto, alkylthio, arylthio, formyl, alkylcarbonyl, arylcarbonyl, cyano and nitro; or $R^1$ and $R^2$ join together to form a substituted or unsubstituted heterocycle;

X and Y are the same or different and are one or more groups selected from the group consisting of hydrogen, halogen, hydroxy, substituted or unsubstituted alkoxy, substituted or unsubstituted aryloxy, substituted or unsubstituted alkyl, substituted or unsubstituted cycloalkyl, substituted or unsubstituted aryl, mercapto, substituted or unsubstituted alkylthio, substituted or unsubstituted arylthio, carboxyl, an ester of carboxyl, an amide of carboxyl, cyano and nitro;

p is 0, 1 or 2; and
q is 0 or 1.

2. The compound or a pharmaceutically acceptable salt thereof as claimed in claim 1, wherein $R^1$ and $R^2$ are the same or different and are hydrogen, substituted or unsubstituted alkoxy, unsubstituted alkyl, substituted or unsubstituted cycloalkyl, substituted or unsubstituted aryl, substituted or unsubstituted heterocycle, substituted or unsubstituted alkylamino, substituted or unsubstituted arylamino or an alkyl substituted by one or more groups selected from the group consisting of halogen, hydroxy, alkoxy, aryloxy, cycloalkyl, alkenyl, unsubstituted aryl, aryl substituted by halogen, aryl substituted by alkoxy, a heterocycle, amino, alkylamino, arylamino, mercapto, alkylthio, arylthio, formyl, alkylcarbonyl, arylcarbonyl, cyano and nitro; or $R^1$ and $R^2$ join, together to form a substituted or unsubstituted heterocycle;

X and Y are one or more groups selected from the group consisting of hydrogen, halogen, substituted or unsubstituted alkoxy, substituted or unsubstituted alkyl, substituted or unsubstituted alkylthio, carboxyl, an ester of carboxyl, an amide of carboxyl and cyano; and p is 0 or 1.

3. The compound or a pharmaceutically acceptable salt thereof as claimed in claim 1, wherein $R^1$ is hydrogen, substituted alkoxy, unsubstituted alkyl, unsubstituted cycloalkyl, substituted or unsubstituted aryl, substituted or unsubstituted heterocycle, unsubstituted alkylamino, substituted arylamino or an alkyl substituted by one or more groups selected from the group consisting of halogen, hydroxy, alkoxy, aryloxy, cycloalkyl, alkenyl, unsubstituted aryl, aryl substituted by halogen, aryl substituted by alkoxy, a heterocycle, amino, alkylamino, arylamino, mercapto, alkylthio, arylthio, formyl, alkylcarbonyl, arylcarbonyl, cyano and nitro;

$R^2$ is hydrogen, unsubstituted alkyl or an alkyl substituted by one or more groups selected from the group consisting of halogen, hydroxy, alkoxy, aryloxy, cycloalkyl, alkenyl, unsubstituted aryl, aryl substituted by halogen, aryl substituted by alkoxy, a heterocycle, amino, alkylamino, arylamino, mercapto, alkylthio, arylthio, formyl, alkylcarbonyl, arylcarbonyl, cyano and nitro; or
$R^1$ and $R^2$ join together to form a substituted or unsubstituted heterocycle;

X is one or more groups selected from the group consisting of hydrogen, halogen and unsubstituted alkyl;
Y is one or more groups selected from the group consisting of hydrogen, halogen, substituted or unsubstituted alkoxy, unsubstituted alkyl, unsubstituted alkylthio, carboxyl, an ester of carboxyl, an amide of carboxyl and cyano; and
p is 0 or 1.

4. A compound or a pharmaceutically acceptable salt thereof, the compound being selected from the group consisting of
  N-(4-chlorophenyl)-2-(4-pyridylmethylthio)benzamide,
  N-(3-chlorophenyl)-2-(4-pyridylmethylthio)benzamide,
  N-(4-dimethylaminophenyl)-2-(4-pyridylmethylthio)benzamide,
  N-(3-isopropylphenyl)-2-(4-pyridylmethylthio)benzamide,
  N-(3,4-dimethoxyphenyl)-2-(4-pyridylmethylthio)benzamide,
  2-(4-pyridylmethylthio)-N-(3-quinolyl)benzamide,
  N-(4-chlorophenyl)-5-fluoro-2-(4-pyridylmethylthio)benzamide,
  N-(4-chloro-3-methylphenyl)-2-(4-pyridylmethylthio)benzamide,
  N-(5-chloro-2,4-dimethoxyphenyl)-2-(4-pyridylmethylthio)benzamide,
  N-(3,5-dimethylphenyl)-2-(4-pyridylmethylthio)benzamide,
  N-(4-bromo-3-methylphenyl)-2-(4-pyridylmethylthio)benzamide and
  N-(3-isoquinolyl)-2-(4-pyridylmethylthio)benzamide.

5. A pharmaceutical composition comprising a pharmaceutically effective amount of the compound or a pharmaceutically acceptable salt thereof as claimed in claim 1 in combination with a pharmaceutical carrier.

6. A method of treating a disease selected from the group consisting of rheumatoid arthritis, age-related macular degeneration, diabetic retinopathy, retinopathy of prematurity, retinal vein occlusion, polyploid choroidal angiopathy, diabetic macular edema, psoriasis vulgaris and pultaceous arteriosclerosis, comprising administering to a patient an effective amount for treatment of the compound or a pharmaceutically acceptable salt thereof as claimed in claim 1.

7. A method of treating a disease selected from the group consisting of rheumatoid arthritis, age-related macular degeneration, diabetic retinopathy, retinopathy of prematurity, retinal vein occlusion, polyploid choroidal angiopathy, diabetic macular edema, psoriasis vulgaris and pultaceous arteriosclerosis, comprising administering to a patient an effective amount for treatment of the compound or a pharmaceutically acceptable salt thereof as claimed in claim 4.

* * * * *